(12) United States Patent
Kramarczyk et al.

(10) Patent No.: US 11,406,703 B2
(45) Date of Patent: Aug. 9, 2022

(54) HUMAN CYTOMEGALOVIRUS VACCINE

(71) Applicant: ModernaTX, Inc., Cambridge, MA (US)

(72) Inventors: Jack F. Kramarczyk, Somerville, MA (US); Kimberly Hassett, Cambridge, MA (US); Shinu John, Cambridge, MA (US); Phil White, Cambridge, MA (US); Andrea Carfi, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 17/411,896

(22) Filed: Aug. 25, 2021

(65) Prior Publication Data
US 2022/0062408 A1  Mar. 3, 2022

Related U.S. Application Data

(60) Provisional application No. 63/136,177, filed on Jan. 11, 2021, provisional application No. 63/079,421, filed on Sep. 16, 2020, provisional application No. 63/070,134, filed on Aug. 25, 2020.

(51) Int. Cl.
| | | |
|---|---|---|
| *A61K 39/245* | (2006.01) | |
| *C12N 7/00* | (2006.01) | |
| *A61K 39/00* | (2006.01) | |

(52) U.S. Cl.
CPC .............. *A61K 39/245* (2013.01); *C12N 7/00* (2013.01); *A61K 2039/53* (2013.01); *A61K 2039/6018* (2013.01); *C12N 2710/16134* (2013.01); *C12N 2710/16171* (2013.01)

(58) Field of Classification Search
CPC .............. A61K 39/245; A61K 2039/53; A61K 2039/6018; C12N 7/00; C12N 2710/16134; C12N 2710/16171
See application file for complete search history.

(56) References Cited

U.S. PATENT DOCUMENTS

| | | | |
|---|---|---|---|
| 3,906,092 A | 9/1975 | Hilleman et al. | |
| 6,074,645 A | 6/2000 | Diamond et al. | |
| 6,162,620 A | 12/2000 | Smith et al. | |
| 6,207,161 B1 | 3/2001 | Pande et al. | |
| 6,448,389 B1 | 9/2002 | Gonczol et al. | |
| 6,500,419 B1 | 12/2002 | Hone et al. | |
| 6,514,948 B1 | 2/2003 | Raz et al. | |
| 6,713,070 B1 | 3/2004 | Plachter et al. | |
| 6,843,992 B2 | 1/2005 | Diamond et al. | |
| 7,001,890 B1 | 2/2006 | Wagner et al. | |
| 7,204,990 B1 | 4/2007 | Kemble et al. | |
| 7,387,782 B2 | 6/2008 | Zaia et al. | |
| 7,410,795 B2 | 8/2008 | Hermanson et al. | |
| 7,419,674 B2 | 9/2008 | Chulay et al. | |
| 8,173,362 B2 | 5/2012 | Shenk et al. | |
| 8,217,016 B2 | 7/2012 | Hoerr et al. | |
| 8,425,898 B2 | 4/2013 | Sampson et al. | |
| 8,673,317 B2 | 3/2014 | Hermanson et al. | |
| 8,691,966 B2 | 4/2014 | Kariko et al. | |
| 8,710,200 B2 | 4/2014 | Schrum et al. | |
| 8,734,853 B2 | 5/2014 | Sood et al. | |
| 8,754,062 B2 | 6/2014 | De Fougerolles et al. | |
| 8,822,663 B2 | 9/2014 | Schrum et al. | |
| 8,877,206 B2 | 11/2014 | Chen et al. | |
| 8,999,380 B2 | 4/2015 | Bancel et al. | |
| 9,149,543 B2 | 10/2015 | Hecker et al. | |
| 9,221,891 B2 | 12/2015 | Bancel et al. | |
| 9,243,041 B2 | 1/2016 | Weiner et al. | |
| 9,283,287 B2 | 3/2016 | Bancel et al. | |
| 9,303,079 B2 | 4/2016 | Bancel et al. | |
| 9,464,124 B2 | 10/2016 | Bancel et al. | |
| 9,486,517 B2 | 11/2016 | Becke et al. | |
| 9,512,456 B2 | 12/2016 | Wang et al. | |
| 9,533,047 B2 | 1/2017 | de Fougerolles et al. | |
| 9,597,380 B2 | 3/2017 | Chakraborty et al. | |
| 9,764,026 B2 | 9/2017 | Sampson et al. | |
| 9,803,199 B2 | 10/2017 | Koizumi et al. | |
| 9,868,691 B2 | 1/2018 | Benenato et al. | |
| 9,872,900 B2 | 1/2018 | Ciaramella et al. | |
| 10,022,435 B2 | 7/2018 | Ciaramella et al. | |
| 10,064,934 B2 | 9/2018 | Ciaramella et al. | |
| 10,064,935 B2 | 9/2018 | Ciaramella et al. | |
| 10,124,055 B2 | 11/2018 | Ciaramella et al. | |

(Continued)

FOREIGN PATENT DOCUMENTS

| | | |
|---|---|---|
| AU | 2015210364 A1 | 3/2017 |
| CA | 2473135 | 6/2003 |

(Continued)

OTHER PUBLICATIONS

John S, Yuzhakov O, Woods A, Deterling J, Hassett K, Shaw CA, Ciaramella G. Multi-antigenic human cytomegalovirus mRNA vaccines that elicit potent humoral and cell-mediated immunity. Vaccine. Mar. 14, 2018;36(12):1689-1699. doi: 10.1016/j.vaccine.2018. 01.029. Epub Feb. 15, 2018. PMID: 29456015. (Year: 2018).*

Maruggi G, Zhang C, Li J, Ulmer JB, Yu D. mRNA as a Transformative Technology for Vaccine Development to Control Infectious Diseases. Mol Ther. Apr. 10, 2019;27(4):757-772. doi: 10.1016/j. ymthe.2019.01.020. Epub Feb. 7, 2019. (Year: 2019).*

Zeng C., Zhang C., Walker P.G., Dong Y. (Jun. 2, 2020) Formulation and Delivery Technologies for mRNA Vaccines. In: . Current Topics in Microbiology and Immunology. Springer, Berlin, Heidelberg. https://doi.org/10.1007/82_2020_217 (Year: 2020).*

International Search Report and Written Opinion for International Application No. PCT/US2021/047541 dated Oct. 26, 2021.

(Continued)

*Primary Examiner* — Rachel B Gill
(74) *Attorney, Agent, or Firm* — Wolf, Greenfield & Sacks, P.C.

(57) ABSTRACT

Aspects of the disclosure relate to methods for producing an antigen-specific immune response to human cytomegalovirus (hCMV) in a subject by administering mRNA vaccines.

30 Claims, 31 Drawing Sheets

Specification includes a Sequence Listing.

(56) References Cited

U.S. PATENT DOCUMENTS

| | | |
|---|---|---|
| 10,207,010 B2 | 2/2019 | Besin et al. |
| 10,232,055 B2 | 3/2019 | Kariko et al. |
| 10,273,269 B2 | 4/2019 | Ciaramella |
| 10,286,086 B2 | 5/2019 | Roy et al. |
| 10,385,088 B2 | 8/2019 | Fraley et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 11,045,540 B2 | 6/2021 | Ciaramella |
| 11,103,578 B2 | 8/2021 | Ciaramella et al. |
| 2003/0092653 A1 | 5/2003 | Kisich et al. |
| 2005/0032730 A1 | 2/2005 | Von Der Mulbe et al. |
| 2005/0059624 A1 | 3/2005 | Hoerr et al. |
| 2005/0170508 A1 | 8/2005 | Huang et al. |
| 2005/0250723 A1 | 11/2005 | Hoerr et al. |
| 2006/0172003 A1 | 8/2006 | Meers et al. |
| 2007/0280929 A1 | 12/2007 | Hoerr et al. |
| 2008/0025944 A1 | 1/2008 | Hoerr et al. |
| 2008/0171711 A1 | 7/2008 | Hoerr et al. |
| 2010/0112042 A1 | 5/2010 | Polisky et al. |
| 2010/0130588 A1 | 5/2010 | Yaworski et al. |
| 2010/0203076 A1 | 8/2010 | Fotin-Mleczek et al. |
| 2010/0239608 A1 | 9/2010 | Von Der Mulbe et al. |
| 2010/0249208 A1 | 9/2010 | Hecker et al. |
| 2010/0291156 A1 | 11/2010 | Barner et al. |
| 2010/0305196 A1 | 12/2010 | Probst et al. |
| 2011/0250225 A1 | 10/2011 | Fotin-Mleczek et al. |
| 2011/0256175 A1 | 10/2011 | Hope et al. |
| 2011/0269950 A1 | 11/2011 | Von Der Mulbe et al. |
| 2012/0009221 A1 | 1/2012 | Hoerr et al. |
| 2012/0101148 A1 | 4/2012 | Aking et al. |
| 2012/0219573 A1 | 8/2012 | Baumhof et al. |
| 2012/0263648 A1 | 10/2012 | Shapiro et al. |
| 2013/0022538 A1 | 1/2013 | Rossi |
| 2013/0102034 A1 | 4/2013 | Schrum et al. |
| 2013/0121988 A1 | 5/2013 | Hoerr et al. |
| 2013/0142818 A1 | 6/2013 | Baumhof et al. |
| 2013/0158021 A1 | 6/2013 | Dong et al. |
| 2013/0183355 A1 | 7/2013 | Jain et al. |
| 2013/0195867 A1 | 8/2013 | Hoerr et al. |
| 2013/0195967 A1 | 8/2013 | Guild et al. |
| 2013/0195969 A1 | 8/2013 | Geall et al. |
| 2013/0202684 A1 | 8/2013 | Geall et al. |
| 2013/0236974 A1 | 9/2013 | De Fougerolles |
| 2013/0243848 A1 | 9/2013 | Lobovkina et al. |
| 2013/0245103 A1 | 9/2013 | de Fougerolles et al. |
| 2013/0259923 A1 | 10/2013 | Bancel et al. |
| 2013/0266640 A1 | 10/2013 | de Fougerolles et al. |
| 2013/0295043 A1 | 11/2013 | Kallen et al. |
| 2013/0336998 A1 | 12/2013 | Kallen et al. |
| 2014/0037660 A1 | 2/2014 | Folin-Mleczek et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0206753 A1 | 7/2014 | Guild et al. |
| 2014/0227346 A1 | 8/2014 | Geall et al. |
| 2014/0271829 A1 | 9/2014 | Lilja et al. |
| 2014/0308304 A1 | 10/2014 | Manoharan et al. |
| 2014/0308308 A1 | 10/2014 | Anderson et al. |
| 2014/0348863 A1 | 11/2014 | Bianchi et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0118183 A1 | 4/2015 | Baumhof et al. |
| 2015/0141499 A1 | 5/2015 | Bancel et al. |
| 2015/0307542 A1 | 10/2015 | Roy et al. |
| 2015/0307850 A1 | 10/2015 | Fu et al. |
| 2015/0315541 A1 | 11/2015 | Bancel et al. |
| 2015/0322115 A1 | 11/2015 | Welinitz et al. |
| 2015/0335732 A1 | 11/2015 | Sampson et al. |
| 2015/0359879 A1 | 12/2015 | Welinitz et al. |
| 2015/0376115 A1 | 12/2015 | Ansell et al. |
| 2016/0022580 A1 | 1/2016 | Ramsay et al. |
| 2016/0024140 A1 | 1/2016 | Issa et al. |
| 2016/0024141 A1 | 1/2016 | Issa et al. |
| 2016/0151284 A1 | 1/2016 | Heyes et al. |
| 2016/0032273 A1 | 2/2016 | Shahrokh et al. |
| 2016/0038612 A1 | 2/2016 | Hoge et al. |
| 2016/0159864 A1 | 6/2016 | Carfi et al. |
| 2016/0213771 A1 | 7/2016 | Sampson et al. |
| 2016/0243221 A1 | 8/2016 | Hoge et al. |
| 2016/0271272 A1 | 9/2016 | Bancel et al. |
| 2016/0296619 A1 | 10/2016 | Orlinger et al. |
| 2016/0317647 A1 | 11/2016 | Ciaramella et al. |
| 2016/0331828 A1 | 11/2016 | Ciaramella et al. |
| 2016/0376224 A1 | 12/2016 | Du et al. |
| 2017/0043037 A1 | 2/2017 | Kariko et al. |
| 2017/0065675 A1 | 3/2017 | Bancel et al. |
| 2017/0119874 A1 | 5/2017 | Lanzavecchia et al. |
| 2017/0143848 A1 | 5/2017 | Calias et al. |
| 2017/0202979 A1 | 7/2017 | Chakraborty et al. |
| 2017/0204152 A1 | 7/2017 | Nelson et al. |
| 2017/0210697 A1 | 7/2017 | Benenato et al. |
| 2017/0239371 A1 | 8/2017 | Guild et al. |
| 2017/0130255 A1 | 10/2017 | Wang et al. |
| 2017/0320916 A1 | 11/2017 | Carfi et al. |
| 2017/0362278 A1 | 12/2017 | Carfi et al. |
| 2018/0000953 A1 | 1/2018 | Almarsson et al. |
| 2018/0002393 A1 | 1/2018 | Bancel et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273467 A1 | 9/2018 | Benenato et al. |
| 2018/0273977 A1 | 9/2018 | Mousavi et al. |
| 2018/0274009 A1 | 9/2018 | Marquardt et al. |
| 2018/0280496 A1 | 10/2018 | Ciaramella et al. |
| 2018/0289792 A1 | 10/2018 | Ciaramella et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0312549 A1 | 11/2018 | Ciaramella |
| 2018/0318409 A1 | 11/2018 | Valiante et al. |
| 2018/0363019 A1 | 12/2018 | Hoge |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0099481 A1 | 4/2019 | Ciaramella et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0241633 A1 | 8/2019 | Fotin-Mleczek et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0309337 A1 | 10/2019 | Rabideau et al. |
| 2019/0314292 A1 | 10/2019 | Benenato et al. |
| 2019/0314493 A1 | 10/2019 | Ciaramella et al. |
| 2019/0336452 A1 | 11/2019 | Brader |
| 2019/0336595 A1 | 11/2019 | Ciaramella |
| 2019/0351040 A1 | 11/2019 | Valiante et al. |
| 2019/0367561 A1 | 12/2019 | Cui et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |

(56) References Cited

U.S. PATENT DOCUMENTS

| | | |
|---|---|---|
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129608 A1 | 4/2020 | Ciaramella et al. |
| 2020/0129615 A1 | 4/2020 | Ciaramella et al. |
| 2020/0163878 A1 | 5/2020 | Baumhof et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2021/0023199 A1 | 1/2021 | Kallen et al. |
| 2021/0030866 A1 | 2/2021 | Kallen et al. |
| 2021/0046173 A1 | 2/2021 | Ciaramella et al. |
| 2021/0163919 A1 | 6/2021 | Issa et al. |
| 2021/0187097 A1 | 6/2021 | Ciaramella et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2021/0309976 A1 | 10/2021 | Dousis et al. |

FOREIGN PATENT DOCUMENTS

| | | | |
|---|---|---|---|
| EP | | 1026253 | 8/2000 |
| EP | | 1083232 | 2/2005 |
| EP | | 1905844 A2 | 2/2008 |
| EP | | 2548960 A1 | 1/2013 |
| EP | | 3310384 A1 | 4/2018 |
| WO | WO 1987/005326 A1 | | 9/1987 |
| WO | WO 1990/011092 | | 10/1990 |
| WO | WO 1993/014778 | | 8/1993 |
| WO | WO 1995/024485 | | 9/1995 |
| WO | WO 1995/026204 | | 10/1995 |
| WO | WO 1995/033835 | | 12/1995 |
| WO | WO 1998/033510 A1 | | 2/1998 |
| WO | WO 1999/033982 | | 7/1999 |
| WO | WO 2001/093836 A2 | | 12/2001 |
| WO | WO 2003/059381 | | 7/2003 |
| WO | WO 2004/058166 A2 | | 7/2004 |
| WO | WO 2004/076645 A2 | | 9/2004 |
| WO | WO 2005/007689 A1 | | 1/2005 |
| WO | WO 2005/009346 | | 2/2005 |
| WO | WO 2005/034979 A2 | | 4/2005 |
| WO | WO 2005/120152 A1 | | 12/2005 |
| WO | WO 2006/056027 A1 | | 6/2006 |
| WO | WO 2006/071903 | | 7/2006 |
| WO | WO 2006/095259 | | 9/2006 |
| WO | WO 2007/051303 A1 | | 5/2007 |
| WO | WO 2007/095976 A2 | | 8/2007 |
| WO | WO 2007/146024 A2 | | 12/2007 |
| WO | WO 2008/052770 A2 | | 5/2008 |
| WO | WO 2008/103276 A2 | | 8/2008 |
| WO | WO 2009/030254 A1 | | 3/2009 |
| WO | WO 2009/030481 A1 | | 3/2009 |
| WO | WO 2009/095226 | | 8/2009 |
| WO | WO 2009/127060 A1 | | 10/2009 |
| WO | WO 2009/127230 A1 | | 10/2009 |
| WO | WO 2009/155535 A2 | | 12/2009 |
| WO | WO 2010/037408 A1 | | 4/2010 |
| WO | WO 2010/037539 A1 | | 4/2010 |
| WO | WO 2010/042877 A1 | | 4/2010 |
| WO | WO 2010/053572 A2 | | 5/2010 |
| WO | WO 2010/054406 A1 | | 5/2010 |
| WO | WO 2010/088927 A1 | | 8/2010 |
| WO | WO 2011/005799 A2 | | 1/2011 |
| WO | WO 2011/026641 A9 | | 3/2011 |
| WO | WO 2011/068810 A1 | | 6/2011 |
| WO | WO 2011/069529 A1 | | 6/2011 |
| WO | WO 2011/069586 A1 | | 6/2011 |
| WO | WO 2011/140627 A1 | | 11/2011 |
| WO | WO 2011/144358 A1 | | 11/2011 |
| WO | WO 2012/006376 A2 | | 1/2012 |
| WO | WO 2012/019630 A1 | | 2/2012 |
| WO | WO 2012/019780 A1 | | 2/2012 |
| WO | WO 2012/034025 A1 | | 3/2012 |
| WO | WO 2012/051211 A2 | | 4/2012 |
| WO | WO 2012/106377 A2 | | 8/2012 |
| WO | WO 2012/116714 A1 | | 9/2012 |
| WO | WO 2012/116715 A1 | | 9/2012 |
| WO | WO 2012/116810 A1 | | 9/2012 |
| WO | WO 2012/116811 A1 | | 9/2012 |
| WO | WO 2013/006838 A1 | | 1/2013 |
| WO | WO 2013/006842 A2 | | 1/2013 |
| WO | WO 2013/036465 A2 | | 3/2013 |
| WO | WO 2013/055905 A1 | | 4/2013 |
| WO | WO 2013/068847 A2 | | 5/2013 |
| WO | WO 2013/090186 A1 | | 6/2013 |
| WO | WO 2013/096812 A1 | | 6/2013 |
| WO | WO 2013/102203 A1 | | 7/2013 |
| WO | WO 2013/120629 A1 | | 8/2013 |
| WO | WO 2013/151666 A2 | | 10/2013 |
| WO | WO 2013/185069 A1 | | 12/2013 |
| WO | WO 2014/005959 A1 | | 1/2014 |
| WO | WO 2014/018117 A1 | | 1/2014 |
| WO | WO-2014/068001 A1 | | 5/2014 |
| WO | WO 2014/089239 A1 | | 6/2014 |
| WO | WO 2014/089486 A1 | | 6/2014 |
| WO | WO 2014/152027 A1 | | 9/2014 |
| WO | WO 2014/152774 A1 | | 9/2014 |
| WO | WO 2014/152940 A1 | | 9/2014 |
| WO | WO 2014/160243 A1 | | 10/2014 |
| WO | WO 2014/172045 A1 | | 10/2014 |
| WO | WO 2014/182661 A2 | | 11/2014 |
| WO | WO 2015/005253 A1 | | 1/2015 |
| WO | WO 2015/024668 A2 | | 2/2015 |
| WO | WO 2015/061467 A1 | | 4/2015 |
| WO | WO 2015/089340 A1 | | 6/2015 |
| WO | WO 2015/095340 A1 | | 6/2015 |
| WO | WO 2015/095346 A1 | | 6/2015 |
| WO | WO 2015/110659 A1 | | 7/2015 |
| WO | WO 2015/161926 A1 | | 10/2015 |
| WO | WO 2015/082570 A1 | | 11/2015 |
| WO | WO 2015/165480 A1 | | 11/2015 |
| WO | WO 2015/170287 A1 | | 11/2015 |
| WO | WO 2015/181142 A1 | | 12/2015 |
| WO | WO 2015/199952 A1 | | 12/2015 |
| WO | WO 2016/004318 A1 | | 1/2016 |
| WO | WO 2016/037053 A1 | | 3/2016 |
| WO | WO 2016/067239 A1 | | 5/2016 |
| WO | WO 2016/092460 A2 | | 6/2016 |
| WO | WO 2016/116904 A1 | | 7/2016 |
| WO | WO 2016/116905 A1 | | 7/2016 |
| WO | WO 2016/130693 A1 | | 8/2016 |
| WO | WO 2016/133881 A1 | | 8/2016 |
| WO | WO 2016/164762 A1 | | 10/2016 |
| WO | WO 2017/070613 A1 | | 10/2016 |
| WO | WO 2016/184822 A1 | | 11/2016 |
| WO | WO 2016/201377 A1 | | 12/2016 |
| WO | WO 2016/203025 A1 | | 12/2016 |
| WO | WO 2017/015457 A1 | | 1/2017 |
| WO | WO 2017/019935 A1 | | 2/2017 |
| WO | WO 2017/020026 A1 | | 2/2017 |
| WO | WO 2017/153936 | | 3/2017 |
| WO | WO 2017/062513 A1 | | 4/2017 |
| WO | WO 2017/066789 A1 | | 4/2017 |
| WO | WO 2017/070601 A1 | | 4/2017 |
| WO | WO 2017/075531 A1 | | 5/2017 |
| WO | WO 2017/127750 A1 | | 7/2017 |
| WO | WO 2017/191274 A2 | | 11/2017 |
| WO | WO 2017/201333 A1 | | 11/2017 |
| WO | WO 2017/201340 A1 | | 11/2017 |
| WO | WO 2017/201342 A1 | | 11/2017 |
| WO | WO 2017/201347 A1 | | 11/2017 |
| WO | WO 2017/201349 A1 | | 11/2017 |
| WO | WO 2017/208191 A1 | | 12/2017 |
| WO | WO 2018/075980 A1 | | 4/2018 |
| WO | WO-2018075980 A1 * | | 4/2018 ............ A61K 39/12 |
| WO | WO 2018/078053 A1 | | 5/2018 |
| WO | WO 2018/081459 A1 | | 5/2018 |
| WO | WO 2018/089851 A1 | | 5/2018 |
| WO | WO 2018/107088 A1 | | 6/2018 |
| WO | WO 2018/111967 A1 | | 6/2018 |
| WO | WO 2018/144082 A1 | | 8/2018 |
| WO | WO 2018/144778 A1 | | 8/2018 |
| WO | WO 2018/157009 A1 | | 8/2018 |
| WO | WO 2018/170245 A1 | | 9/2018 |

(56) References Cited

FOREIGN PATENT DOCUMENTS

| | | |
|---|---|---|
| WO | WO 2018/170256 A1 | 9/2018 |
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |
| WO | WO 2018/187590 A2 | 10/2018 |
| WO | WO 2018/200737 A1 | 11/2018 |
| WO | WO 2018/232355 A1 | 12/2018 |
| WO | WO 2018/232357 A1 | 12/2018 |
| WO | WO 2019/036670 A1 | 2/2019 |
| WO | WO 2019/036682 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2019/148101 A1 | 8/2019 |
| WO | WO 2020/006242 A1 | 1/2020 |
| WO | WO 2020/056370 A1 | 3/2020 |
| WO | WO 2020/061284 A1 | 3/2020 |
| WO | WO 2020/061295 A1 | 3/2020 |
| WO | WO 2020/061367 A1 | 3/2020 |
| WO | WO 2020/097291 A1 | 5/2020 |
| WO | WO 2020/172239 A1 | 8/2020 |
| WO | WO 2020/185811 A1 | 9/2020 |
| WO | WO 2020/190750 A1 | 9/2020 |
| WO | WO 2020/243561 A1 | 12/2020 |
| WO | WO 2021/030533 A1 | 2/2021 |
| WO | WO 2021/050864 A1 | 3/2021 |
| WO | WO 2021/055811 A1 | 3/2021 |
| WO | WO 2021/155243 A1 | 8/2021 |
| WO | WO 2021/159040 A2 | 8/2021 |
| WO | WO 2021/159130 A2 | 8/2021 |
| WO | WO 2021/211343 A1 | 10/2021 |
| WO | WO 2021/222304 A1 | 11/2021 |
| WO | WO 2021/231929 A1 | 11/2021 |
| WO | WO 2021/231963 A1 | 11/2021 |

OTHER PUBLICATIONS

[No Author Listed], "Messenger RNA", Internet: Wikipedia. Jun. 19, 2013, XP002699196, Retrieved from the Internet: URL: http://en.wikipedia.org/wiki/Messenger RNA.

[No Author Listed], Clinical Trial NCT03382405. "Safety, Reactogenicity, and Immunogenicity of Cytomegalovirus Vaccines mRNA-1647 and mRNA-1443 in Healthy Adults." First posted Dec. 22, 2017. Retrieved online Nov. 13, 2020 from https://www.clinicaltrials.gov/ct2/show/study/NCT03382405?term=modernatx&draw=3&rank=14.

[No Author Listed], 'Moderna Announces Additional Positive Phase 1 Data from Cytomegalovirus (CMV) Vaccine (mRNA-1647) and First Participant Dosed in Phase 2 Study', Jan. 9, 2020, retrieved from the internet on Sep. 28, 2021 from https://www.businesswire.com/news/home/20200109005801/en/Moderna-Announces-Additional-Positive-Phase-1-Data-from-Cytomegalovirus-CMV-V accine-mRNA-1647-and-First-Participant-Dosed-in-Phase-2-Study.

[No Author Listed], 'Moderna Announces Positive Interim Results from Phase 1 Cytomegalovirus (CMV) Vaccine (mRNA-1647) Study and Progress Toward Phase 2 and Pivotal Trials', Sep. 12, 2019, retrieved from the internet on Sep. 28, 2021 from https://investors.modernatx.com/news-releases/news-release-details/moderna-announces-positive-interim-results-phase-1.

Anderson et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.

Andries et al., N(1)-methylpseudouridine-incorporated mRNA outperforms pseudouridine-incorporated mRNA by providing enhanced protein expression and reduced immunogenicity in mammalian cell lines and mice. J Control Release. Nov. 10, 2015;217:337-44. doi: 10.1016/j.jconrel.2015.08.051. Epub Sep. 3, 2015.

Archer, S.J., Induction of a T-cell specific antigen on bone marrow lymphocytes with thymus RNA. Immunology. Jan. 1978;34(1):123-9.

Ashley, D.M. et al., Bone marrow-generated dendritic cells pulsed with tumor extracts or tumor RNA induce antitumor immunity against central nervous system tumors. J Exp Med. Oct. 6, 1997; 186(7): 1177-82.

Bettinger, T. et al., Peptide-mediated RNA delivery: a novel approach for enhanced transfection of primary and post-mitotic cells. Nucleic Acids Res. Sep. 15, 2001;29(18):3882-91.

Bogers et al., Potent immune responses in rhesus macaques induced by nonviral delivery of a self-amplifying RNA vaccine expressing HIV type 1 envelope with a cationic nanoemulsion.J Infect Dis. Mar. 15, 2015;211(6):947-55. doi: 10.1093/infdis/jiu522. Epub Sep. 18, 2014.

Bonehill, A., et al., Single-step antigen loading and activation of dendritic cells by mRNA electroporation for the purpose of therapeutic vaccination in melanoma patients. Clin Cancer Res. May 2009; 15(10): 3366-3375.

Bowie et al., Deciphering the message in protein sequences: tolerance to amino acid substitutions. Science. Mar. 16, 1990;247(4948):1306-10.

Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.

Brito et al., Self-amplifying mRNA vaccines. Adv Genet. 2015;89:179-233. doi: 10.1016/bs.adgen.2014.10.005. Epub Dec. 4, 2014.

Cairns et al., Patient-Specific Neutralizing Antibody Responses to Herpes Simplex Virus Are Attributed to Epitopes on gD, GB, or Both and Can Be Type Specific. J Virol. Sep. 2015;89(18):9213-31. doi: 10.1128/JVI.01213-15. Epub Jun. 24, 2015.

Chen et al., Influence of Particle Size on the in Vivo Potency of Lipid Nanoparticle Formulations of siRNA. J Control Release. Aug. 10, 2016;235:236-244. doi: 10.1016/j.jconrel.2016.05.059. Epub May 26, 2016.

Chiuppesi et al., Vaccine-Derived Neutralizing Antibodies to the Human Cytomegalovirus gH/gL Pentamer Potently Block Primary Cytotrophoblast Infection. J Virol. Dec. 2015;89(23):11884-98. doi: 10.1128/JVI.01701-15. Epub Sep. 16, 2015.

Conry, R.M. et al., Characterization of a messenger RNA polynucleotide vaccine vector. Cancer Res. Apr. 1, 1995 ;55 (7):1397-1400.

Cosman et al., ULBPs, Novel MHC Class I-Related Molecules, Bind to CMV Glycoprotein UL 16 and Stimulate NK Cytotoxicity through the NKG2D Receptor, Immunity,2001, vol. 14, No vol. pp. 123-133.

Cullis et al., Lipid Nanoparticle Systems for Enabling Gene Therapies. Mol Ther. Jul. 5, 2017;25(7):1467-1475. doi: 10.1016/j.ymthe. 2017.03.013. Epub Apr. 13, 2017.

Dahlman et al., In vivo endothelial siRNA delivery using polymeric nanoparticles with low molecular weight, Nature Nanotechnology, 2014, No vol.#, pp. 1-8.

Davison, Human herpesvirus 5 strain Merlin, complete genome. GenBank: AY446894.2, Dep. Jul. 2, 2013.

Davison. UL 128 [Human herpesvirus 5], GenBank: AAR31335. Dep. Dec. 20, 2003.

Deering et al., Nucleic Acid Vaccines: Prospects for Non-Viral Delivery of mRNA Vaccines, Expert Opinion, 2014, vol. 11, No. 6, pp. 1-15.

Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.

Durbin et al., RNAs Containing Modified Nucleotides Fail To Trigger RIG-I Conformational Changes for Innate Immune Signaling. mBio. Sep. 20, 2016;7(5):e00833-16. doi: 10.1128/mBio.00833-16.

Ernsting et al., Factors controlling the pharmacokinetics, biodistribution and intratumoral penetration of nanoparticles. J Control Release. Dec. 28, 2013;172(3):782-94. doi: 10.1016/j.jconrel.2013.09.013. Epub Sep. 25, 2013.

Ewert et al., Cationic liposome-nucleic acid complexes for gene delivery and silencing: pathways and mechanisms for plasmid DNA and siRNA. Top Curr Chem. 2010;296:191-226.

(56) References Cited

OTHER PUBLICATIONS

Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
Genini et al., Serum Antibody Response to the gH/gL/pUL128-131 Five-Protein Complex of Human Cytomegalovirus (HCMV) in Primary and Reactivated HCMV Infections. J Clin Virol. Oct. 2011;52(2):113-8. doi: 10.1016/j.jcv.2011.06.018. Epub Aug. 4, 2011.
Gerna et al., Human cytomegalovirus (HCMV) infection/re-infection: development of a protective HCMV vaccine.New Microbiol. Jan. 2019;42(1):1-20. Epub Jan. 21, 2019.
Gilboa, E. et al., Cancer immunotherapy with mRNA-transfected dendritic cells. lmmunol Rev. Jun. 2004;199:251-63.
Gindy et al., Stabilization of Ostwald ripening in low molecular weight amino lipid nanoparticles for systemic delivery of siRNA therapeutics. Mol Pharm. Nov. 3, 2014;11(11):4143-53. doi: 10.1021/mp500367k. Epub Oct. 15, 2014.
Gjetting et al., In vitro and in vivo effects of polyethylene glycol (PEG)-modified lipid in DOTAP/cholesterol-mediated gene transfection. Int J Nanomedicine. Aug. 9, 2010;5:371-83.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.
Hajj et al., Tools for translation: non-viral materials for therapeutic mRNA delivery. Nat Rev Mat. Sep. 2017;2:17056.
Hartmann et al., Handbook of RNA Biochemistry, Second Edition, "Part I RNA Synthesis and Detection." 2014. p. 1-27.
Hassett et al., Optimization of Lipid Nanoparticles for Intramuscular Administration of mRNA Vaccines. Mol Ther Nucleic Acids. Apr. 15, 2019;15:1-11. Epub Feb. 7, 2019.
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Hecker, Nonviral, cationic lipid-mediated delivery of mRNA. Methods Mol Biol. 2013;969:73-88. doi: 10.1007/978-1-62703-260-5_5.
Heiser, A. et al., Induction of polyclonal prostate cancer-specific CTL using dendritic cells transfected with amplified tumor RNA. J lmmunol. Mar. 1, 2001; 166(5):2953-60.
Hoerr, I. et al., In vivo application of RNA leads to induction of specific cytotoxic T lymphocytes and antibodies. EurJ lmmunol. Jan. 2000;30(1):1-7.
Hoerr, I. et al., Stabilized Messenger RNA (RNActiveTM) as a Tool for Innovative Gene Delivery. Tissue Engineering. Apr. 2007; 13(4): 865-925.
Hoerr, More than a messenger: A new class of drugs-mRNA-based therapeutics. Genetic Engineering & Biotechnology News. Jun. 18, 2013. http://www.genengnews.com/gen-articles/more-than-a-messenger-a-new-class-of-drugs-mrna-based-therapeutics/4916/ [last accessed Mar. 25, 2016].
Holtkamp, S. et al., Modification of antigen-encoding RNA increases stability, translational efficacy, and T-cell stimulatory capacity of dendritic cells. Blood. Dec. 15, 2006;108(13):4009-17.
Jirikowski, G.F., et al., Reversal of diabetes insipidus in Brattleboro Rats: lntrahypothalamic injection of vasopressin mRNA. Science. Feb. 1992; 255(5047): 996-998.
John et al., Multi-antigenic human cytomegalovirus mRNA vaccines that elicit potent humoral and cell-mediated immunity. Vaccine. Mar. 14, 2018;36(12):1689-1699. doi:10.1016/j.vaccine.2018.01.029. Epub Feb. 15, 2018.
Johnston et al., Status of vaccine research and development of vaccines for herpes simplex virus. Vaccine. Jun. 3, 2016;34(26):2948-2952. doi: 10.1016/j.vaccine.2015.12.076. Epub Mar. 11, 2016.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.
Kanapathipillai, et al., Nanoparticle targeting of anti-cancer drugs that alter intracellular signaling or influence the tumor microenvironment, Adv. Drug Deliv. Rev. (2014), , pp. 1-12.
Kariko, K., et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093/nar/gkr695. Epub Sep. 2, 2011.
Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.
Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.
Kisich et al., Antimycobacterial agent based on mRNA encoding human beta-defensin 2 enables primary macrophages to restrict growth of *Mycobacterium tuberculosis*.Infect Immun. Apr. 2001;69(4):2692-9.
Koelle et al., Recent progress in herpes simplex virus immunobiology and vaccine research. Clin Microbiol Rev. Jan. 2003;16(1):96-113. doi: 10.1128/CMR.16.1.96-113.2003.
Kowalski et al., Delivering the Messenger: Advances in Technologies for Therapeutic mRNA Delivery. Mol Ther. Apr. 10, 2019;27(4):710-728. doi: 10.1016/j.ymthe.2019.02.012.
Kozielski, Kristen L. et al., Bioreducible Cationic Polymer-Based Nanoparticles for Efficient and Environmentally Triggered Cytoplasmic siRNA Delivery to Primary Human Brain Cancer Cells, ACS Nano, 2014, vol. 8,'No. 4',pp. 3232-3241.
Kreiter, S., et al., lntranodal vaccination with naked antigen-encoding RNA elicits potent prophylactic and therapeutic antitumoral immunity. Cancer Res. 2010; 70: 9031-9040.
Kreiter, S., et al., Tumor vaccination using messenger RNA: prospects of a future therapy. Curr Opinion in lmmun. Jun. 2011; 23(3): 399-406.
Kuhn, A.N., et al., mRNA as a versatile tool for exogenous protein expression. Current Gene Therapy. Oct. 2012; 12 (5): 347-361.
Kumar et al., Shielding of Lipid Nanoparticles for siRNA Delivery: Impact on Physicochemical Properties, Cytokine Induction, and Efficacy. Mol Ther Nucleic Acids. Nov. 18, 2014;3(11):e210. doi: 10.1038/mtna.2014.61.
Kurimoto et al., PEG-OligoRNA Hybridization of mRNA for Developing Sterically Stable Lipid Nanoparticles toward In Vivo Administration. Molecules. Apr. 3, 2019;24(7): 1303.
Leitner, W.W. et al., DNA and RNA-based vaccines: principles, progress and prospects. Vaccine. Dec. 10, 1999;18 (9-10):765-77.
Leroueil et al., Wide varieties of cationic nanoparticles induce defects in supported lipid bilayers. Nano Lett. Feb. 2008;8(2):420-4. doi: 10.1021/n10722929. Epub Jan. 25, 2008.
Li, L. et al., Overcoming obstacles to develop effective and safe siRNA therapeutics. Expert Opin Biol Ther. May 2009; 9(5): 609-19.
Lin et al., Lipid-based nanoparticles in the systemic delivery of siRNA. Nanomedicine (Lond). Jan. 2014;9(1):105-20. doi: 10.2217/nnm.13.192.
Lorenzi, J.C., et al., Intranasal vaccination with messenger RNA as a new approach in gene therapy: Use against tuberculosis. BMC Biotechnol. Oct. 2010; 10(77): 1-11.
Magini et al., Self-Amplifying mRNA Vaccines Expressing Multiple Conserved Influenza Antigens Confer Protection against Homologous and Heterosubtypic Viral Challenge. PLoS One. Aug. 15, 2016;11(8):e0161193. doi: 10.1371/journal.pone.0161193. eCollection 2016.

(56) References Cited

OTHER PUBLICATIONS

Maier et al., Biodegradable Lipids Enabling Rapidly Eliminated Lipid Nanoparticles for Systemic Delivery of RNAi Therapeutics. Mol Ther. Aug. 2013; 21(8): 1570-1578.
Martinon, F. et al., Induction of virus-specific cytotoxic T lymphocytes in vivo by liposome-entrapped mRNA. EurJ lmmunol. Jul. 1993;23(7):1719-22.
McVoy et al., A cytomegalovirus DNA vaccine induces antibodies that block viral entry into fibroblasts and epithelial cells. Vaccine . Dec. 16, 2015;33(51):7328-7336. doi: 10.1016/j.vaccine.2015.10.078. Epub Oct. 24, 2015.
McVoy, Cytomegalovirus vaccines. Clin Infect Dis. Dec. 2013;57 Suppl 4:S196-9. doi: 10.1093/cid/cit587.
Michel et al., Cationic Nanoliposomes Meet mRNA: Efficient Delivery of Modified mRNA Using Hemocompatible and Stable Vectors for Therapeutic Applications. Mol Ther Nucleic Acids. Sep. 15, 2017;8:459-468. doi: 10.1016/j.omtn.2017.07.013. Epub Jul. 25, 2017.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mitchell, DA et al., RNA transfected dendritic cells as cancer vaccines. Curr Opin Mal Ther. Apr. 2000;2(2):176-81.
Mitchell, DA et al., RNA-transfected dendritic cells in cancer immunotherapy. J Clin Invest. Nov. 2000;106 (9):1065-9.
Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.
Muller, M.R. et al., Transfection of dendritic cells with RNA induces CD4- and COB-mediated T cell immunity against breast carcinomas and reveals the immunodominance of presented T cell epitopes. J lmmunol. Jun. 15, 2003;170 (12):5892-6.
Oberli et al., Lipid Nanoparticle Assisted mRNA Delivery for Potent Cancer Immunotherapy. Nano Lett. Mar. 8, 2017;17(3):1326-1335. doi: 10.1021/acs.nanolett.6b03329. Epub Dec. 5, 2016.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.
Pardi et al., mRNA vaccines—a new era in vaccinology. Nat Rev Drug Discov. Apr. 2018;17(4):261-279. doi: 10.1038/nrd.2017.243. Epub Jan. 12, 2018.
Pardi et al., Nucleoside-modified mRNA vaccines induce potent T follicular helper and germinal center B cell responses. J Exp Med. Jun. 4, 2018;215(6):1571-1588. doi: 10.1084/jem.20171450. Epub May 8, 2018.
Pass et al., Vaccine prevention of maternal cytomegalovirus infection. N Engl J Med. Mar. 19, 2009;360(12):1191-9. doi: 10.1056/NEJMoa0804749.
Patel et al., Naturally-occurring cholesterol analogues in lipid nanoparticles induce polymorphic shape and enhance intracellular delivery of mRNA. Nat Commun. Feb. 20, 2020;11(1):983. doi: 10.1038/s41467-020-14527-2.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Phua et al., Messenger RNA (mRNA) nanoparticle tumour vaccination. Nanoscale. Jul. 21, 2014;6(14):7715-29. doi: 10.1039/c4nr01346h. Review.
Poveda et al., Establishing Preferred Product Characterization for the Evaluation of RNA Vaccine Antigens. Vaccines (Basel). Sep. 27, 2019;7(4):131. doi: 10.3390/vaccines7040131.
Pulford, B., et al., Liposome-siRNA-peptide complexes cross the blood-brain barrier and significantly decrease PrP'C on neuronal cells and PrP'RES in infected cell cultures. PLoS One. 201 O; 5(6): e11085.
Rabinovich, P.M., et al., Synthetic messenger RNA as a tool for gene therapy. Hum. Gene Ther. Oct. 2006; 17: 1027-1035.

Ramamoorth et al., Non viral vectors in gene therapy—an overview. J Clin Diagn Res. Jan. 2015; 9(1): GE01-GE06.
Reap et al., Cellular and humoral immune responses to alpha virus replicon vaccines expressing cytomegalovirus pp65, IE1, and GB proteins. Clin Vaccine Immunol. Jun. 2007;14(6):748-55. Epub Apr. 18, 2007.
Reichmuth et al., mRNA Vaccine Delivery Using Lipid Nanoparticles. Ther Deliv. 2016;7(5):319-34. doi: 10.4155/tde-2016-0006.
Rittig et al., Intradermal vaccinations with RNA coding for TAA generate CD8+ and CD4+ immune responses and induce clinical benefit in vaccinated patients. Mol Ther. May 2011;19(5):990-9. doi: 10.1038/mt.2010.289. Epub Dec. 28, 2010.
Sabnis et al., A Novel Amino Lipid Series for mRNA Delivery: Improved Endosomal Escape and Sustained Pharmacology and Safety in Non-human Primates. Mol Ther. Jun. 6, 2018;26(6):1509-1519. doi: 10.1016/j.ymthe.2018.03.010. Epub Mar. 14, 2018.
Sahin et al., mRNA-based therapeutics—developing a new class of drugs. Nat Rev Drug Discov. Oct. 2014;13(10):759-80. doi: 10.1038/nrd4278. Epub Sep. 19, 2014.
Schlake et al., Developing mRNA-vaccine technologies. RNA Biol. Nov. 2012;9(11):1319-30. doi: 10.4161/rna.22269. Epub Oct. 12, 2012.
Schleiss et al., Additive Protection against Congenital Cytomegalovirus Conferred by Combined Glycoprotein B/pp65 Vaccination Using a Lymphocytic Choriomeningitis Virus Vector. Clin Vaccine Immunol. Jan. 5, 2017;24(1). pii: e00300-16. doi: 10.1128/CVI.00300-16. Print Jan. 2017.
Schleiss, Cyotmegalovirus vaccines under clinical development. J Virus Erad. Oct. 5, 2016;2(4):198-207.
Schmitt, W.E. et al., In vitro induction of a bladder cancer-specific T-cell response by mRNA-transfected dendritic cells. J Cancer Res Clin Oncol. 2001 ;127(3):203-6.
Schott, J.W., et al., Viral and non-viral approaches for transient delivery of mRNA and proteins. Current Gene Ther. 2011; 11 (5): 382-398.
Segura, J., et al., Monitoring gene therapy by external imaging of mRNA: Pilot study on murine erythropoietin. Ther Drug Monit. Oct. 2007; 29(5): 612-8.
Semple, S.C., et al., Rational design of cationic lipids for siRNA delivery. Nat Biotechnol. Feb. 2010; 28(2): 172-176.
Sirin et al. AB-Bind: Antibody binding mutational database for computational affinity predictions. Protein Sci. Feb. 2016;25(2):393-409. doi: 10.1002/pro.2829. Epub Nov. 6, 2015.
Smits, E., et al., RNA-based gene transfer for adult stem cells and T cells. Leukemia. 2004; 18:1898-1902.
Sohn, R.L., et al., In-vivo particle mediated delivery of mRNA to mammalian tissues: ballistic and biological effects. Wound Rep and Regen. Jul.-Aug. 2001; 287-296.
Stanton et al., Human herpesvirus 5 transgenic strain Merlin, complete genome. GenBank: GU179001. Dep. Dec. 13, 2009.
Strong, V.T. et al., Incorporation of beta-globin untranslated regions into a Sindbis virus vector for augmentation of heterologous mRNA expression. Gene Ther. Jun. 1997;4(6):624-7.
Sullenger, BA et al., Emerging clinical applications of RNA. Nature. Jul. 11, 2002;418(6894):252-8.
Sun et al., Human herpesvirus 5 isolate D-947 UL131A, UL130, and UL128 genes, complete cds. GenBank: GU568344. Dep. Apr. 20, 2010.
Szebeni et al., Activation of complement by therapeutic liposomes and other lipid excipient-based therapeutic products: prediction and prevention. Adv Drug Deliv Rev. Sep. 16, 2011;63(12):1020-30. doi: 10.1016/j.addr.2011.06.017. Epub Jul. 14, 2011.
Szebeni et al., Complement activation as a bioequivalence issue relevant to the development of generic liposomes and other nanoparticulate drugs. Biochem Biophys Res Commun. Dec. 18, 2015;468(3):490-7. doi: 10.1016/j.bbrc.2015.06.177. Epub Jul. 14, 2015.
Szebeni, Complement activation-related pseudoallergy: a stress reaction in blood triggered by nanomedicines and biologicals. Mol Immunol. Oct. 2014;61(2):163-73. doi: 10.1016/j.molimm.2014.06.038. Epub Aug. 12, 2014.

(56) References Cited

OTHER PUBLICATIONS

Tavernier, G., et al., mRNA as gene therapeutic: How to control protein expression. J. of Controlled Release. Mar. 2011; 150(3): 238-247.
Terapa et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir. 0c03039. Epub Jan. 13, 2021.
Teufel, R. et al., Human peripheral blood mononuclear cells transfected with messenger RNA stimulate antigen-specific cytotoxic T-lymphocytes in vitro. Cell Mol Life Sci. Aug. 2005;62(15):1755-62.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015. 103. Epub Jun. 8, 2015.
Torrecilla et al., Lipid Nanoparticles as Carriers for RNAi Against Viral Infections: Current Status and Future Perspectives. Biomed Res Int. 2014;2014:161794. doi: 10.1155/2014/161794. Epub Aug. 12, 2014.
Tripathy et al., Long-term expression of erythropoietin in the systemic circulation of mice after intramuscular injection of a plasmid DNA vector, Proc. Natl. Acad. Sci. USA 93, 1996, pp. 10876-10880.
Uzgun, S., et al., PEGylation improves nanoparticle formation and transfection efficiency of messenger RNA. Pharm Res. Sep. 2011; 28(9); 2223-2232.
Van Den Bosch et al., Simultaneous activation of Viral Antigen-specific Memory CD4+ and CD8+ T-cells using mRNA—electroporated CD40-activaled autologous B-cells. J Immunother. Sep./Oct. 2006; 29, 512-23.
Vici et al., Immunologic treatments for precancerous lesions and uterine cervical cancer. J Exp Clin Cancer Res. Mar. 26, 2014;33:29. doi: 10.1186/1756-9966-33-29.
Wang et al., Chapter 3: Lipid Nanoparticles for the Delivery of Nucleic Acids. Book: Nanoparticulate Drug Delivery Systems: Strategies, Technologies, and Applications. 2013. 29 pages.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Wen et al., Human cytomegalovirus gH/gL/UL128/UL130/UL131A complex elicits potently neutralizing antibodies in mice. Vaccine. Jun. 24, 2014;32(30):3796-804. doi: 10.1016/j.vaccine. 2014.05.004. Epub May 14, 2014.
Winkler et al., Changing the antigen binding specificity by single point mutations of an anti-p24 (HIV-1) antibody. J Immunol. Oct. 15, 2000;165(8):4505-14.
Wong et al., An mRNA vaccine for influenza. Nat Biotechnol. Dec. 2012;30(12):1202-4. doi: 10.1038/nbt.2439.
Wussow et al., Human cytomegalovirus vaccine based on the envelope gH/gL pentamer complex. PLoS Pathog. Nov. 20, 2014;10(11):e1004524. doi: 10.1371/journal.ppat.1004524. eCollection Nov. 2014.
Wussow et al., Neutralization of Human Cytomegalovirus Entry into Fibroblasts and Epithelial Cells. Vaccines (Basel). Oct. 31, 2017;5(4):39. doi: 10.3390/vaccines5040039.
Xue et al., Lipid-Based Nanocarriers for RNA Delivery. Curr Pharm Des. 2015;21(22):3140-7.
Yamamoto et al., Current prospects for mRNA gene delivery, European Journal of Pharmaceutics and Biopharmaceutics 71 (2009) 484-489.
YP_0181566. Davison et al., Human betaherpesvirus 5 (HHV-5; HCMB). Dep. Sep. 27, 2002, Updated Jul. 2, 2013.
YP_018555. Davison et al., Human betaherpesvirus 5 (HHV-5; HCMB). Dep. Sep. 27, 2002, Updated Jul. 2, 2013.
YP_018565. Davison et al., Human betaherpesvirus 5 (HHV-5; HCMB). Dep. Sep. 27, 2002, Updated Jul. 2, 2013.
YP_081514. Davison et al., Human betaherpesvirus 5 (HHV-5; HCMB). Dep. Sep. 27, 2002, Updated Jul. 2, 2013.
YP_081523. Davison et al., Human betaherpesvirus 5 (HHV-5; HCMB). Dep. Sep. 27, 2002, Updated Jul. 2, 2013.
Zhao et al., Chapter Two: Lipid Nanoparticles for Gene Delivery. Book: Advances in Genetics. Elsevier, 2014. 24 pages.
Zhao et al., Nanoparticle vaccines. Vaccine. Jan. 9, 2014;32(3):327-37. doi: 10.1016/j.vaccine.2013.11.069. Epub Dec. 2, 2013.
Zhou, W.Z. et al., RNA melanoma vaccine: induction of antitumor immunity by human glycoprotein 100 mRNA immunization. Hum Gene Ther. Nov. 1, 1999;10(16):2719-24.
Zou et al., Lipid-mediated delivery of RNA is more efficient than delivery of DNA in non-dividing cells. Int J Pharm. Apr. 15, 2010;389(1-2):232-43. doi: 10.1016/j.ijpharm.2010.01.019. Epub Jan. 18, 2010.

* cited by examiner

SEQUENCE LISTING

<160> NUMBER OF SEQ ID NOS: 30

<210> SEQ ID NO 1
<211> LENGTH: 2887
<212> TYPE: RNA
<213> ORGANISM: Artificial Sequence
<220> FEATURE:
<223> OTHER INFORMATION: Synthetic

<400> SEQUENCE: 1

| | | | | | |
|---|---|---|---|---|---|
| gggaauuaag | agagaaaaga | agaguaagaa | gaaauauaag | agccaccaug | gaauccagga | 60 |
| ucuggugccu | gguagucugc | guuaacuugu | guaucgucug | ucugggugcu | gcgguuuccu | 120 |
| caucuucuac | ucguggaacu | ucugcuacuc | acagucacca | uuccucucau | acgacgucug | 180 |
| cugcucacuc | ucgauccggu | ucagucucuc | aacgcguaac | uucuucccaa | acggucagcc | 240 |
| augguguuaa | cgagaccauc | uacaacacua | cccucaagua | cggagaugug | gugggggguca | 300 |
| auaccaccaa | guaccccuau | cgcgugaguuu | cuauggccca | gggauacggau | cuuauucgcu | 360 |
| uugaacguaa | uaucgucugc | accucgauga | agcccaucaa | ugaagaccug | gacgagggca | 420 |
| ucaugguggu | cuacaaacgc | aacaucgucg | cgcacaccuu | uaaggaacga | gucuaccaga | 480 |
| agguuuugac | guucgucgu | agcuacgcuu | acauccacac | cacuuaucug | cugggcagca | 540 |
| acacggaaua | cguggcgccu | ccuaugaugu | agauucauca | uaucaacagc | cacagucagu | 600 |
| gcuacaguuc | cuacagccgc | guuauagcag | gcacgguuuu | cguggcuuau | cauagggaca | 660 |
| gcuaugaaaa | caaaaccaug | caauuaaugc | ccgacgauua | uuccaacacc | cacaguaccc | 720 |
| guuacgugac | ggucaaggau | caaugcaca | gccgcggcag | caccuggcuc | uaucgugaga | 780 |
| ccuguaaucu | gaauuguaug | gugaccauca | cuacugcgcg | cuccaaauau | ccuuaucauu | 840 |
| uuuucgccac | uuccacgggu | gacgugguug | acauuucucc | uuucuacaac | ggaaccaauc | 900 |
| gcaaugccag | cuacuuugga | gaaaacgccg | acaaguuuuu | cauuuuuccg | aacuacacua | 960 |
| ucgucuccga | cuuuggaaga | ccgaauucug | cguuagagac | ccacagguug | guggcuuuuc | 1020 |
| uugaacugc | ggacucggug | aucuccuggg | auauacagga | cgaaaagaau | gucacuuguc | 1080 |
| aacucacuuu | cugggaagcc | ucggaacgca | ccauucguuc | cgaagccgag | gacucguauc | 1140 |
| acuuuucuuc | ugccaaaaug | accgccacuu | ucuuaucaa | gaagcaagag | gugaacaugu | 1200 |
| ccgacucugc | gcuggacugc | guacgugaug | aggcuauaaa | uaaguuacag | cagauuuuca | 1260 |
| auacuucaua | caaucaaaca | uaugaaaaau | auggaaacgu | guccgucuuu | gaaaccacug | 1320 |
| gugguuuggu | aguguucugg | caagguauca | agcaaaaauc | ucugguggaa | cucgaacguu | 1380 |
| uggccaaccg | cuccagucug | aaucuuacuc | auaauagaac | caaaagaagu | acagauggca | 1440 |
| acaaugcaac | ucauuuaucc | aacauggaau | cggugcacaa | ucuggucuac | gcccagcugc | 1500 |
| aguucaccua | ugacacguug | cgcgguuaca | ucaaccgggc | gcuggcgcaa | aucgcagaag | 1560 |
| ccuggugugu | ggaucaacgg | cgcacccuag | aggucuucaa | ggaacucagc | aagaucaacc | 1620 |
| cgucagccau | ucucucggcc | auuuacaaca | aaccgauugc | cgcgcguuuc | augggugaug | 1680 |
| ucuugggccu | ggccagcugc | gugaccauca | accaaaccag | cgucaaggug | cugcgugaua | 1740 |
| ugaacgugaa | ggagucgcca | ggacgcugcu | acucacgacc | cgggucauc | uuuaauuucg | 1800 |
| ccaacagcuc | uacgugcag | uacgucaac | ugggcgagga | caacgaaauc | cuguggggca | 1860 |
| accaccgcac | ugaggaaugu | cagcuuccca | gccucaagau | cuucaucgcc | gggaacucgg | 1920 |
| ccuacgagua | cguggacuac | cucuucaaac | gcaugauuga | ccagcagagu | aucuccaccg | 1980 |
| ucgacagcau | gaucgcccug | gauaucgacc | cgcuggaaaa | uaccgacuuc | aggguacugg | 2040 |

```
aacuuuacuc gcagaaagag cugcguucca gcaacguuuu ugaccucgaa gagaucaugc    2100
gcgaauucaa cucguacaag cagcggguaa aguacgugga ggacaaggua gucgacccgc    2160
uaccgcccua ccucaagggu cuggacgacc ucaugagcgg ccugggcgcc gcgggaaagg    2220
ccguuggcgu agccauuggg gccguggugu gcgcggugge cuccguggue gaaggcguuu    2280 ccaccuuccu caaaaacccc uucggagcgu ucaccaucau ccucgugggc auagcuguag    2340
ucauuaucac uuauuugauc uauacucgac agcggcguuu ugcacgcag ccgcugcaga    2400 accucuuucc cuaucgguug uccgccgacg ggaccaccgu gacgucgggc agcaccaaag    2460
acacgucguu acaggcuccg ccuuccuacg aggaaagugu uuauaauucu ggucgcaaag    2520
gaccgggacc accgucgucu gaugcaucca cggcggcucc gccuuacacc aacgagcagg    2580
cuuaccagau gcuucuggcc cuggcccguc uggacgcaga gcagcgagcg cagcagaacg    2640
guacagauuc uuuggacgga cggacuggca cgcaggacaa gggacagaag cccaaccuac    2700
uagaccgacu cgcacaucgc aaaaacggcu accgacacuu gaaagacucu gacgaagaag    2760
agaacgucug auaauaggcu ggagccucgg uggccaugcu ucuugccccu ugggccuccc    2820 cccagcccu ccuccccuuc cugcacccgu accccgugg ucuuugaaua aagucugagu    2880
gggcggc                                                             2887

<210> SEQ ID NO 2
<211> LENGTH: 679
<212> TYPE: RNA
<213> ORGANISM: Artificial Sequence
<220> FEATURE:
<223> OTHER INFORMATION: Synthetic

<400> SEQUENCE: 2
gggaaauaag agagaaaaga agaguaagaa gaaauauaag agccaccaug aguccaaag     60 aucugacgcc guucuugacg gcguugugge ugcuauuggg ucacagccgc gugccgcggg    120
ugcgcgcaga agaauguugc gaauucauaa acgucaacca cccgccggaa cgcuguuacg    180
auuucaaaau gugcaaucgc uucaccgucg cgcugcggug uccggacggc gaagucugcu    240
acagucccga gaaaacggcu gagauucgcg ggaucgucac caccaugacc cauucauuga    300
cacgccaggu cguacacaac aaaacgacga gcugcaacua caauccguua uaccucgaag    360
cugacgggcg aauacgcugc ggcaaaguaa acgacaaggc gcaguaccug cugggcgccg    420
cuggcagcgu uccuaucga uggaucaauc uggaaucgac caagauaacc cggaucgugg    480
gccuggauca guaccuggag agcguuaaga aacacaaacg gcuggaugug ugccgcgcua    540
aaaugggcua uaugcugcag ugauaauagg cuggagccuc gguggccaug cuucuugccc    600
cuugggccuc cccccagccc cuccucccu uccugcaccc guaccccegu ggucuuugaa    660 uaaagucuga gugggcggc                                                679

<210> SEQ ID NO 3
<211> LENGTH: 808
<212> TYPE: RNA
<213> ORGANISM: Artificial Sequence
<220> FEATURE:
<223> OTHER INFORMATION: Synthetic

<400> SEQUENCE: 3
gggaaauaag agagaaaaga agaguaagaa gaaauauaag agccaccaug cugcggcuuc     60
ugcuucguca ccacuuucac ugccugcuuc ugugcgcggu uugggcaacg cccgucuagg    120
```

| | |
|---|---:|
| cgucuccgug gucgacgcua acagcaaacc agaauccguc cccgccaugg ucuaaacuga | 180 |
| cguauuccaa accgcaugac gcggcgacgu uuuacugucc uuuucucuau cccucgcccc | 240 |
| cacgaucccc cuugcaauuc ucggggwucc agcggguauc aacggguccc gaguqucgca | 300 |
| acgagacccu guaucugcug uacaaccggg aaggccagac cuugguggag agaagcucca | 360 |
| ccugggugaa aaaggugauc ugguaccuga gcggucggaa ccaaaccauc cuccaacgga | 420 |
| ugccccgaac ggcuucgaaa ccgagcgacg gaaacgugca gaucagcgug aagacgcca | 480 |
| agauuuuugg agcgcacaug gugcccaagc agaccaagcu gcuacgcuuc gucgucaacg | 540 |
| auggcacacg uuaucagaug ugugugauga gcuggagag cugggcucac gucuuccggg | 600 |
| acuacagcgu gucuuuucag gugcgauuga cguucaccga ggccaauaac cagacuuaca | 660 |
| ccuucugcac ccaucccaau cucaucguuu gauaauaggc uggagccucg guggccaugc | 720 |
| uucuugcccc uugggccucc cccagcccc uccucccuu ccugcacccg uaccccgug | 780 |
| gucuuugaau aaagucugag ugggcggc | 808 |

```
<210> SEQ ID NO 4
<211> LENGTH: 553
<212> TYPE: RNA
<213> ORGANISM: Artificial Sequence
<220> FEATURE:
<223> OTHER INFORMATION: Synthetic

<400> SEQUENCE: 4
```

| | |
|---|---:|
| gggaauaaag agagaaaaga agaguaagaa gaaauauaag agccaccaug cggcugugguc | 60 |
| ggguguggcu gucuguuugu cugucgccg uggugcuggg ucagugccag cgggaaaccg | 120 |
| cggaaaagaa cgauuauuac cgaguaccgc auuacuggga cgcgugcucu cgcgcgcugc | 180 |
| ccgaccaaac ccguuacaag uauguggaac agcucgugga ccucacguug aacuaccacu | 240 |
| acgaugcgag ccacggcuug gacaacuuug acgugcucaa gagaaucaac gugaccgagg | 300 |
| ugucguugcu caucagcgac uuuagacguc agaaccgucg cggcggcacc aacaaaagga | 360 |
| ccacguucaa cgccgccggu ucgcuggcgc cacacgcccg gagccucgag uucagcgugc | 420 |
| ggcucuuugc caacugauaa uaggcuggag ccucggguggc caugcuucu gccccuuggg | 480 |
| ccuccccca gccccuccuc cccuuccugc acccguaccc ccguggucuu ugaauaaagu | 540 |
| cugagugggc ggc | 553 |

```
<210> SEQ ID NO 5
<211> LENGTH: 2392
<212> TYPE: RNA
<213> ORGANISM: Artificial Sequence
<220> FEATURE:
<223> OTHER INFORMATION: Synthetic

<400> SEQUENCE: 5
```

| | |
|---|---:|
| gggaauaaag agagaaaaga agaguaagaa gaaauauaag agccaccaug cggccaggcc | 60 |
| uccccuccua ccucaucauc cucgccgucu gucucuucag ccaccuacuu ucgcacgau | 120 |
| auggcgcaga agccguaucc gaaccgcugg acaaagcguu ucaccuacug cucaacaccu | 180 |
| acggagacc cauccgcuuc cugcgugaaa uaccacca guuaccuac aacagcagcc | 240 |
| uccguaacag cacggucguc agggaaaacg ccaucaguuu caacuucuuc caaagcuaua | 300 |
| aucaauacua uguauuccau augccucgau gucucuuugc ggguccucug gcggagcagu | 360 |
| uucugaacca gguagaucug accgaaaccc uggaagaua ccaacagaga cuuaacacuu | 420 |
| acgcgcuggu auccaaagac cuggccagcu accgaucuuu cucgcagcag cuaaaggcac | 480 |

```
aagacagccu aggugaacag cccaccacug ugccaccgcc cauugaccug ucaauaccuc    540 acguuggau gccaccgcaa accacuccac acggcuggac agaaucacau accaccucag    600
gacuacaccg accacacuuu aaccagaccu guauccucuu ugauggacac gaucuacuau    660
ucagcaccgu cacaccuugu uugcaccaag gcuuuaccu caucgacgaa cuacguuacg    720
uuaaaauaac acugaccgag gacuucuucg uaguuacggu guccauagac gacgacacac    780
ccaugcugcu uaucuucggc caucuuccac gcguacuuuu caaagcgccc uaucaacgcg    840
acaacuuuau acuacgacaa acugagaaac acgagcuccu ggugcuaguu aagaaagauc    900
aacugaaccg ucacucuuau cucaaagacc cggacuuucu ugacgccgca cuugacuuca    960
acuaccuaga ccucagcgca cuacuacgua acagcuuuca ccguuacgcc guggauguac   1020
ucaagagcgg ucgaugucag augcuggacc gccgcacggu agaaauggcc uucgccuacg   1080
cauuagcacu guucgcagca gcccgacaag aagaggccgg cgcccaaguc uccgucccac   1140
gggcccuaga ccgccaggcc gcacucuuac aaauacaaga auuuaugauc accugccucu   1200
cacaaacacc accacgcacc acguugcugc uguauccac ggccguggac cuggccaaac    1260
gagcccuuug gacaccgaau cagaucaccg acaucaccag ccucguacgc cuggucuaca   1320
uacucucuaa acagaaucag caacaucuca uccccccaaug ggcacacga cagaucgccg   1380 acuuugcccu aaaacuacac aaaacgcacc uggccucuuu ucuuucagcc uucgcacgcc   1440
aagaacucua cccuauggc agccucgucc acuccaugcu gguacauacg acggagagac   1500
gcgaaaucuu caucguagaa acgggccucu guucauuggc cgagcuauca cacuuuacgc   1560
aguuguuagc ucauccacac cacgaauacc ucagcgaccu guacacaccc uguuccagua   1620
gcgggcgacg cgaucacucg cucgaacgcc ucacgcgucu cuuccccgau gccaccgucc   1680
ccgcuaccgu ucccgccgcc cucuccaucc uaucuaccau gcaaccaagc acgcuggaaa   1740
ccuuccccga ccuguuuugc uugccgcucg gcgaauccuu cuccgcgcug accgucuccg   1800
aacacgucag uuauaucgua acaaaccagu accgaucaa agguaucucc uacccugucu    1860
ccaccaccgu cguaggccag agccucauca ucacccagac ggacagucaa acuaaaugcg   1920
aacugacgcg caacaugcau accacacaca gcaucacagu ggcgcucaac auuucgcuag   1980
aaaacugcgc cuuuugccaa agcgcccugc uagaauacga cgacgcaa ggcgucauca     2040 acaucaugua caugcacgac ucggacacg uccuuuucgc ccuggaucc uacaacgaag     2100 ugguggucuc aucuccgcga acucacuacc ucaugcuuuu gaagaacggu acgguacuag   2160
aaguaacuga cgucgucgug gacgccaccg acagucgucu ccucaugaug uccgucuacg   2220
cgcuaucggc caucaucggc aucuaucugc ucuaccgcau gcucaagaca ugcugauaau   2280
aggcuggagc cucggguggcc augcuucuug cccccuuggg cucccccag ccccuccucc    2340 ccuuccugca cccguacccc cguggucuuu gaauaaaguc ugagugggcg gc            2392
```

<210> SEQ ID NO 6
<211> LENGTH: 1000
<212> TYPE: RNA
<213> ORGANISM: Artificial Sequence
<220> FEATURE:
<223> OTHER INFORMATION: Synthetic

<400> SEQUENCE: 6

```
gggaaauaag agagaaaaga agaguaagaa gaaauauaag agccaccaug ugccgccgcc     60
cggauugcgg cuucucuuuc ucaccuggac cggugauacu gcuguggugu ugccuucugc    120
```

| | |
|---|---:|
| ugcccauugu uuccucagcc gccgucagcg ucgcuccuac cgccgccgag aaagucccg | 180 |
| cggagugccc cgaacuaacg cgccgaugcu uguugggugu ggguguuugag ggugacaagu | 240 |
| augaaaguug gcugcgcccg uuggugaaug uuaccgggcg cgauggcccg cuaucgcaac | 300 |
| uuauccguua ccgucccguu acgccggagg ccgccaacuc cgucuguug gacgaggcuu | 360 |
| uccuggacac ucuggcccug cuguacaaca auccggauca auugcgggcc cugcugacgc | 420 |
| uguugagcuc ggacacagcg ccgcgcugga ugacggugau gcgcggcuac agcgagugcg | 480 |
| gcgauggcuc gccggccgug uacacgugcg uggacgaccu gugccgcggc uacgaccuca | 540 |
| cgcgacuguc auacgggcgc agcaucuucg cggaacacgu guuaggcuuc gagcugguc | 600 |
| caccgucucu cuuuaacgug gugguggcca uacgcaacga agccacgcgu accaaccgcg | 660 |
| ccgugcgucu gcccgugagc accgcugccg cgcccgaggg caucacgcuc uuuuacggcc | 720 |
| uguacaacgc agugaaggaa uucugccugc gucaccagcu ggacccgccg cugcuacgcc | 780 |
| accuagauaa auacuacgcc ggacugccgc ccgagcugaa gcagacgcgc gucaaccugc | 840 |
| cggcucacuc gcgcuauggc ccucaagcag uggaugcucg cugauaauag gcuggagccu | 900 |
| cgguggccau gcuucuugcc ccuugggccu ccccccagcc ccuccuccc uuccugcacc | 960 |
| cguaccccg uggucuuuga auaaagucug aguggcggc | 1000 |

<210> SEQ ID NO 7
<211> LENGTH: 2721
<212> TYPE: RNA
<213> ORGANISM: Artificial Sequence
<220> FEATURE:
<223> OTHER INFORMATION: Synthetic

<400> SEQUENCE: 7

| | |
|---|---:|
| auggaaucca ggaucugguu ccugguaguc ugcguuaacu uguguaucgu cugucugggu | 60 |
| gcugcgguuu ccucaucuuc uacucgugga acuucugcua cucacaguca ccauuccucu | 120 |
| cauacgacgu cugcugcuca cucucgaucc gguucagucu cucaacgcgu aacuucuucc | 180 |
| caaacgguca gccaugguug uaacgagacc aucuacaaca cuacccucaa guacggagau | 240 |
| gugguggggg ucaauaccac caaguacccc uaucgcgugu guucuauggc ccagggguacg | 300 |
| gaucuuauuc gcuuugaacg uaauaucguc ugcaccucga ugaagcccau caaugaagac | 360 |
| cuggacgagg gcaucauggu ggucuacaaa cgcaacaucg ucgcgcacac cuuuaaggua | 420 |
| cgagucuacc agaagguuuu gacguuucgu cguagcuacg cuuacaucca caccacuuau | 480 |
| cugcugggca gcaacacgga auacguggcg ccuccuaugu gggagauuca ucauaucaac | 540 |
| agccacaguc agugcuacag uuccuacagc cgcguuauag caggcacggu uuucguggcu | 600 |
| uaucauaggg acagcuauga aaacaaaacc augcaauuaa ugcccgacga uuauccaac | 660 |
| acccacagua cccguuacgu gacggucaag gaucaauggc acagccgcgg cagcaccugg | 720 |
| cucuaucgug agaccuguaa ucugaauugu auggugacca ucacuacgc gcgcuccaaa | 780 |
| uaccuuauc auuuuucgc cacuuccacg ggugacgugg uugacauuuc ccuuucuac | 840 |
| aacggaacca aucgcaaugc cagcuacuuu ggagaaaacg ccgacaaguu uucauuuuu | 900 |
| ccgaacuaca cuaucgucuc cgacuuugga agaccgaauu cugcguuaga cccacagg | 960 |
| uuggugcuu uucuugaacg ugcggacucg gugaucuccu gggauauaca ggacgaaaag | 1020 |
| aaugucacuu gucaacucac uuucgggaa gccucggaac gcaccaucg uuccgaagcc | 1080 |
| gaggacucgu aucacuuuuc uucugccaaa augaccgcca cuucuuauc uaagaagcaa | 1140 |
| gaggugaaca ugucccgacuc ugcgcuggac ugcguacgug augaggcuau aaauaaguua | 1200 |

| | |
|---|---|
| cagcagauuu ucaauacuuc auacaaucaa acauaugaaa aauauggaaa cguguccguc | 1260 |
| uuugaaacca cuggugguuu gguagugunc uggcaaggua ucaagcaaaa aucucugguu | 1320 |
| gaacucgaac guunggccaa ccgcuccagu cugaaucuua ucauaauag aaccaaaaga | 1380 |
| aguacagaug gcaacaaugc aaccauuuua uccaacaugg aaucggugca caaucugguc | 1440 |
| uacgcccagc ugcaguucac cuaugacacg uugcgcgguu acaucaaccg ggcgcuggcg | 1500 |
| caaaucgcag aagccuggug uguggaucaa cggcgcaccc uagaggucuu caaggaacuc | 1560 |
| agcaagauca cccgucagc cauucucucg gccauuuaca acaaaccgau ugccgcgcgu | 1620 |
| uucauggguug augucuuggg ccuggccagc ugcgugacca ucaaccaaac cagcgucaag | 1680 |
| gugcugcgug auaugaacgu gaaggagucg ccaggacgcu gcuacucacg acccgugguc | 1740 |
| aucuuuaauu ucgccaacag cucguacgug caguacgguc aacugggcga ggacaacgaa | 1800 |
| auccguuugg gcaaccaccg cacugaggaa ugucagcuuc ccagccucaa gaucuucauc | 1860 |
| gccgggaacu cggccuacga guacguggac uaccucuuca aacgcaugau ugaccucagc | 1920 |
| aguaucucca ccgucgacag caugaucgcc cuggauaucg acccgcugga aaauaccgac | 1980 |
| uucaggguac uggaacuuua ucgcagaaaa gagcugcguu ccagcaacgu uuuugaccuc | 2040 |
| gaagagauca ugcgcgaauu caacucguac aagcagcggg uaaaguacgu ggaggacaag | 2100 |
| guagucgacc cgcuaccgcc cuaccucaag ggucuggacg accucaugag cggccugggc | 2160 |
| gccgcgggaa aggccguugg cguagccauu ggggccgugg guggcgcggu ggccuccgug | 2220 |
| gucgaaggcg uugccacccuu ccucaaaaac cccuucggag cguucaccau caucucgug | 2280 |
| gccauagcug uagucauuau cacuuauuug aucauauacuc gacagcggcg uuugugcacg | 2340 |
| cagccgcugc agaaccucuu ucccuaucug guguccgccg acgggaccac cgugacgucg | 2400 |
| ggcagcacca aagacacguc guuacaggcu ccgccuuccu acgaggaaag uguuuauaau | 2460 |
| ucuggucgca aaggaccggg accaccgucg ucugaugcau ccacggcggc uccgccuuac | 2520 |
| accaacgagc aggcuuacca gaugcuucug gcccuggccc gucuggacgc agagcagcga | 2580 |
| gcgcagcaga acguacaga uucuuuggac ggacggacug gcacgcagga caagggacag | 2640 |
| aagcccaacc uacuagaccg acugcgacau cgcaaaaacg cuaccgaca cuugaaagac | 2700 |
| ucugacgaag aagagaacgu c | 2721 |

<210> SEQ ID NO 8
<211> LENGTH: 513
<212> TYPE: RNA
<213> ORGANISM: Artificial Sequence
<220> FEATURE:
<223> OTHER INFORMATION: Synthetic

<400> SEQUENCE: 8

| | |
|---|---|
| augagucca aagaucugac gccguucuug acggcguugu ggcugcuauu gggucacagc | 60 |
| cgcgugccgc gggugcgcgc agaagaaugu ugcgaauuca uaaacgucaa ccacccgccg | 120 |
| gaacgcuguu acgauuucaa aaugugcaau cgcuucaccg ucgcgcugcg gugccggac | 180 |
| ggcgaagucu gcuacagucc cgagaaaacg cgcugagauuc gcgggaucgu caccaccaug | 240 |
| acccauucau ugacacgcca ggucuacac aacaaacuga cgagcugcaa cuacaauccg | 300 |
| uuauaccucg aagcugacgg gcgaauacgc ugcggcaaag uaaacgacaa ggcgcaguac | 360 |
| cugcuggggcg ccgcuggcag cguucccuau cgauggauca aucuggaaua cgacaagaua | 420 |
| acccggaucg uggccuggaa ucaguaccug gagagcguua agaaacacaa acggcuggau | 480 |

| | | |
|---|---|---|
| gugugccgcg cuaaaauggg cuauaugcug cag | | 513 |

<210> SEQ ID NO 9
<211> LENGTH: 642
<212> TYPE: RNA
<213> ORGANISM: Artificial Sequence
<220> FEATURE:
<223> OTHER INFORMATION: Synthetic

<400> SEQUENCE: 9

| | |
|---|---|
| augcugcggc uucugcuucg ucaccacuuu cacugccugc uucugugcgc gguuugggca | 60 |
| acgcccuguc uggcgucucc gggucgacg cuaacagcaa accagaauc guccccgcca | 120 |
| uggucuaaac ugacguauuc caaaccgcau gacgcggcga cguuuuacug uccuuuucuc | 180 |
| uaucccucgc ccccacgauc ccccuugcaa uucgcgggu uccagcgggu caacgggu | 240 |
| cccgagaguc gcaacgagac ccuguaucug cuguacaacc gggaaggcca gaccuuggu | 300 |
| gagagaagcu ccaccugggu gaaaaggug aucggguacc ugagcggucg gaaccaaacc | 360 |
| auccuccaac ggaugccccg aacggcuucg aaaccgagcg acgaaacgu gcagaucagc | 420 |
| guggaagacg ccaagauuuu uggagcgcac augugccca agcagaccaa gcugcuacgc | 480 |
| uucgucguca acgauggcac acguuauacag augugugua ugaagcugga gagcugggcu | 540 |
| cacgucuucc gggacuacag cgugucuuuu caggugcgau ugacguucac cgaggccaau | 600 |
| aaccagacuu acaccuucug cacccaucc aaucucaucg uu | 642 |

<210> SEQ ID NO 10
<211> LENGTH: 387
<212> TYPE: RNA
<213> ORGANISM: Artificial Sequence
<220> FEATURE:
<223> OTHER INFORMATION: Synthetic

<400> SEQUENCE: 10

| | |
|---|---|
| augcggcugu ucggguugug gcugucuguu ugucugugcg ccgugguugcu gggucagugc | 60 |
| cagcgggaaa ccgcggaaaa gaacgauuau uaccgaguac cgcauuacug ggacgcgugc | 120 |
| ucucgcgcgc ugcccgacca aacccguuac aaguaugugg aacagcucgu ggaccucacg | 180 |
| uugaacuacc acuacgaugc gagccacggc uuggacaacu uugacgugcu caagagaauc | 240 |
| aacgugaccg aggugucguu gcucaucagc gacuuuagac gucagaaccg ucgcggcggc | 300 |
| accaacaaaa ggaccacguu caacgccgcc gguucgcugg cgccacacgc ccggagcccuc | 360 |
| gaguucagcg ugcggcucuu ugccaac | 387 |

<210> SEQ ID NO 11
<211> LENGTH: 2226
<212> TYPE: RNA
<213> ORGANISM: Artificial Sequence
<220> FEATURE:
<223> OTHER INFORMATION: Synthetic

<400> SEQUENCE: 11

| | |
|---|---|
| augcggccag gccuccccuc cuaccucauc auccucgccg ucugucucuu cagccaccua | 60 |
| cuuucgucac gauauggcgc agaagccgua uccgaaccgc uggacaaagc guuucaccua | 120 |
| cugcucaaca ccuacgggag acccauccgc uuccugcgug aaaauaccac ccagugucc | 180 |
| uacaacagca gccuccguaa cagcacgguc gucaggaaa acgccaucag uuucaacuuc | 240 |
| uuccaaagcu auaaucaaua cuauguauuc cauaugccuc gaugucucuu ugcgggccu | 300 |
| cuggcggagc aguuucugaa ccagguagau cugaccgaaa cccuggaaag auaccaacag | 360 |

```
agacuuaaca cuuacgcgcu gguauccaaa gaccuggcca gcuaccgauc uuucucgcag    420
cagcuaaagg cacaagacag ccuaggugaa cagcccacca cugugccacc gcccauugac    480
cugucaauac cucacguuug gaugccaccg caaaccacuc cacacggcug gacagaauca    540
cauaccaccu caggacuaca ccgaccacac uuuaaccaga ccuguauccu cuuugaugga    600
cacgaucuac uauucagcac cgucacaccu uguuugcacc aaggcuuuua ccucaucgac    660
gaacuacguu acguuaaaau aacacugacc gaggacuucu ucguaguuac ggugccaua     720 gacgacgaca cacccaugcu gcuuaucuuc ggccaucuuc cacgcguacu uuucaaagcg    780
cccuaucaac gcgacaacuu uauacuacga caaacgagac aacgagcu  ccggugcua      840 guuaagaaag aucaacugaa ccgucacucu uaucucaaag acccggacuu cuugacgcc     900 gcacuugacu caacuaccu agaccucagc gcauacuac guaacagcuu ucaccguuac      960
gccguggaug uacucaagag cggucgaugu cagaugcugg accgccgcac gguagaaaug   1020
gccuucgccu acgcauuagc acguucgca gcagcccgac aagaagaggc cggcgcccaa    1080
gucuccgucc cacgggcccu agaccgccag gccgcacucu acaaauaca agaauuuaug    1140 aucaccugcc ucucacaaac accaccacgc accacguugc ugcuguaucc cacggccgug   1200
gaccuggcca aacgagcccu uuggacaccg aaucagauca ccgacaucac cagccucgua   1260
cgccuggucu acauacucuc uaaacagaau cagcaacauc ucauccccca augggcacua   1320
cgacagaucg ccgacuuugc ccuaaaacua cacaaaacgc accuggccuc uuuucuuuca   1380
gccuucgcac gccaagaacu cuaccucaug ggcagccucg uccacuccau gcugguacau   1440
acgacggaga gacgcgaaau cuucaucgua gaaacgggcc ucguucauu ggccgagcua    1500 ucacacuuua cgcaguuguu agcucaucca caccacgaau accucagcga ccuguacaca   1560
cccuguucca guagcgggcg acgcgaucac ucgcucgaac gccucacgcg ucucuucccc   1620
gaugccaccg uccccgcuac cguucccgcc gcccucucca uccuaucuac caugcaacca   1680
agcacgcugg aaaccuuccc cgaccuguuu ugcuugccgc ucggcgaauc cuucuccgcg   1740
cugaccgucu ccgaacacgu caguuauauc guaacaaacc aguaccgau  caaagguauc   1800 uccuacccug ucuccaccac cgucguaggc cagagccuca ucauccca  gacgacagu     1860 caaacuaaau gcgaacugac gcgcaacaug cauaccacac acagcaucac agugggcgcuc   1920 aacauuucgc uagaaaacug cgccuuugc caaagcgccc ugcuagaaua cgacgacacg     1980
caaggcguca ucaacaucau guacaugcac gacucggacg acguccuuuu cgcccuggau   2040
cccuacaacg aaguggugu cucaucuccg cgaacucacu accucaugcu uuugaagaac    2100
gguacgguac uagaaguaac ugacgucguc guggacgcca ccgacagucg ucuccucaug   2160 augccgucu acgcgcuauc ggccaucauc ggcaucuauc ugcucuaccg caugcucaag    2220
acaugc                                                              2226
```

<210> SEQ ID NO 12
<211> LENGTH: 834
<212> TYPE: RNA
<213> ORGANISM: Artificial Sequence
<220> FEATURE:
<223> OTHER INFORMATION: Synthetic

<400> SEQUENCE: 12

```
augugccgcc gcccggauug cggcuucucu uucucaccug gaccggugau acugcugugg    60
uguugccuuc ugcugcccau uguuccuca gccgccguca gcgucgcucc uaccgccgcc    120
```

```
gagaaagucc cgcggagug  ccccgaacua acgcgccgau gcuuguuggg ugagguguuu    180
gagggugaca aguaugaaag uuggcugcgc ccguuggguga auguuaccgg gcgcgauggc    240
ccgcuaucgc aacuuauccg uuaccguccc guuacgccgg aggccgccaa cuccgugcug    300
uuggacgagg cuuccugga cacucuggcc cugcuguaca acaauccgga ucaauugcgg     360
gcccugcuga cgcuguugag cucggacaca gcgccgcgcu ggaugacggu gaugcgcggc    420
uacagcgagu gcggcgaugg cucgccggcc guguacacgu gcguggacga ccugugccgc    480
ggcuacgacc ucacgcgacu gucauacggg cgcagcaucu ucacggaaca cguguuaggc    540
uucgagcugg ugccaccguc ucucuuuaac guggugugg ccauacgcaa cgaagccacg     600
cguaccaacc gcgccgugcg ucugcccgug agcaccgcug ccgcgcccga gggcaucacg    660
cucuuuuacg gccuguacaa cgcagugaag gaauucugcc ugcgucacca gcuggacccg    720
ccgcugcuac gccaccuaga uaaauacuac gccggacugc cgcccgagcu gaagcagacg    780
cgcgucaacc ugccggcuca cucgcgcuau ggcccucaag caguggaugc ucgc          834
```

<210> SEQ ID NO 13  
<211> LENGTH: 47  
<212> TYPE: RNA  
<213> ORGANISM: Artificial Sequence  
<220> FEATURE:  
<223> OTHER INFORMATION: Synthetic

<400> SEQUENCE: 13

```
gggaaauaag agagaaaaga agaguaagaa gaaauauaag agccacc                   47
```

<210> SEQ ID NO 14  
<211> LENGTH: 119  
<212> TYPE: RNA  
<213> ORGANISM: Artificial Sequence  
<220> FEATURE:  
<223> OTHER INFORMATION: Synthetic

<400> SEQUENCE: 14

```
ugauaauagg cuggagccuc gguggccaug cuucuugccc cuugggccuc ccccagccc      60 cucccccccu uccugcaccc guaccccgu ggucuuugaa uaaagucuga gugggcggc      119
```

<210> SEQ ID NO 15  
<211> LENGTH: 907  
<212> TYPE: PRT  
<213> ORGANISM: Artificial Sequence  
<220> FEATURE:  
<223> OTHER INFORMATION: Synthetic

<400> SEQUENCE: 15

Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr

-continued

```
              100                 105                 110
Ser Met Lys Pro Ile Asn Glu Asp Leu Asp Glu Gly Ile Met Val Val
            115                 120                 125

Tyr Lys Arg Asn Ile Val Ala His Thr Phe Lys Val Arg Val Tyr Gln
            130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
            195                 200                 205

Lys Thr Met Gln Leu Met Pro Asp Asp Tyr Ser Asn Thr His Ser Thr
            210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
            275                 280                 285

Tyr Phe Gly Glu Asn Ala Asp Lys Phe Phe Ile Phe Pro Asn Tyr Thr
            290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
            355                 360                 365

Ala Lys Met Thr Ala Thr Phe Leu Ser Lys Lys Gln Glu Val Asn Met
            370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
            435                 440                 445

Ser Ser Leu Asn Leu Thr His Asn Arg Thr Lys Arg Ser Thr Asp Gly
            450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
            515                 520                 525
```

-continued

```
Leu Ser Ala Ile Tyr Asn Lys Pro Ile Ala Ala Arg Phe Met Gly Asp
            530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
                580                 585                 590

Gly Gln Leu Gly Glu Asp Asn Glu Ile Leu Leu Gly Asn His Arg Thr
            595                 600                 605

Glu Glu Cys Gln Leu Pro Ser Leu Lys Ile Phe Ile Ala Gly Asn Ser
            610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
                660                 665                 670

Arg Ser Ser Asn Val Phe Asp Leu Glu Glu Ile Met Arg Glu Phe Asn
            675                 680                 685

Ser Tyr Lys Gln Arg Val Lys Tyr Val Glu Asp Lys Val Val Asp Pro
            690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Gly Ala Phe Thr Ile Ile Leu Val Ala Ile Ala Val Val Ile Ile Thr
            755                 760                 765

Tyr Leu Ile Tyr Thr Arg Gln Arg Arg Leu Cys Thr Gln Pro Leu Gln
            770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
            820                 825                 830

Ala Ser Thr Ala Ala Pro Pro Tyr Thr Asn Glu Gln Ala Tyr Gln Met
            835                 840                 845

Leu Leu Ala Leu Ala Arg Leu Asp Ala Glu Gln Arg Ala Gln Gln Asn
850                 855                 860

Gly Thr Asp Ser Leu Asp Gly Arg Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Asn Val
            900                 905

<210> SEQ ID NO 16
<211> LENGTH: 171
<212> TYPE: PRT
<213> ORGANISM: Artificial Sequence
<220> FEATURE:
```

<223> OTHER INFORMATION: Synthetic

<400> SEQUENCE: 16

```
Met Ser Pro Lys Asp Leu Thr Pro Phe Leu Thr Ala Leu Trp Leu Leu
1               5                   10                  15

Leu Gly His Ser Arg Val Pro Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170
```

<210> SEQ ID NO 17
<211> LENGTH: 214
<212> TYPE: PRT
<213> ORGANISM: Artificial Sequence
<220> FEATURE:
<223> OTHER INFORMATION: Synthetic

<400> SEQUENCE: 17

```
Met Leu Arg Leu Leu Arg His His Phe His Cys Leu Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
        35                  40                  45

Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175
```

```
Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
            195                 200                 205

His Pro Asn Leu Ile Val
    210

<210> SEQ ID NO 18
<211> LENGTH: 129
<212> TYPE: PRT
<213> ORGANISM: Artificial Sequence
<220> FEATURE:
<223> OTHER INFORMATION: Synthetic

<400> SEQUENCE: 18

Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn

<210> SEQ ID NO 19
<211> LENGTH: 742
<212> TYPE: PRT
<213> ORGANISM: Artificial Sequence
<220> FEATURE:
<223> OTHER INFORMATION: Synthetic

<400> SEQUENCE: 19

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
            20                  25                  30

Pro Leu Asp Lys Ala Phe His Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125
```

```
Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Ser Gly Arg Arg
        515                 520                 525

Asp His Ser Leu Glu Arg Leu Thr Arg Leu Phe Pro Asp Ala Thr Val
    530                 535                 540
```

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
            565                 570                 575

Ser Phe Ser Ala Leu Thr Val Ser Glu His Val Ser Tyr Ile Val Thr
                580                 585                 590

Asn Gln Tyr Leu Ile Lys Gly Ile Ser Tyr Pro Val Ser Thr Thr Val
            595                 600                 605

Val Gly Gln Ser Leu Ile Ile Thr Gln Thr Asp Ser Gln Thr Lys Cys
610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
            645                 650                 655

Tyr Asp Asp Thr Gln Gly Val Ile Asn Ile Met Tyr Met His Asp Ser
                660                 665                 670

Asp Asp Val Leu Phe Ala Leu Asp Pro Tyr Asn Glu Val Val Val Ser
            675                 680                 685

Ser Pro Arg Thr His Tyr Leu Met Leu Leu Lys Asn Gly Thr Val Leu
690                 695                 700

Glu Val Thr Asp Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
            740

<210> SEQ ID NO 20
<211> LENGTH: 278
<212> TYPE: PRT
<213> ORGANISM: Artificial Sequence
<220> FEATURE:
<223> OTHER INFORMATION: Synthetic

<400> SEQUENCE: 20

Met Cys Arg Arg Pro Asp Cys Gly Phe Ser Phe Ser Pro Gly Pro Val
1               5                   10                  15

Ile Leu Leu Trp Cys Cys Leu Leu Pro Ile Val Ser Ser Ala Ala
            20                  25                  30

Val Ser Val Ala Pro Thr Ala Ala Glu Lys Val Pro Ala Glu Cys Pro
            35                  40                  45

Glu Leu Thr Arg Arg Cys Leu Leu Gly Glu Val Phe Glu Gly Asp Lys
50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Ala
            85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
            115                 120                 125

Asp Thr Ala Pro Arg Trp Met Thr Val Met Arg Gly Tyr Ser Glu Cys
130                 135                 140

Gly Asp Gly Ser Pro Ala Val Tyr Thr Cys Val Asp Asp Leu Cys Arg
145                 150                 155                 160

```
Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Pro Glu Gly Ile Thr Leu Phe Tyr Gly
    210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275
```

```
<210> SEQ ID NO 21
<211> LENGTH: 8
<212> TYPE: RNA
<213> ORGANISM: Artificial Sequence
<220> FEATURE:
<223> OTHER INFORMATION: Synthetic

<400> SEQUENCE: 21 uuugaauu                                                            8

<210> SEQ ID NO 22
<211> LENGTH: 9
<212> TYPE: RNA
<213> ORGANISM: Artificial Sequence
<220> FEATURE:
<223> OTHER INFORMATION: Synthetic
<220> FEATURE:
<221> NAME/KEY: misc_RNA
<222> LOCATION: (8)..(8)
<223> OTHER INFORMATION: n may be U or A
<220> FEATURE:
<221> NAME/KEY: misc_RNA
<222> LOCATION: (9)..(9)
<223> OTHER INFORMATION: n may be U or A

<400> SEQUENCE: 22 uuauuuann                                                           9

<210> SEQ ID NO 23
<211> LENGTH: 11
<212> TYPE: RNA
<213> ORGANISM: Artificial Sequence
<220> FEATURE:
<223> OTHER INFORMATION: Synthetic

<400> SEQUENCE: 23
gggauccuac c                                                       11

<210> SEQ ID NO 24
<211> LENGTH: 20
<212> TYPE: PRT
<213> ORGANISM: Artificial Sequence
<220> FEATURE:
<223> OTHER INFORMATION: Synthetic

<400> SEQUENCE: 24

Met Glu Thr Pro Ala Gln Leu Leu Phe Leu Leu Leu Leu Trp Leu Pro
```

Asp Thr Thr Gly
            20

<210> SEQ ID NO 25
<211> LENGTH: 30
<212> TYPE: PRT
<213> ORGANISM: Artificial Sequence
<220> FEATURE:
<223> OTHER INFORMATION: Synthetic

<400> SEQUENCE: 25

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly
            20                  25                  30

<210> SEQ ID NO 26
<211> LENGTH: 18
<212> TYPE: PRT
<213> ORGANISM: Artificial Sequence
<220> FEATURE:
<223> OTHER INFORMATION: Synthetic

<400> SEQUENCE: 26

Met Asp Trp Thr Trp Ile Leu Phe Leu Val Ala Ala Ala Thr Arg Val
1               5                   10                  15

His Ser

<210> SEQ ID NO 27
<211> LENGTH: 24
<212> TYPE: PRT
<213> ORGANISM: Artificial Sequence
<220> FEATURE:
<223> OTHER INFORMATION: Synthetic

<400> SEQUENCE: 27

Met Leu Gly Ser Asn Ser Gly Gln Arg Val Val Phe Thr Ile Leu Leu
1               5                   10                  15

Leu Leu Val Ala Pro Ala Tyr Ser
            20

<210> SEQ ID NO 28
<211> LENGTH: 17
<212> TYPE: PRT
<213> ORGANISM: Artificial Sequence
<220> FEATURE:
<223> OTHER INFORMATION: Synthetic

<400> SEQUENCE: 28

Met Lys Cys Leu Leu Tyr Leu Ala Phe Leu Phe Ile Gly Val Asn Cys
1               5                   10                  15

Ala

<210> SEQ ID NO 29
<211> LENGTH: 15
<212> TYPE: PRT
<213> ORGANISM: Artificial Sequence
<220> FEATURE:
<223> OTHER INFORMATION: Synthetic

<400> SEQUENCE: 29

Met Trp Leu Val Ser Leu Ala Ile Val Thr Ala Cys Ala Gly Ala
1               5                   10                  15

```
<210> SEQ ID NO 30
<211> LENGTH: 9
<212> TYPE: RNA
<213> ORGANISM: Artificial Sequence
<220> FEATURE:
<223> OTHER INFORMATION: Synthetic

<400> SEQUENCE: 30 ccrccaugg                                                              9
```

HUMAN CYTOMEGALOVIRUS VACCINE

RELATED APPLICATIONS

This application claims the benefit under 35 U.S.C. § 119(e) of U.S. Provisional Application Ser. No. 63/070,134, filed Aug. 25, 2020, entitled "Human Cytomegalovirus Vaccine," U.S. Provisional Application Ser. No. 63/079,421, filed Sep. 16, 2020, entitled "Human Cytomegalovirus Vaccine," and U.S. Provisional Application Ser. No. 63/136,117, filed Jan. 11, 2021, entitled "Human Cytomegalovirus Vaccine," each of which is incorporated by reference herein in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. The ASCII file, created on Aug. 12, 2021, is named M137870132US03-SEQ-EAS.txt and is 46,859 bytes in size.

BACKGROUND

Cytomegalovirus (CMV) is a member of the Herpesviridae family of viruses. CMV is primarily acquired through contact with infectious mucosal secretions or in utero, and establishes latency after primary infection. Overall, CMV seroprevalence in the United States is 50.4%, but rates of 60% to 100% have been reported in resource-poor areas.

CMV is the most common congenital viral infection, as it affects 30,000 to 40,000 infants in the United States annually (0.6% to 2% of live births). Although congenital CMV infection in the first trimester is associated with the most adverse pregnancy outcomes, symptomatic congenital CMV can result from infection at any time during pregnancy. Approximately 30% to 35% of mothers with primary CMV infection during pregnancy will transmit the virus to the fetus; 12% of these newborns will have symptomatic disease, and approximately 4% will die in the first year of life. In addition, approximately half of CMV-infected infants who are symptomatic at birth will develop late complications such as intellectual disability, sensorineural hearing loss, and developmental delay. Due to the significant effect that congenital CMV infection has on pediatric health, a 2017 Institute of Medicine Report places development of a CMV vaccine for the prevention of congenital CMV infection in its highest priority category.

In individuals on chronic immunosuppressive medications after solid organ or hematopoietic stem cell transplantation, CMV infection that leads to graft rejection or end-organ disease is associated with high mortality. In the United States, approximately 30,000 adults receive solid organ transplants and 22,000 receive hematopoietic cell transplants annually. Overall, 8% to 40% of solid organ transplants and 3% to 6% of hematopoietic cell transplant patients who receive antiviral prophylaxis will develop post-transplant complications due to CMV. Major complications of CMV infection in transplant recipients include acute or chronic rejection of the transplanted tissue and invasive diseases such as colitis, hepatitis, and encephalitis.

SUMMARY

A significant unmet medical need is a safe and effective method for the prevention of congenital CMV infection. Another unmet medical need is the prevention of CMV infection in individuals on chronic immunosuppressive medications after solid organ or hematopoietic stem cell transplantation.

A messenger ribonucleic acid (mRNA)-based vaccine platform has been developed based on the principle and observations that target viral proteins or antigens can be produced in vivo by delivery and cellular uptake of the corresponding synthetic viral mRNA from delivery of an immunogenic composition formulated in a lipid nanoparticle. The mRNA then undergoes intracellular ribosomal translation to endogenously express the viral protein antigens encoded by the vaccine immunogenic composition comprising synthetic viral mRNA. These mRNA-based vaccines do not enter the cellular nucleus or interact with the human genome, are nonreplicating, and are expressed transiently. mRNA vaccines and immunogenic compositions thereby offer a mechanism to stimulate the endogenous production of structurally intact, properly folded and with human glycosylated viral glycoproteins and protein antigens in a manner that precisely mimics wild-type viral infection and is able to induce highly targeted immune responses against infectious pathogens such as CMV.

Aspects of the disclosure relate to hCMV immunogenic compositions comprising (a) a messenger ribonucleic acid (mRNA) polynucleotide comprising an open reading frame encoding a hCMV gH polypeptide; (b) a mRNA polynucleotide comprising an open reading frame encoding a hCMV gL polypeptide; (c) a mRNA polynucleotide comprising an open reading frame encoding a hCMV UL128 polypeptide; (d) a mRNA polynucleotide comprising an open reading frame encoding a hCMV UL130 polypeptide; (e) a mRNA polynucleotide comprising an open reading frame encoding a hCMV UL131A polypeptide; and (f) a mRNA polynucleotide comprising an open reading frame encoding a hCMV gB polypeptide, wherein: the molar ratio of (a):(f) within the immunogenic composition is about 1:1; the molar ratio of (b):(c):(d):(e) within the immunogenic composition is about 1:1:1:1; and the molar ratio of each of (a) and (f) to any one of (b), (c), (d) or (e) within the immunogenic composition is about 1.5:1 to 2:1.

In some embodiments, the molar ratio of (a):(b):(c):(d):(e):(f) is about 2:1:1:1:1:2. In some embodiments, the hCMV immunogenic composition is maintained as a liquid formulation until use in administration to patients. In some embodiments, the hCMV immunogenic composition is maintained as a lyophilized formulation until use in administration to patients.

In some embodiments, the hCMV immunogenic composition is stable for at least three months when stored at a temperature of greater than 0° C. and less than or equal to 10° C. In some embodiments, the hCMV immunogenic composition is stable for at least twelve to eighteen months when stored at a temperature of greater than 0° C. and less than or equal to 10° C. In some embodiments, the hCMV immunogenic composition is stable for at least twenty-four months when stored at a temperature of greater than 0° C. and less than or equal to 10° C. In some embodiments, the hCMV immunogenic composition is stable for at least three months when stored at a temperature of about 5° C. In some embodiments, the hCMV immunogenic composition is stable for at least twelve to eighteen months when stored at a temperature of about 5° C. In some embodiments, the hCMV immunogenic composition is stable for at least twenty-four months when stored at a temperature of about 5° C.

In some embodiments, the hCMV immunogenic composition has increased stability relative to an hCMV immunogenic composition in which (a)-(f) are present in approximately equivalent masses. In some embodiments, the hCMV immunogenic composition has increased stability when stored for at least three months at a temperature of greater than 0° C. and less than or equal to 10° C. relative to an hCMV immunogenic composition in which (a)-(f) are present in approximately equivalent masses. In some embodiments, the hCMV immunogenic composition has increased stability when stored for at least twenty-four months at a temperature of greater than 0° C. and less than or equal to 10° C. relative to an hCMV immunogenic composition in which (a)-(f) are present in approximately equivalent masses.

In some embodiments, the hCMV immunogenic composition has increased pentamer expression relative to an hCMV immunogenic composition in which (a)-(f) are present in approximately equivalent masses. In some embodiments, the hCMV immunogenic composition induces increased pentamer antibody levels relative to an hCMV immunogenic composition in which (a)-(f) are present in approximately equivalent masses. In some embodiments, the hCMV immunogenic composition has increased gB expression relative to an hCMV immunogenic composition in which (a)-(f) are present in approximately equivalent masses. In some embodiments, the hCMV immunogenic composition induces increased gB antibody levels relative to an hCMV immunogenic composition in which (a)-(f) are present in approximately equivalent masses.

In some embodiments, the mRNA polynucleotides of (a)-(f) are formulated in at least one lipid nanoparticle in an amount sufficient to induce an antigen-specific immune response to hCMV or a hCMV antigen in a subject. In some embodiments, the mRNA polynucleotides of (a)-(f) are formulated in at least one lipid nanoparticle and lyophilized in an amount sufficient to induce an antigen-specific immune response to hCMV or a hCMV antigen in a subject.

In some embodiments, at least one of the mRNA polynucleotides of (a)-(f) comprises a chemical modification. In some embodiments, at least 80% of the uracil in the open reading frame of mRNA polynucleotides (a)-(f) have a chemical modification selected from N1-methyl-pseudouridine or N1-ethyl-pseudouridine. In some embodiments, the chemical modification is in the carbon-5 position of the uracil. In some embodiments, at least one of the mRNA polynucleotides of (a)-(f) further comprises at least one 5' terminal cap, 7mG(5')ppp(5')N1mpNp.

In some embodiments, the lipid nanoparticle comprises a mixture of lipids comprising: an ionizable amino lipid; cholesterol; 1,2-distearoyl-sn-glycero-3-phosphocholine (DSPC); and 1,2 dimyristoyl-sn-glycerol, methoxypolyethyleneglycol (DMG-PEG). In some embodiments, the ionizable amino lipid comprises Compound I:

In some embodiments, the lipid nanoparticle comprises a mixture of lipids comprising 20-60 mol % ionizable amino lipid, 25-55 mol % cholesterol, 5-25 mol % DSPC, and 0.5-15 mol % DMG-PEG. In some embodiments, the lipid nanoparticle comprises a mixture of lipids comprising 45-55 mol % ionizable amino lipid, 35-40 mol % cholesterol, 5-15 mol % DSPC, and 1-2 mol % DMG-PEG. In some embodiments, the lipid nanoparticle comprises a mixture of lipids comprising 50 mol % ionizable amino lipid, 38.5 mol % cholesterol, 10 mol % DSPC, and 1.5 mol % DMG-PEG. In some embodiments, the lipid nanoparticle comprises a mixture of lipids comprising 49 mol % ionizable amino lipid, 38.5 mol % cholesterol, 10 mol % DSPC, and 2.5 mol % DMG-PEG. In some embodiments, the lipid nanoparticle comprises a mixture of lipids comprising 48 mol % ionizable amino lipid, 38.5 mol % cholesterol, 11 mol % DSPC, and 2.5 mol % DMG-PEG. In some embodiments, the lipid nanoparticle comprises a mixture of lipids comprising 47 mol % ionizable amino lipid, 38.5 mol % cholesterol, 11.5 mol % DSPC, and 3 mol % DMG-PEG.

In some embodiments, the molar ratio of mRNAs (a):(b):(c):(d):(e):(f) is about 2:1:1:1:1:2 and results in 10%, 20%, 30% 40% or 50% less lipid administered to patients compared to when an equal mass of mRNAs (a):(b):(c):(d):(e):(f) is administered. In some embodiments, the molar ratio of mRNAs (a):(b):(c):(d):(e):(f) is about 2:1:1:1:1:2 and results in 30% less lipid administered to patients compared to when an equal mass of mRNAs (a):(b):(c):(d):(e):(f) is administered. In some embodiments, the molar ratio of mRNAs (a):(b):(c):(d):(e):(f) is about 2:1:1:1:1:2 and results in 40% less lipid administered to patients compared to when an equal mass of mRNAs (a):(b):(c):(d):(e):(f) is administered. In some embodiments, the molar ratio of mRNAs (a):(b):(c):(d):(e):(f) is about 2:1:1:1:1:2 and results in 50% less lipid administered to patients compared to when an equal mass of mRNAs (a):(b):(c):(d):(e):(f) is administered.

In some embodiments, the mRNA encoding hCMV gH protein comprises a nucleotide sequence having at least 90% identity to the nucleotide sequence of sequence of SEQ ID NO: 5, the mRNA encoding hCMV gL protein comprises a nucleotide sequence having at least 90% identity to the nucleotide sequence of sequence of SEQ ID NO: 6, the mRNA encoding hCMV UL128 protein comprises a nucleotide sequence having at least 90% identity to the nucleotide sequence of sequence of SEQ ID NO: 2, the mRNA encoding hCMV UL130 protein comprises a nucleotide sequence having at least 90% identity to the nucleotide sequence of sequence of SEQ ID NO: 3, the mRNA encoding hCMV UL131A protein comprises a nucleotide sequence having at least 90% identity to the nucleotide sequence of sequence of SEQ ID NO: 4, and/or the mRNA encoding hCMV gB protein comprises a nucleotide sequence having at least 90% identity to the nucleotide sequence of sequence of SEQ ID NO: 1.

(Compound I)

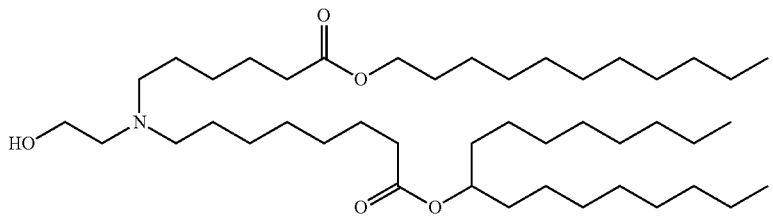

In some embodiments, the mRNA encoding hCMV gH protein comprises the nucleotide sequence of sequence of SEQ ID NO: 5, the mRNA encoding hCMV gL protein comprises the nucleotide sequence of sequence of SEQ ID NO: 6, the mRNA encoding hCMV UL128 protein comprises the nucleotide sequence of sequence of SEQ ID NO: 2, the mRNA encoding hCMV UL130 protein comprises the nucleotide sequence of sequence of SEQ ID NO: 3, the mRNA encoding hCMV UL131A protein comprises the nucleotide sequence of sequence of SEQ ID NO: 4, and/or the mRNA encoding hCMV gB protein comprises the nucleotide sequence of sequence of SEQ ID NO: 1.

In some embodiments, the open reading frame encoding the hCMV gH polypeptide comprises a sequence having at least 90% identity to the sequence of SEQ ID NO: 11, the open reading frame encoding the hCMV gL polypeptide comprises a sequence having at least 90% identity to the sequence of SEQ ID NO: 12, the open reading frame encoding the hCMV UL128 polypeptide comprises a sequence having at least 90% identity to the sequence of SEQ ID NO: 8, the open reading frame encoding the hCMV UL130 polypeptide comprises a sequence having at least 90% identity to the sequence of SEQ ID NO: 9, the open reading frame encoding the hCMV UL131A polypeptide comprises a sequence having at least 90% identity to the of sequence of SEQ ID NO: 10, and/or the open reading frame encoding the hCMV gB polypeptide comprises a sequence having at least 90% identity to the sequence of SEQ ID NO: 7.

In some embodiments, the open reading frame encoding the hCMV gH polypeptide comprises SEQ ID NO: 11, the open reading frame encoding the hCMV gL polypeptide comprises SEQ ID NO: 12, the open reading frame encoding the hCMV UL128 polypeptide comprises SEQ ID NO: 8, the open reading frame encoding the hCMV UL130 polypeptide comprises SEQ ID NO: 9, the open reading frame encoding the hCMV UL131A polypeptide comprises SEQ ID NO: 10, and/or the open reading frame encoding the hCMV gB polypeptide comprises the sequence of SEQ ID NO: 7.

In some embodiments, each of the mRNA polynucleotides of (a)-(f) further comprises a polyA tail. In some embodiments, the polyA tail is 100 nucleotides in length.

In some embodiments, the hCMV gH polypeptide comprises an amino acid sequence having at least 90% identity to the amino acid sequence of SEQ ID NO: 19, the hCMV gL polypeptide comprises an amino acid sequence having at least 90% identity to the amino acid sequence of SEQ ID NO: 20, the hCMV UL128 polypeptide comprises an amino acid sequence having at least 90% identity to the amino acid sequence of SEQ ID NO: 16, the hCMV UL130 polypeptide comprises an amino acid sequence having at least 90% identity to the amino acid sequence of SEQ ID NO: 17, the hCMV UL131A polypeptide comprises an amino acid sequence having at least 90% identity to the amino acid sequence of SEQ ID NO: 18, and/or the hCMV gB polypeptide comprises an amino acid sequence having at least 90% identity to the amino acid sequence of SEQ ID NO: 15.

In some embodiments, the hCMV gH polypeptide comprises the amino acid sequence of SEQ ID NO: 19, the hCMV gL polypeptide comprises the amino acid sequence of SEQ ID NO: 20, the hCMV UL128 polypeptide comprises the amino acid sequence of SEQ ID NO: 16, the hCMV UL130 polypeptide comprises the amino acid sequence of SEQ ID NO: 17, the hCMV UL131A polypeptide comprises the amino acid sequence of SEQ ID NO: 18, and/or the hCMV gB polypeptide comprises the amino acid sequence of SEQ ID NO: 15.

Aspects of the disclosure relate to methods for producing an antigen-specific immune response to hCMV in a subject comprising administering to a human subject an effective amount of an hCMV immunogenic composition described herein to thereby induce an antigen-specific immune response to hCMV or a hCMV antigen in the human subject.

In some embodiments, the hCMV immunogenic composition is administered via intramuscular injection. In some embodiments, the human subject is CMV-seropositive prior to being administered the hCMV mRNA vaccine. In some embodiments, the human subject is CMV-seronegative prior to being administered the hCMV mRNA vaccine. In some embodiments, the hCMV immunogenic composition is administered at a dose of 25 μg-300 μg mRNA. In some embodiments, the hCMV immunogenic composition is administered at a dose of 50 μg-150 μg mRNA. In some embodiments, the hCMV immunogenic composition is administered at a dose of 50 μg. In some embodiments, the hCMV immunogenic composition is administered at a dose of 100 μg. In some embodiments, the hCMV immunogenic composition is administered at a dose of 150 μg.

In some embodiments, the hCMV immunogenic composition is administered at least once, at least twice, or at least three times. In some embodiments, the hCMV immunogenic composition is administered with a primary immunization followed by one booster immunization. In some embodiments, the hCMV immunogenic composition is administered with a primary immunization followed by two booster immunizations.

In some embodiments, the effective amount is sufficient to produce serum neutralizing anti-CMV antibody titers against epithelial cell infection on any of day 29, day 56, day 84, day 168, or day 196 after administration of the hCMV immunogenic composition. In some embodiments, the effective amount is sufficient to produce serum neutralizing anti-CMV antibody titers against fibroblast infection on any of day 29, day 56, day 84, day 168, or day 196 after administration of the hCMV immunogenic composition. In some embodiments, the effective amount is sufficient to produce serum neutralizing anti-CMV antibody titers against epithelial cell infection on any of day 29, day 56, day 84, day 168, or day 196 after immunization and associated geometric mean ratio (GMR) of post-baseline/baseline titers at one or more time points after administration of the hCMV immunogenic composition. In some embodiments, the effective amount is sufficient to produce serum neutralizing anti-CMV antibody titers against fibroblast infection on any of day 29, day 56, day 84, day 168, or day 196 after immunization and associated geometric mean ratio (GMR) of post-baseline/baseline titers at one or more time points after administration of the hCMV immunogenic composition. In some embodiments, the proportion of participants with ≥2-fold, ≥3-fold, or ≥4-fold increases in neutralizing antibody (nAb) over baseline against epithelial cell infection is at least 50%, at least 60%, at least 70% at least 80%, or at least 90% at one time point after administration of the hCMV immunogenic composition. In some embodiments, the proportion of participants with ≥2-fold, ≥3-fold, or ≥4-fold increases in neutralizing antibody (nAb) over baseline against fibroblast infection is at least 50%, at least 60%, at least 70% at least 80%, or at least 90% at one time point after administration of the hCMV immunogenic composition.

Aspects of the disclosure relate to methods for producing an antigen-specific immune response to human cytomegalovirus (hCMV) in a subject comprising administering to a human subject an effective amount of the hCMV immunogenic composition comprising (a) a messenger ribonucleic acid (mRNA) polynucleotide comprising an open reading frame encoding a hCMV gH polypeptide; (b) a mRNA polynucleotide comprising an open reading frame encoding a hCMV gL polypeptide; (c) a mRNA polynucleotide comprising an open reading frame encoding a hCMV UL128 polypeptide; (d) a mRNA polynucleotide comprising an open reading frame encoding a hCMV UL130 polypeptide; (e) a mRNA polynucleotide comprising an open reading frame encoding a hCMV UL131A polypeptide; and (f) a mRNA polynucleotide comprising an open reading frame encoding a hCMV gB polypeptide, to thereby induce an antigen-specific immune response to hCMV or a hCMV antigen in the human subject, wherein the hCMV immunogenic composition is administered at a dose of 25 µg-300 µg mRNA, and wherein the proportion of human subjects with ≥2 fold, ≥3-fold, ≥4-fold, ≥5-fold, ≥6-fold, ≥7-fold, ≥8-fold, ≥9-fold, ≥10-fold, ≥11-fold, ≥12-fold, or ≥13-fold increase in neutralizing antibody (nAb) over baseline against epithelial cell infection is at least 50%, at least 60%, at least 70% at least 80%, or at least 90% at one time point after administration of the hCMV immunogenic composition.

Further aspects of the disclosure relate to methods for producing an antigen-specific immune response to human cytomegalovirus (hCMV) in a subject comprising administering to a human subject an effective amount of the hCMV immunogenic composition comprising (a) a messenger ribonucleic acid (mRNA) polynucleotide comprising an open reading frame encoding a hCMV gH polypeptide; (b) a mRNA polynucleotide comprising an open reading frame encoding a hCMV gL polypeptide; (c) a mRNA polynucleotide comprising an open reading frame encoding a hCMV UL128 polypeptide; (d) a mRNA polynucleotide comprising an open reading frame encoding a hCMV UL130 polypeptide; (e) a mRNA polynucleotide comprising an open reading frame encoding a hCMV UL131A polypeptide; and (f) a mRNA polynucleotide comprising an open reading frame encoding a hCMV gB polypeptide, to thereby induce an antigen-specific immune response to hCMV or a hCMV antigen in the human subject, wherein the hCMV immunogenic composition is administered at a dose of 25 µg-300 µg mRNA, and wherein the proportion of human subjects with ≥2 fold increase in neutralizing antibody (nAb) over baseline against fibroblast infection is at least 50%, at least 60%, at least 70% at least 80%, or at least 90% at one time point after administration of the hCMV immunogenic composition.

Aspects of the disclosure relate to methods for producing an antigen-specific immune response to human cytomegalovirus (hCMV) in a subject comprising administering to a human subject an effective amount of the hCMV immunogenic composition comprising (a) a messenger ribonucleic acid (mRNA) polynucleotide comprising an open reading frame encoding a hCMV gH polypeptide; (b) a mRNA polynucleotide comprising an open reading frame encoding a hCMV gL polypeptide; (c) a mRNA polynucleotide comprising an open reading frame encoding a hCMV UL128 polypeptide; (d) a mRNA polynucleotide comprising an open reading frame encoding a hCMV UL130 polypeptide; (e) a mRNA polynucleotide comprising an open reading frame encoding a hCMV UL131A polypeptide; and (f) a mRNA polynucleotide comprising an open reading frame encoding a hCMV gB polypeptide, to thereby induce an antigen-specific immune response to hCMV or a hCMV antigen in the human subject, wherein the hCMV immunogenic composition is administered at a dose of 25 µg-300 µg mRNA, and wherein the proportion of human subjects with ≥2-fold, ≥3-fold, ≥4-fold, ≥5-fold, ≥6-fold, ≥7-fold, ≥8-fold, ≥9-fold, or ≥10-fold increase in anti-pentamer binding antibody (bAb) over baseline is at least 50%, at least 60%, at least 70% at least 80%, or at least 90% at one time point after administration of the hCMV immunogenic composition.

Further aspects of the disclosure relate to methods for producing an antigen-specific immune response to human cytomegalovirus (hCMV) in a subject comprising administering to a human subject an effective amount of the hCMV immunogenic composition comprising (a) a messenger ribonucleic acid (mRNA) polynucleotide comprising an open reading frame encoding a hCMV gH polypeptide; (b) a mRNA polynucleotide comprising an open reading frame encoding a hCMV gL polypeptide; (c) a mRNA polynucleotide comprising an open reading frame encoding a hCMV UL128 polypeptide; (d) a mRNA polynucleotide comprising an open reading frame encoding a hCMV UL130 polypeptide; (e) a mRNA polynucleotide comprising an open reading frame encoding a hCMV UL131A polypeptide; and (f) a mRNA polynucleotide comprising an open reading frame encoding a hCMV gB polypeptide, to thereby induce an antigen-specific immune response to hCMV or a hCMV antigen in the human subject, wherein the hCMV immunogenic composition is administered at a dose of 25 µg-300 µg mRNA, and wherein the proportion of human subjects with ≥2-fold increase in anti-gB binding antibody (Ab) over baseline is at least 50%, at least 60%, at least 70% at least 80%, or at least 90% at one time point after administration of the hCMV immunogenic composition.

In some embodiments, the geometric mean ratio (GMR) of neutralizing antibodies against epithelial cell infection measured in a human subject is about 8-14 at one time point after administration of the hCMV immunogenic composition. In some embodiments, the geometric mean ratio (GMR) of anti-pentamer binding antibody (bAb) in a human subject is about 6-10 at one time point after administration of the hCMV immunogenic composition.

In some embodiments, the geometric mean ratio (GMR) of neutralizing antibodies against fibroblast infection in a human subject is about 2 at one time point after administration of the hCMV immunogenic composition. In some embodiments, the geometric mean ratio (GMR) of anti-gB binding antibody (Ab) in a human subject is about 2 at one time point after administration of the hCMV immunogenic composition.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2A provides a graph showing that the rate of degradation ($k_{observed}$) of each mRNA component of the vaccine correlates with the length of the mRNA construct. As shown in FIG. 2A, higher degradation rates were associated with the larger mRNA molecules gH and gB. FIG. 2B shows the amount of each mRNA component in a 100 µg RNA dose of an immunogenic composition comprising hCMV mRNA where the mRNA components were included based on equal mass (left column) or based on a pre-specified molar ratio (right column) The amount is shown in two ways, by mass (µg) and by mole (nanomole).

FIG. 6A shows the amount of each mRNA molecule in µg and picomoles when the hCMV mRNA immunogenic composition is based on an equal mass ratio or a proposed molar ratio. FIG. 6B shows a dose response of anti-gB antibodies as the relative molar content is modulated in the series of hCMV mRNA immunogenic compositions. Increased antibody response is observed with increased gB content. FIG. 6C shows a dose response of anti-pentamer antibodies as the relative molar content is modulated in the series of hCMV mRNA immunogenic compositions. Increased antibody response is observed with increased gH content. FIG. 6D shows dose response of anti-pentamer antibodies as the relative molar content is modulated in the series of hCMV mRNA immunogenic compositions. In Lot #1, #2, and #3, the UL131A is the limiting pentamer component, and in those groups, an increased antibody response is observed with increased UL131A content. In Lot #4, the gH is the limiting pentamer component and the UL131A was dosed in significant excess. The molar content of the pentamer-limiting gH in Lot #4 equals the molar content of pentamer-limiting UL131A in Lot #1, yet the antibody response of Lot #4 is less than the antibody response of Lot #1 indicating that excess gH is beneficial to maximize the antibody response. The hCMV pentamer is formed with gH as the basal component from which the other pentamer polypeptides may assemble onto. Thus, when gH is lacking, pentamer formation is hampered.

FIG. 8A shows neutralizing antibodies (nAb) against epithelial cell infection (primarily pentamer specific nAb). FIG. 8B shows neutralizing antibodies (nAb) against fibroblast cell infection (primarily gB specific nAb).

FIG. 9A shows neutralizing antibodies (nAb) against epithelial cell infection. FIG. 9B shows neutralizing antibodies (nAb) against fibroblast cell infection. The normal gaussian distribution shown is a theoretical distribution of batches based on purity.

FIG. 15A shows a dose response of anti-gB antibodies. FIG. 15B shows a dose response of anti-pentamer antibodies. The scale refers to the size of the batch used to manufacture mRNA using In Vitro Transcription (IVT).

FIG. 16A shows that large scale lyophilized formulation based on molar ratio (1 g scale) elicited higher CMV neutralizing antibody titers than small scale liquid formulation based on equal mass ratio (0.03 g scale) in epithelial cells. FIG. 16B shows that large scale lyophilized formulation based on molar ratio (1 g scale) elicited high CMV neutralizing antibody titers at a dose of 2 μg mRNA.

DETAILED DESCRIPTION

Figure 1A:
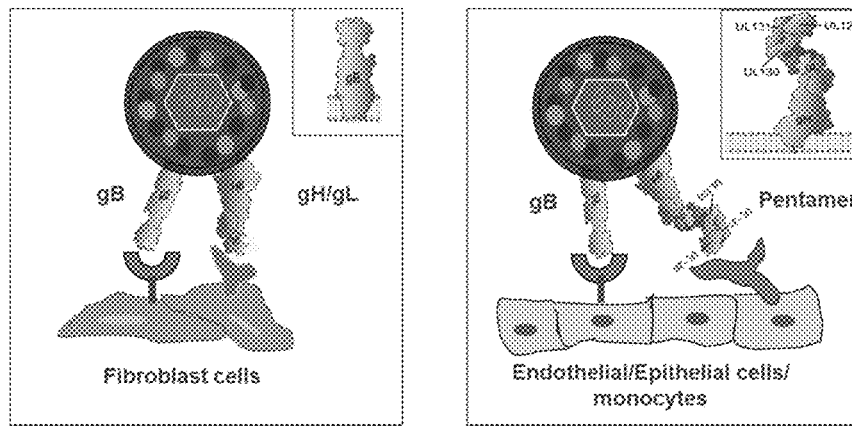
FIGS. 1A and 1B provide schematics showing that the hCMV immunogenic compositions described herein include mRNAs encoding viral antigens gB and the pentamer (gH/gL/UL128/UL130/UL131A). CMV tropism is associated with distinct glycoproteins. gB and the pentamer are important targets of neutralizing antibodies. The majority of neutralizing antibodies in seropositive individuals are against pentamer.

HCMV immunogenic compositions (e.g., vaccines such as mRNA vaccines) containing mRNAs encoding the hCMV pentamer (gH, gL, UL128, UL130, and UL131A) and gB at equal mass ratios (e.g., an mRNA mass ratio for gH:gL:UL128:UL130:UL131A:gB of approximately 1:1:1:1:1:1) have been shown to be efficacious in inducing neutralizing antibodies against hCMV in a Phase I clinical trial study. However, the use of an equal mass ratio for all the mRNA components results in some mRNA components being over-represented on a molar basis and others being under-represented due to their differences in molecular weight. Surprisingly, it is shown herein that specifying the molar ratios of specific mRNA components within a hCMV immunogenic composition that includes gH, gL, UL128, UL130, UL131A, and gB leads to improved properties. In particular, using an approximately equal molar ratio of gL, UL128, UL130, and UL131A, while increasing the molar ratios of gB and/or gH relative to the other mRNA components within an hCMV immunogenic composition improved pentamer expression, improved gB expression, improved anti-pentamer antibody response, and improved anti-gB antibody response. Additionally, such a molar ratio allows for increased shelf life of hCMV immunogenic compositions by maintaining product potency.

The rationale for modifying mRNA ratios within a multivalent hCMV mRNA vaccine is based at least in part on the molar stoichiometry of hCMV pentamer formation once the mRNAs within the vaccine are translated into proteins. Providing the individual mRNA constructs in a ratio that matches the molar stoichiometry allows maximum protein expression per mass of mRNA dosed to the patient. gB and gH are the largest glycoprotein components in the immunogenic composition and gH is the basal structure that the smaller pentamer proteins complex onto to form mature pentamer. Further, adjusting the ratio based on relative rates of mRNA degradation during storage, which are dependent at least in part on the mRNA construct length, allows optimal functional performance throughout the duration of the drug product shelf life. As shown in the Examples, the largest mRNA can serve as a surrogate for potency of the entire vaccine batch. As long as the gB component remained above 49% unmodified by degradation, the immunogenicity of the entire vaccine was intact. A modified ratio containing approximately equal molar amounts of UL128, gL, UL130, and UL131A and excess (e.g., at least 1.5×, or at least 2×) molar amount of gB and gH was demonstrated herein to be efficacious in vitro and in mice. For a given total dose, hCMV immunogenic compositions (e.g., mRNA vaccines) based on molar ratios can result in increased potency as shown by protein expression and/or improved antibody response compared to hCMV mRNA vaccines based on equal mass ratios.

In some embodiments, hCMV immunogenic compositions (e.g., mRNA vaccines) based on molar ratios can result in about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more than 50% increase in potency. In certain embodiments, hCMV immunogenic compositions (e.g., mRNA vaccines) based on molar ratios can result in about 40% increase in potency. In some embodiments, hCMV immunogenic compositions (e.g., mRNA vaccines) based on molar ratios can result in about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more than 50% decrease in cost of goods. In certain embodiments, hCMV immunogenic compositions (e.g., mRNA vaccines) based on molar ratios can result in about 40% decrease in cost of goods. In some embodiments, hCMV immunogenic compositions (e.g., mRNA vaccines) based on molar ratios can result in increased tolerability because of about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more than 50% lower lipid dosing. In certain embodiments, hCMV immunogenic compositions (e.g., mRNA vaccines) based on molar ratios can result in increased tolerability because of about 40% lower lipid dosing.

Antigens

Antigens are proteins or polysaccharides capable of inducing an immune response (e.g., causing an immune system to produce antibodies against the antigens). Herein, use of the term antigen encompasses immunogenic proteins and immunogenic fragments that induce (or are capable of inducing) an immune response to hCMV, unless otherwise stated. It should be understood that the term "protein" encompasses peptides and the term "antigen" encompasses antigenic fragments.

HCMV includes several surface glycoproteins that are involved in viral attachment and entry into different cell types. The pentameric complex (PC), composed of gH/gL/UL128/UL130/UL131A (Hahn et al., 2004; Ryckman et al., 2008; Wang and Shenk, 2005b, each of which are incorporated herein by reference), mediates entry into endothelial cells, epithelial cells, and myeloid cells.

HCMV proteins UL128, UL130, and UL131A assemble with gH and gL proteins to form a heterologous pentameric complex, designated gH/gL/UL128-131A, found on the surface of the HCMV. Natural variants and deletion and mutational analyses have implicated proteins of the gH/gL/UL128-131A complex with the ability to infect certain cell types, including for example, endothelial cells, epithelial cells, and leukocytes.

HCMV enters cells by fusing its envelope with either the plasma membrane (fibroblasts) or the endosomal membrane (epithelial and endothelial cells). HCMV initiates cell entry by attaching to the cell surface heparan sulfate proteoglycans using envelope glycoprotein M (gM) or gB. This step is followed by interaction with cell surface receptors that trigger entry or initiate intracellular signaling. The entry receptor function is provided by gH/gL glycoprotein complexes. Different gH/gL complexes are known to facilitate entry into epithelial cells, endothelial cells, or fibroblasts. For example, while entry into fibroblasts requires gH/gL heterodimer, entry into epithelial and endothelial cells requires the pentameric complex gH/gL/UL128/UL130/UL131 in addition to gH/gL. Thus, different gH/gL complexes engage distinct entry receptors on epithelial/endothelial cells and fibroblasts. Receptor engagement is followed by membrane fusion, a process mediated by gB and gH/gL. Early antibody studies have supported critical roles for both gB and gH/gL in hCMV entry. gB is essential for entry and cell spread. gB and gH/gL are necessary and sufficient for cell fusion and thus constitute the "core fusion machinery" of HCMV, which is conserved among other herpesviruses. Thus, the four glycoprotein complexes play a crucial role in viral attachment, binding, fusion and entry into the host cell.

Studies involving the gH/gL/UL128-131A complex have shown that hCMV glycoproteins gB, gH, gL, gM, and gN, as well as UL128, UL130, and UL131A proteins, are immunogenic and involved in the immunostimulatory response in a variety of cell types. Moreover, UL128, UL13, and UL131A genes are relatively conserved among hCMV isolates and therefore represent an attractive target for vaccination. Furthermore, recent studies have shown that antibodies to epitopes within the pentameric gH/gL/UL128-131 complex neutralize entry into endothelial, epithelial, and other cell types, thus blocking the ability of hCMV to infect several cell types.

Without wishing to be bound by any theory, the majority of neutralizing antibodies may be directed against envelope glycoproteins (Britt et al., 1990; Fouts et al., 2012; Macagno et al., 2010; Marshall et al., 1992, incorporated herein by reference), whereas robust T cell responses may be directed against the tegument protein pp65 and nonstructural proteins such as IE1 and IE2 (Blanco-Lobo et al., 2016; Borysiewicz et al., 1988; Kern et al., 2002, incorporated herein by reference).

HCMV envelope glycoprotein complexes (e.g., gH/gL/UL128/UL130/UL131A) represent major antigenic targets of antiviral immune responses. Embodiments of the present disclosure provide RNA (e.g., mRNA) vaccines that include polynucleotides encoding an HCMV antigen, in particular an HCMV antigen from one of the HCMV glycoprotein complexes. Embodiments of the present disclosure provide RNA (e.g., mRNA) vaccines that include at least one polynucleotide encoding at least one hCMV antigenic polypeptide. The HCMV RNA vaccines provided herein may be used to induce a balanced immune response, comprising both cellular and humoral immunity, without many of the risks associated with DNA vaccines and live attenuated vaccines.

The entire contents of International Application No. PCT/US2015/027400 (WO 2015/164674), entitled "Nucleic Acid Vaccines," International Application No. PCT/US2016/058310 (WO2017/070613), entitled "HUMAN CYTOMEGALOVIRUS VACCINE," International Application No. PCT/US2017/057748 (WO2018/075980), entitled "HUMAN CYTOMEGALOVIRUS VACCINE," U.S. Pat. No. 10,064,935, entitled "HUMAN CYTOMEGALOVIRUS VACCINE," U.S. Pat. No. 10,383,937, entitled "HUMAN CYTOMEGALOVIRUS VACCINE," and U.S. Pat. No. 10,064,935, entitled "HUMAN CYTOMEGALOVIRUS VACCINE," and U.S. Pat. No. 10,716,846, entitled "HUMAN CYTOMEGALOVIRUS VACCINE," are incorporated herein by reference.

hCMV antigens of immunogenic compositions (e.g., vaccines such as mRNA vaccines) of the present disclosure are provided in Table 13 herein. In some embodiments, the hCMV immunogenic composition (e.g., mRNA vaccine) comprises: (a) a messenger ribonucleic acid (mRNA) polynucleotide comprising an open reading frame encoding a hCMV gH polypeptide; (b) a mRNA polynucleotide comprising an open reading frame encoding a hCMV gL polypeptide; (c) a mRNA polynucleotide comprising an open reading frame encoding a hCMV UL128 polypeptide; (d) a mRNA polynucleotide comprising an open reading frame encoding a hCMV UL130 polypeptide; (e) a mRNA polynucleotide comprising an open reading frame encoding a hCMV UL131A polypeptide; and (f) a mRNA polynucleotide comprising an open reading frame encoding a hCMV gB. In some embodiments, the hCMV vaccine components comprise the sequences provided in Table 13.

In some embodiments, the mRNA encoding hCMV gH protein comprises a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the nucleotide sequence of sequence of SEQ ID NO: 5.

In some embodiments, the mRNA encoding hCMV gL protein comprises a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the nucleotide sequence of sequence of SEQ ID NO: 6.

In some embodiments, the mRNA encoding hCMV UL128 protein comprises a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the nucleotide sequence of sequence of SEQ ID NO: 2.

In some embodiments, the mRNA encoding hCMV UL130 protein comprises a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the nucleotide sequence of sequence of SEQ ID NO: 3.

In some embodiments, the mRNA encoding hCMV UL131A protein comprises a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the nucleotide sequence of sequence of SEQ ID NO: 4.

In some embodiments, the mRNA encoding hCMV gB protein comprises a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the nucleotide sequence of sequence of SEQ ID NO: 1.

In some embodiments, the mRNA encoding the hCMV gH polypeptide comprises the nucleotide sequence of SEQ ID NO: 5. In some embodiments, the mRNA encoding the hCMV gL polypeptide comprises an open reading frame (ORF) of the nucleotide sequence of SEQ ID NO: 6. In some embodiments, the mRNA encoding the hCMV UL128 polypeptide comprises the nucleotide sequence of SEQ ID NO: 2. In some embodiments, the mRNA encoding the hCMV UL130 polypeptide comprises the nucleotide sequence of SEQ ID NO: 3. In some embodiments, the mRNA encoding the hCMV UL131A polypeptide comprises the nucleotide sequence of SEQ ID NO: 4. In some embodiments, the mRNA encoding the hCMV gB polypeptide comprises the nucleotide sequence of SEQ ID NO: 1.

In some embodiments, the open reading frame encoding the hCMV gH polypeptide comprises a sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the sequence of SEQ ID NO: 11.

In some embodiments, the open reading frame encoding the hCMV gL polypeptide comprises a sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the sequence of SEQ ID NO: 12.

In some embodiments, the open reading frame encoding the hCMV UL128 polypeptide comprises a sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the sequence of SEQ ID NO: 8.

In some embodiments, the open reading frame encoding the hCMV UL130 polypeptide comprises a sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the sequence of SEQ ID NO: 9.

In some embodiments, the open reading frame encoding the hCMV UL131A polypeptide comprises a sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the of sequence of SEQ ID NO: 10.

In some embodiments, the mRNA encoding the hCMV gH polypeptide comprises an open reading frame (ORF) of the nucleotide sequence of SEQ ID NO: 11. In some embodiments, the mRNA encoding the hCMV gL polypeptide comprises an open reading frame (ORF) of the nucleotide sequence of SEQ ID NO: 12. In some embodiments, the mRNA encoding the hCMV UL128 polypeptide comprises an open reading frame (ORF) of the nucleotide sequence of SEQ ID NO: 8. In some embodiments, the mRNA encoding the hCMV UL130 polypeptide comprises an open reading frame (ORF) of the nucleotide sequence of SEQ ID NO: 9. In some embodiments, the mRNA encoding the hCMV UL131A polypeptide comprises an open reading frame (ORF) of the nucleotide sequence of SEQ ID NO: 10. In some embodiments, the mRNA encoding the hCMV gB polypeptide comprises an open reading frame (ORF) of the nucleotide sequence of SEQ ID NO: 7.

In some embodiments, the hCMV gB polypeptide comprises a sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the sequence of SEQ ID NO: 7.

In some embodiments, the hCMV gH polypeptide comprises an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the amino acid sequence of SEQ ID NO: 19 In some embodiments, the hCMV gL polypeptide comprises an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the amino acid sequence of SEQ ID NO: 20.

In some embodiments, the hCMV UL128 polypeptide comprises an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the amino acid sequence of SEQ ID NO: 16.

In some embodiments, the hCMV UL130 polypeptide comprises an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the amino acid sequence of SEQ ID NO: 17.

In some embodiments, the hCMV UL131A polypeptide comprises an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the amino acid sequence of SEQ ID NO: 18.

In some embodiments, the hCMV gB polypeptide comprises an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or more than 99% identity, to the amino acid sequence of SEQ ID NO: 15.

In some embodiments, the hCMV gH polypeptide comprises the amino acid sequence of SEQ ID NO: 19. In some embodiments, the hCMV gL polypeptide comprises the amino acid sequence of SEQ ID NO: 20. In some embodiments, the hCMV UL128 polypeptide comprises the amino acid sequence of SEQ ID NO: 16. In some embodiments, the hCMV UL130 polypeptide comprises the amino acid sequence of SEQ ID NO: 17. In some embodiments, the hCMV UL131A polypeptide comprises the amino acid sequence of SEQ ID NO: 18. In some embodiments, the hCMV gB polypeptide comprises the amino acid sequence of SEQ ID NO: 15.

In some embodiments, the mRNA components of a hCMV immunogenic composition (e.g., mRNA vaccine) are present in equal masses. In other embodiments, the mRNA components of a hCMV immunogenic composition (e.g., mRNA vaccine) are not present in equal masses. It was discovered herein that inclusion of the mRNA components in equal masses led to the underrepresentation of some of the longer mRNA constructs due at least in part to degradation. Accordingly, as explained in the Examples, an alternative approach based on molar ratios of mRNA components was developed herein for formulation of mRNA components of a hCMV immunogenic composition (e.g., mRNA vaccine).

In some embodiments, the hCMV immunogenic composition (e.g., mRNA vaccine) comprises (a) a messenger ribonucleic acid (mRNA) polynucleotide comprising an open reading frame encoding a hCMV gH polypeptide; (b) a mRNA polynucleotide comprising an open reading frame encoding a hCMV gL polypeptide; (c) a mRNA polynucleotide comprising an open reading frame encoding a hCMV UL128 polypeptide; (d) a mRNA polynucleotide comprising an open reading frame encoding a hCMV UL130 polypeptide; (e) a mRNA polynucleotide comprising an open reading frame encoding a hCMV UL131A polypeptide; and (f) a mRNA polynucleotide comprising an open reading frame encoding a hCMV gB polypeptide, wherein: the molar ratio of (a):(f) within the immunogenic composition is about 1:1; the molar ratio of (b):(c):(d):(e) within the immunogenic composition is about 1:1:1:1; and the molar ratio of each of (a) and (f) to any one of (b), (c), (d) or (e) within the immunogenic composition is about 1.5:1 to 2:1 (e.g., 1.5:1 to 2:1, 1.5:1 to 1.9:1, 1.5:1 to 1.8:1, 1.5:1 to 1.7:1, 1.5:1 to 1.6:1, 1.6:1 to 2:1, 1.6:1 to 1.9:1, 1.6:1 to 1.8:1, 1.6:1 to 1.7:1, 1.7:1 to 2:1, 1.7:1 to 1.9:1, 1.7:1 to 1.8:1, 1.8:1 to 2:1, 1.8:1 to 1.9:1, or 1.9:1 to 2:1).

In some embodiments, the molar ratio of each of (a) and (f) to any one of (b), (c), (d) or (e) within the immunogenic composition is about 1.5:1 to 2:1 (e.g., 1.5:1, 1.6:1, 1.7:1, 1.8:1, 1.9:1, or 2:1). In some embodiments, the molar ratio of (a) to any one of (b), (c), (d) or (e) within the immunogenic composition is about 1.5:1 to 2:1 (e.g., 1.5:1, 1.6:1, 1.7:1, 1.8:1, 1.9:1, or 2:1). In some embodiments, the molar ratio of (f) to any one of (b), (c), (d) or (e) within the immunogenic composition is about 1.5:1 to 2:1 (e.g., 1.5:1, 1.6:1, 1.7:1, 1.8:1, 1.9:1, or 2:1). In some embodiments, the molar ratio of (a) to any one of (b), (c), (d) or (e) within the immunogenic composition is about 1.5:1 to 2:1 (e.g., 1.5:1, 1.6:1, 1.7:1, 1.8:1, 1.9:1, or 2:1), and the molar ratio of (f) to any one of (b), (c), (d) or (e) within the immunogenic composition is about 1.5:1 to 2:1 (e.g., 1.5:1, 1.6:1, 1.7:1, 1.8:1, 1.9:1, or 2:1). In some embodiments, the molar ratio of (a):(b):(c):(d):(e):(f) is about 1.5:1:1:1:1:1.5. In some embodiments, the molar ratio of (a):(b):(c):(d):(e):(f) is about 2:1:1:1:1:2.

In some embodiments, mRNAs associated with hCMV immunogenic compositions described herein may further comprise a 5' cap (e.g., 7mG(5')ppp(5')NlmpNp), a polyA tail (e.g., ~100 nucleotides), or a 5' cap and a polyA tail.

It should be understood that the hCMV immunogenic compositions (e.g., mRNA vaccines) of the present disclosure may comprise a signal sequence. It should also be understood that the hCMV mRNA vaccines of the present disclosure may include any 5' untranslated region (UTR)

and/or any 3' UTR. Exemplary UTR sequences are provided in Table 13; however, other UTR sequences may be used or exchanged for any of the UTR sequences described herein. UTRs may also be omitted from the vaccine constructs provided herein.

Without wishing to be bound by any theory, the hCMV immunogenic compositions (e.g., mRNA vaccines) described herein, in which molar ratios are used to determine the amounts of each mRNA component, may have increased stability relative to hCMV immunogenic compositions (e.g., mRNA vaccines) in which the mRNA components are present in equal masses. This increased stability can help to ensure that the hCMV immunogenic compositions are stable throughout the shelf-life of a drug product containing these compositions and are still sufficiently efficacious for administration to a subject until the specified expiry date of the drug product.

Stability of mRNA constructs can be measured by any means known to one of ordinary skill in the art. In some embodiments, stability of mRNA constructs is calculated based on measuring degradation and/or purity of the mRNA construct. Longer mRNA constructs within hCMV immunogenic compositions described herein, such as gH and gB are expected to degrade faster than the shorter mRNA constructs within the same hCMV immunogenic compositions. Accordingly, in some embodiments, stability of hCMV immunogenic compositions described herein is measured by measuring the degradation and/or purity of gH and/or gB. "Purity," as used herein, refers to the amount of full-length intact mRNA (e.g., mRNA encoding gB) relative to the total input of the mRNA (e.g., mRNA encoding gB) on mass basis.

In some embodiments, all of the mRNA components of hCMV immunogenic compositions described herein maintain a purity of at least 45% (e.g., at least 45%, at least 46%, at least 47%, at least 48%, at least 49%, at least 50%, at least 60%, at least 70%, at least 80%, or more) throughout the projected shelf-life (e.g., up to 2 years) under proper storage conditions (e.g., at a temperature of greater than 0° C. and less than or equal to 10° C.). In some embodiments, gH and/or gB maintain a purity of at least 45% (e.g., at least 45%, at least 46%, at least 47%, at least 48%, at least 49%, at least 50%, at least 60%, at least 70%, at least 80%, or more) throughout the projected shelf-life (e.g., up to 2 years) under proper storage conditions (e.g., at a temperature of greater than or equal to −80° C. and less than or equal to 10° C. such as −80, −70, −40, −20, 0, 5, or 10° C.).

In some embodiments, the hCMV immunogenic composition (e.g., mRNA vaccine) is stable for at least three months (e.g., at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, at least 24 months, at least 25 month, at least 26 months, at least 27 months, at least 28 months, at least 29 months, at least 30 months, at least 31 months, at least 32 months, at least 33 months, at least 34 months, at least 35 months, at least 36 months or more) when stored at a temperature of greater than or equal to −80° C. and less than or equal to 10° C. In some embodiments, the hCMV immunogenic composition (e.g., mRNA vaccine) is stored at a temperature of about −80, −70, −40, −20, 0, 5, or 10° C. In some embodiments, the immunogenic composition (e.g., vaccine) is stored at a temperature of about −80° C. In some embodiments, the immunogenic composition (e.g., vaccine) is stored at a temperature of about −20° C. In some embodiments, the immunogenic composition (e.g., vaccine) is stored at a temperature of about 5° C. In some embodiments, the hCMV immunogenic composition (e.g., mRNA vaccine) is stable for at least three months (e.g., at least 3 months, at least 6 months, at least 9 months, at least 12 months, at least 15 months, at least 18 months, at least 21 months, at least 24 months, at least 30 months, or at least 36 months) when stored at a temperature of about −80, −20, or 5° C.

In some embodiments, the hCMV immunogenic composition (e.g., mRNA vaccine) is stable for at least twelve to eighteen months when stored at a temperature of greater than or equal to −80° C. and less than or equal to 10° C. (e.g., −80, −70, −40, −20, 0, 5, or 10° C.). In some embodiments, the hCMV immunogenic composition (e.g., mRNA vaccine) is stable for at least twelve to eighteen months when stored at a temperature of about −80° C. In some embodiments, the hCMV immunogenic composition (e.g., mRNA vaccine) is stable for at least twelve to eighteen months when stored at a temperature of about −20° C. In some embodiments, the hCMV immunogenic composition (e.g., mRNA vaccine) is stable for at least twelve to eighteen months when stored at a temperature of about 5° C.

In some embodiments, hCMV immunogenic compositions (e.g., mRNA vaccines) described herein in which mRNA components are based on specified molar ratios have increased stability (e.g., increased by at least 20%, at least 50%, at least 80%, at least 100%, at least 2-fold, at least 5-fold, at least 10-fold or more) relative to an hCMV immunogenic composition in which the mRNA components are present in approximately equivalent masses. In some embodiments, the hCMV immunogenic compositions (e.g., mRNA vaccines) described herein in which mRNA components are based on specified molar ratios have increased stability (e.g., increased by at least 20%, at least 50%, at least 80%, at least 100%, at least 2-fold, at least 5-fold, at least 10-fold or more) relative to an hCMV immunogenic composition in which the mRNA components are present in approximately equivalent masses when stored for at least three months e.g., at least 3 months, at least 6 months, at least 9 months, at least 12 months, at least 15 months, at least 18 months, at least 21 months, at least 24 months or at least 36 months) at a temperature of greater than or equal to −80° C. and less than or equal to 10° C. (e.g., −80, −70, −40, −20, 0, 5, or 10° C.).

In some embodiments, hCMV immunogenic compositions (e.g., mRNA vaccines) described herein in which mRNA components are based on specified molar ratios have increased stability (e.g., increased by at least 20%, at least 50%, at least 80%, at least 100%, at least 2-fold, at least 5-fold, at least 10-fold or more) relative to an hCMV immunogenic composition in which the mRNA components are present in approximately equivalent masses when stored for at least twenty-four months at a temperature of greater than or equal to −80° C. and less than or equal to 10° C. (e.g., −80, −70, −40, −20, 0, 5, or 10° C.). In some embodiments, hCMV immunogenic compositions (e.g., mRNA vaccines) described herein in which mRNA components are based on specified molar ratios have increased stability (e.g., increased by at least 20%, at least 50%, at least 80%, at least 100%, at least 2-fold, at least 5-fold, at least 10-fold or more) relative to an hCMV immunogenic composition in which the mRNA components are present in approximately equivalent masses when stored for at least twenty-four months at a temperature of about −80, −20, or 5° C.

In some embodiments, hCMV immunogenic compositions (e.g., mRNA vaccines) described herein in which mRNA components are based on specified molar ratios result in increased (e.g., increased by at least 10%, at least 20%, at least 50%, at least 90%, at least 2-fold, or at least 10-fold) pentamer expression (e.g., in vitro or in vivo) relative to an hCMV immunogenic composition in which the mRNAs are present in approximately equivalent masses.

In some embodiments, hCMV immunogenic compositions (e.g., mRNA vaccines) described herein in which mRNA components are based on specified molar ratios result in increased (e.g., increased by at least 10%, at least 20%, at least 50%, at least 90%, at least 2-fold, or at least 10-fold) gB expression (e.g., in vitro or in vivo) relative to an hCMV immunogenic composition in which the mRNAs are present in approximately equivalent masses.

In some embodiments, hCMV immunogenic compositions (e.g., mRNA vaccines) described herein in which mRNA components are based on specified molar ratios induces increased (e.g., increased by at least 10%, at least 20%, at least 50%, at least 90%, at least 2-fold, or at least 10-fold) anti-pentamer antibody level relative to an hCMV immunogenic composition in which the mRNAs are present in approximately equivalent masses.

In some embodiments, hCMV immunogenic compositions (e.g., mRNA vaccines) described herein in which mRNA components are based on specified molar ratios induces increased (e.g., increased by at least 10%, at least 20%, at least 50%, at least 90%, at least 2-fold, or at least 10-fold) anti-gB antibody level relative to an hCMV immunogenic composition in which the mRNAs are present in approximately equivalent masses.

Nucleic Acids

The hCMV immunogenic compositions (e.g., mRNA vaccines) of the present disclosure comprise at least one (one or more) ribonucleic acid (RNA) having an open reading frame encoding at least one hCMV antigen. In some embodiments, the RNA is a messenger RNA (mRNA) having an open reading frame encoding at least one hCMV antigen. In some embodiments, the RNA (e.g., mRNA) further comprises a (at least one) 5' UTR, 3' UTR, a polyA tail and/or a 5' cap.

Nucleic acids comprise a polymer of nucleotides (nucleotide monomers), also referred to as polynucleotides. Nucleic acids may be or may include, for example, deoxyribonucleic acids (DNAs), ribonucleic acids (RNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) and/or chimeras and/or combinations thereof.

Messenger RNA (mRNA) is any ribonucleic acid that encodes a (at least one) protein (a naturally-occurring, non-naturally-occurring, or modified polymer of amino acids) and can be translated to produce the encoded protein in vitro, in vivo, in situ or ex vivo. The skilled artisan will appreciate that, except where otherwise noted, nucleic acid sequences set forth in the instant application may recite "T"s in a representative DNA sequence but where the sequence represents RNA (e.g., mRNA), the "T"s would be substituted for "U"s. Thus, any of the DNAs disclosed and identified by a particular sequence identification number herein also disclose the corresponding RNA (e.g., mRNA) sequence complementary to the DNA, where each "T" of the DNA sequence is substituted with "U."

An open reading frame (ORF) is a continuous stretch of DNA or RNA beginning with a start codon (e.g., methionine (ATG or AUG)) and ending with a stop codon (e.g., TAA, TAG or TGA, or UAA, UAG or UGA). An ORF typically encodes a protein. It will be understood that the sequences disclosed herein may further comprise additional elements, e.g., 5' and 3' UTRs, but that those elements, unlike the ORF, need not necessarily be present in a vaccine of the present disclosure.

Variants

In some embodiments, the hCMV immunogenic composition (e.g., mRNA vaccine) of the present disclosure comprises mRNAs encoding an hCMV antigen variant. Antigen or other polypeptide variants refers to molecules that differ in their amino acid sequence from a wild-type, native or reference sequence. The antigen/polypeptide variants may possess substitutions, deletions, and/or insertions at certain positions within the amino acid sequence, as compared to a native or reference sequence. Ordinarily, variants possess at least 50% identity to a wild-type, native or reference sequence. In some embodiments, variants share at least 80%, or at least 90% identity with a wild-type, native or reference sequence.

Variant antigens/polypeptides encoded by nucleic acids of the disclosure may contain amino acid changes that confer any of a number of desirable properties, e.g., that enhance their immunogenicity, enhance their expression, and/or improve their stability or PK/PD properties in a subject. Variant antigens/polypeptides can be made using routine mutagenesis techniques and assayed as appropriate to determine whether they possess the desired property. Assays to determine expression levels and immunogenicity are well known in the art. Similarly, PK/PD properties of a protein variant can be measured using art recognized techniques, e.g., by determining expression of antigens in a vaccinated subject over time and/or by looking at the durability of the induced immune response. The stability of protein(s) encoded by a variant nucleic acid may be measured by assaying thermal stability or stability upon urea denaturation or may be measured using in silico prediction. Methods for such experiments and in silico determinations are known in the art.

In some embodiments, an hCMV immunogenic composition (e.g., mRNA vaccine) comprises an mRNA ORF having a nucleotide sequence identified by any one of the sequences provided herein (see e.g., Table 13), or having a nucleotide sequence at least 80%, at least 85%, at least 90%, at least 95%, at least 96%, at least 97%, at least 98%, or at least 99% identical (including all values in between) to a nucleotide sequence identified by any one of the sequence provided herein.

The term "identity" refers to a relationship between the sequences of two or more polypeptides (e.g. antigens) or polynucleotides (nucleic acids), as determined by comparing the sequences. Identity also refers to the degree of sequence relatedness between or among sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related antigens or nucleic acids can be readily calculated by known methods. "Percent (%) identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide (e.g., antigen) have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm.

As such, polynucleotides encoding peptides or polypeptides containing substitutions, insertions and/or additions, deletions and covalent modifications with respect to reference sequences, in particular the polypeptide (e.g., antigen) sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support. In some embodiments, sequences for (or encoding) signal sequences, termination sequences, transmembrane domains, linkers, multimerization domains (such as, e.g., foldon regions) and the like may be substituted with alternative sequences that achieve the same or a similar function. In some embodiments, cavities in the core of proteins can be filled to improve stability, e.g., by introducing larger amino acids. In other embodiments, buried hydrogen bond networks may be replaced with hydrophobic resides to improve stability. In yet other embodiments, glycosylation sites may be removed and replaced with appropriate residues. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an RNA (e.g., mRNA) vaccine.

As recognized by those skilled in the art, protein fragments, functional protein domains, and homologous proteins are also considered to be within the scope of hCMV antigens of interest. For example, provided herein is any protein fragment (meaning a polypeptide sequence at least one amino acid residue shorter than a reference antigen sequence but otherwise identical) of a reference protein, provided that the fragment is immunogenic and confers a protective immune response to the hCMV pathogen. In addition to variants that are identical to the reference protein but are truncated, in some embodiments, an antigen includes 2, 3, 4, 5, 6, 7, 8, 9, 10, or more mutations, relative to any of the sequences provided or referenced herein. Antigens/antigenic polypeptides can range in length from about 4, 6, or 8 amino acids to full length proteins.

Stabilizing Elements

Naturally-occurring eukaryotic mRNA molecules can contain stabilizing elements, including, but not limited to untranslated regions (UTR) at their 5'-end (5' UTR) and/or at their 3'-end (3' UTR), in addition to other structural features, such as a 5'-cap structure or a 3'-poly(A) tail. Both the 5' UTR and the 3' UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing.

In some embodiments, the hCMV immunogenic composition (e.g., mRNA vaccine) includes at least one RNA polynucleotide having an open reading frame encoding at least one antigenic polypeptide having at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G (5')ppp(5')G (New England BioLabs, Ipswich, Mass.). 5'-capping of modified RNA may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes may be derived from a recombinant source.

The 3'-poly(A) tail is typically a stretch of adenine nucleotides added to the 3'-end of the transcribed mRNA. It can, in some instances, comprise up to about 400 adenine nucleotides. In some embodiments, the length of the 3'-poly (A) tail may be an essential element with respect to the stability of the individual mRNA.

In some embodiments, the hCMV immunogenic composition (e.g., mRNA vaccine) includes one or more stabilizing elements. Stabilizing elements may include for instance a histone stem-loop. A 32 kDa stem-loop binding protein (SLBP) has been reported. It is associated with the histone stem-loop at the 3-end of the histone messages in both the nucleus and the cytoplasm. Its expression level is regulated by the cell cycle; it peaks during the S-phase, when histone mRNA levels are also elevated. The protein has been shown to be essential for efficient 3-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the hCMV immunogenic composition (e.g., mRNA vaccine) includes a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. The synergistic effect of the combination of poly(A) and at least one histone stem-loop does not depend on the order of the elements or the length of the poly(A) sequence.

In some embodiments, the hCMV immunogenic composition (e.g., mRNA vaccine) does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. In some embodiments, the nucleic acid does not include an intron.

The hCMV immunogenic composition (e.g., mRNA vaccine) may or may not contain an enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as it is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In some embodiments, the hCMV immunogenic composition (e.g., mRNA vaccine) has one or more AU-rich sequences removed. These sequences, sometimes referred to as AURES are destabilizing sequences found in the 3'UTR. The AURES may be removed from the RNA vaccines. Alternatively the AURES may remain in the RNA vaccine.

Signal Peptides

In some embodiments, an hCMV immunogenic composition (e.g., mRNA vaccine) comprises an mRNA having an ORF that encodes a signal peptide fused to the hCMV antigen. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by a ER-resident signal peptidase of the host cell, or they remain uncleaved and function as a membrane anchor. A signal peptide may also facilitate the targeting of the protein to the cell membrane.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

Signal peptides from heterologous genes (which regulate expression of genes other than hCMV antigens in nature) are known in the art and can be tested for desired properties and then incorporated into a nucleic acid of the disclosure. In some embodiments, the signal peptide may comprise one of the following sequences: MDSKGSSQKGSRLLLLL-VVSNLLLPQGVVG (SEQ ID NO: 25), MDWTWIL-FLVAAATRVHS (SEQ ID NO: 26); METPAQLLFLLLL-WLPDTTG (SEQ ID NO: 13); MLGSNSGQRVVFTILLLLVAPAYS (SEQ ID NO: 27); MKCLLYLAFLFIGVNCA (SEQ ID NO: 28); MWLVSLAIVTACAGA (SEQ ID NO: 29).

Sequence Optimization

In some embodiments, an ORF encoding an antigen of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence ORF (e.g., a naturally-occurring or wild-type mRNA sequence encoding a hCMV antigen). In some embodiments, a codon optimized sequence shares less than 90% sequence identity to a naturally-occurring or wild-type sequence (e.g., a naturally-occurring or wild-type mRNA sequence encoding a hCMV antigen). In some embodiments, a codon optimized sequence shares less than 85% sequence identity to a naturally-occurring or wild-type sequence (e.g., a naturally-occurring or wild-type mRNA sequence encoding a hCMV antigen). In some embodiments, a codon optimized sequence shares less than 80% sequence identity to a naturally-occurring or wild-type sequence (e.g., a naturally-occurring or wild-type mRNA sequence encoding a hCMV antigen). In some embodiments, a codon optimized sequence shares less than 75% sequence identity to a naturally-occurring or wild-type sequence (e.g., a naturally-occurring or wild-type mRNA sequence encoding hCMV antigen).

In some embodiments, a codon optimized mRNA sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a hCMV antigen). In some embodiments, a codon optimized sequence shares between 65% and 75% or about 80% sequence identity to a naturally-occurring or wild-type sequence (e.g., a naturally-occurring or wild-type mRNA sequence encoding a hCMV antigen).

In some embodiments, a codon-optimized mRNA sequence encodes an antigen that is as immunogenic as, or more immunogenic than (e.g., at least 10%, at least 20%, at least 30%, at least 40%, at least 50%, at least 100%, or at least 200% more), than a hCMV antigen encoded by a non-codon-optimized sequence.

When transfected into mammalian host cells, the modified mRNAs have a stability of between 12-18 hours, or greater than 18 hours, e.g., 24, 36, 48, 60, 72, or greater than 72 hours and are capable of being expressed by the mammalian host cells.

In some embodiments, a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than RNA containing a larger amount of adenine (A) and thymine (T) or uracil (U) nucleotides. As an example, WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Chemically Unmodified Nucleotides

In some embodiments, at least one RNA (e.g., mRNA) of an hCMV immunogenic composition (e.g., mRNA vaccine) of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Chemical Modifications

The hCMV immunogenic compositions (e.g., mRNA vaccines) of the present disclosure comprise, in some embodiments, at least one nucleic acid (e.g., RNA) having an open reading frame encoding at least one hCMV antigen, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleoside of the disclosure is one as is generally known or recognized in the art. Non-limiting examples of such naturally occurring modified nucleotides and nucleosides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise 1-methyl-pseudouridine (m1nψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a mRNA of the disclosure comprises 1-methyl-pseudouridine (m1ψ) substitutions at one or more or all uridine positions of the nucleic acid.

In some embodiments, a mRNA of the disclosure comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, a mRNA of the disclosure comprises pseudouridine (ψ) substitutions at one or more or all uridine positions of the nucleic acid.

In some embodiments, a mRNA of the disclosure comprises pseudouridine (ψ) substitutions at one or more or all uridine positions of the nucleic acid and 5-methyl cytidine substitutions at one or more or all cytidine positions of the nucleic acid.

In some embodiments, a mRNA of the disclosure comprises uridine at one or more or all uridine positions of the nucleic acid.

In some embodiments, mRNAs are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the polyA tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The mRNAs may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

Untranslated Regions (UTRs)

The mRNAs of the present disclosure may comprise one or more regions or parts which act or function as an untranslated region. Where mRNAs are designed to encode at least one antigen of interest, the nucleic acid may comprise one or more of these untranslated regions (UTRs). Wild-type untranslated regions of a nucleic acid are transcribed but not translated. In mRNA, the 5' UTR starts at the transcription start site and continues to the start codon but does not include the start codon; whereas, the 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5'UTR and 3'UTR sequences are known and available in the art.

A 5' UTR is region of an mRNA that is directly upstream (5') from the start codon (the first codon of an mRNA transcript translated by a ribosome). A 5' UTR does not encode a protein (is non-coding). Natural 5'UTRs have features that play roles in translation initiation. They harbor signatures like Kozak sequences which are commonly known to be involved in the process by which the ribosome initiates translation of many genes. Kozak sequences have the consensus CCR(A/G)CCAUGG (SEQ ID NO: 30), where R is a purine (adenine or guanine) three bases upstream of the start codon (AUG), which is followed by another 'G'. 5'UTR also have been known to form secondary structures which are involved in elongation factor binding.

In some embodiments of the disclosure, a 5' UTR is a heterologous UTR, i.e., is a UTR found in nature associated with a different ORF. In another embodiment, a 5' UTR is a synthetic UTR, i.e., does not occur in nature. Synthetic UTRs include UTRs that have been mutated to improve their properties, e.g., which increase gene expression as well as those which are completely synthetic. Exemplary 5' UTRs include *Xenopus* or human derived α-globin or β-globin (U.S. Pat. Nos. 8,278,063; 9,012,219), human cytochrome b-245 α polypeptide, and hydroxysteroid (17b) dehydrogenase, and Tobacco etch virus (U.S. Pat. Nos. 8,278,063, 9,012,219). CMV immediate-early 1 (IE1) gene (US20140206753, WO2013/185069), the sequence GGGAUCCUACC (SEQ ID NO: 18) (WO2014144196) may also be used. In another embodiment, 5' UTR of a TOP gene is a 5' UTR of a TOP gene lacking the 5' TOP motif (the oligopyrimidine tract) (e.g., WO/2015101414, WO2015101415, WO/2015/062738, WO2015024667, WO2015024667; 5' UTR element derived from ribosomal protein Large 32 (L32) gene (WO/2015101414, WO2015101415, WO/2015/062738), 5' UTR element derived from the 5'UTR of an hydroxysteroid (17-β) dehydrogenase 4 gene (HSD17B4) (WO2015024667), or a 5' UTR element derived from the 5' UTR of ATP5A1 (WO2015024667) can be used. In some embodiments, an internal ribosome entry site (IRES) is used instead of a 5' UTR.

In some embodiments, a 5' UTR of the present disclosure comprises a nucleotide sequence of SEQ ID NO: 13.

A 3' UTR is region of an mRNA that is directly downstream (3') from the stop codon (the codon of an mRNA transcript that signals a termination of translation). A 3' UTR does not encode a protein (is non-coding). Natural or wild type 3' UTRs are known to have stretches of adenosines and uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) (SEQ ID NO: 18) nonamers. Molecules containing this type of AREs include GM-CSF and TNF-α. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

3' UTRs may be heterologous or synthetic. With respect to 3' UTRs, globin UTRs, including *Xenopus* β-globin UTRs and human β-globin UTRs are known in the art (U.S. Pat. Nos. 8,278,063, 9,012,219, US20110086907). A modified β-globin construct with enhanced stability in some cell types by cloning two sequential human β-globin 3'UTRs head to tail has been developed and is well known in the art (US2012/0195936, WO2014/071963). In addition α2-globin, α1-globin, UTRs and mutants thereof are also known in the art (WO2015101415, WO2015024667). Other 3' UTRs described in the mRNA constructs in the non-patent literature include CYBA (Ferizi et al., 2015) and albumin (Thess et al., 2015). Other exemplary 3' UTRs include that of bovine or human growth hormone (wild type or modified) (WO2013/185069, US20140206753, WO2014152774), rabbit β globin and hepatitis B virus (HBV), α-globin 3' UTR and Viral VEEV 3' UTR sequences are also known in the art. In some embodiments, the sequence UUUGAAUU (WO2014144196) is used. In some embodiments, 3' UTRs of human and mouse ribosomal protein are used. Other examples include rps9 3'UTR (WO2015101414), FIG. 4 (WO2015101415), and human albumin 7 (WO2015101415).

In some embodiments, a 3' UTR of the present disclosure comprises a nucleotide sequence of SEQ ID NO: 14.

Those of ordinary skill in the art will understand that 5'UTRs that are heterologous or synthetic may be used with any desired 3' UTR sequence. For example, a heterologous 5'UTR may be used with a synthetic 3'UTR with a heterologous 3' UTR.

Combinations of features may be included in flanking regions and may be contained within other features. For example, the ORF may be flanked by a 5' UTR which may contain a strong Kozak translational initiation signal and/or a 3' UTR which may include an oligo(dT) sequence for templated addition of a poly-A tail. 5' UTR may comprise a first polynucleotide fragment and a second polynucleotide fragment from the same and/or different genes such as the 5' UTRs described in US Patent Application Publication No. 20100293625 and PCT/US2014/069155, herein incorporated by reference in their entireties.

In Vitro Transcription of RNA cDNA encoding the polynucleotides described herein may be transcribed using an in vitro transcription (IVT) system. In vitro transcription of RNA is known in the art and is described in International Publication WO/2014/152027, which is incorporated by reference herein in its entirety.

In some embodiments, the RNA transcript is generated using a non-amplified, linearized DNA template in an in vitro transcription reaction to generate the RNA transcript.

In some embodiments, the template DNA is isolated DNA. In some embodiments, the template DNA is cDNA. In some embodiments, the cDNA is formed by reverse transcription of a RNA polynucleotide, for example, but not limited to hCMV mRNA. In some embodiments, cells, e.g., bacterial cells, e.g., E. coli, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5' to and operably linked to the gene of interest.

In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

When RNA transcripts are being generated, the 5' UTR may comprise a promoter sequence. Such promoter sequences are known in the art. It should be understood that such promoter sequences will not be present in a vaccine of the disclosure.

A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a nucleic acid includes 200 to 3,000 nucleotides. For example, a nucleic acid may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

In some embodiments, the RNA transcript is capped via enzymatic capping. In some embodiments, the RNA comprises 5' terminal cap, for example, 7mG(5')ppp(5')NlmpNp.

Chemical Synthesis

Solid-phase chemical synthesis. Nucleic acids of the present disclosure may be manufactured in whole or in part using solid phase techniques. Solid-phase chemical synthesis of nucleic acids is an automated method wherein molecules are immobilized on a solid support and synthesized step by step in a reactant solution. Solid-phase synthesis is useful in site-specific introduction of chemical modifications in the nucleic acid sequences.

Liquid Phase Chemical Synthesis. The synthesis of nucleic acids of the present disclosure by the sequential addition of monomer building blocks may be carried out in a liquid phase.

Combination of Synthetic Methods. The synthetic methods discussed above each has its own advantages and limitations. Attempts have been conducted to combine these methods to overcome the limitations. Such combinations of methods are within the scope of the present disclosure. The use of solid-phase or liquid-phase chemical synthesis in combination with enzymatic ligation provides an efficient way to generate long chain nucleic acids that cannot be obtained by chemical synthesis alone.

Ligation of Nucleic Acid Regions or Subregions

Assembling nucleic acids by a ligase may also be used. DNA or RNA ligases promote intermolecular ligation of the 5' and 3' ends of polynucleotide chains through the formation of a phosphodiester bond. Nucleic acids such as chimeric polynucleotides and/or circular nucleic acids may be prepared by ligation of one or more regions or subregions. DNA fragments can be joined by a ligase catalyzed reaction to create recombinant DNA with different functions. Two oligodeoxynucleotides, one with a 5' phosphoryl group and another with a free 3' hydroxyl group, serve as substrates for a DNA ligase.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, Mass.), poly-T beads, LNATM oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR.

Quantification

In some embodiments, the nucleic acids of the present disclosure may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (ThermoFisher, Waltham, Mass.). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Lipid Nanoparticles (LNPs)

In some embodiments, the hCMV immunogenic compositions (e.g., mRNA vaccines) of the disclosure are formulated in one or more lipid nanoparticles (LNPs). Lipid nanoparticles typically comprise ionizable amino (cationic) lipid, non-cationic lipid, sterol and PEG lipid components along with the nucleic acid cargo of interest. The lipid nanoparticles of the disclosure can be generated using components, compositions, and methods as are generally known in the art; see, for example, PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entireties.

Vaccines of the present disclosure are typically formulated in lipid nanoparticles. The vaccines can be made, for example, using mixing processes such as microfluidics and T-junction mixing of two fluid streams, one of which contains the mRNA and the other has the lipid components. In some embodiments, the vaccines are prepared by combining an ionizable amino lipid, a phospholipid (such as DOPE or DSPC), a PEG lipid (such as 1,2-dimyristoyl-OT-glycerol methoxypoly ethylene glycol, also known as PEG-DMG), and a structural lipid (such as cholesterol) in an alcohol (e.g., ethanol). The lipids may be combined to yield desired molar ratios and diluted with water and alcohol (e.g., ethanol) to a final lipid concentration of between about 5.5 mM and about 25 mM, for example.

Vaccines including mRNA and a lipid component may be prepared, for example, by combining a lipid solution with an mRNA solution at lipid component to mRNA wt:wt ratios of between about 5:1 and about 50:1. The lipid solution may be rapidly injected using a microfluidic based system (e.g., NanoAssemblr) at flow rates between about 10 ml/min and about 18 ml/min, for example, into the mRNA solution to produce a suspension (e.g., with a water to alcohol ratio between about 1:1 and about 4:1).

Vaccines can be processed by dialysis to remove the alcohol (e.g., ethanol) and achieve buffer exchange. Formulations may be dialyzed against phosphate buffered saline (PBS), pH 7.4, for example, at volumes greater than that of the primary product (e.g., using Slide-A-Lyzer cassettes (Thermo Fisher Scientific Inc., Rockford, Ill.)) with a molecular weight cutoff of 10 kD, for example. The forgoing exemplary method induces nanoprecipitation and particle formation. Alternative processes including, but not limited to, T-junction and direct injection, may be used to achieve the same nanoprecipitation.

Vaccines of the present disclosure are typically formulated in lipid nanoparticles. In some embodiments, the lipid nanoparticle comprises at least one ionizable amino lipid, at least one non-cationic lipid, at least one sterol, and/or at least one polyethylene glycol (PEG)-modified lipid.

The lipid nanoparticles of the present disclosure are comprised of a mixture of lipids and the amounts are measured according to the mole faction or the mole percent of each lipid component in the lipid nanoparticle. Mole percent is obtained by multiplying the mole fraction by 100%. The mRNA and any water are not represented where the lipid mixture is accounted for numerically.

In some embodiments, the lipid nanoparticle comprises a mixture of lipids comprising 20-60 mol % ionizable amino lipid. For example, the lipid nanoparticle may comprise a mole percent of 20-50 mol %, 20-40 mol %, 20-30 mol %, 30-60 mol %, 30-50 mol %, 30-40 mol %, 40-60 mol %, 40-50 mol %, or 50-60 mol % ionizable amino lipid. In some embodiments, the lipid nanoparticle comprises 20 mol %, 30 mol %, 40 mol %, 50 mol %, or 60 mol % ionizable amino lipid.

The ionizable amino lipid may sometimes be referred to in the literature as a cationic lipid, but this document adopts the ionizable amino lipid nomenclature to reflect that the lipid in question is only cationic under certain pH conditions.

In some embodiments, the lipid nanoparticle comprises a mixture of lipids comprising 5-25 mol % non-cationic lipid. For example, the lipid nanoparticle may comprise a non-cationic lipid comprising 5-20 mol %, 5-15 mol %, 5-10 mol %, 10-25 mol %, 10-20 mol %, 10-25 mol %, 15-25 mol %, 15-20 mol %, or 20-25 mol % non-cationic lipid. In some embodiments, the lipid nanoparticle comprises a mixture of lipids comprising 5 mol %, 10 mol %, 15 mol %, 20 mol %, or 25 mol % non-cationic lipid.

In some embodiments, the lipid nanoparticle comprises a mixture of lipids comprising 25-55 mol % sterol. For example, the lipid nanoparticle may comprise a sterol comprising 25-50 mol %, 25-45 mol %, 25-40 mol %, 25-35 mol %, 25-30 mol %, 30-55 mol %, 30-50 mol %, 30-45 mol %, 30-40 mol %, 30-35 mol %, 35-55 mol %, 35-50 mol %, 35-45 mol %, 35-40 mol %, 40-55 mol %, 40-50 mol %, 40-45 mol %, 45-55 mol %, 45-50 mol %, or 50-55 mol % sterol. In some embodiments, the lipid nanoparticle comprises a mole percent of 25 mol %, 30 mol %, 35 mol %, 40 mol %, 45 mol %, 50 mol %, or 55 mol % sterol.

In some embodiments, the lipid nanoparticle comprises a mixture of lipids comprising 0.5-15 mol % PEG-modified lipid. For example, the lipid nanoparticle may comprise a mole percent of 0.5-10 mol %, 0.5-5 mol %, 1-15 mol %, 1-10 mol %, 1-5 mol %, 2-15 mol %, 2-10 mol %, 2-5 mol %, 5-15 mol %, 5-10 mol %, or 10-15 mol % PEG-modified lipid. In some embodiments, the lipid nanoparticle comprises a mole percent of 0.5 mol %, 1 mol %, 2 mol %, 3 mol %, 4 mol %, 5 mol %, 6 mol %, 7 mol %, 8 mol %, 9 mol %, 10 mol %, 11 mol %, 12 mol %, 13 mol %, 14 mol %, or 15 mol % PEG-modified lipid.

In some embodiments, the lipid nanoparticle comprises a molar ratio of 20-60% ionizable amino lipid, 5-25% non-cationic lipid, 25-55% sterol, and 0.5-15% PEG-modified lipid.

In some embodiments, the lipid nanoparticle comprises a mixture of lipids comprising 49 mol % ionizable amino lipid, 38.5 mol % cholesterol, 10 mol % DSPC, and 2.5 mol % DMG-PEG. In some embodiments, the lipid nanoparticle comprises a mixture of lipids comprising 48 mol % ionizable amino lipid, 38.5 mol % cholesterol, 11 mol % DSPC, and 2.5 mol % DMG-PEG. In some embodiments, the lipid nanoparticle comprises a mixture of lipids comprising 47 mol % ionizable amino lipid, 38.5 mol % cholesterol, 11.5 mol % DSPC, and 3 mol % DMG-PEG.

In some embodiments, an ionizable amino lipid of the disclosure comprises a compound having structure:

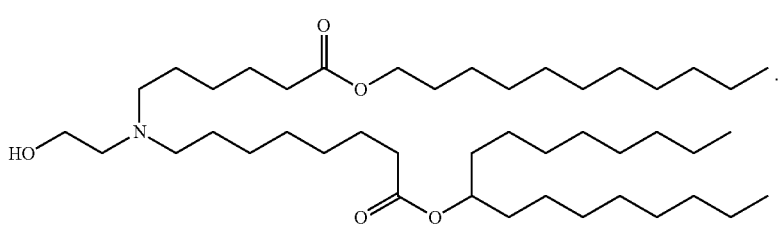

(Compound I)

In some embodiments, an ionizable amino lipid of the disclosure comprises a compound having structure:

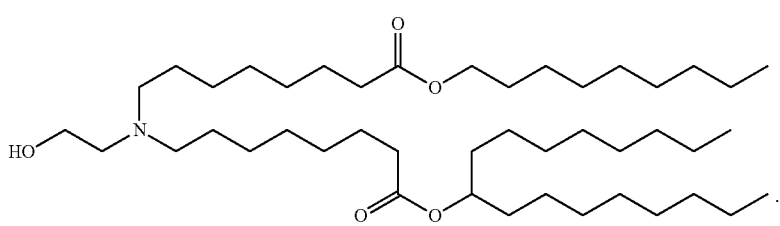

(Compound II)

In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine,1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is DMG-PEG, PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable amino lipid of Compound 1, wherein the non-cationic lipid is DSPC, the structural lipid is cholesterol, and the PEG lipid is DMG-PEG.

In some embodiments, the lipid nanoparticle comprises 45-55 mole percent ionizable amino lipid. For example, the lipid nanoparticle may comprise 45, 46, 47, 48, 49, 50, 51, 52, 53, 54, or 55 mole percent ionizable amino lipid.

In some embodiments, the lipid nanoparticle comprises 5-15 mole percent DSPC. For example, the lipid nanoparticle may comprise 5, 6, 7, 8, 9, 10, 11, 12, 13, 14, or 15 mole percent DSPC.

In some embodiments, the lipid nanoparticle comprises 35-40 mole percent cholesterol. For example, the lipid nanoparticle may comprise 35, 36, 37, 38, 39, or 40 mole percent cholesterol.

In some embodiments, the lipid nanoparticle comprises 1-2 mole percent DMG-PEG. For example, the lipid nanoparticle may comprise 1, 1.5, or 2 mole percent DMG-PEG.

In some embodiments, the lipid nanoparticle comprises 50 mole percent ionizable amino lipid, 10 mole percent DSPC, 38.5 mole percent cholesterol, and 1.5 mole percent DMG-PEG.

In some embodiments, a LNP of the disclosure comprises an N:P ratio of from about 2:1 to about 30:1.

In some embodiments, a LNP of the disclosure comprises an N:P ratio of about 6:1.

In some embodiments, a LNP of the disclosure comprises an N:P ratio of about 3:1.

In some embodiments, a LNP of the disclosure comprises a wt/wt ratio of the ionizable amino lipid component to the RNA of from about 10:1 to about 100:1.

In some embodiments, a LNP of the disclosure comprises a wt/wt ratio of the ionizable amino lipid component to the RNA of about 20:1.

In some embodiments, a LNP of the disclosure comprises a wt/wt ratio of the ionizable amino lipid component to the RNA of about 10:1.

In some embodiments, a LNP of the disclosure has a mean diameter from about 50 nm to about 150 nm.

In some embodiments, a LNP of the disclosure has a mean diameter from about 70 nm to about 120 nm.

Multivalent Vaccines

The hCMV immunogenic composition (e.g., mRNA vaccine), as provided herein, may include mRNA or multiple mRNAs encoding two or more antigens of the same or different hCMV species. In some embodiments, the hCMV immunogenic composition (e.g., mRNA vaccine) includes an RNA or multiple RNAs encoding two or more antigens. In some embodiments, the mRNA of a hCMV immunogenic composition (e.g., mRNA vaccine) may encode 1, 2, 3, 4, 5, 6, 7, 8, 9, 10, 11, 12, or more antigens.

In some embodiments, the hCMV immunogenic composition (e.g., mRNA vaccine) comprises at least one RNA encoding an hCMV gH, an hCMV gL, an hCMV UL128, an hCMV UL130, an hCMV UL131A, and an hCMV gB.

In some embodiments, two or more different RNAs (e.g., mRNAs) encoding antigens may be formulated in the same lipid nanoparticle. In other embodiments, two or more different RNAs encoding antigens may be formulated in separate lipid nanoparticles (e.g., each RNA formulated in a single lipid nanoparticle). The lipid nanoparticles may then be combined and administered as a single vaccine composition (e.g., comprising multiple RNA encoding multiple antigens) or may be administered separately.

Pharmaceutical Formulations

Provided herein are compositions (e.g., pharmaceutical compositions), methods, kits and reagents for prevention or treatment of hCMV in humans and other mammals, for example. hCMV immunogenic compositions (e.g., mRNA vaccines) can be used as therapeutic or prophylactic agents. They may be used in medicine to prevent and/or treat infectious disease.

In some embodiments, the hCMV immunogenic compositions (e.g., mRNA vaccines) containing mRNA as described herein can be administered to a subject (e.g., a mammalian subject, such as a human subject), and the RNA polynucleotides are translated in vivo to produce an antigenic polypeptide (antigen).

An "effective amount" of a hCMV immunogenic composition (e.g., mRNA vaccine) is based, at least in part, on the target tissue, target cell type, means of administration, physical characteristics of the RNA (e.g., length, nucleotide composition, and/or extent of modified nucleosides), other components of the vaccine, and other determinants, such as age, body weight, height, sex and general health of the subject. Typically, an effective amount of a hCMV immunogenic composition (e.g., mRNA vaccine) provides an induced or boosted immune response as a function of antigen production in the cells of the subject. In some embodiments, an effective amount of the hCMV immunogenic composition (e.g., mRNA vaccine) containing RNA polynucleotides having at least one chemical modifications are more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation and/or expression from the polynucleotide, decreased nucleic acid degradation (as demonstrated, for example, by increased duration of protein translation from a modified polynucleotide), or altered antigen specific immune response of the host cell.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, immunological compositions (e.g., RNA vaccines including polynucleotides and their encoded polypeptides) in accordance with the present disclosure may be used for treatment or prevention of hCMV infection. The hCMV immunogenic composition (e.g., mRNA vaccine) may be administered prophylactically or therapeutically as part of an active immunization scheme to healthy individuals or early in infection during the incubation phase or during active infection after onset of symptoms. In some embodiments, the amount of the hCMV immunogenic composition (e.g., mRNA vaccine) of the present disclosure provided to a cell, a tissue or a subject may be an amount effective for immune prophylaxis.

The hCMV immunogenic composition (e.g., mRNA vaccine) may be administered with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 4 months, 5 months, 6 months or 1 year. In some embodiments, more than one (e.g., 1, 2, 3, or more) boosters are administered. In some embodiments, two boosters are administered (e.g., one around the beginning of month 2 and one around the beginning of month 6) following the initial administration.

In some embodiments, the hCMV immunogenic composition (e.g., mRNA vaccine) may be administered intramuscularly (e.g., to deltoid muscle), intranasally or intradermally, similarly to the administration of inactivated vaccines known in the art.

The hCMV immunogenic composition (e.g., mRNA vaccine) may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers, better neutralizing immunity, produce more durable immune responses, and/or produce responses earlier than commercially available vaccines.

Provided herein are pharmaceutical compositions including the hCMV immunogenic composition (e.g., mRNA vaccine) and/or complexes optionally in combination with one or more pharmaceutically acceptable excipients.

The hCMV immunogenic composition (e.g., mRNA vaccine) may be formulated or administered alone or in conjunction with one or more other components. For instance, the hCMV immunogenic composition (e.g., mRNA vaccine) may comprise other components including, but not limited to, adjuvants.

In some embodiments, the hCMV immunogenic composition (e.g., mRNA vaccine) does not include an adjuvant (they are adjuvant free). In some embodiments, the hCMV immunogenic composition (e.g., mRNA vaccine) includes an adjuvant. Any known adjuvant suitable for use in vaccines may be used. In some embodiments, the hCMV immunogenic composition (e.g., mRNA vaccine) includes an MF59 adjuvant system (e.g., as described in O'Hagan et al., Expert Rev Vaccines. 2007 October; 6(5):699-710, incorporated herein by reference).

The hCMV immunogenic composition (e.g., mRNA vaccine) may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, the hCMV immunogenic compositions (e.g., mRNA vaccines) are administered to humans, such as human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigens.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, the hCMV immunogenic composition (e.g., mRNA vaccine) is formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with the hCMV immunogenic composition (e.g., mRNA vaccine) (e.g., for transplantation into a subject), hyaluronidase, nanoparticle mimics and combinations thereof.

In some embodiments, the hCMV immunogenic composition (e.g., mRNA vaccine) described herein is formulated in a LNP formulation and lyophilized. The lyophilized composition can be reconstituted with appropriate solution for administration. In some embodiments, the lyophilized composition is reconstituted a solution containing 0.9% sodium chloride. In some embodiments, the reconstituted composition is then diluted with tris sucrose Diluent SD-0724 to a concentration for delivery of an appropriate dose level in an appropriate volume (e.g., 0.5 mL).

Dosing/Administration

Provided herein are compositions (e.g., pharmaceutical compositions), methods, kits and reagents for prevention and/or treatment of hCMV infection in humans and other mammals. The hCMV immunogenic composition (e.g., mRNA vaccine) can be used as therapeutic or prophylactic agents. In some aspects, the hCMV immunogenic compositions (e.g., mRNA vaccines) of the disclosure are used to provide prophylactic protection from hCMV. In some aspects, the hCMV immunogenic compositions (e.g., mRNA vaccines) of the disclosure are used to treat a hCMV infection. In some embodiments, the hCMV immunogenic composition (e.g., mRNA vaccine) of the present disclosure is used in the priming of immune effector cells, for example, to activate peripheral blood mononuclear cells (PBMCs) ex vivo, which are then infused (re-infused) into a subject.

A subject may be any mammal, including non-human primate and human subjects. Typically, a subject is a human subject.

In some embodiments, the hCMV immunogenic composition (e.g., mRNA vaccine) is administered to a subject (e.g., a mammalian subject, such as a human subject) in an effective amount to induce an antigen-specific immune response. The RNA encoding the hCMV antigen is expressed and translated in vivo to produce the antigen, which then stimulates an immune response in the subject. The subject may be hCMV seropositive (e.g., has previously had a natural hCMV infection) or hCMV seronegative (e.g., has not previously had a natural hCMV infection) prior of being administered the hCMV mRNA vaccine.

Prophylactic protection from hCMV can be achieved following administration of the hCMV immunogenic composition (e.g., mRNA vaccine) of the present disclosure. Vaccines can be administered once, twice, three times, four times or more but it is likely sufficient to administer the vaccine once (optionally followed by one or more boosters). It is possible, although less desirable, to administer the vaccine to an infected individual to achieve a therapeutic response. Dosing may need to be adjusted accordingly.

A method of eliciting an immune response in a subject against hCMV is provided in aspects of the present disclosure. The method involves administering to the subject a hCMV immunogenic composition (e.g., mRNA vaccine) described herein, thereby inducing in the subject an immune response specific to a hCMV antigen (e.g., the hCMV gH, gL, UL128, UL130, UL131A and/or gB). In some embodiments, the immune response is the induction of neutralizing antibodies against a hCMV antigen (e.g., the hCMV gH, gL, UL128, UL130, UL131A and/or gB). In some embodiments, the anti-antigen antibody titer in the subject is increased following vaccination relative to anti-antigen antibody titer in a subject vaccinated with a prophylactically effective dose of a traditional vaccine against the hCMV. An "anti-antigen antibody" is a serum antibody the binds specifically to the antigen.

In some embodiments, a prophylactically effective dose is an effective dose that prevents infection with the virus at a clinically acceptable level. In some embodiments, the effective dose is a dose listed in a package insert for the vaccine. In some embodiments, an effective dose is sufficient to produce detectable levels of hCMV antigen (e.g., gH, gL, UL128, UL130, UL131A and/or gB polypeptide) as measured in serum of the subject administered the hCMV immunogenic composition (e.g., mRNA vaccine) at 1-72 hours (e.g., 1-72 hours, 1-60 hours, 1-45 hours, 1-30 hours, 1-15 hours, 15-72 hours, 15-60 hours, 15-45 hours, 15-30 hours, 30-72 hours, 30-60 hours, 30-45 hours, 45-72 hours, 45-60 hours, or 60-72 hours) post administration. In some embodiments, the effective dose is sufficient to produce neutralization titer produced by neutralizing antibody against the hCMV antigen (e.g., gH, gL, UL128, UL130, UL131A and/or gB polypeptide) as measured in serum of the subject administered the hCMV immunogenic composition (e.g., mRNA vaccine) at 1-72 hours (e.g., 1-72 hours, 1-60 hours, 1-45 hours, 1-30 hours, 1-15 hours, 15-72 hours, 15-60 hours, 15-45 hours, 15-30 hours, 30-72 hours, 30-60 hours, 30-45 hours, 45-72 hours, 45-60 hours, or 60-72 hours) post administration.

A traditional vaccine, as used herein, refers to a vaccine other than the mRNA vaccines of the present disclosure. For instance, a traditional vaccine includes, but is not limited, to live microorganism vaccines, killed microorganism vaccines, subunit vaccines, protein antigen vaccines, DNA vaccines, virus like particle (VLP) vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments, the anti-antigen antibody titer in the subject is increased 1 log to 10 log following vaccination relative to anti-antigen antibody titer in a subject vaccinated with a prophylactically effective dose of a traditional vaccine against the hCMV or an unvaccinated subject. In some embodiments, the anti-antigen antibody titer in the subject is increased 1 log, 2 log, 3 log, 4 log, 5 log, or 10 log following vaccination relative to anti-antigen antibody titer in a subject vaccinated with a prophylactically effective dose of a traditional vaccine against the hCMV or an unvaccinated subject.

A method of eliciting an immune response in a subject against hCMV is provided in other aspects of the disclosure. The method involves administering to the subject the hCMV immunogenic composition (e.g., mRNA vaccine) described herein, thereby inducing in the subject an immune response specific to hCMV antigen, wherein the immune response in the subject is equivalent to an immune response in a subject vaccinated with a traditional vaccine against the hCMV at 2 times to 100 times the dosage level relative to the RNA vaccine.

In some embodiments, the immune response in the subject is equivalent to an immune response in a subject vaccinated with a traditional vaccine at twice the dosage level relative to the hCMV immunogenic composition (e.g., mRNA vaccine). In some embodiments, the immune response in the subject is equivalent to an immune response in a subject vaccinated with a traditional vaccine at three times the dosage level relative to the hCMV immunogenic composition (e.g., mRNA vaccine). In some embodiments, the immune response in the subject is equivalent to an immune response in a subject vaccinated with a traditional vaccine at 4 times, 5 times, 10 times, 50 times, or 100 times the dosage level relative to the hCMV immunogenic composition (e.g., mRNA vaccine). In some embodiments, the immune response in the subject is equivalent to an immune response in a subject vaccinated with a traditional vaccine at 10 times to 1000 times the dosage level relative to the hCMV immunogenic composition (e.g., mRNA vaccine). In some embodiments, the immune response in the subject is equivalent to an immune response in a subject vaccinated with a traditional vaccine at 100 times to 1000 times the dosage level relative to the hCMV immunogenic composition (e.g., mRNA vaccine).

In other embodiments, the immune response is assessed by determining [protein] antibody titer in the subject. In other embodiments, the ability of serum or antibody from an immunized subject is tested for its ability to neutralize viral uptake or reduce hCMV transformation of human B lymphocytes. In other embodiments, the ability to promote a robust T cell response(s) is measured using art recognized techniques.

Other aspects the disclosure provide methods of eliciting an immune response in a subject against hCMV by administering to the subject the hCMV mRNA vaccine comprising at least one RNA polynucleotide having an open reading frame encoding at least one hCMV antigen, thereby inducing in the subject an immune response specific to hCMV antigen, wherein the immune response in the subject is induced 2 days to 10 weeks earlier relative to an immune response induced in a subject vaccinated with a prophylactically effective dose of a traditional vaccine against hCMV. In some embodiments, the immune response in the subject is induced in a subject vaccinated with a prophylactically effective dose of a traditional vaccine at 2 times to 100 times the dosage level relative to the RNA vaccine.

In some embodiments, the immune response in the subject is induced 2 days, 3 days, 1 week, 2 weeks, 3 weeks, 5 weeks, or 10 weeks earlier relative to an immune response induced in a subject vaccinated with a prophylactically effective dose of a traditional vaccine.

The hCMV immunogenic composition (e.g., mRNA vaccine) may be administered by any route which results in a therapeutically effective outcome. These include, but are not limited, to intradermal, intramuscular, intranasal, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. The hCMV immunogenic composition (e.g., mRNA vaccine) is typically formulated in dosage unit form for ease of administration and uniformity of dosage. It will be understood, however, that the total daily usage of the hCMV immunogenic composition (e.g., mRNA vaccine) may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, the hCMV immunogenic composition (e.g., mRNA vaccine) is administered at a dose of about 1 µg, 2 µg, 3 µg, 4 µg, 5 µg, 6 µg, 7 µg, 8 µg, 9 µg, 10 µg, 11 µg, 12 µg, 13 µg, 14 µg, 15 µg, 16 µg, 17 µg, 18 µg, 19 µg, 20 µg, 21 µg, 22 µg, 23 µg, 24 µg 25 µg, 26 µg, 27 µg, 28 µg, 29 µg, 30 µg, 31 µg, 32 µg, 33 µg, 34 µg, 35 µg, 36 µg, 37 µg, 38 µg, 39 µg, 40 µg, 41 µg, 42 µg, 43 µg, 44 µg, 45 µg, 46 µg, 47 µg, 48 µg, 49 µg, 50 µg, 51 µg, 52 µg, 53 µg, 54 µg, 55 µg, 56 µg, 57 µg, 58 µg, 59 µg, 60 µg, 61 µg, 62 µg, 63 µg, 64 µg, 65 µg, 66 µg, 67 µg, 68 µg, 69 µg, 70 µg, 71 µg, 72 µg, 73 µg, 74 µg, 75 µg, 76 µg, 77 µg, 78 µg, 79 µg, 80 µg, 81 µg, 82 µg, 83 µg, 84 µg, 85 µg, 86 µg, 87 µg, 88 µg, 89 µg, 90 µg, 95 µg, 100 µg, 110 µg, 120 pig, 130 µg, 140 µg, 150 µg, 160 µg, 170 µg, 180 µg, 190 µg, 200 µg, 250 µg, 300 µg, 350 µg, 400 µg, 450 µg, or 500 µg, including all values in between.

As used herein, the dose of the hCMV immunogenic composition (e.g., mRNA vaccine) of the present disclosure refers to total µg mRNA in a formulation of lipid nanoparticles. As used herein, "Total µg mRNA" refers to total dose, or the nominal dose, for a single administration with the understanding that RNA impurities, degraded mRNA, and otherwise inactive mRNA are still counted in the total. The weight of the lipid components is not included when referring to dose in the present disclosure.

In some embodiments, the hCMV immunogenic composition (e.g., mRNA vaccine) is administered at a dose of about 50-150 µg. In some embodiments, only one dose is administered, while in other embodiments, multiple doses (e.g., one, two, or three doses) are administered. In embodiments wherein multiple doses are administered, the dose between the first dose and a subsequent dose can be the same or different. In some embodiments, the effective amount of the hCMV immunogenic composition (e.g., mRNA vaccine including mRNAs encoding gH/gL/UL128/UL130/UL131A/gB), as provided herein, may be as low as 150 µg, administered for example as a single dose.

In some embodiments, the effective amount of hCMV immunogenic composition (e.g., mRNA vaccine) is a single dose of 50-150 µg. For example, the effective amount of hCMV immunogenic composition (e.g., mRNA vaccine) may be a single dose of 50 µg, 51 µg, 52 µg, 53 µg, 54 µg, 55 µg, 56 µg, 57 µg, 58 µg, 59 µg, 60 µg, 61 µg, 62 µg, 63 µg, 64 µg, 65 µg, 66 µg, 67 µg, 68 µg, 69 µg, 70 µg, 71 µg, 72 µg, 73 µg, 74 µg, 75 µg, 76 µg, 77 µg, 78 µg, 79 µg, 80 µg, 81 µg, 82 µg, 83 µg, 84 µg, 85 µg, 86 µg, 87 µg, 88 µg, 89 µg, 90 µg, 95 µg, 100 µg, 110 µg, 120 µg, 130 µg, 140 µg, or 150 µg, including all values in between. In some embodiments, the effective amount of the hCMV immunogenic composition (e.g., mRNA vaccine) is a single dose of 50 µg. In some embodiments, the effective amount of the hCMV immunogenic composition (e.g., mRNA vaccine) is a single dose of 100 µg. In some embodiments, the effective amount of the hCMV immunogenic composition (e.g., mRNA vaccine) is a single dose of 150 µg.

In some embodiments, the effective amount of the hCMV immunogenic composition (e.g., mRNA vaccine) is either 50 µg, 100 µg or 150 µg. In some embodiments, the effective dose is administered as a primary immunization followed by a single boost of the same effective dose. In some embodiments, the effective dose is administered as a primary immunization followed by two sequential booster immunizations of the same effective dose. In some embodiments, the effective dose is 50 µg of hCMV immunogenic composition (e.g., mRNA vaccine) and is administered as a primary immunization of 50 µg followed by two sequential booster immunizations of 50 µg. In some embodiments, the effective dose is 100 µg hCMV immunogenic composition (e.g., mRNA vaccine) and is administered as a primary immunization of 100 µg followed by two sequential booster immunizations of 100 µg. In some embodiments, the effective dose is 150 µg of hCMV immunogenic composition (e.g., mRNA vaccine) and is administered as a primary immunization of 150 µg followed by two sequential booster immunizations of 150 µg. In some embodiments, the booster immunizations should be at least two weeks apart.

In some embodiments, the effective amount of hCMV immunogenic composition (e.g., mRNA vaccine) is two doses of 50-150 µg. For example, the effective amount of hCMV immunogenic composition (e.g., mRNA vaccine) may be two doses of 50 µg, 51 µg, 52 µg, 53 µg, 54 µg, 55 µg, 56 µg, 57 µg, 58 µg, 59 µg, 60 µg, 61 µg, 62 µg, 63 µg, 64 µg, 65 µg, 66 µg, 67 µg, 68 µg, 69 µg, 70 µg, 71 µg, 72 µg, 73 µg, 74 µg, 75 µg, 76 µg, 77 µg, 78 µg, 79 µg, 80 µg, 81 µg, 82 µg, 83 µg, 84 µg, 85 µg, 86 µg, 87 µg, 88 µg, 89 µg, 90 µg, 95 µg, 100 µg, 110 µg, 120 µg, 130 µg, 140 µg, or 150 µg, including all values in between. In some embodiments, the effective amount of the hCMV immunogenic composition (e.g., mRNA vaccine) is two doses of 50 µg. In some embodiments, the effective amount of the hCMV immunogenic composition (e.g., mRNA vaccine) is two doses of 100 µg. In some embodiments, the effective amount of the hCMV immunogenic composition (e.g., mRNA vaccine) is two doses of 150 µg.

In some embodiments, the effective amount of hCMV immunogenic composition (e.g., mRNA vaccine) is three doses of 50-150 µg. For example, the effective amount of hCMV immunogenic composition (e.g., mRNA vaccine) may be three doses of 50 µg, 51 µg, 52 µg, 53 µg, 54 µg, 55 µg, 56 µg, 57 µg, 58 µg, 59 µg, 60 µg, 61 µg, 62 µg, 63 µg, 64 µg, 65 µg, 66 µg, 67 µg, 68 µg, 69 µg, 70 µg, 71 µg, 72 µg, 73 µg, 74 µg, 75 µg, 76 µg, 77 µg, 78 µg, 79 µg, 80 µg, 81 µg, 82 µg, 83 µg, 84 µg, 85 µg, 86 µg, 87 µg, 88 µg, 89 µg, 90 µg, 95 µg, 100 µg, 110 µg, 120 µg, 130 µg, 140 µg, or 150 µg, including all values in between. In some embodiments, the effective amount of the hCMV immunogenic composition (e.g., mRNA vaccine) is three doses of 50 µg. In some embodiments, the effective amount of the hCMV immunogenic composition (e.g., mRNA vaccine) is three doses of 100 µg. In some embodiments, the effective amount of the hCMV immunogenic composition (e.g., mRNA vaccine) is three doses of 150 µg.

In some embodiments, the effective amount of the hCMV immunogenic composition (e.g., mRNA vaccine) is more than 3 (e.g., 4, 5 or more) doses of 50 µg-150 µg. In some embodiments, the effective amount of the hCMV immunogenic composition (e.g., mRNA vaccine) is more than 3 (e.g., 4, 5 or more) doses of 50 µg. In some embodiments, the effective amount of the hCMV immunogenic composition (e.g., mRNA vaccine) is more than 3 (e.g., 4, 5 or more) doses of 100 µg. In some embodiments, the effective amount of the hCMV immunogenic composition (e.g., mRNA vaccine) is more than 3 (e.g., 4, 5 or more) doses of 150 µg.

In some embodiments, the effective amount of the hCMV immunogenic composition (e.g., mRNA vaccine) relates to the amount of integral mRNA in the composition. As used herein, "integral mRNA" refers to intact mRNA transcripts that are capable of producing hCMV antigens and/or inducing an immune response against an antigen in a subject. The amount of integral mRNA in a hCMV immunogenic composition (e.g., mRNA vaccine) is related to the length, rate of degradation, and the length of time from which the immunogenic composition is produced. When the effective amount is determined from clinical results, that dose can be referred to in terms of the total mRNA present (i.e. the total dose) or in terms of the integral mRNA present in the hCMV immunogenic composition (e.g., mRNA vaccine).

In some embodiments, the effective amount of the hCMV immunogenic composition (e.g., mRNA vaccine) is a single dose of 5-35 pmol (e.g., 5-35, 5-30, 5-25, 5-20, 5-15, 5-10, 10-35, 10-30, 10-25, 10-20, 10-15, 15-35, 15-30, 15-25, 15-20, 20-35, 20-30, 20-25, 25-35, 25-30, or 30-35 pmol) pentamer components and 4-50 pmol (e.g., 4-50, 10-50, 10-40, 10-30, 10-20, 20-50, 20-40, 20-30, 30-50, 30-40, or 40-50 pmol) gB mRNA. In some embodiments, the effective amount of the hCMV immunogenic composition (e.g., mRNA vaccine) is a single dose of 10-30 pmol (e.g., 10-30, 10-20, or 20-30 pmol) pentamer components and 15-45 pmol (e.g., 15-45, 15-30, or 30-45 pmol) gB mRNA. In some embodiments, the effective amount of the hCMV immunogenic composition (e.g., mRNA vaccine) is a single dose of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 pmol (including all values in between) pentamer components and 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 pmol (including all values in between) gB mRNA.

In certain embodiments, an effective amount or dose of the hCMV immunogenic composition (e.g. mRNA vaccine) does not require that the pmoles of each component are equal. For example, larger picomolar doses of the mRNAs encoding the integral transmembrane domain containing components such as gH and gB may be required to ensure that these components do not become limiting. In addition, in some embodiments the picomolar dose of each of the 6 mRNA may be individually determined because of stability or other biochemical or biophysical requirements.

In some embodiments, the effective amount of the hCMV immunogenic composition (e.g., mRNA vaccine) is two doses of 5-35 pmol (e.g., 5-35, 5-30, 5-25, 5-20, 5-15, 5-10, 10-35, 10-30, 10-25, 10-20, 10-15, 15-35, 15-30, 15-25, 15-20, 20-35, 20-30, 20-25, 25-35, 25-30, or 30-35 pmol) pentamer components and 4-50 pmol (e.g., 4-50, 10-50, 10-40, 10-30, 10-20, 20-50, 20-40, 20-30, 30-50, 30-40, or 40-50 pmol) gB mRNA. In some embodiments, the effective amount of the hCMV immunogenic composition (e.g., mRNA vaccine) is two doses of 10-30 pmol (e.g., 10-30, 10-20, or 20-30 pmol) pentamer components and 15-45 pmol (e.g., 15-45, 15-30, or 30-45 pmol) integral gB mRNA. In some embodiments, the effective amount of the hCMV immunogenic composition (e.g., mRNA vaccine) is two doses of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 pmol (including all values in between) pentamer components and 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 pmol (including all values in between) gB mRNA.

In some embodiments, the effective amount of the hCMV immunogenic composition (e.g., mRNA vaccine) is three doses of 5-35 pmol (e.g., 5-35, 5-30, 5-25, 5-20, 5-15, 5-10, 10-35, 10-30, 10-25, 10-20, 10-15, 15-35, 15-30, 15-25, 15-20, 20-35, 20-30, 20-25, 25-35, 25-30, or 30-35 pmol) pentamer components and 4-50 pmol (e.g., 4-50, 10-50, 10-40, 10-30, 10-20, 20-50, 20-40, 20-30, 30-50, 30-40, or 40-50 pmol) integral gB mRNA. In some embodiments, the effective amount of the hCMV immunogenic composition (e.g., mRNA vaccine) is three doses of 10-30 pmol (e.g., 10-30, 10-20, or 20-30 pmol) pentamer components and 15-45 pmol (e.g., 15-45, 15-30, or 30-45 pmol) integral gB mRNA. In some embodiments, the effective amount of the hCMV immunogenic composition (e.g., mRNA vaccine) is three doses of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 pmol (including all values in between) pentamer components and 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 pmol (including all values in between) integral gB mRNA.

In some embodiments, the effective amount of the hCMV immunogenic composition (e.g., mRNA vaccine) is more than three (e.g., 4, 5, or more) doses of 5-35 pmol (e.g., 5-35, 5-30, 5-25, 5-20, 5-15, 5-10, 10-35, 10-30, 10-25, 10-20, 10-15, 15-35, 15-30, 15-25, 15-20, 20-35, 20-30, 20-25, 25-35, 25-30, or 30-35 pmol) pentamer components and 4-50 pmol (e.g., 4-50, 10-50, 10-40, 10-30, 10-20, 20-50, 20-40, 20-30, 30-50, 30-40, or 40-50 pmol) of integral gB mRNA. In some embodiments, the effective amount of the hCMV immunogenic composition (e.g., mRNA vaccine) is more than three (e.g., 4, 5, or more) doses of 10-30 pmol (e.g., 10-30, 10-20, or 20-30 pmol) pentamer components and 15-45 pmol (e.g., 15-45, 15-30, or 30-45 pmol) integral gB mRNA. In some embodiments, the effective amount of the hCMV immunogenic composition (e.g., mRNA vaccine) is more than three (e.g., 4, 5, or more) doses of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 pmol (including all values in between) pentamer components and 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 pmol (including all values in between) integral gB mRNA.

In some embodiments, in certain of the integral mRNA doses described herein, the hCMV immunogenic composition (e.g., mRNA vaccine) contains mRNAs at a gB:gH:gL:UL128:UL130:UL131A molar ratio of 2:2:1:1:1:1.

In some embodiments, one, two, three, or more than three doses (of any of the doses described herein) of the hCMV immunogenic composition (e.g., mRNA vaccine) are administered to a subject. In some embodiments, one, two, or three doses (of any of the doses described herein) of the hCMV immunogenic composition (e.g., mRNA vaccine) are administered to a subject. In some embodiments, the doses are administered on day 1, around the beginning of month 2 (e.g., day 29), and around the beginning of month 6 (e.g., day 169).

In some embodiments, a dose of hCMV immunogenic composition (e.g., mRNA vaccine) is administered to a subject on day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 53, day 54, day 55, day 56, day 57, day 58, day 59, day 60, day 61, day 62, day 63, day 64, day 65, day 66, day 67, day 68, day 69, day 70, day 71, day 72, day 73, day 74, day 75, day 76, day 77, day 78, day 79, day 80, day 81, day 82, day 83, day 84, day 85, day 86, day 87, day 88, day 89, day 90, day 91, day 92, day 93, day 94, day 95, day 96, day 97, day 98, day 99, day 100, day 101, day 102, day 103, day 104, day 105, day 106, day 107, day 108, day 109, day 110, day 111, day 112, day 113, day 114, day 115, day 116, day 117, day 118, day 119, day 120, day 121, day 122, day 123, day 124, day 125, day 126, day 127, day 128, day 129, day 130, day 131, day 132, day 133, day 134, day 135, day 136, day 137, day 138, day 139, day 140, day 141, day 142, day 143, day 144, day 145, day 146, day 147, day 148, day 149, day 150, day 151, day 152, day 153, day 154, day 155, day 156, day 157, day 158, day 159, day 160, day 161, day 162, day 163, day 164, day 165, day 166, day 167, day 168, day 169, day 170, day 171, day 172, day 173, day 174, day 175, day 176, day 177, day 178, day 179, day 180, day 181, day 182, day 183, day 184, day 185, day 186, day 187, day 188, day 189, day 190, day 191, day 192, day 193, day 194, day 195, day 196, day 197, day 198, day 199.

In some embodiments, a dose of hCMV immunogenic composition (e.g., mRNA vaccine) is administered to a subject after day 199.

The hCMV mRNA vaccines described herein can be formulated into a dosage form described herein or known in the art, such as an intranasal, intratracheal, or injectable (e.g., intravenous, intraocular, intravitreal, intramuscular, intradermal, intracardiac, intraperitoneal, and subcutaneous).

Vaccine Efficacy

Some aspects of the present disclosure provide formulations of the hCMV mRNA vaccine, wherein the hCMV mRNA vaccine is formulated in an effective amount to produce an antigen specific immune response in a subject (e.g., production of antibodies specific to an anti-hCMV antigen). "An effective amount" is a dose of the hCMV mRNA vaccine effective to produce an antigen-specific immune response. Also provided herein are methods of inducing an antigen-specific immune response in a subject.

As used herein, an immune response to a vaccine or LNP of the present disclosure is the development in a subject of a humoral and/or a cellular immune response to a (one or more) hCMV protein(s) present in the vaccine. For purposes of the present disclosure, a "humoral" immune response refers to an immune response mediated by antibody molecules, including, e.g., secretory (IgA) or IgG molecules, while a "cellular" immune response is one mediated by T-lymphocytes (e.g., CD4+ helper and/or CD8+ T cells (e.g., CTLs) and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves and antigen-specific response by helper T-cells. Helper T-cells act to help stimulate the function, and focus the activity nonspecific effector cells against cells displaying peptide antigens in association with MHC molecules on their surface. A cellular immune response also leads to the production of cytokines, chemokines, and other such molecules produced by activated T-cells and/or other white blood cells including those derived from CD4+ and CD8+ T-cells.

In some embodiments, the antigen-specific immune response is characterized by measuring an anti-hCMV antigen antibody titer produced in a subject administered the hCMV mRNA vaccine as provided herein. An antibody titer is a measurement of the amount of antibodies within a subject, for example, antibodies that are specific to a particular antigen (e.g., an anti-hCMV antigen) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the hCMV mRNA vaccine.

In some embodiments, an anti-hCMV antigen antibody titer produced in a subject is increased by at least 1 log relative to a control. For example, anti-hCMV antigen antibody titer produced in a subject may be increased by at least 1.5, at least 2, at least 2.5, at least 3 log, at least 4 log, or at least 5 log, or more, relative to a control. In some embodiments, the anti-hCMV antigen antibody titer produced in the subject is increased by 1, 1.5, 2, 2.5, 3, 3.5, 4, 4.5, or 5 log relative to a control. In some embodiments, the anti-hCMV antigen antibody titer produced in the subject is increased by 1-5 log relative to a control. For example, the anti-hCMV antigen antibody titer produced in a subject may be increased by 1-1.5, 1-2, 1-2.5, 1-3, 1-4, 1-5, 1.5-2, 1.5-2.5, 1.5-3, 1.5-4, 1.5-5, 2-2.5, 2-3, 2-4, 2-5, 2.5-3, 2.5-4, 2.5-5, 3-4, 3-5, or 4-5 log relative to a control.

In some embodiments, the anti-hCMV antigen antibody titer produced in a subject is increased at least 2 times relative to a control. For example, the anti-hCMV antigen antibody titer produced in a subject may be increased at least 3 times, at least 4 times, at least 5 times, at least 6 times, at least 7 times, at least 8 times, at least 9 times, or at least 10 times relative to a control. In some embodiments, the anti-hCMV antigen antibody titer produced in the subject is increased 2, 3, 4, 5, 6, 7, 8, 9, or 10 times relative to a control. In some embodiments, the anti-hCMV antigen antibody titer produced in a subject is increased 2-10 times relative to a control. For example, the anti-hCMV antigen antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

In some embodiments, an antigen-specific immune response is measured as a ratio of geometric mean titer (GMT), referred to as a geometric mean ratio (GMR), of serum neutralizing antibody titers to hCMV. A geometric mean titer (GMT) is the average antibody titer for a group of subjects calculated by multiplying all values and taking the nth root of the number, where n is the number of subjects with available data.

In some embodiments, administration of an effective amount of the hCMV immunogenic composition (e.g., mRNA vaccine) elicits serum neutralizing antibody titers against hCMV. In some embodiments, administration a single dose (e.g., any of the doses described herein), or multiple doses, of the hCMV immunogenic composition (e.g., mRNA vaccine) elicits serum neutralizing antibody titers against hCMV.

In some embodiments, an effective amount of the hCMV immunogenic composition (e.g., mRNA vaccine) described herein is sufficient to produce geometric mean titer (GMT) of serum neutralizing anti-CMV antibodies against epithelial cell hCMV infection on day 1, day 29, day 56, day 84, day 168, or day 196 after immunization, and associated GMR of post-baseline/baseline titers. In some embodiments, an effective amount of the hCMV immunogenic composition (e.g., mRNA vaccine) described herein is sufficient to produce serum neutralizing antibody titers against fibroblast hCMV infection on day 1, day 29, day 56, day 84, day 168, or day 196 after immunization, and GMR of post-baseline/baseline titers.

In some embodiments, the GMT of serum neutralizing antibodies to hCMV increases in the subject administered the hCMV immunogenic composition (e.g., mRNA vaccine) by at least 2-fold (e.g., at least 2-fold, at least 3-fold, at least 4-fold), relative to baseline. In some embodiments, the GMT of serum neutralizing antibodies to hCMV increases in the subject by 2-fold to 10-fold after administering a single dose (e.g., a single dose of ≥50 μg, such as 50 μg, 100 g, or 150 μg) of the hCMV immunogenic composition (e.g., mRNA vaccine), relative to baseline. In some embodiments, the GMT of serum neutralizing antibodies to hCMV increases in the subject by 2-fold to 10-fold after administering two doses (e.g., two doses of ≥50 μg, such as 50 μg, 100 μg, or 150 μg) of the hCMV immunogenic composition (e.g., mRNA vaccine), relative to baseline. In some embodiments, the GMT of serum neutralizing antibodies to hCMV increases in the subject by 2-fold to 10-fold after administering three doses (e.g., three doses of 250 μg, such as 50 μg, 100 μg, or 150 μg) of the hCMV immunogenic composition (e.g., mRNA vaccine), relative to baseline.

In some embodiments, neutralizing antibody (nAb) GMTs against epithelial cell infection are increased at least 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, or 51-fold over baseline GMTs at a timepoint after administration of an hCMV immunogenic composition. In some embodiments, the timepoint is after administration of two doses of the immunogenic composition. In some embodiments, the timepoint is after administration of three doses of the immunogenic composition.

In some embodiments, the proportion of human subjects with ≥2 fold, ≥3-fold, ≥4-fold, ≥5-fold, ≥6-fold, ≥7-fold, ≥8-fold, ≥9-fold, ≥10-fold, ≥11-fold, ≥12-fold, or ≥13-fold increases in nAb over baseline against epithelial cell infection is at least 50%, at least 60%, at least 70% at least 80%, or at least 90% at a time point after administration of the hCMV immunogenic composition.

In some embodiments, administration of an effective amount of the hCMV immunogenic composition (e.g., mRNA vaccine) elicits serum neutralizing antibody titers against hCMV gB protein. In some embodiments, administration a single dose (e.g., any of the doses described herein), or multiple doses, of the hCMV immunogenic composition (e.g., mRNA vaccine) elicits serum neutralizing antibody titers against hCMV gB protein.

In some embodiments, the GMT of serum neutralizing antibodies to hCMV gB protein increases in the subject administered the hCMV immunogenic composition (e.g., mRNA vaccine) by at least 2-fold (e.g., at least 2-fold, at least 3-fold, at least 4-fold), relative to baseline. In some embodiments, the GMT of serum neutralizing antibodies to hCMV gB protein increases in the subject by 2-fold to 10-fold after administering a single dose (e.g., a single dose of ≥50 μg, such as 50 μg, 100 μg, or 150 μg) of the hCMV immunogenic composition (e.g., mRNA vaccine), relative to baseline. In some embodiments, the GMT of serum neutralizing antibodies to hCMV gB protein increases in the subject by 2-fold to 10-fold after administering two doses (e.g., two doses of ≥50 μg, such as 50 μg, 100 μg, or 150 μg) of the hCMV immunogenic composition (e.g., mRNA vaccine), relative to baseline. In some embodiments, the GMT of serum neutralizing antibodies to hCMV gB protein increases in the subject by 2-fold to 10-fold after administering three doses (e.g., three doses of ≥50 μg, such as 50 μg, 100 μg, or 150 μg) of the hCMV immunogenic composition (e.g., mRNA vaccine), relative to baseline.

In some embodiments, the proportion of human subjects with ≥2-fold increase in nAb over baseline against fibroblast infection is at least 50%, at least 60%, at least 70% at least 80%, or at least 90% at a time point after administration of the hCMV immunogenic composition.

In some embodiments, administration of an effective amount of the hCMV immunogenic composition (e.g., mRNA vaccine) elicits antigen-specific T-cell response against hCMV. In some embodiments, administration a single dose (e.g., any of the doses described herein), or multiple doses, of the hCMV immunogenic composition (e.g., mRNA vaccine) elicits antigen-specific T-cell response against hCMV. In some embodiments, administration of an effective amount of the hCMV immunogenic composition (e.g., mRNA vaccine) elicits antigen-specific T-cell response against hCMV gB protein. In some embodiments, administration a single dose (e.g., any of the doses described herein), or multiple doses, of the hCMV immunogenic composition (e.g., mRNA vaccine) elicits antigen-specific T-cell response against hCMV gB protein. In some embodiments, administration of an effective amount of the hCMV immunogenic composition (e.g., mRNA vaccine) elicits antigen-specific T-cell response against hCMV pentamer. In some embodiments, administration a single dose (e.g., any of the doses described herein), or multiple doses, of the hCMV immunogenic composition (e.g., mRNA vaccine) elicits antigen-specific T-cell response against hCMV pentamer. In some embodiments, the T-cell response (e.g., against hCMV, hCMV gB protein, or hCMV pentamer) comprises interferon-γ (IFN-γ) secretion.

A control/baseline, in some embodiments, is the anti-hCMV antigen antibody titer produced in a subject who has not been administered the hCMV mRNA vaccine. In some embodiments, a control/baseline is an anti-hCMV antigen antibody titer produced in a subject who has a natural hCMV infection, i.e., a subject who is hCMV seropositive prior to being administered the hCMV mRNA vaccine. In some embodiments, a control/baseline is an anti-hCMV antigen antibody titer produced in a subject who is hCMV seronegative prior to being administered the hCMV mRNA vaccine. In some embodiments, the GMT of serum neutralizing antibodies to hCMV increases in a dose-dependent manner.

In some embodiments, the GMT of binding antibody response to hCMV pentamer (anti-pentamer antibody titer) increases in the subject administered the hCMV immunogenic composition (e.g., mRNA vaccine) by at least 2-fold (e.g., at least 2-fold, at least 3-fold, at least 4-fold), relative to baseline. In some embodiments, the GMT of binding antibody response to hCMV pentamer increases in the subject by 2-fold to 10-fold after administering a single dose (e.g., a single dose of 250 gg, such as 50 µg, 100 gg, or 150 µg) of the hCMV immunogenic composition (e.g., mRNA vaccine), relative to baseline. In some embodiments, the GMT of binding antibody response to hCMV pentamer increases in the subject by 2-fold to 10-fold after administering two doses (e.g., two doses of 250 gg, such as 50 µg, 100 µg, or 150 µg) of the hCMV immunogenic composition (e.g., mRNA vaccine), relative to baseline. In some embodiments, the GMT of binding antibody response to hCMV increases in the subject by 2-fold to 10-fold after administering three doses (e.g., three doses of ≥50 µg, such as 50 µg, 100 µg, or 150 µg) of the hCMV immunogenic composition (e.g., mRNA vaccine), relative to baseline.

In some embodiments, anti-pentamer binding antibody (bAb) GMTs are increased at least 2-fold, 3-fold, 4-fold, 5-fold, 6-fold, 7-fold, 8-fold, 9-fold, or 10-fold over baseline GMTs at a timepoint after administration of an hCMV immunogenic composition. In some embodiments, the timepoint is after administration of two doses of the immunogenic composition. In some embodiments, the timepoint is after administration of three doses of the immunogenic composition.

In some embodiments, the proportion of human subjects with ≥2-fold, ≥3-fold, ≥4-fold, ≥5-fold, ≥6-fold, ≥7-fold, ≥8-fold, ≥9-fold, or ≥10-fold increases in anti-pentamer binding antibody (bAb) over baseline is at least 50%, at least 60%, at least 70% at least 80%, or at least 90% at one time point after administration of the hCMV immunogenic composition.

In some embodiments, the GMT of binding antibody response to gB increases in the subject administered the hCMV immunogenic composition (e.g., mRNA vaccine) by at least 2-fold (e.g., at least 2-fold, at least 3-fold, at least 4-fold), relative to baseline. In some embodiments, the GMT of binding antibody response to anti-gB increases in the subject by 2-fold to 10-fold after administering a single dose (e.g., a single dose of ≥50 µg, such as 50 µg, 100 µg, or 150 µg) of the hCMV immunogenic composition (e.g., mRNA vaccine), relative to baseline. In some embodiments, the GMT of binding antibody response to anti-gB increases in the subject by 2-fold to 10-fold after administering two doses (e.g., two doses of ≥50 µg, such as 50 µg, 100 µg, or 150 µg) of the hCMV immunogenic composition (e.g., mRNA vaccine), relative to baseline. In some embodiments, the GMT of binding antibody response to anti-gB increases in the subject by 2-fold to 10-fold after administering three doses (e.g., three doses of ≥50 µg, such as 50 µg, 100 µg, or 150 µg) of the hCMV immunogenic composition (e.g., mRNA vaccine), relative to baseline.

In some embodiments, anti-gB binding antibody (Ab) GMTs are increased at least 2-fold, 3-fold, 4-fold, 5-fold, 6-fold, 7-fold, 8-fold, 9-fold, or 10-fold over baseline GMTs at a timepoint after administration of an hCMV immunogenic composition. In some embodiments, the timepoint is after administration of a single dose of the immunogenic composition. In some embodiments, the timepoint is after administration of two doses of the immunogenic composition. In some embodiments, the timepoint is after administration of three doses of the immunogenic composition. In some embodiments the GMT response reaches a maximum within about 10 days to 2 weeks after a dose is administered.

In some embodiments, the proportion of human subjects with ≥2-fold increase in anti-gB binding antibody (Ab) over baseline is at least 50%, at least 60%, at least 70% at least 80%, or at least 90% at one time point after administration of the hCMV immunogenic composition.

In some embodiments, the ability of the hCMV mRNA vaccine to be effective is measured in a murine model. For example, the hCMV mRNA vaccine may be administered to a murine model and the murine model assayed for induction of neutralizing antibody titers. Viral challenge studies may also be used to assess the efficacy of a vaccine of the present disclosure. For example, the hCMV mRNA vaccine may be administered to a murine model, the murine model challenged with hCMV, and the murine model assayed for survival and/or immune response (e.g., neutralizing antibody response, T cell response (e.g., cytokine response)).

In some embodiments, an effective amount of the hCMV mRNA vaccine is a dose that is reduced compared to the standard of care dose of a recombinant hCMV protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified hCMV protein vaccine, or a live attenuated or inactivated hCMV mRNA vaccine, or a hCMV VLP vaccine, that a physician/clinician or other medical professional would administer to a subject to treat or prevent hCMV, or a hCMV-related condition, while following the standard of care guideline for treating or preventing hCMV, or a hCMV-related condition.

In some embodiments, the anti-hCMV antigen antibody titer produced in a subject administered an effective amount of the hCMV mRNA vaccine is equivalent to an anti-hCMV antigen antibody titer produced in a control subject administered a standard of care dose of a recombinant or purified hCMV protein vaccine, or a live attenuated or inactivated hCMV mRNA vaccine, or a hCMV VLP vaccine.

Vaccine efficacy may be assessed using standard analyses (see, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

Efficacy=(ARU−ARV)/ARU×100; and

Efficacy=(1−RR)×100.

Likewise, vaccine effectiveness may be assessed using standard analyses (see, e.g., Weinberg et al., J Infect Dis. 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

Effectiveness=(1−OR)×100.

In some embodiments, efficacy of the hCMV mRNA vaccine is at least 60% relative to unvaccinated control subjects. For example, efficacy of the hCMV mRNA vaccine may be at least 65%, at least 70%, at least 75%, at least 80%, at least 85%, at least 95%, at least 98%, or 100% relative to unvaccinated control subjects.

Sterilizing Immunity. Sterilizing immunity refers to a unique immune status that prevents effective pathogen infection into the host. In some embodiments, the effective amount of an hCMV mRNA vaccine of the present disclosure is sufficient to provide sterilizing immunity in the subject for at least 1 year. For example, the effective amount of the hCMV mRNA vaccine of the present disclosure may be sufficient to provide sterilizing immunity in the subject for at least 2 years, at least 3 years, at least 4 years, or at least 5 years. In some embodiments, the effective amount of the hCMV mRNA vaccine of the present disclosure is sufficient to provide sterilizing immunity in the subject at an at least 5-fold lower dose relative to control. For example, the effective amount may be sufficient to provide sterilizing immunity in the subject at an at least 10-fold lower, 15-fold, or 20-fold lower dose relative to a control.

Detectable Antigen. In some embodiments, the effective amount of the hCMV mRNA vaccine of the present disclosure is sufficient to produce detectable levels of hCMV antigen as measured in serum of the subject at 1-72 hours post administration.

Titer. An antibody titer is a measurement of the amount of antibodies within a subject, for example, antibodies that are specific to a particular antigen (e.g., an anti-hCMV antigen). Antibody titer is typically expressed as the inverse of the greatest dilution that provides a positive result. Enzyme-linked immunosorbent assay (ELISA) is a common assay for determining antibody titers, for example.

In some embodiments, the effective amount of the hCMV mRNA vaccine of the present disclosure is sufficient to produce a 1,000-10,000 neutralizing antibody titer produced by neutralizing antibody against the hCMV antigen as measured in serum of the subject at 1-72 hours post administration. In some embodiments, the effective amount is sufficient to produce a 1,000-5,000 neutralizing antibody titer produced by neutralizing antibody against the hCMV antigen as measured in serum of the subject at 1-72 hours post administration. In some embodiments, the effective amount is sufficient to produce a 5,000-10,000 neutralizing antibody titer produced by neutralizing antibody against the hCMV antigen as measured in serum of the subject at 1-72 hours post administration.

In some embodiments, the neutralizing antibody titer is at least 100 $NT_{50}$. For example, the neutralizing antibody titer may be at least 200, 300, 400, 500, 600, 700, 800, 900 or 1000 $NT_{50}$. In some embodiments, the neutralizing antibody titer is at least 10,000 $NT_{50}$.

In some embodiments, the neutralizing antibody titer is at least 100 neutralizing units per milliliter (NU/mL). For example, the neutralizing antibody titer may be at least 200, 300, 400, 500, 600, 700, 800, 900 or 1000 NU/mL. In some embodiments, the neutralizing antibody titer is at least 10,000 NU/mL.

In some embodiments, an anti-hCMV antigen antibody titer produced in the subject is increased by at least 1 log relative to a control. For example, an anti-hCMV antigen antibody titer produced in the subject may be increased by at least 2, 3, 4, 5, 6, 7, 8, 9 or 10 log relative to a control.

In some embodiments, an anti-hCMV antigen antibody titer produced in the subject is increased at least 2 times relative to a control. For example, an anti-hCMV antigen antibody titer produced in the subject is increased by at least 3, 4, 5, 6, 7, 8, 9 or 10 times relative to a control.

In some embodiments, a geometric mean, which is the nth root of the product of n numbers, is generally used to describe proportional growth. Geometric mean, in some embodiments, is used to characterize antibody titer produced in a subject.

EXAMPLES

In order that the invention described in this application may be more fully understood, the following examples are set forth. The examples described in this application are offered to illustrate the systems and methods provided in this application and are not to be construed in any way as limiting their scope.

Figure 1B:
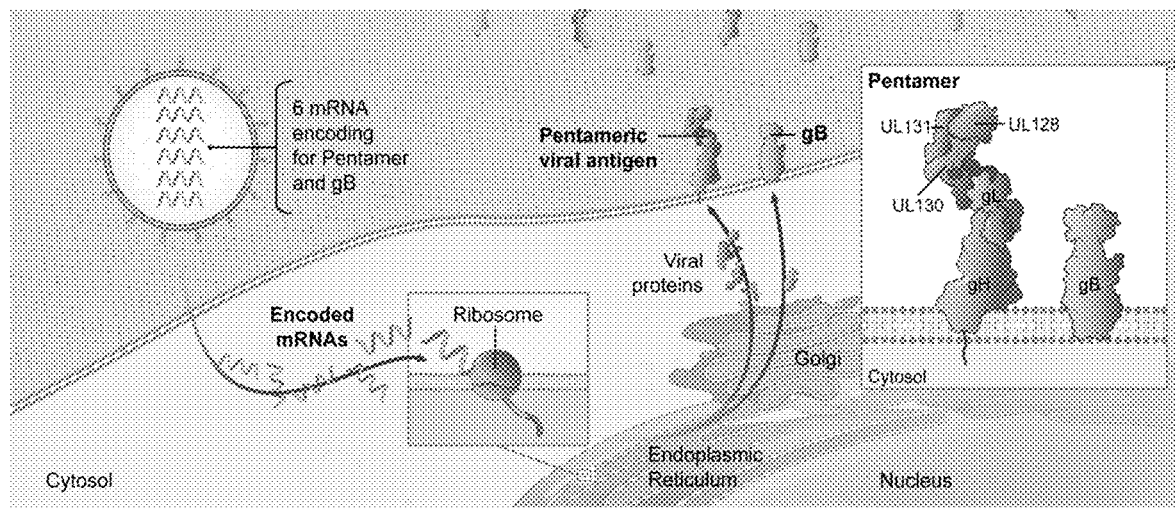

Example 1: Selecting Optimal Ratio of mRNA Constructs in a hCMV mRNA Immunogenic Composition Allows Maximal Potency Throughout Shelf Life hCMV mRNA vaccines containing mRNAs encoding all of the components of the hCMV pentamer (gH, gL, UL128, UL130, and UL131A) and gB (FIGS. 1A and 1B) at an equal mass ratio were found to be efficacious in inducing neutralizing antibodies against hCMV in a Phase I clinical trial study. However, due to the different molecular weights of the individual mRNA constructs, the use of an equal mass ratio results in very different molar doses of the individual mRNA components, with some being present in excess and others being under-represented. In particular, the largest mRNA constructs, corresponding to gB and gH are under-represented on a molar basis in an equal mass ratio formulation.

It was hypothesized that providing the individual mRNA constructs in a ratio that matches the molar stoichiometry could allow for maximum protein expression per mass of mRNA dosed to a patient. It was also hypothesized that the larger mRNA constructs, corresponding to gB and gH, may degrade faster than the smaller mRNA constructs and this degradation may become limiting to the overall stability of the mRNA based vaccine. Accordingly, it was investigated whether further adjusting the molar ratios of mRNA components based on predicted relative rates of mRNA degradation during storage could allow for optimal functional performance throughout the duration of the drug product shelf life.

A formulation comprising equal molar amounts of UL128, gL, UL130, and UL131A, and 2× molar amounts of gB and gH, was investigated and compared to the previously-used equal mass ratio in in vitro and in vivo studies. It was surprisingly found that for a given total dose, formulating the mRNA components based on a proposed molar ratio of the hCMV mRNA vaccine components resulted in increased protein expression of both of the larger glycoprotein antigens (gB and pentamer). The increased expression of gB and pentamer was measured in in vitro cell culture experiments, and also resulted in improved antibody response of both anti-gB and anti-pentamer IgG when administered to mice, compared to the use of equal mass ratios.

Figure 2A:
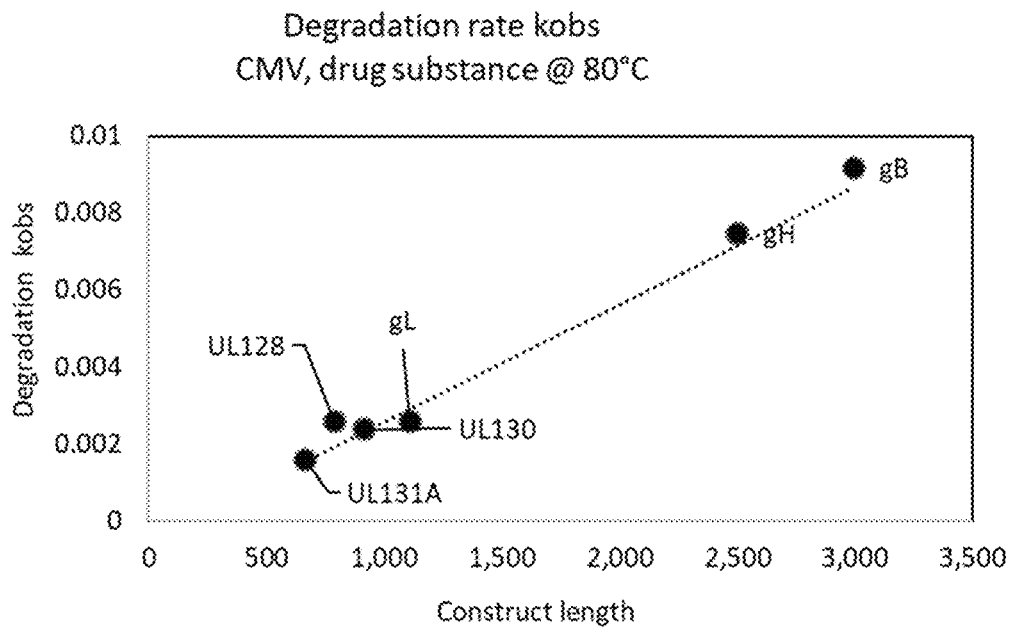
FIGS. 2A and 2B provide graphs showing components within a hCMV immunogenic composition (e.g., hCMV mRNA vaccine), including mRNAs encoding gB, gH, gL, UL128, UL130, and UL131A.
Figure 2B:
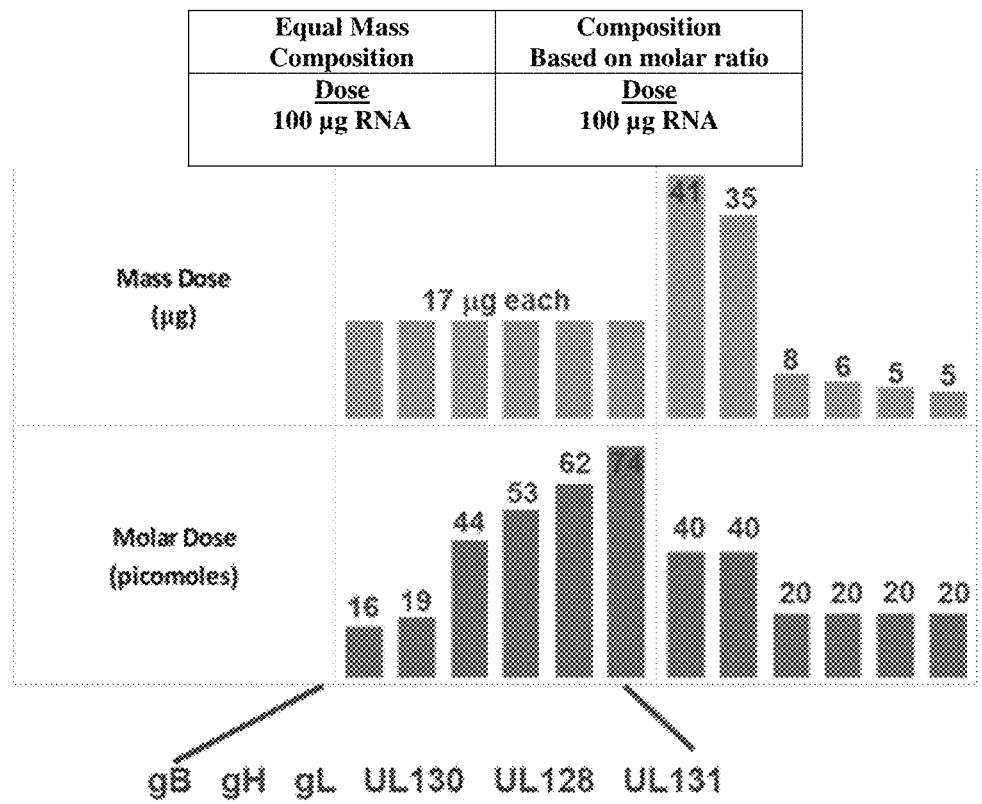
Figure 3A:
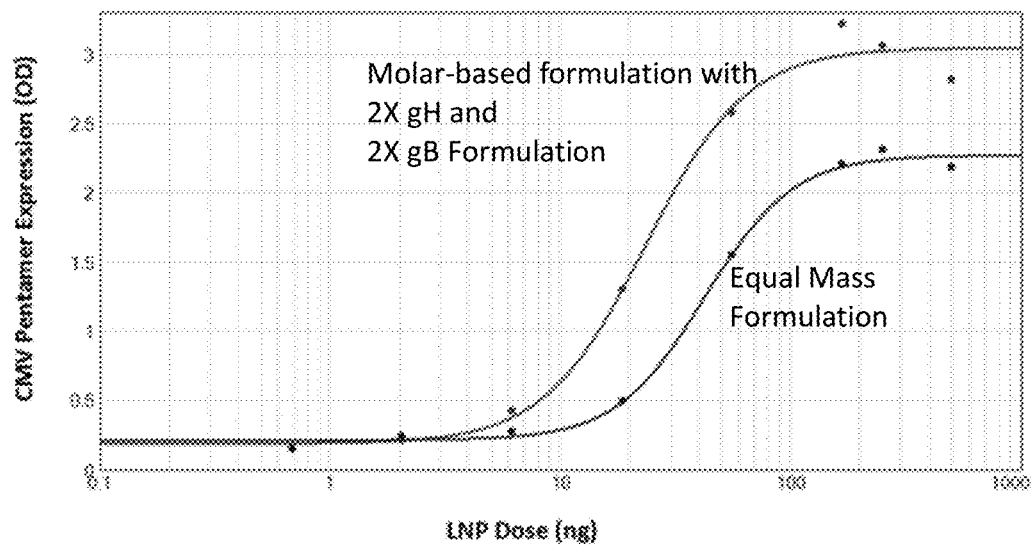
FIGS. 3A-3B provide graphs showing that a molar ratio of hCMV mRNA components that includes 2×gH and 2×gB relative to each of gL, UL128, UL130, and UL131A increases the expression level of the hCMV pentamer and hCMV gB in vitro (as indicated by Emax) and increases the relative potency of the hCMV pentamer and hCMV gB, relative to use of an equal mass ratio for the hCMV mRNA components.
Figure 3B:
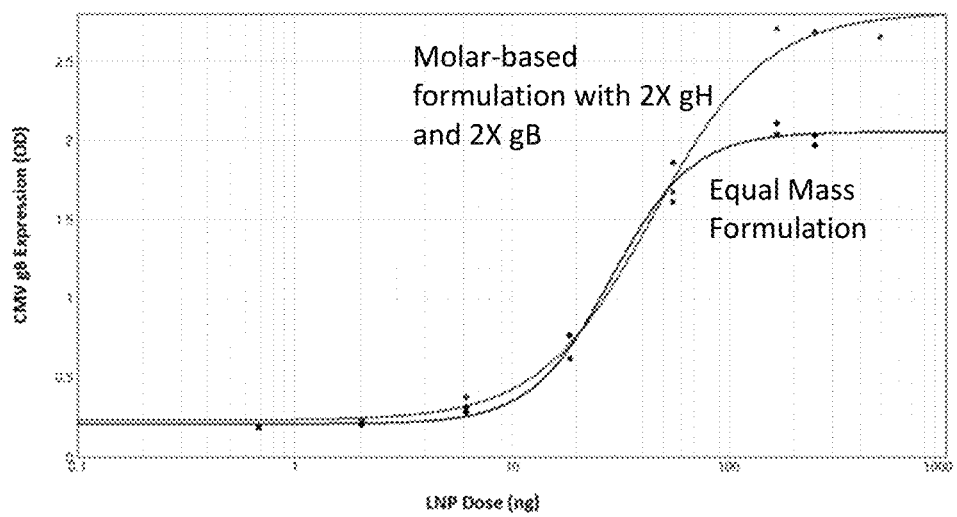
Figure 4:
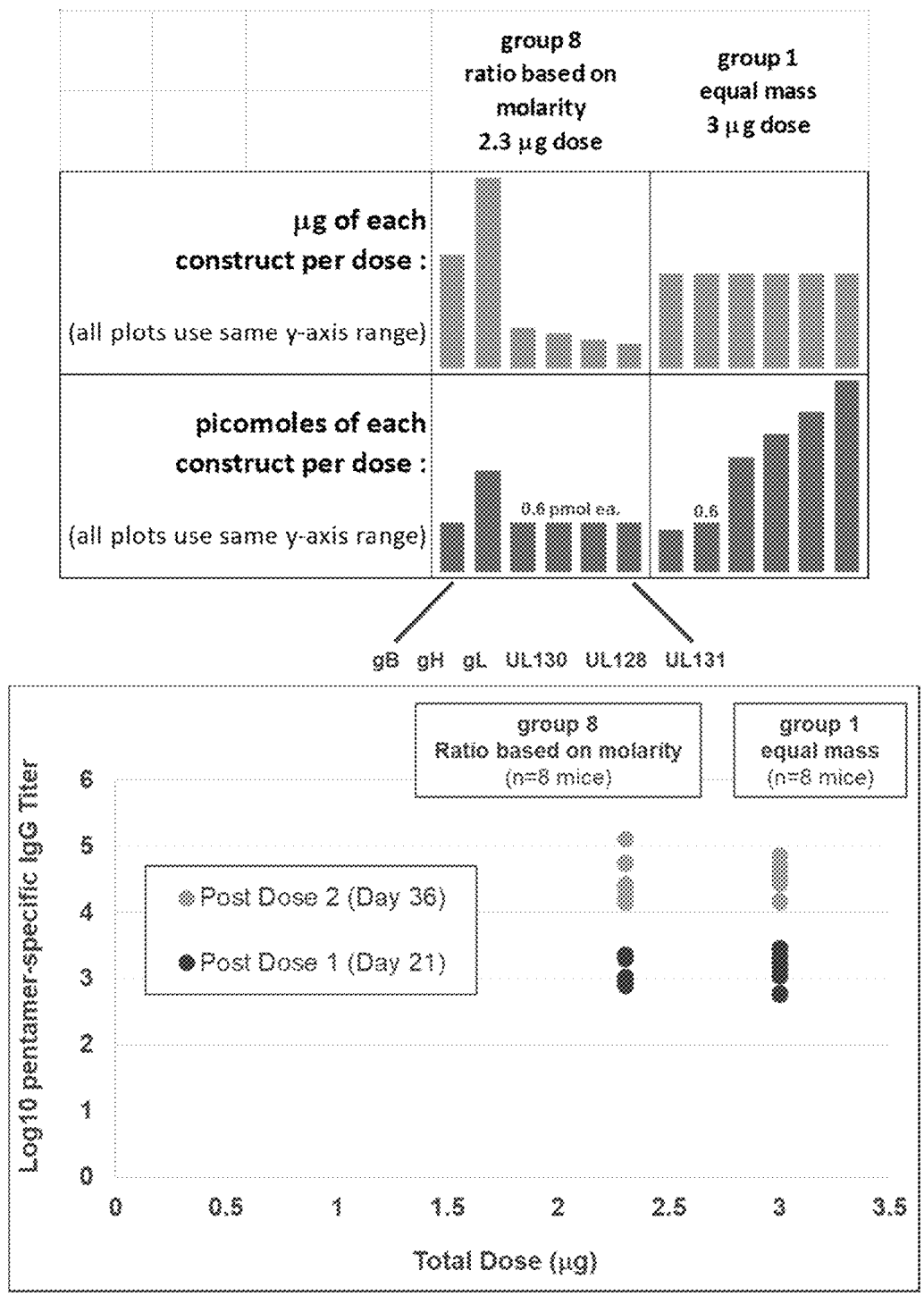
FIG. 4 provides graphs showing a formulation designed based on molar content can maintain strong antibody response in mice even when dosing significantly less gL, UL130, UL128, and UL131. In the top panel, the content of the two formulations (group 8 and group 1) are shown in mass (mg) and in moles (picomoles) and the height of the bar reflects the relative amount of each mRNA. In group 1 the content of gH is the limiting factor to producing the pentamer (0.6 picomoles per dose). In group 8, the content of each of gL, UL130, UL128, and UL131 was designed to also be 0.6 picomoles per dose, thus matching the pentamer dose to group 1 on a molar basis. In the bottom panel, the pentamer-specific antibody response is graphed as a function of total mass dose for groups 8 and 1. The response level is similar, while group 8 employed a lower total dose (2.3 mg vs 3 mg) and significantly less gL, UL130, UL128, and UL131. Further, gB is 1.2× in group 8 relative to group 1.

Without wishing to be bound by any theory, the formulation comprising equal molar amounts of gL, UL128, UL130, and UL131A, and 2× molar amounts of gB and gH compensates for pentamer protein stoichiometry and differential rates of mRNA degradation. See FIG. 2A. In addition to calculating doses of individual components on a molar basis, a further improvement was obtained by simultaneously adding 2× molar amounts of gH and gB, relative to the 1× equimolar amounts of the mRNAs encoding proteins that complex with gH such as gL, UL128, UL130, and UL131A. The vaccine formulated in this way results in elevated molar doses of these high molecular weight mRNA components relative to the other lower molecular weight mRNA components. This design was in contrast to when the mRNA components were formulated based on an equal mass ratio (FIG. 2B). In FIG. 3, in vitro expression data shown in two separate examples that in comparison to equal mass formulations, pentamer expression was increased for formulations based on molar stoichiometry with 2×gH. The increased expression was observed by an increased Emax. Surprisingly, an hCMV mRNA immunogenic composition based on the molar ratios described above achieved equivalent or slightly higher antibody response in mice using lower total doses than an hCMV mRNA immunogenic composition based on an equal mass (FIG. 4).

Figure 5:
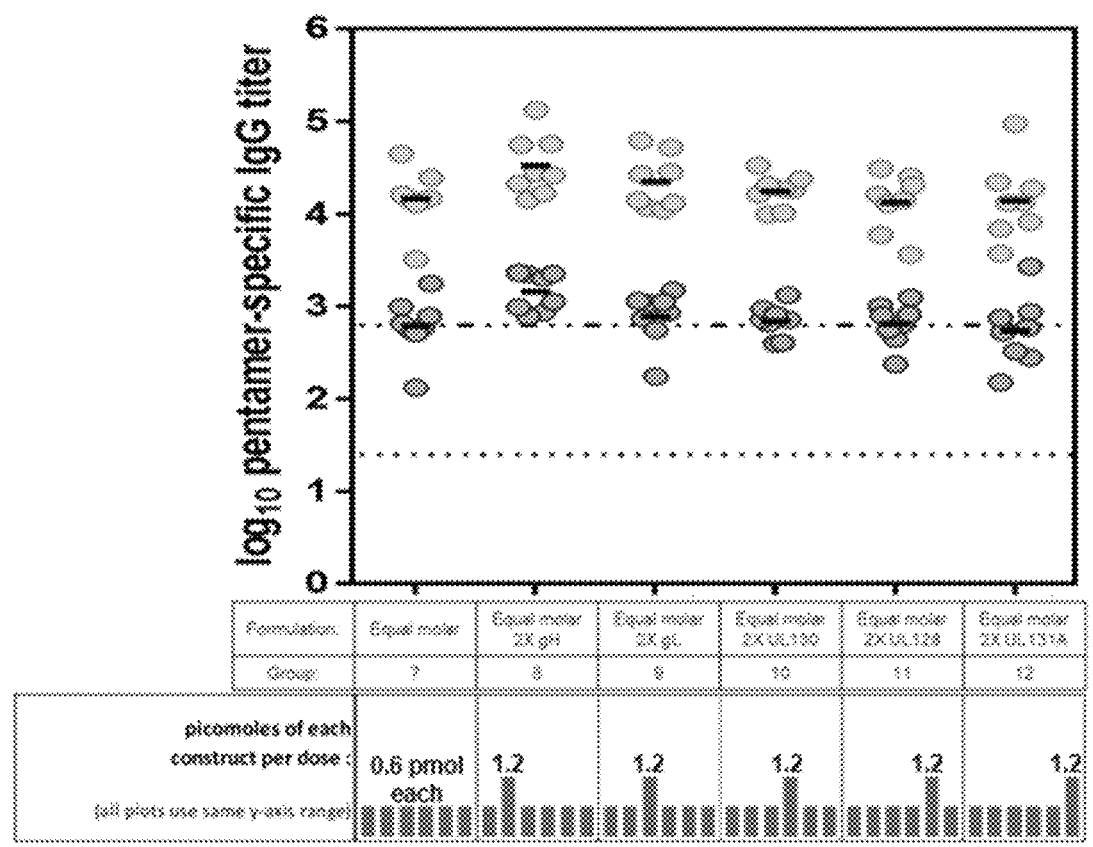
FIG. 5 provides a graph showing the effects on anti-pentamer IgG response of augmenting the molar ratio of each hCMV pentamer component individually. The results show that excess gH increases anti-pentamer IgG in mice.
Figure 6A:
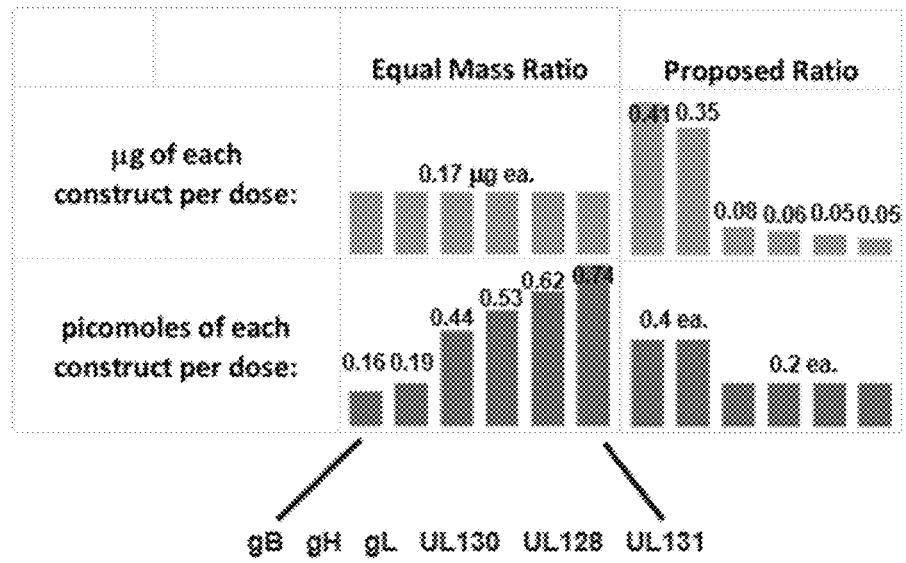
FIGS. 6A-6D provide graphs showing dose responses of anti-gB antibodies and anti-pentamer antibodies in mice for three formulations (Lot #1, 2, and 3) based on specified molar ratios of the mRNA components compared to equal mass ratios (Lot #4).
Figure 6A:
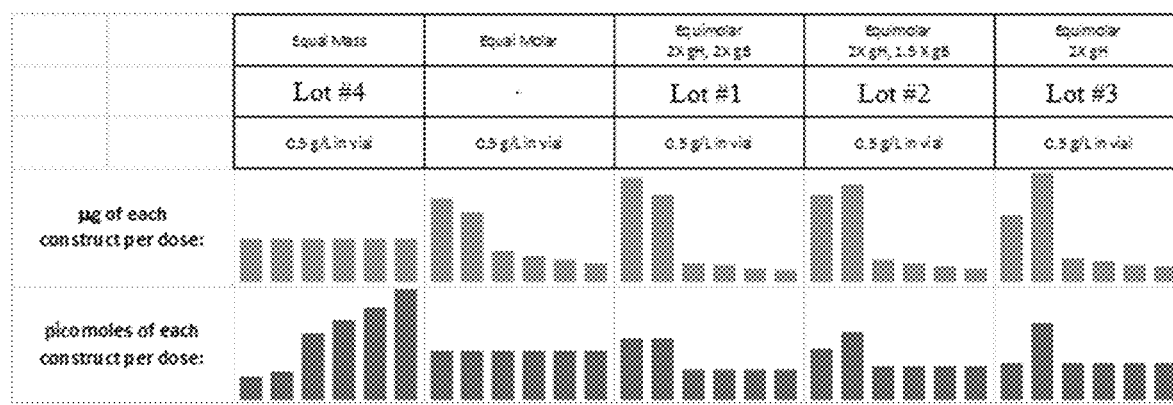
Figure 6B:
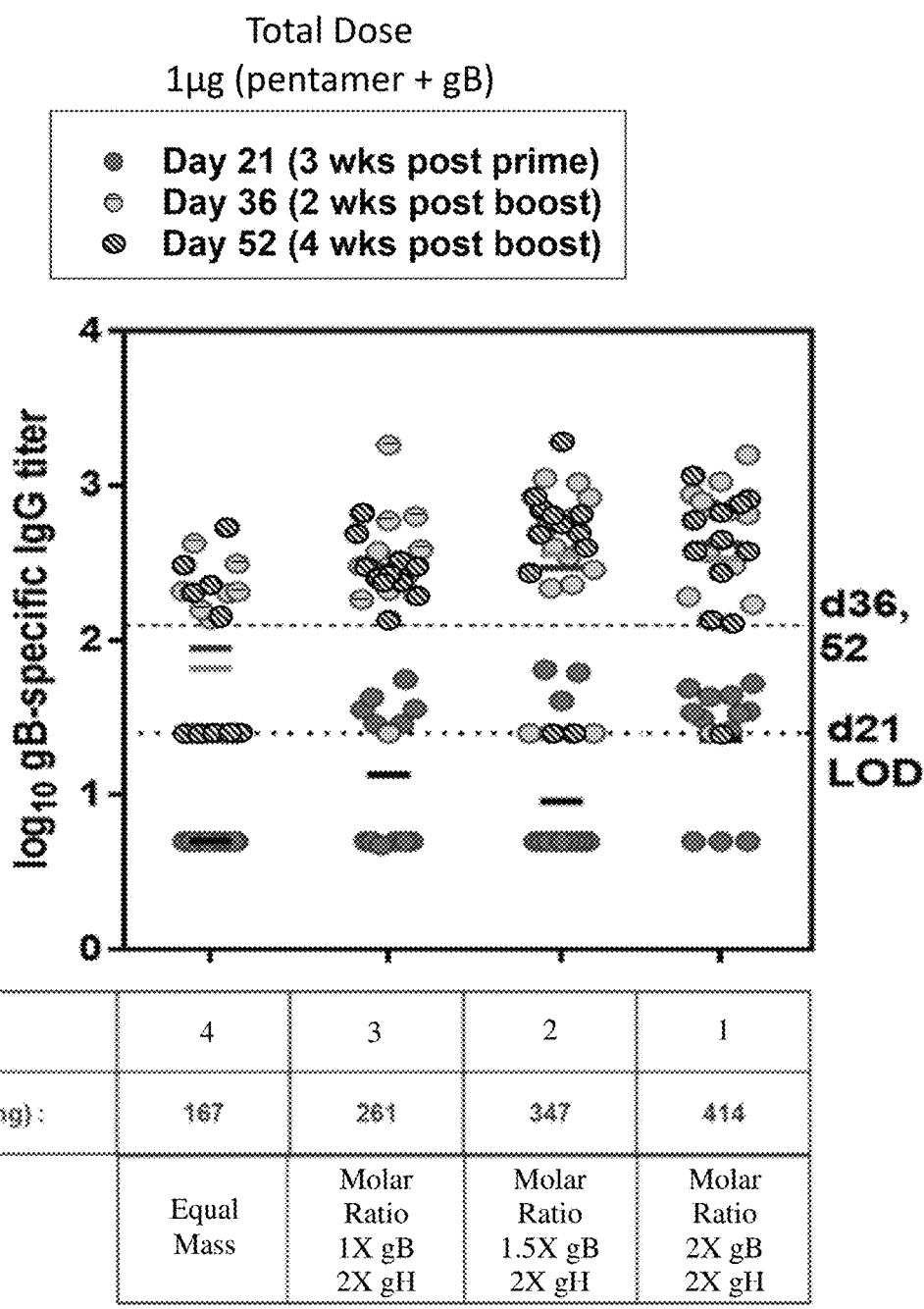
Figure 6C:
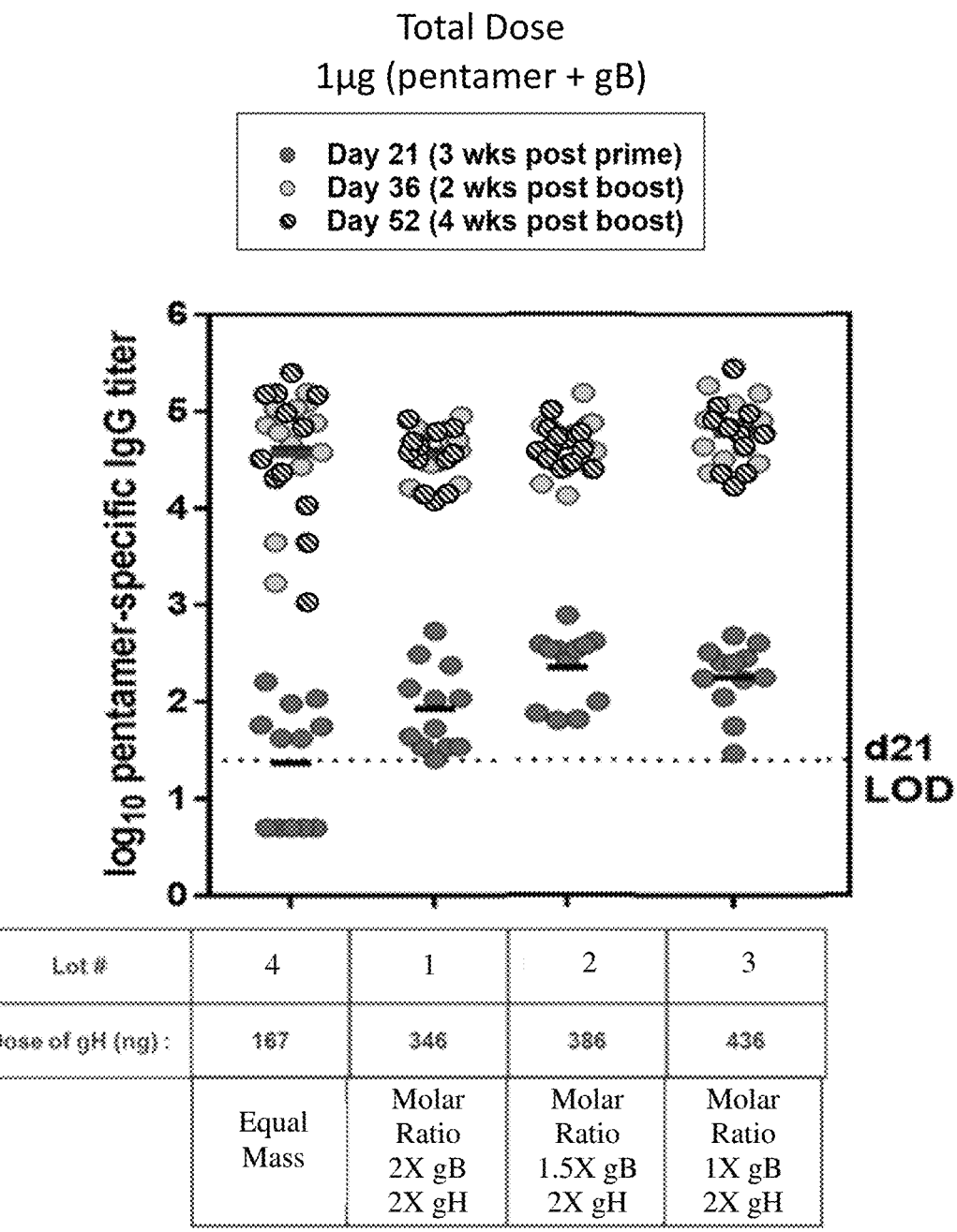
Figure 6D:
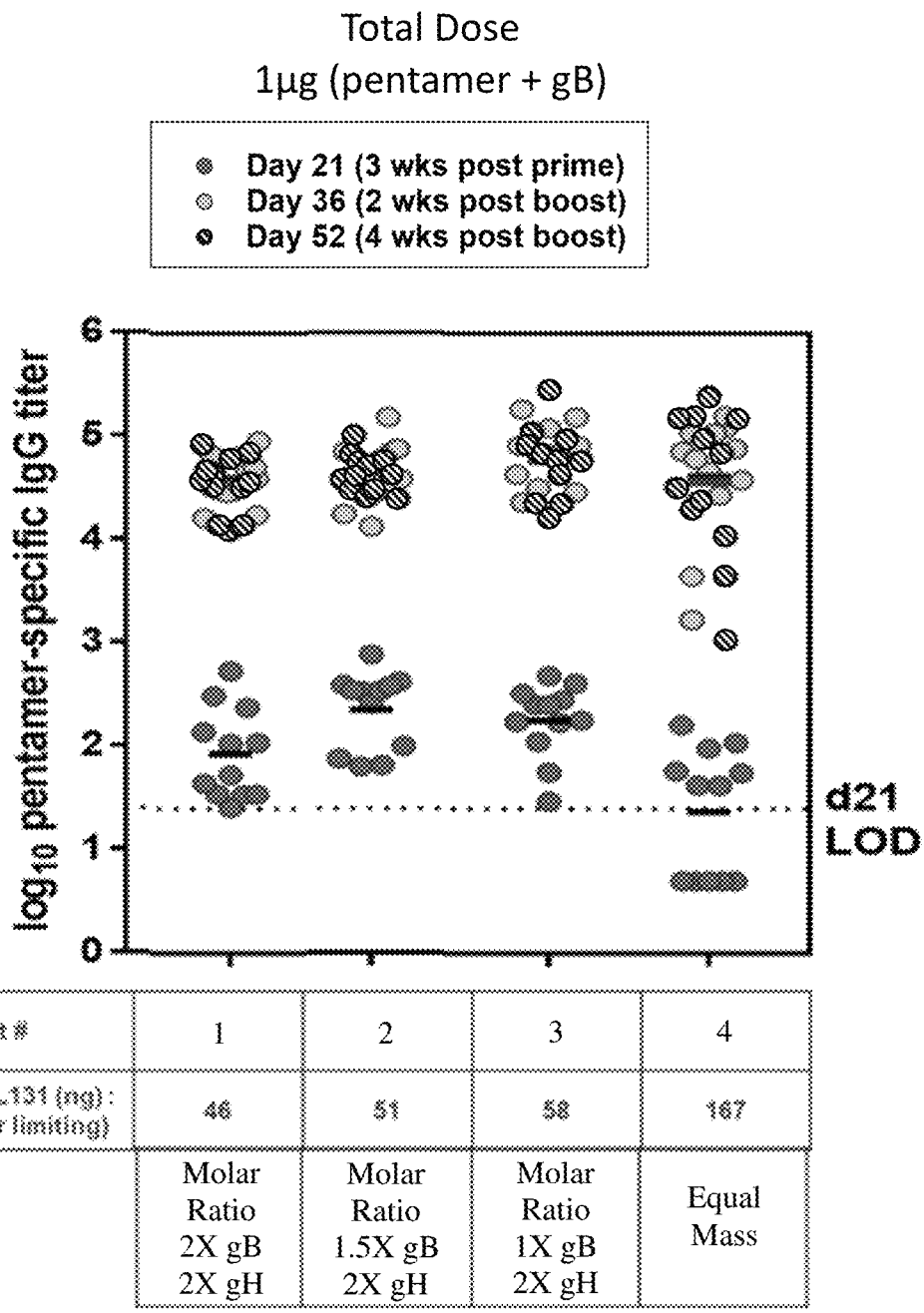

It was found that when each mRNA construct was tested by increasing its molar ratio to 2× to create an excess of the added construct, while the other mRNA components were present in an equal molar ratio, an excess of gH had the biggest effect on increasing anti-pentamer IgG response in mice (FIG. 5). Significantly, it was found that a lower total dose of the hCMV mRNA immunogenic composition was required to demonstrate an increased anti-gB and anti-pentamer antibody response in mice when the mRNA components were formulated based on the molar ratios described herein relative to being formulated based on an equal mass ratio (FIGS. 6A-6D).

Figure 7:
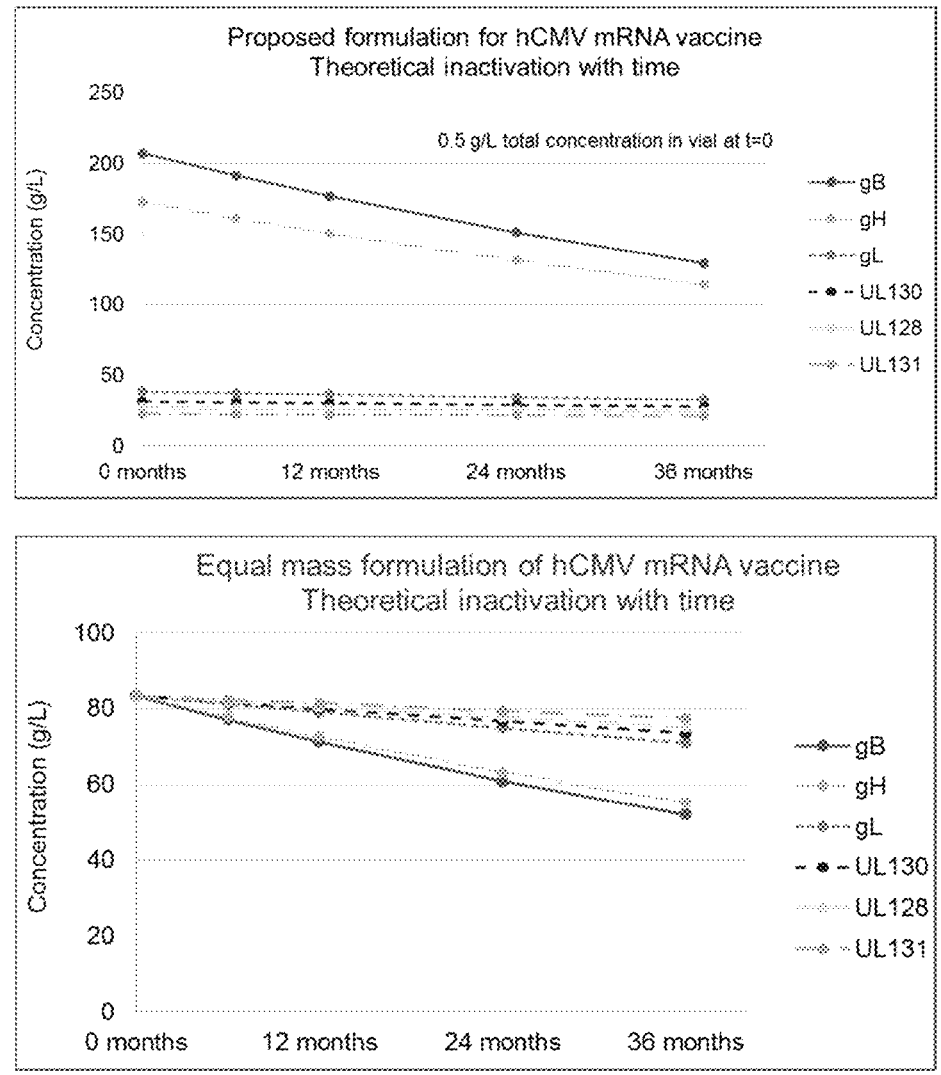
FIG. 7 provides graphs showing theoretical inactivation over time of components within a hCMV mRNA vaccine in which the mRNA components are formulated based on a specified molar ratio of the mRNA components (top panel) or based on equal mass of the components (bottom panel). Rates of inactivation are based on the rate-to-length relationship shown in FIG. 2A. The top panel reveals that in hCMV mRNA vaccines with 2×gB and 2×gH relative to the other mRNA components, gH and gB are predicted to be maintained in excess up to at least 36 months. Whereas the bottom panel shows that in equal mass formulations, gH and gB are not maintained at equal mass proportions as inactivation occurs over time.

Based on calculated theoretical inactivation rates, the proposed molar ratios of mRNA components in the hCMV mRNA immunogenic composition described herein was found to adequately compensate for degradation of the longer mRNA constructs and to maintain excess amounts of gH and gB for at least 36 months, corresponding to the predicted shelf life for a drug product containing these components (FIG. 7). An excess of the longer gH and gB constructs compensated for inactivation with time, while maintaining a maximally potent product (FIG. 7).

The proposed molar ratios of mRNAs in the hCMV mRNA vaccine described herein maximizes potency throughout the duration of the shelf life of the vaccine. Specifically, a composition based on equal molarity of the smaller mRNAs (gL, UL130, UL128, and UL131) with an excess of longer mRNA constructs (gH and gB) capitalizes on the structural stoichiometry of the target protein complex, increases the gB content over equal mass formulations, and compensates for known mechanisms of mRNA inactivation. This approach also provides the potential for a robust dose definition with less mRNA, which could provide lower cost of goods and better tolerability. Furthermore, since gL, UL128, UL130, and UL131 all bind with membrane anchored gH and assemble into a larger glycoprotein complex known as the pentamer, it is advantageous never to have gH in limiting supply compared to the other smaller members of the pentamer. Since gH forms the basal structure of the pentamer and the other smaller proteins need to assemble onto it to form the mature pentamer complex, if the basal component is in short supply, then mature pentamer will also be in short supply.

Example 2: Phase II does Selection Clinical Trial

Figure 8A:
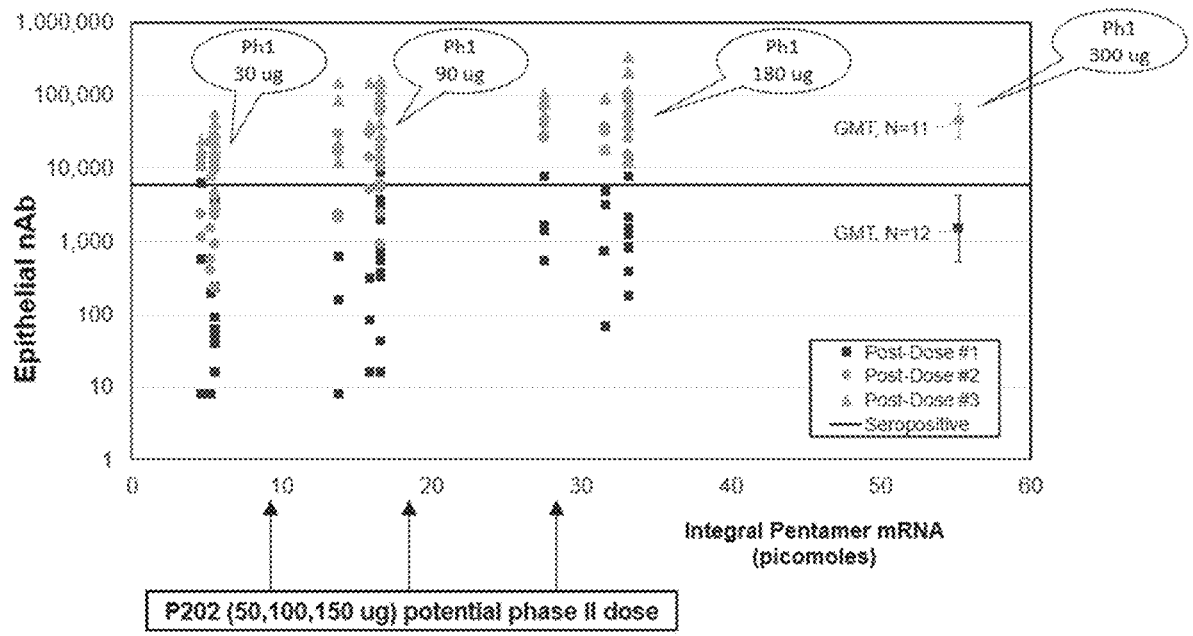
FIGS. 8A-8B provide graphs showing neutralizing antibody response in humans of a hCMV mRNA vaccine in a Phase I clinical trial plotted onto a molar-based X-axis. The plotted values used a hCMV vaccine in which the mRNA components were formulated based on equal mass, but shown here as calculated picomoles. Arrows along the X-axis are provided to demonstrate where on the X-axis an alternate formulation based on micrograms would overlay. Using this X-axis allows two differently designed formulations to be plotted on the same continuous axis to enable dose selection for subsequent trials, whereas plotting against the total mass dose (mg) would create a discontinuous dose response curve between the two formulations. Dose-escalation phases A and B and dose-selection phase B (30, 90, 180 µg) are graphed as individual subjects. Dose selection phase C (300 µg) data are graphed as GMT+−95% confidence interval until study is unblinded.
Figure 8B:
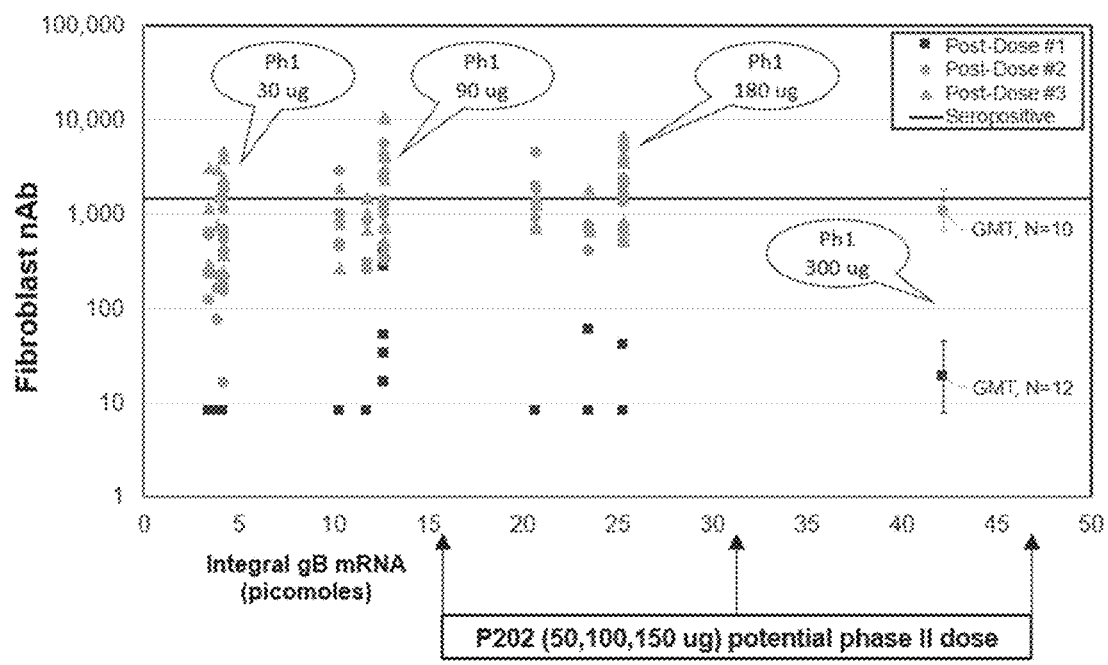

A Phase I clinical trial was conducted using an hCMV mRNA vaccine comprising the pentamer components and gB in an equal mass ratio. Phase I clinical trial data indicated that neutralizing antibody titers against epithelial cell infection (derived from successful pentamer expression and immune response) generally exceeded the neutralizing antibody titers against fibroblast cell infection (derived from successful gB expression and immune response). Therefore, maximizing integral gB neutralizing immune response was a driving factor when evaluating Phase I data and data from naturally infected seropositive patients for designing a dose for subsequent clinical trials. The hCMV Phase I clinical trial data was graphed with a molar-based X-axis to enable comparison between Phase I (equal mass) data and proposed Phase II (molar based) data to be graphed on one continuous x-axis despite the differences in mRNA component concentrations used in the Phase I and Phase II vaccine formulations. Graphing Phase I and Phase II data on the same continuous x-axis enables an inclusive dose response curve which can be used for dose selection for subsequent clinical trials. The x-axes of FIG. 8A and FIG. 8B depict picomoles of integral pentamer mRNA and picomoles of integral gB mRNA, respectively. These values were calculated for each Phase I dose based on the total dose (μg), the ratio of the mRNA in the Drug Product, the actual purity of the Drug Product, and the molecular weight of each mRNA (FIGS. 8A-8B).

The graphs provided in FIGS. 8A and 8B show the neutralizing antibody titers (nAb) against fibroblast (gB) and epithelial cell (pentamer) infection. In both graphs, the seropositive benchmark level is noted by a red horizontal line. The seropositive benchmark level to gB and pentamer is the antibody titer specific for these antigens and found in unvaccinated patients who have been previously infected with hCMV and recovered. Note the benchmark seropositive pentamer titer is much higher than the benchmark gB titer. The data from Phase I Dose-escalation Phases A&B and Phase I Dose-selection Phase B (30, 90, 180 μg) are graphed as individual subjects. The data from Phase I, 300 μg Dose Cohort C post-dose data point 1 (PD1) and post-dose data point 2 (PD2) data are graphed as GMT+−95% confidence interval. In the text box below the X-axis, arrows indicate proposed Phase II (P202) doses calculated using moles but expressed as weight (50, 100, 150 μg) total mRNA in the LNP.

In FIG. 8A, the Phase II (P202) data based on the indicated proposed doses is expected to be between 9-29 picomoles of integral pentamer mRNA, which corresponds to the portion of the dose response curve previously shown to elicit neutralizing antibodies after 2 or 3 doses generally at or above the seropositive benchmark in the Phase I trial. The Phase I ratio readily achieved the seropositive benchmark at 5 picomoles after 3 doses (See Post Dose 3, FIG. 8A) and even had many subjects reach the benchmark seropositive levels after 2 doses (See PD 2, FIGS. 8A & B) at 12 picomoles. Due to the strong neutralizing antibody response induced to pentamer for epithelial cell infection, it was not necessary to design the Phase II formulation such that it extends the dose level out to a higher picomolar dose of pentamer mRNA components. In fact, the Phase II formulation will achieve 9-29 picomoles of integral pentamer mRNA components at a slightly lower total mass per dose. However, the molar based design of the doses enabled the selection of a dose that will reach these benchmark levels and have at least 26 months of product stability. For example, the Phase I Phase C 300 µg dose delivers significantly more integral pentamer than does the Phase II 150 µg dose. See FIG. 8A.

In contrast, in FIG. 8B, the fibroblast nAb data to gB shows that achieving the seropositive benchmark is more challenging for the gB antigen due to reduced immunogenicity relative to pentamer. By 20-25 picomoles of integral gB, not all patients had achieved the seropositive benchmark nAb level after PD2 or PD3. Accordingly, the Phase II mRNA molar ratios described in Example 1 were designed to deliver more gB mRNA per total mass dose, thereby extending the dose curve out to higher picomolar doses of gB mRNA. In fact, the Phase II molar ratio based formulation will deliver 16-47 picomoles of integral gB mRNA at a much lower total mass dose. In this case, the P101C 300 µg dose delivers less integral gB than does the P202 150 µg dose.

Figure 9A:
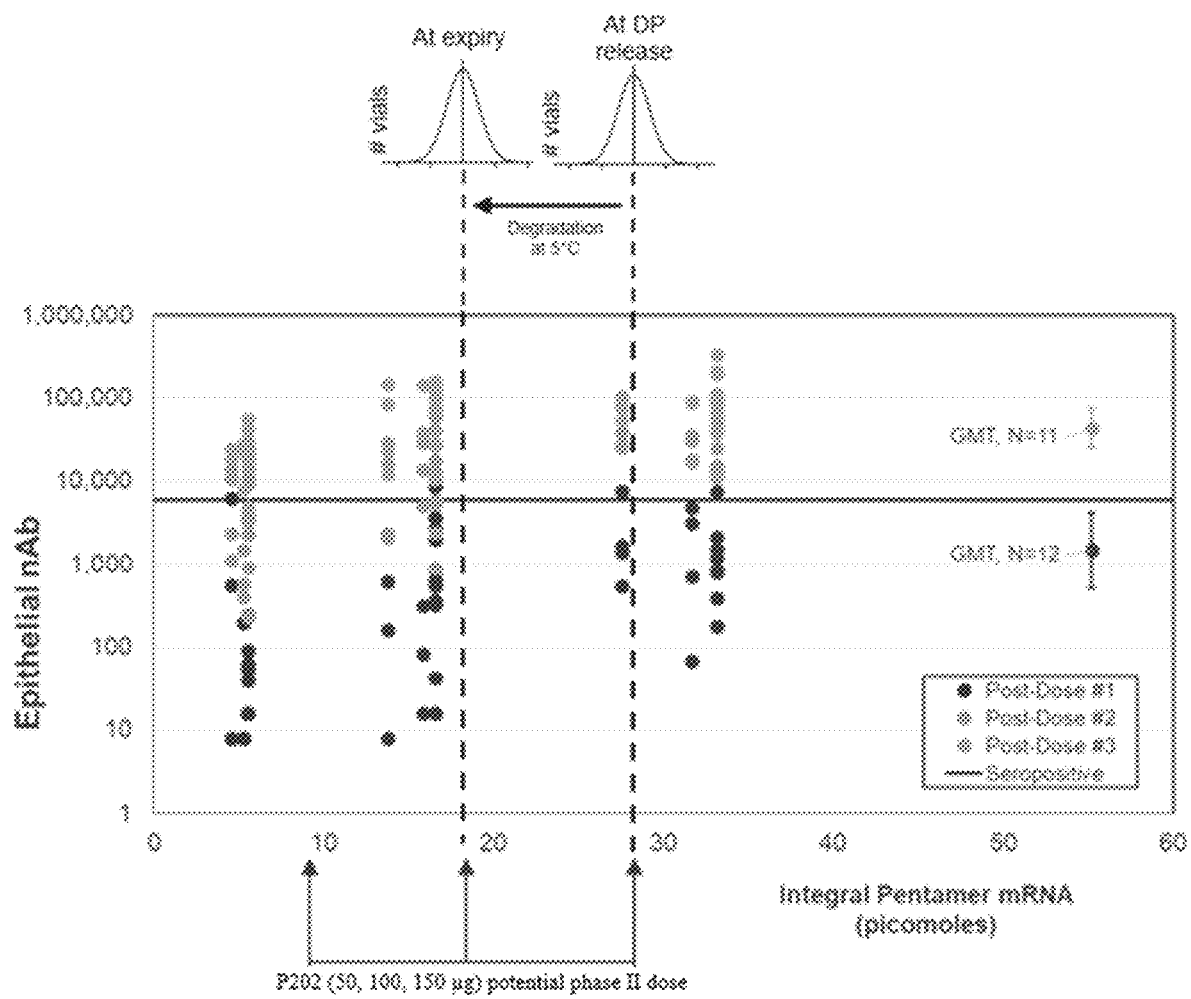
FIGS. 9A-9B provide graphs showing nominal dose selection to ensure vials of hCMV vaccine are efficacious until expiry.
Figure 9B:
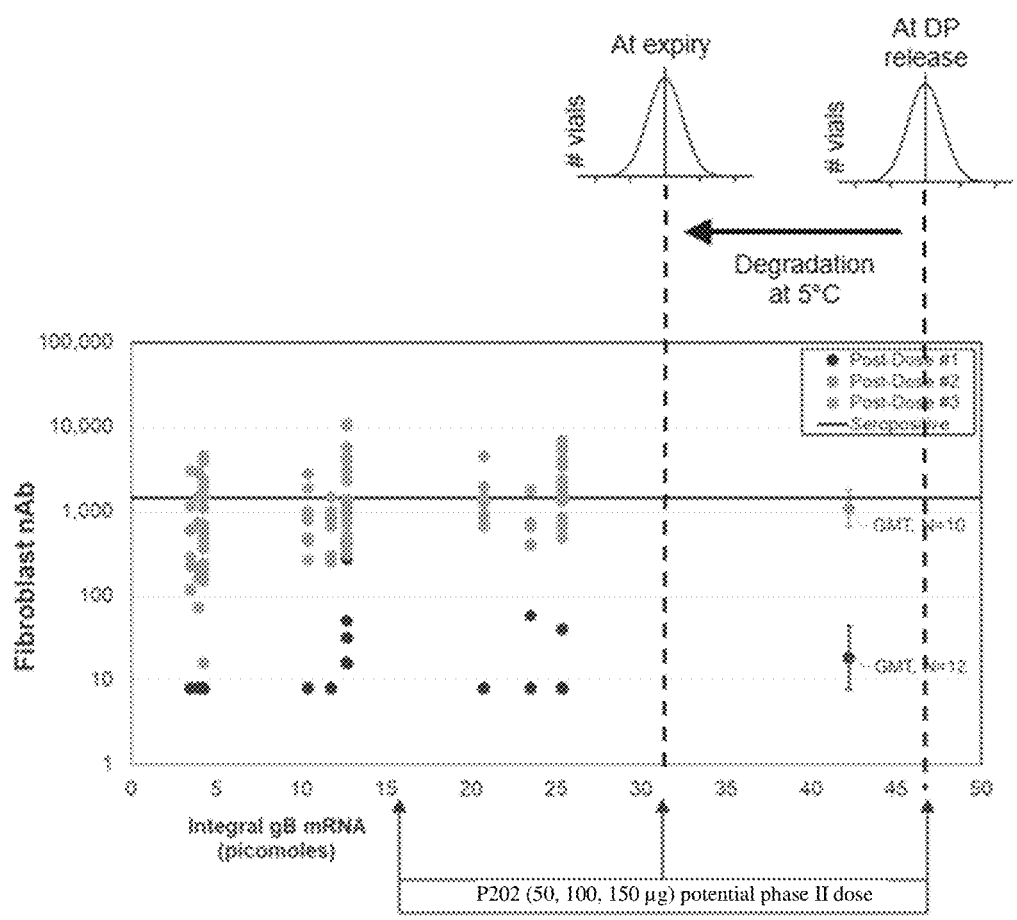

Next, as shown in FIGS. 9A and B, these dose response curves were used to visualize the projected doses for a Phase II clinical trial described herein and along with the data obtained, the visualization technique shown in FIGS. 9A and 9B will also be used for selecting the optimal dose for a Phase III clinical trial. Because pentamer immunogenicity is significantly greater compared to gB immunogenicity, it is expected that maximizing the fibroblast nAb titers to gB will determine the minimum required dose, and if the proposed molar ratio design is followed, the correlating epithelial nAb titers to pentamer will be more than adequate.

Without considering LNP function, other quality attributes, cell function, immune response, and sequence-specific aspects of mRNA and protein, the dose selection strategies provided herein correlate integral transmembrane protein encoding mRNA content and purity to neutralizing antibody response. Based on this study, the dose response curves can be used to define the dose for future clinical studies.

Prediction of the minimum required dose in every vial through expiry includes modelling all elements that are expected to impact the dose strength, such as concentration (e.g., in-process control (IPC) assay and dilution) and purity (e.g., degradation). The IPC assay measures the total mRNA content. Phase III clinical trial subjects and commercial vaccine patients will receive a range of dose strengths. The total dose of integral transmembrane protein encoding mRNA (µg) was calculated as 500 µL mRNA concentration (g/L)×purity (%).

Figure 10:
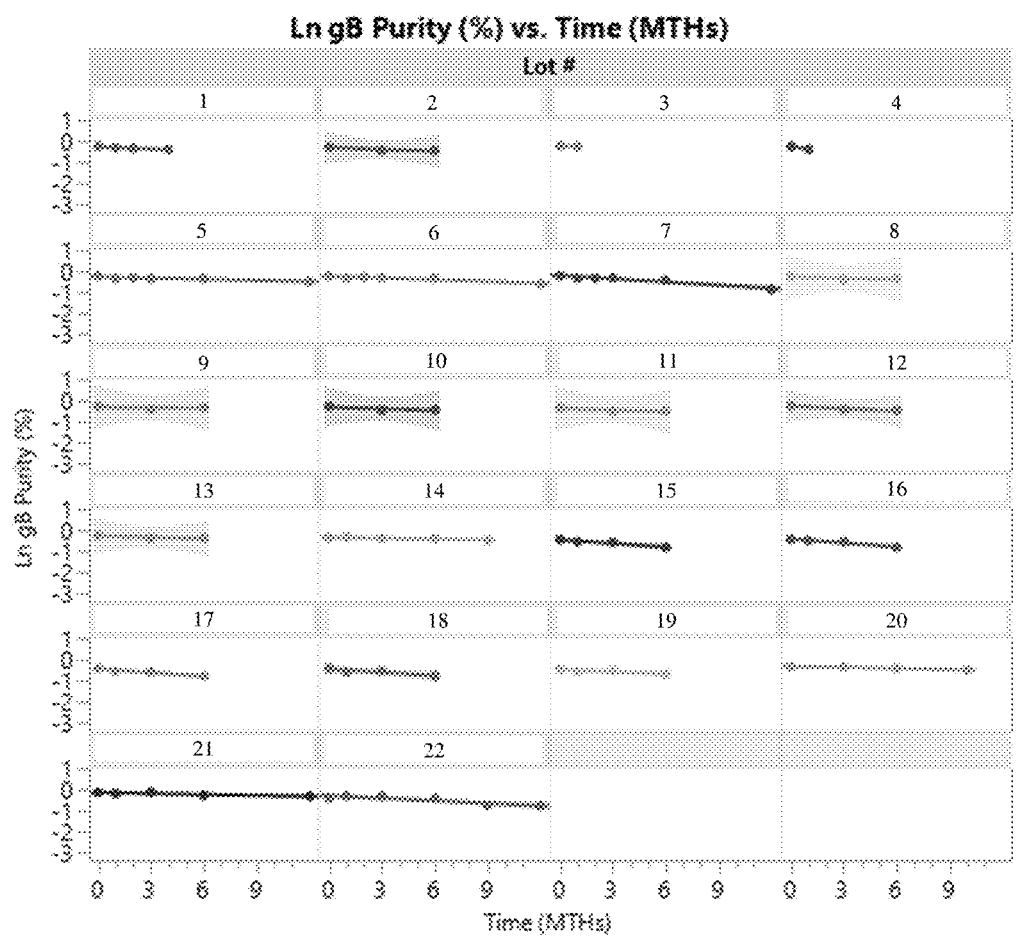
FIG. 10 provides graphs showing modeled degradation of twenty-two batches of a hCMV vaccine at 5° C. based on percent purity of gB over time. The data demonstrate first order kinetics.
Figure 11:
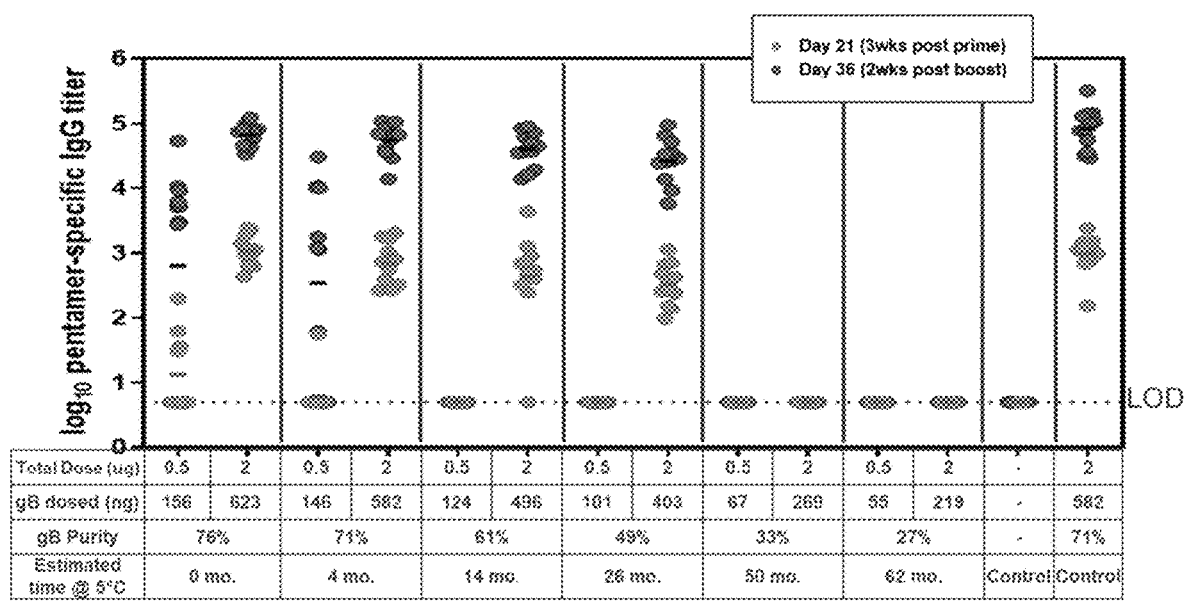
FIG. 11 provides graphs showing anti-pentamer response (top panel) and anti-gB response (lower panel) in mice at various levels of gB purity. The graphs demonstrate that the immune response to both pentamer and gB were not affected until gB purity fell below 49% at around 26 months. This result indicated that gB mRNA can serve as a single indicator for batch potency over time.
Figure 11:
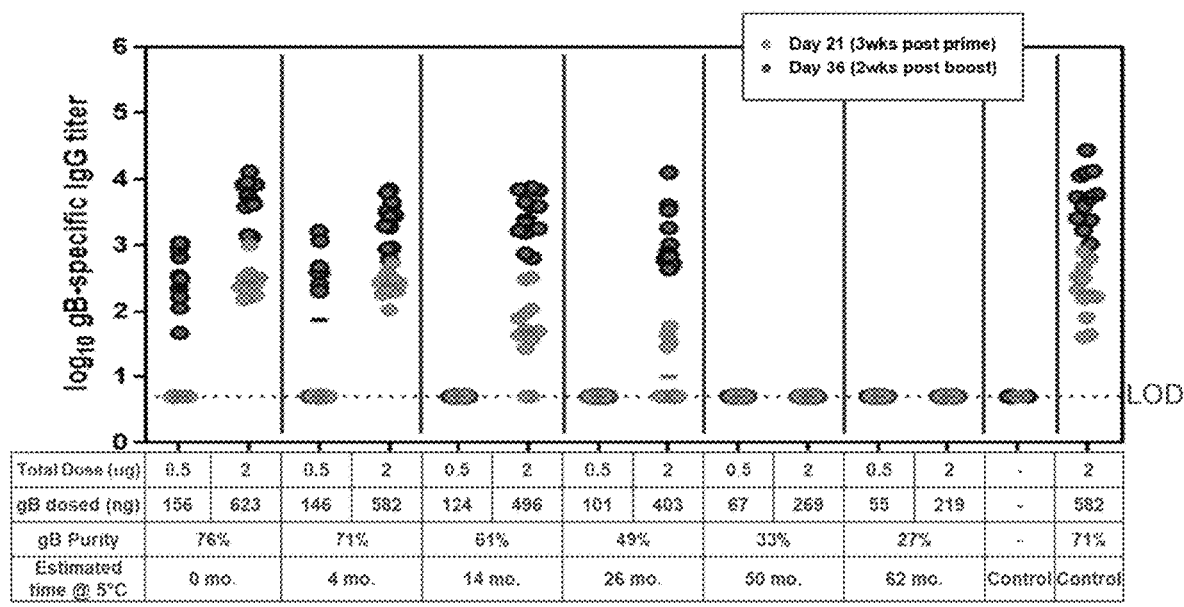

A nominal dose was selected to ensure expiry vials are efficacious (FIGS. 9A-9B). For example, a 150 µg nominal dose (target dose with a distribution), enables two years of 5° C. shelf life for Phase III and commercial supply. At expiry, vials deliver a dose strength in the range of 100 µg nominal dose. FIG. 10 provides degradation modeling at 5° C. The requirement of 50% gB purity at expiry for efficacy was determined because the equal mass ratio hCMV mRNA vaccine antibody response in mouse studies showed a marginal decline when gB purity is decreased to 50% and modeling of the degradation rate predicts that 50% gB represents ~2 years at 5° C. (FIG. 11). Note that immunogenicity targets are maintained until gB purity degrades to below 49% after 26 months in a mouse assay. Relating a change in murine immunogenicity to predict a change in human response depends on dose response curve sensitivity. Doses tested in mice (0.5 & 2 µg) are on the steepest part of the dose response curve. Human dose selection targets saturating nAb levels (less sensitivity to purity is expected). Based on the current modeling, it is expected that the 150 µg dose is immunogenically potent and well tolerated.

Example 3. A Phase II, Randomized, Observer-Blind, Placebo-Controlled, Dose-Finding Trial to Evaluate the Safety and Immunogenicity of the hCMV mRNA Vaccine in Healthy Adults The purpose of this Phase II study was to evaluate the safety and immunogenicity of the hCMV mRNA immunogenic composition in healthy adults (18 through 40 years of age) who were either CMV-seronegative or CMV-seropositive at enrolment. The hCMV mRNA vaccine has demonstrated non-clinical safety and immunogenicity and holds the potential for preventing human primary CMV infection and CMV re-infection/re-activation in CMV-positive individuals.

Description of Study Vaccine

The hCMV mRNA vaccine evaluated in this study against CMV infection consists of 6 distinct mRNA sequences encoding 6 viral protein targets of nAb response to human CMV infection (full length CMV gB and pentameric gH/gL/UL128/UL130/UL131A glycoprotein complex [Pentamer]) in a lipid nanoparticle (LNP) formulation. The 6 mRNAs are present in the hCMV mRNA vaccine at a gL:UL128:UL130:UL131A:gH:gB molar ratio of approximately 1:1:1:1:2:2.

The LNP formulation includes 4 lipid excipients: heptadecan-9-yl 8-((2-hydroxyethyl)(6-oxo-6(undecyloxy)hexyl)amino)octanoate, a cationic ionizable amino lipid, and the commercially-available lipids cholesterol, 1,2-distearoyl-sn-glycero-3-phosphocholine (DSPC), and 1,2-dimyristoyl-sn-glycerol, methoxypolyethyleneglycol (PEG2000 DMG) (Mui et al 2013).

The hCMV mRNA vaccine injection was provided as 520 µg of lyophilized product in single-use glass vials and stored at −25° C. to −15° C. (−13° F. to 5° F.) until use. Following appropriate dose preparation, the hCMV mRNA vaccine injection was administered intramuscularly into the deltoid muscle in a volume of 0.5 mL.

The lyophilized vaccine is reconstituted with 0.6 mL of 0.9% sodium chloride injection (USP), then diluted with tris sucrose diluent SD-0724 to a concentration for delivery of the specified dose level in a volume of 0.5 mL. A 0.9% sodium chloride injection (USP) (normal saline) placebo was administered in a volume of 0.5 mL.

Study Design

The design and dose levels proposed for this Phase II Study were based on accumulated safety and immunogenicity data from an ongoing Phase I study. An interim analysis of safety and immunogenicity data across the 30 µg, 90 µg, and 180 µg dose level cohorts for the Phase I study has shown that the hCMV mRNA vaccine is generally well-tolerated in adults, both CMV-seronegative and CMV-seropositive. In CMV-seronegative participants, neutralizing antibodies (nAbs) against both epithelial cell and fibroblast infection were observed at all dose levels following 2 doses (administered at 0, 2 months) of the hCMV mRNA vaccine and immune response was measured 1 month after the second dose. Additionally, antibody levels against viral proteins necessary for epithelial cell and fibroblast entry were boosted in CMV-seropositive participants at all dose levels following the same vaccination schedule.

The Phase II Study described herein evaluates 3 dose levels of the hCMV mRNA immunogenic composition for safety and immunogenicity in CMV-seronegative and CMV-seropositive adults 18 to 40 years of age using a dose escalation, sequential enrollment design and was intended to allow selection of a single dose for further development.

Figure 12:
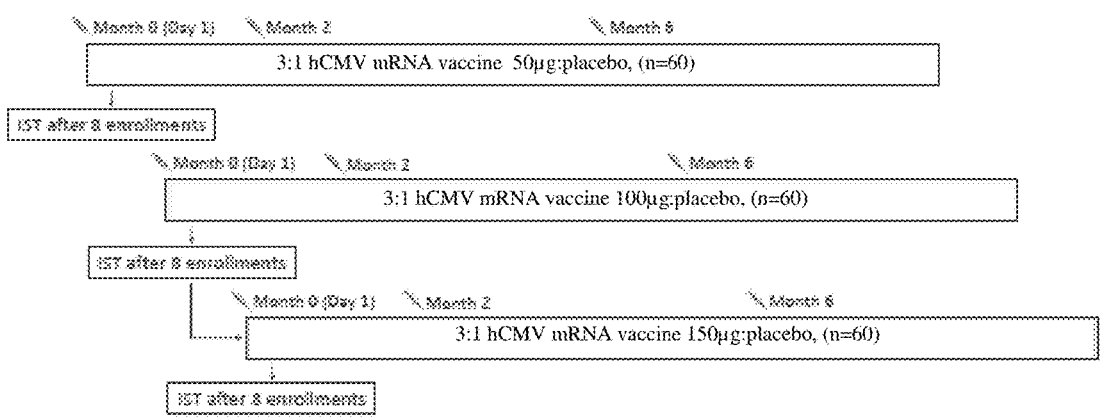
FIG. 12 provides a schematic depicting an overview of the Phase II clinical trial study design. Abbreviations: IST, internal safety team; mRNA, messenger ribonucleic acid.
Figure 12:
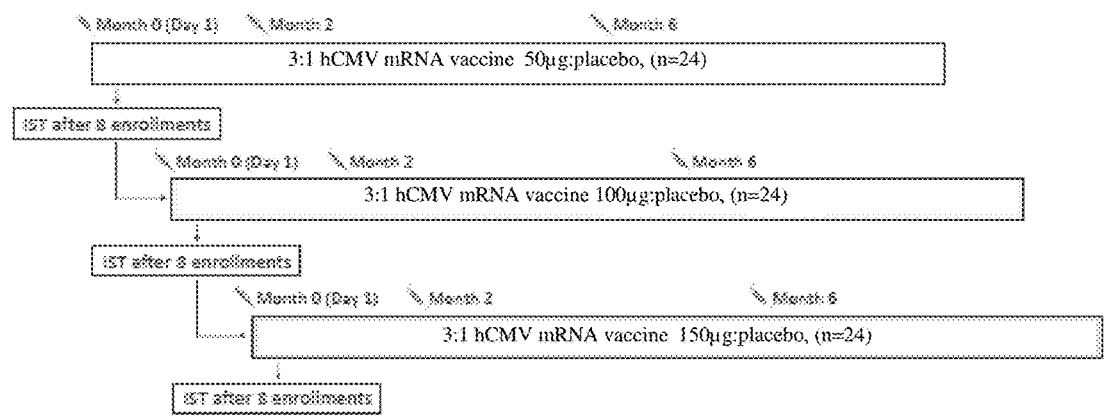

A schematic of the study design is presented in FIG. 12. The study includes two treatment groups, a CMV-seronegative group and a CMV-seropositive group, which are enrolled simultaneously. Randomization was stratified by CMV serostatus via an Interactive Response Technology (IRT) in a sequential manner into 3 different dose levels. At each dose level, subjects are randomized in a 3:1 ratio to receive either hCMV mRNA vaccine or placebo, administered in a 3-vaccination (0, 2, 6-month) schedule.

Treatment Arms

CMV-Seronegative Group

There were 60 subjects at each dose level in the CMV-seronegative group. Dose levels were 50 µg, 100 µg or 150 µg. At each dose level, subjects were randomized in a 3:1 ratio to receive either hCMV mRNA vaccine or placebo, administered in a 3-vaccination (0, 2, 6-month) schedule.

CMV-Seropositive Group

There are 24 subjects at each dose level in the CMV-seropostive group. Dose levels were 50 µg, 100 µg or 150 µg. At each dose level, subjects were randomized in a 3:1 ratio to receive either hCMV mRNA vaccine or placebo, administered in a 3-vaccination (0, 2, 6-month) schedule.

Screening Period

The Screening of each subject occurred during the first visit at the clinic. Screening may have occurred up to 28 days prior to Visit Day 1. The Screening visit may have been performed across 2 separate clinic visits.

Treatment Period

All subjects are administered three doses, at Visits Day 1, Day 56, and Day 168.

Estimated Study Duration

The study duration is approximately 18 months for each subject.

Sample Size

Approximately 252 subjects, including approximately 72 CMV-seropositive subjects and approximately 180 CMV-seronegative subjects were enrolled. The number of proposed subjects was considered sufficient to provide a descriptive summary of the safety and immunogenicity of different dose levels of hCMV mRNA vaccine. A total of 189 subjects received the hCMV mRNA vaccine.

Objectives and Endpoints

Primary Objectives

The primary objectives of the study are as follows:

1. To evaluate the safety of different dose levels of the hCMV mRNA vaccine administered in a 3-vaccination (0, 2, 6-month) schedule.

2. To evaluate neutralizing anti-CMV antibody responses against fibroblast and epithelial cell infection following vaccination with the hCMV mRNA vaccine at different dose levels administered in a 3-vaccination (0, 2, 6-month) schedule.

Secondary Objectives

The secondary objectives of the study are as follows:

1. To evaluate antigen-specific antibody responses following vaccination with the hCMV mRNA vaccine at different dose levels in a 3-vaccination schedule.

2. To evaluate the immunogenicity of the hCMV mRNA vaccine by CMV serostatus at enrollment.

Exploratory Objectives

The exploratory objectives of the study are as follows:

1. To evaluate cell-mediated immune responses following vaccination with the hCMV mRNA vaccine at different dose levels.

2. In CMV-seropositive subjects, to assess possible effects of immunologic response following vaccination with the hCMV mRNA vaccine compared to placebo.

Primary Endpoints

1. Solicited local and systemic ARs through 7 days after each vaccination.

2. Unsolicited AEs through 28 days after each vaccination.

3. Medically-attended adverse events (MAAEs) through 6 months after the last vaccination, and serious adverse events (SAEs) throughout the entire study period.

4. Geometric mean titer (GMT) of serum neutralizing anti-CMV antibodies against epithelial cell infection and against fibroblast infection, and associated geometric mean ratio (GMR) of post-baseline/baseline titers at each timepoint.

5. Proportion of subjects with ≥2-fold, 3-fold, and 4-fold increases in nAb over baseline against epithelial cell infection and against fibroblast infection at each timepoint.

Secondary Endpoints

1. GMT of anti-gB specific IgG and anti-Pentamer specific IgG as measured by enzyme-linked immunosorbent assay (ELISA), and associated GMR of post-baseline/baseline titers at each timepoint.

2. GMT, GMR, and proportion of subjects with ≥2-fold, 3-fold, and 4-fold increases over baseline of serum nAb against epithelial cell infection and against fibroblast infection at each timepoint, and GMT and GMR of antigen-specific IgG (ELISA) at each timepoint, in the CMV-seropositive group and in the CMV-seronegative group.

Exploratory Endpoints 1. gB- and Pentamer-specific interferon (IFN)-γ-secreting T-cells as measured by enzyme-linked immunospot (ELISpot) assay.

2. Exploratory assays to assess for anti-CMV immunologic response or for primary CMV infection may be performed at the discretion of the Sponsor.

Analyses

The following analyses are conducted

1. A 3-month interim analysis of safety and immunogenicity data collected from Visit Day 1 through Day 84 (Month 3) may be performed for each dose level. Available safety or immunogenicity data up to Day 196 (Month 7) may also be summarized as part of these interim analyses. This analysis serves as the basis for selection of the hCMV mRNA vaccine dose level for subsequent trials.

2. A 7-month interim analysis of safety and immunogenicity data collected from Visit Day 1 through Day 196 (Month 7) may be performed for each dose level. Available safety or immunogenicity data up to Day 336 (Month 12) may also be summarized as part of these interim analyses.

3. The final unblinded analysis of safety and immunogenicity data collected from Visit Day 1 through the end of the trial.

Immunogenicity Assessments

Serum neutralizing anti-CMV antibody titers against epithelial cell infection on Day 1, Day 29, Day 56, Day 84, Day 168, Day 196, Day 336, and Day 504, and GMR of post-baseline/baseline titers.

Serum neutralizing anti-CMV antibody titers against fibroblast infection on Day 1, Day 29, Day 56, Day 84, Day 168, Day 196, Day 336, and Day 504, and GMR of post-baseline/baseline titers.

Proportion of subjects with ≥2-fold, 3-fold, and 4-fold increases in nAb against epithelial cell infection on Day 29, Day 56, Day 84, Day 168, Day 196, Day 336, and Day 504, compared with Day 1.

Proportion of subjects with ≥2-fold, 3-fold, and 4-fold increases in nAb against fibroblast infection on Day 29, Day 56, Day 84, Day 168, Day 196, Day 336, and Day 504, compared with Day 1.

Proportion of subjects with nAb against epithelial cell infection above nAb titers associated with natural CMV infection at Day 1, Day 29, Day 56, Day 84, Day 168, Day 196, Day 336, and Day 504.

Proportion of subjects with nAb against fibroblast infection above nAb titers associated with natural CMV infection at Day 1, Day 29, Day 56, Day 84, Day 168, Day 196, Day 336, and Day 504.

GMT of anti-gB IgG as measured by ELISA on Day 1, Day 29, Day 56, Day 84, Day 168, Day 196, Day 336, and Day 504, and GMR of post-baseline/baseline titers.

GMT of anti-Pentamer IgG as measured by ELISA on Day 1, Day 29, Day 56, Day 84, Day 168, Day 196, Day 336, and Day 504, and GMR of post-baseline/baseline titers.

Figure 13:
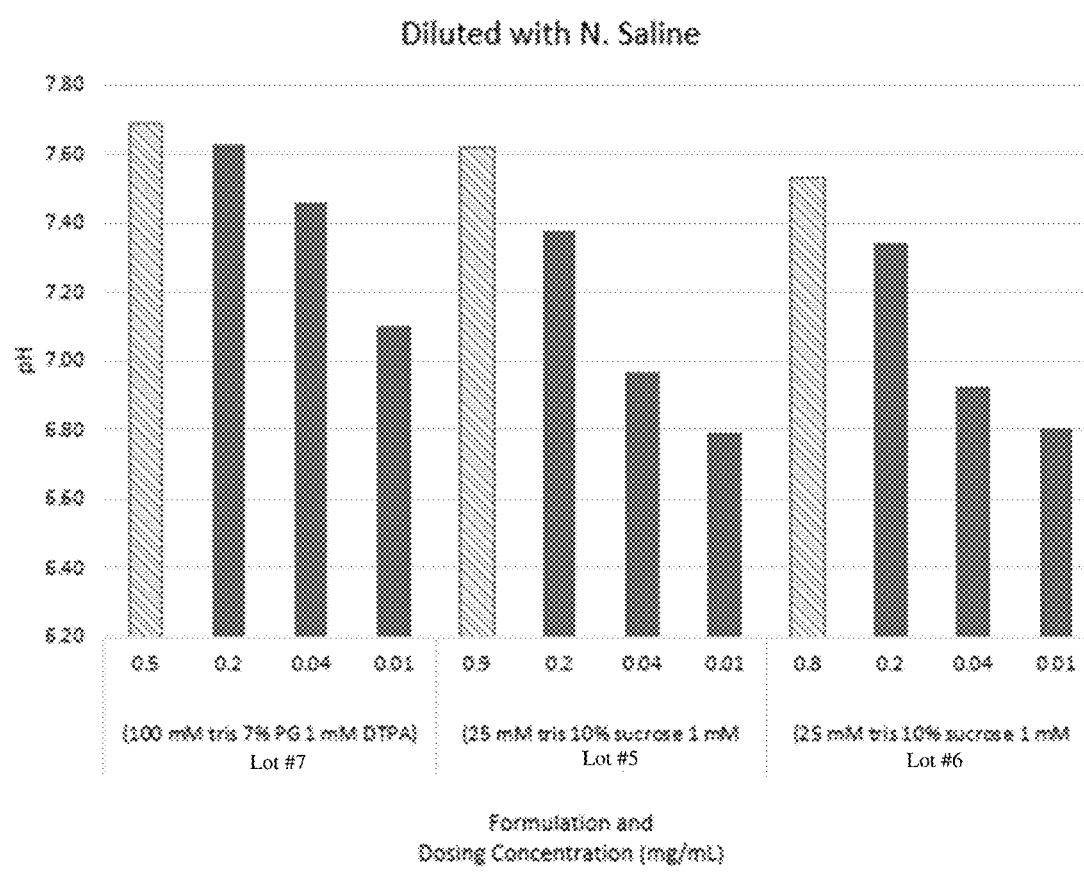
FIG. 13 provides a graph showing a pH shift with high dilutions for lyophilized formulations dose prepared with normal saline (*N. saline*). Commercial USP normal saline has a pH range of 4.5-7.0. and the measured pH of the normal saline is 6.3.

Example 4: Evaluation of Immunogenicity, In Vitro Expression and Analytics Characterization of Phase II Process The immunogenicity, in vitro expression of the hCMV antigens, and analytics characterization of the Phase II process was evaluated at 0.4 g and 1 g scale with lyophilized hCMV RNA vaccine based on molar ratio, and compared with a 0.03 g scale liquid formulation. Lyophilized formulations were prepared with normal Saline (having a measured pH of 6.3) at different doses. A pH shift in the diluted formulations is shown in FIG. 13.

Figure 14A:
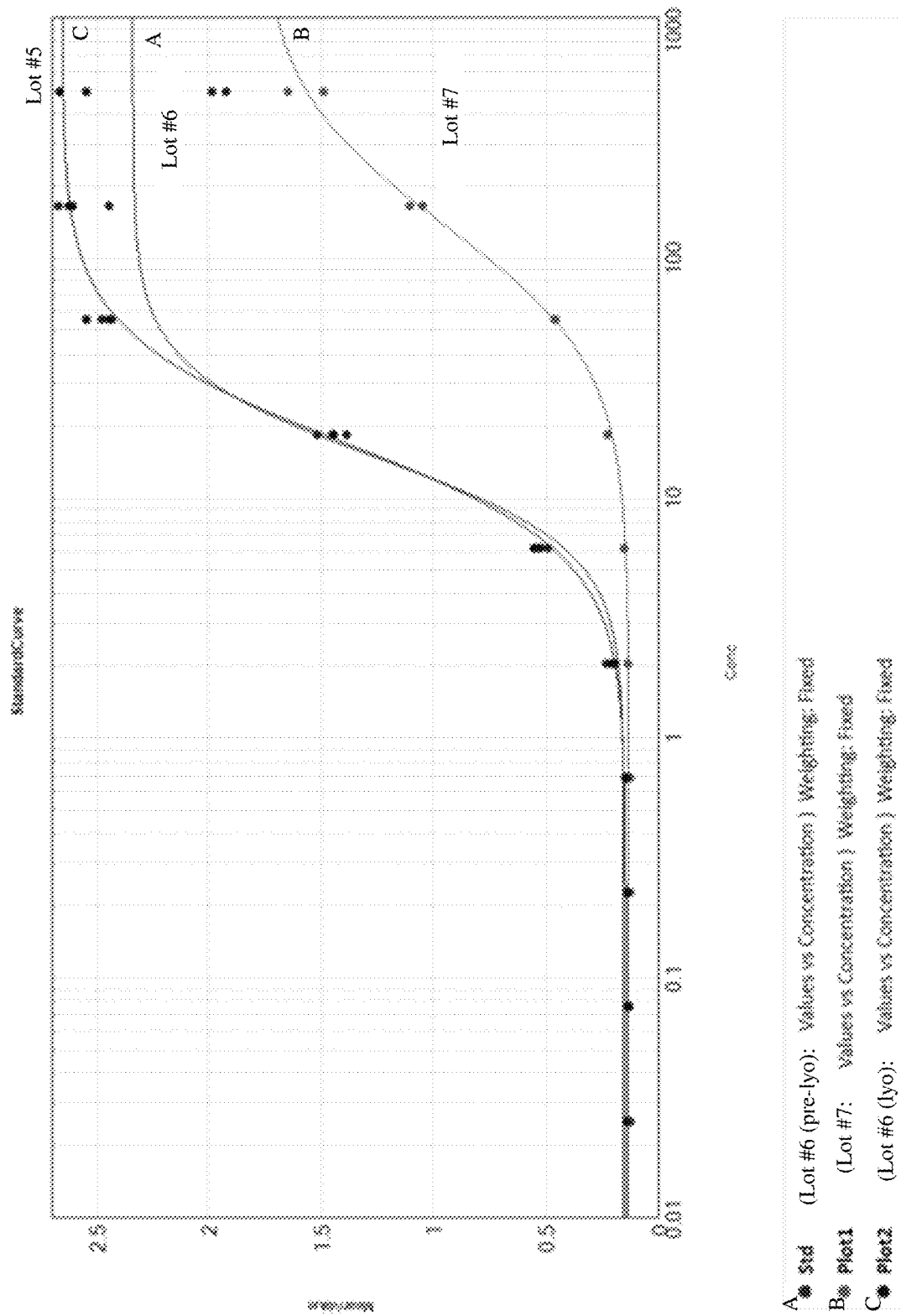
FIGS. 14A-14B provide graphs showing that the two formulations based on molar ratio increase the expression level of the hCMV pentamer and hCMV gB in vitro.
Figure 14B:
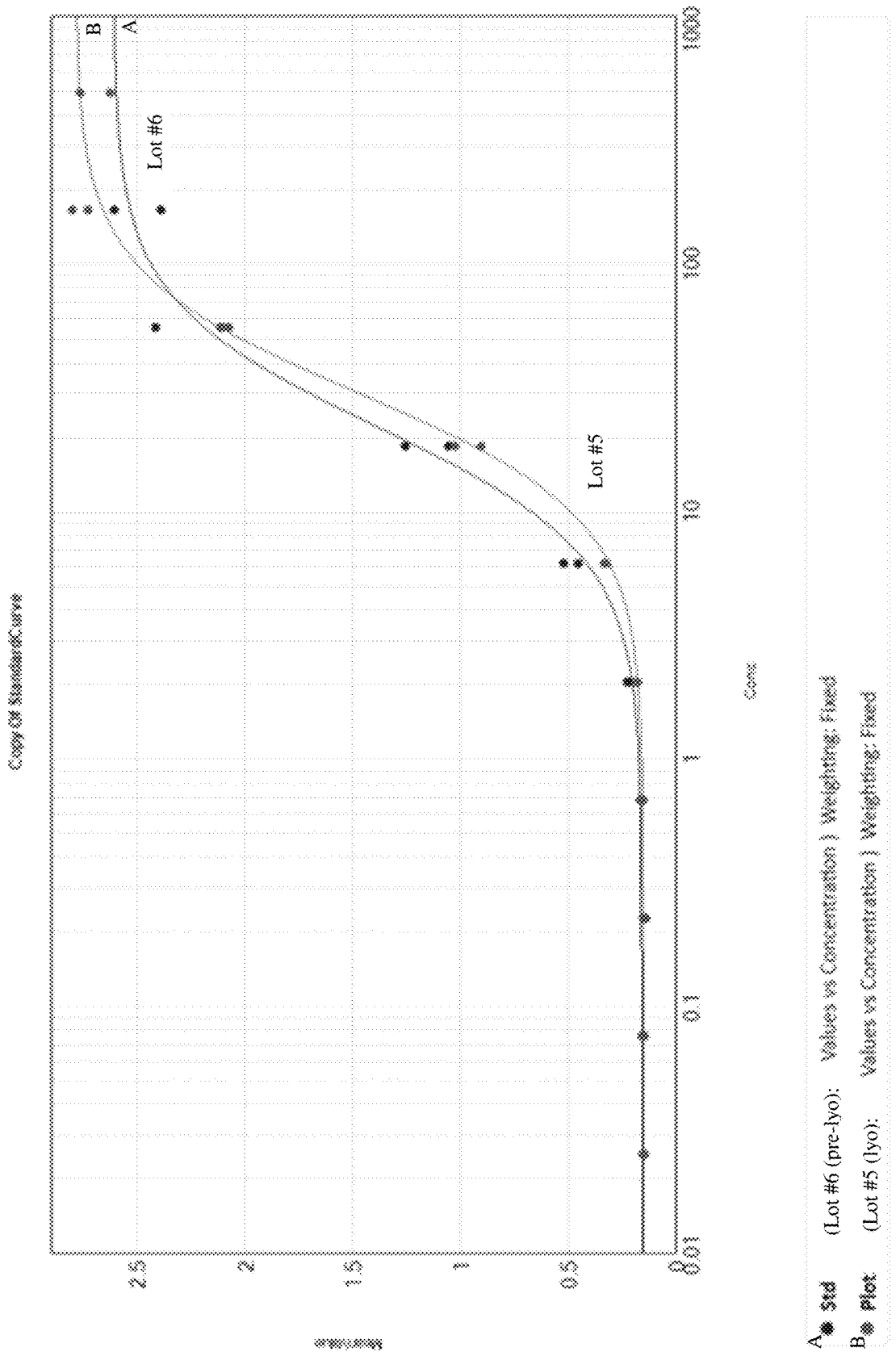

The in vitro expression levels of the hCMV pentamer and hCMV gB were evaluated for two lyophilized formulations (0.4 g and 1 g scale) based on molar ratios of the mRNA components, and a liquid formulation based on equal mass ratios (0.03 g scale). Lyophilized formulations at 0.4 g or 1 g scale resulted in higher in vitro expression of pentamer proteins compared to the 0.03 g scale liquid formulation (FIGS. 14A-14C).

Figure 15A:
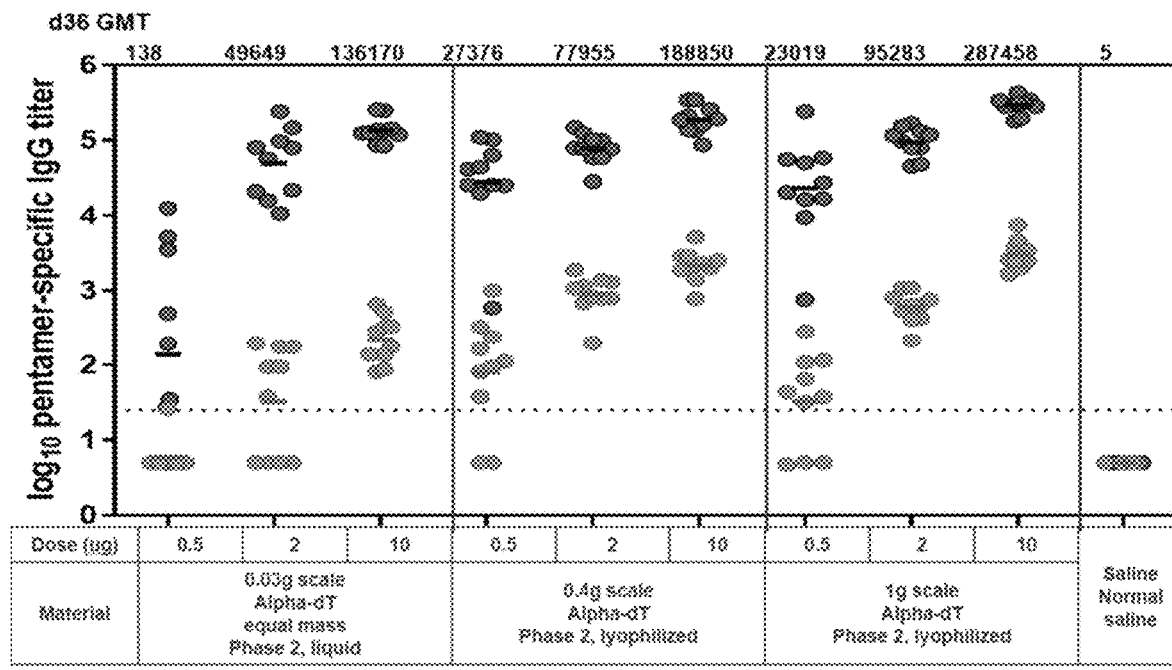
FIGS. 15A-15B provide graphs showing dose responses of anti-gB antibodies and anti-pentamer antibodies in mice for two formulations based on molar ratios of the mRNA components (0.4 g and 1 g scale) compared to equal mass ratios (0.03 g scale).
Figure 15B:
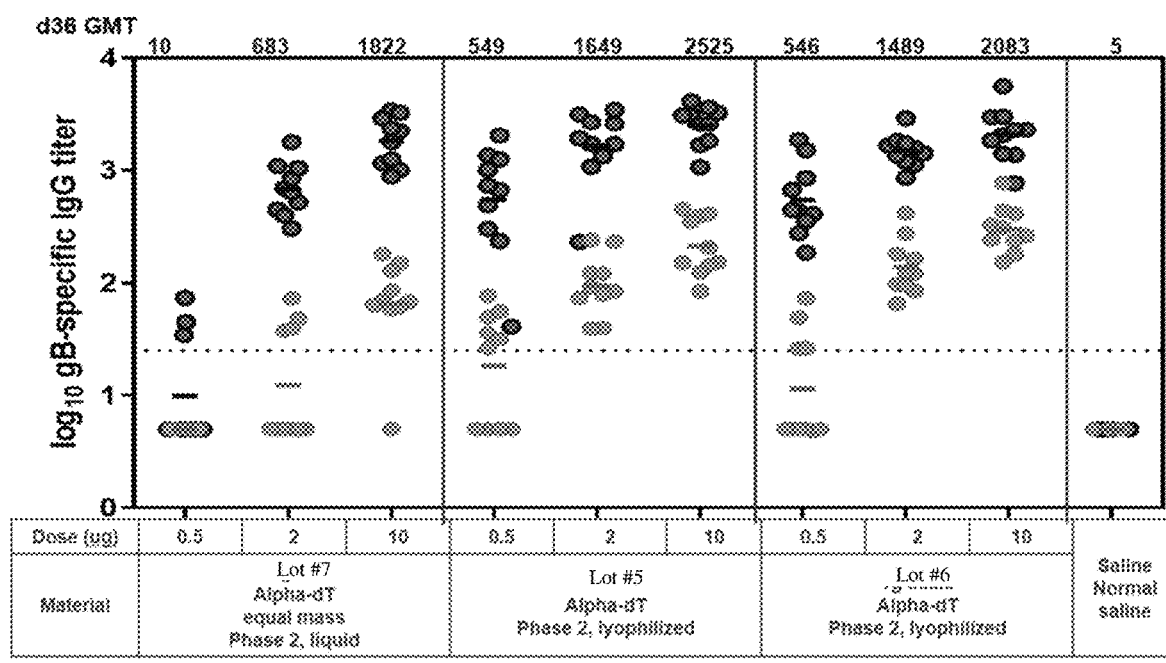

Anti-pentamer IgG titers 21 or 36 days post immunization are shown in FIG. 15A, and anti-gB IgG titers 21 or 36 days post immunization are shown in FIG. 15B. The lyophilized formulations at 0.4 g and 1 g scale resulted in higher (15-20 fold) titers of pentamer-specific and gB-specific IgG compared to the equal mass liquid formulation at 0.03 g scale at 0.5 µg dose. The immune responses from the groups receiving the 1 g scale were comparable to the responses from the 0.4 g scale.

Figure 16A:
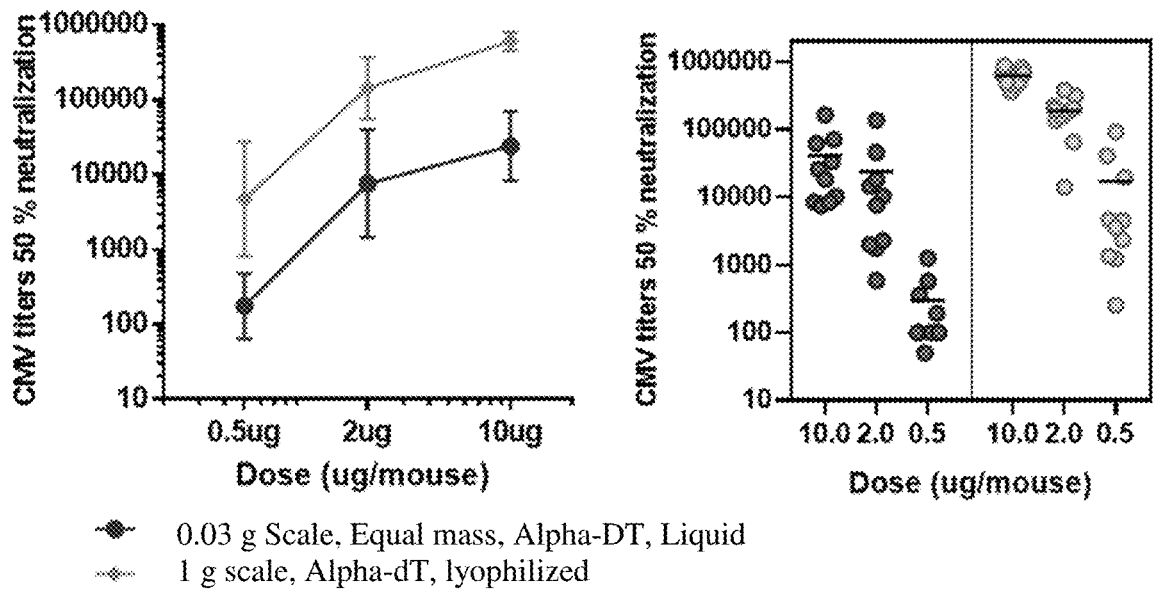
FIGS. 16A-16B provide graphs comparing CMV neutralizing antibody titers elicited by different formulations from different manufacturing batches using either 0.03 g versus 1.0 g scale In Vitro Transcription (IVT) manufacture of mRNA.
Figure 16B:
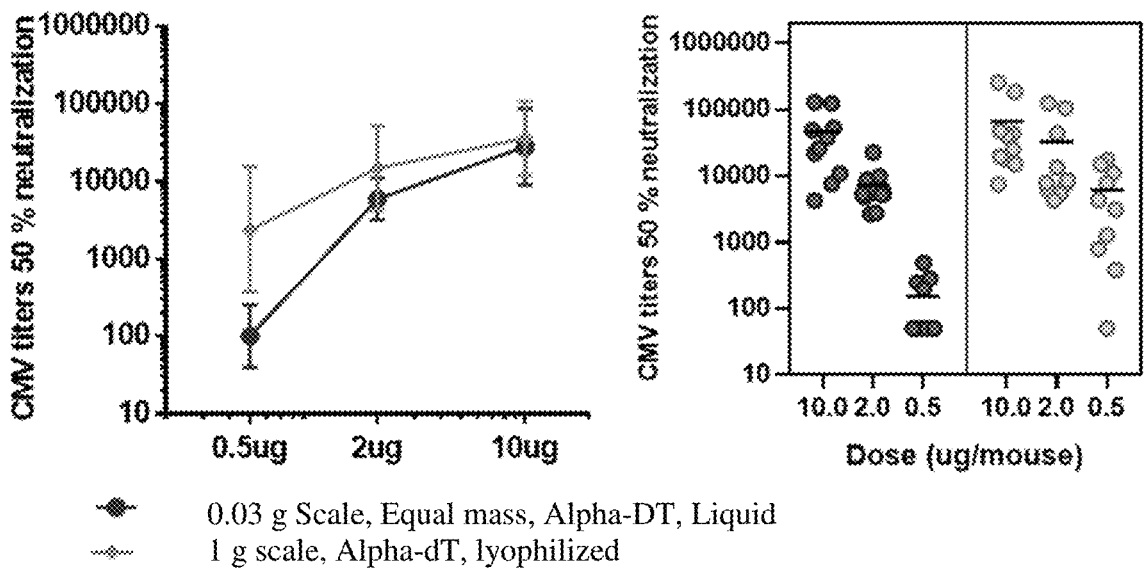

CMV neutralization titers were conducted comparing large scale (1 g) lyophilized formulation with small scale (0.03 g) liquid formulation. The neutralization titers against CMV virus resulted in 26-fold higher using the lyophilized formulation based on molar ratio, compared to the equal mass ratio liquid formulation (FIGS. 16A and 16B).

Example 5: Evaluation of Immunogenicity 1 Month Post-$2^{nd}$ Vaccination in Phase II Study This Example describes results from the 3-month (1-month post-2nd vaccination) interim analysis of immunogenicity of the hCMV mRNA vaccine.

Immunogenicity in CMV-seronegative and CMV-seropositive participants was measured as neutralizing antibody (nAb) responses against epithelial cell infection (a measure of immune response to pentamer antigen) and nAb responses against fibroblast infection (a measure of immune response to gB antigen). Results were summarized by mean, median, min, max, geometric mean titer (GMT), geometric mean ratio (GMR) with respect to baseline, and corresponding 95% confidence intervals for GMT and GMR.

A microneutralization assay for measurement of nAb against epithelial cell infection utilized CMV isolate VR1814 and ARPE-19 cells. A microneutralization assay for measurement of nAb against fibroblast infection utilized CMV isolate AD169 and HEL299 cells.

Baseline Neutralizing Antibody

In CMV-seronegative participants, nAb GMTs against epithelial cell infection and against fibroblast infection at Baseline (prior to the first vaccination) were below the lower limit of quantitation (LLOQ) (reported as 8, representing 0.5×LLOQ) in all treatment groups. This is indicative of the absence of CMV infection prior to immunization.

In CMV-seropositive participants (n=46), the Baseline GMT of nAb against cell infection was 3,924 (95% CI: 2,249, 6,845) and the Baseline GMT of nAb against fibroblast infection was 3,955 (95% CI: 2,197, 7,119). These values represent the nAb GMTs of naturally-acquired immunity for this per-protocol set and a benchmark against which immune responses in the CMV-seronegative group were compared.

Neutralizing Antibody (nAb) Responses

Figure 17:
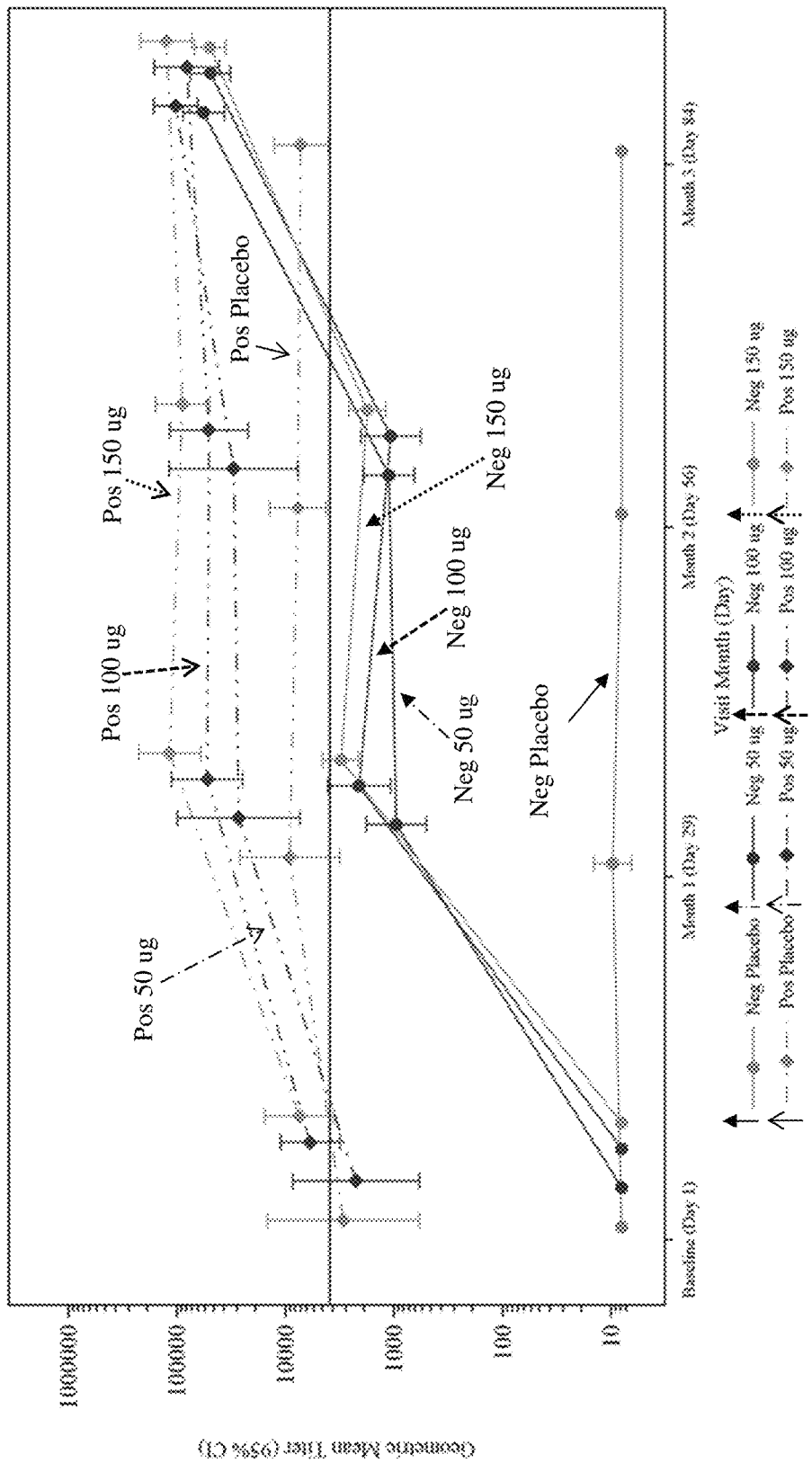
FIG. 17 shows neutralizing antibody titers against epithelial cell infection through month 3 (1 month after the second vaccination) in a Phase II trial, by CMV serostatus and vaccination group, per-protocol set for antibody-mediated immunogenicity. Neg: CMV-seronegative, Pos: CMV-seropositive. 50 μg, 100 μg, and 150 μg refer to the dose of mRNA vaccine. Confidence intervals (CIs) were calculated using t-distribution of the log transformed values. The solid black reference line indicates the baseline GMT of all CMV seropositive subjects at baseline.

In CMV-seronegative participants, neutralizing antibodies against epithelial cell infection (FIG. 17) increased in a dose-related manner after the $1^{st}$ vaccination to GMTs at Month 1 (1 month after $1^{st}$ vaccination) of 955 (95% CI 503, 1,814); 2,100 (95% CI 1,074, 4,110); and 3,109 (95% CI 2,116, 4,568) in the 50 µg, 100 µg, and 150 µg treatment groups, respectively (Table 1). Within each mRNA treatment group, nAb against epithelial cell infection increased further after the 2nd vaccination to GMTs exceeding the seropositive benchmark GMT in all treatment groups, with GMTs at Month 3 (1 month after the 2nd vaccination) of 57,028 (95% CI 36,725, 88,554); 49,302 (95% CI 32,141, 75,627); and 49,706 (95% CI 35,792, 69,029) in the 50 µg, 100 µg, and 150 µg treatment groups, respectively (Table 1).

Figure 18:
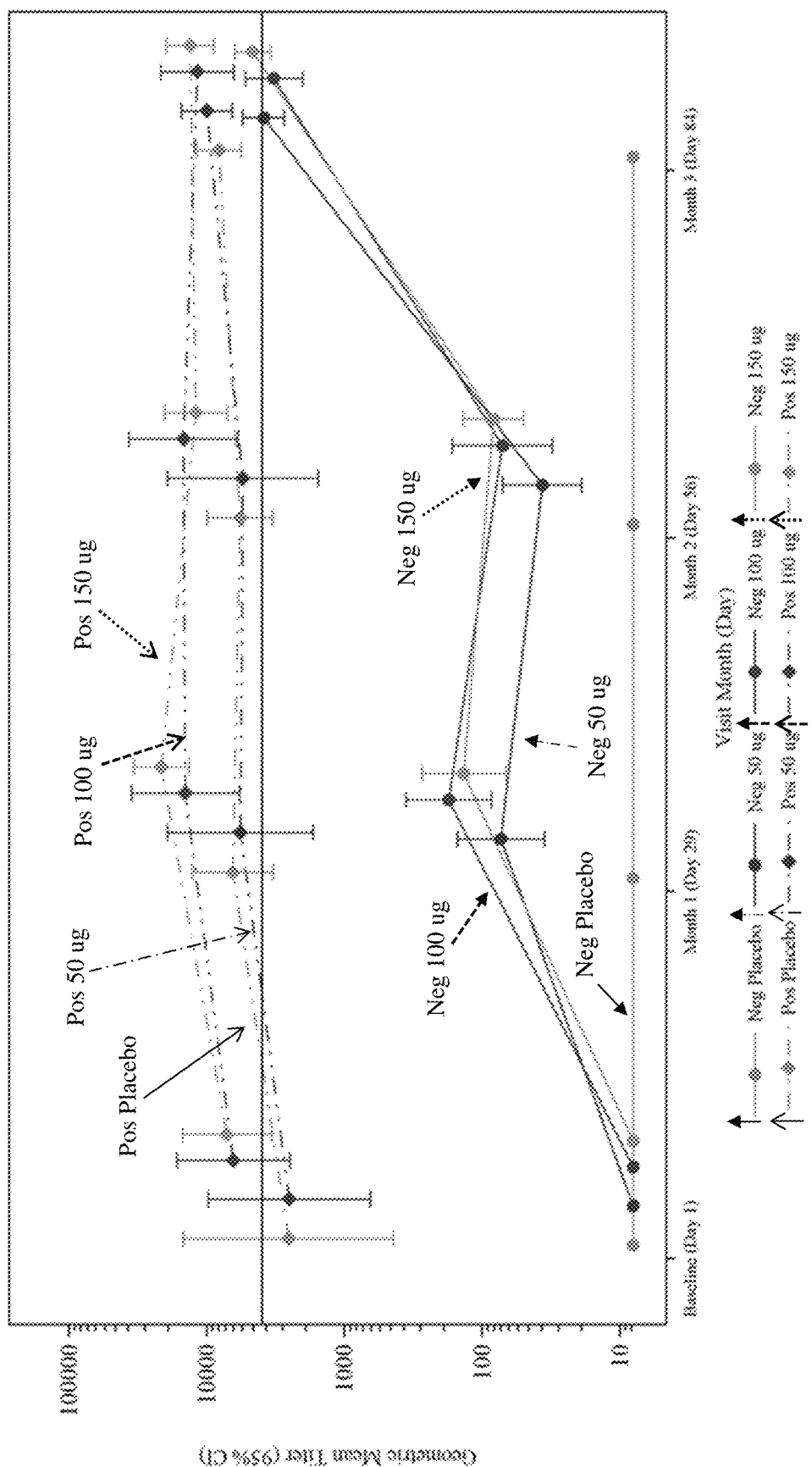
FIG. 18 shows neutralizing antibody titers against fibroblast infection through month 3 (1 month after the second vaccination) in a Phase II trial, by CMV serostatus and vaccination group, per-protocol set for antibody-mediated immunogenicity. Neg: CMV-seronegative, Pos: CMV-seropositive. 50 μg, 100 μg, and 150 μg refer to the dose of mRNA vaccine. Confidence intervals (CIs) were calculated using t-distribution of the log transformed values. The solid black reference line indicates the baseline GMT of all CMV seropositive subjects at baseline.

In CMV-seronegative participants, neutralizing antibodies against fibroblast infection (FIG. 18) increased after the 1st vaccination to GMTs at Month 1 (1 month after the 1st vaccination) of 73 (95% CI 35, 151), 175 (95% CI 86, 356), and 136 (95% CI 68, 272) in the 50 µg, 100 µg, and 150 µg treatment groups, respectively (Table 1). Within each mRNA treatment group, nAb against fibroblast infection increased further after the 2nd vaccination to GMTs approaching or exceeding the seropositive benchmark GMT in all treatment groups, with GMTs at Month 3 (1 month after the 2nd vaccination) of 3,856 (95% CI 2,726, 5,455); 3,242 (95% CI 2,009, 5,233); and 4,638 (95% CI 3,417, 6,296) in the 50 µg, 100 µg, and 150 µg treatment groups, respectively (Table 1).

TABLE 1

Neutralizing Antibody Responses in CMV-Seronegative Participants

CMV-seronegative
Neutralizing Antibodies Against Epithelial Cell Infection
(P202 seropositive cohort baseline GMT = 3,914)

|  | Placebo<br>N = 29 | 50 μg<br>N = 30 | 100 μg<br>N = 23 | 150 μg<br>N = 32 | Total mRNA<br>N = 85 |
|---|---|---|---|---|---|
| GMT Baseline | 8 | 8 | 8 | 8 | 8 |
|  | n = 29 | n = 32 | n = 23 | n = 32 | n = 85 |
| GMT Month 1 | 9.7 | 955 | 2,100 | 3,109 | 1,821 |
| 95% CI | n = 28 | n = 30 | n = 23 | n = 30 | n = 83 |
|  | — | 503; 1,814 | 1,074; 4,110 | 2,116; 4,568 | 1350; 2540 |
| GMT Month 2 | 8 | 1,115 | 1,076 | 1,773 | 1,321 |
| 95% CI | n = 29 | n = 29 | n = 22 | n = 32 | n = 83 |
|  | — | 503; 1,814 | 1,074; 4,110 | 2,116; 4,568 | 8; 32,736 |
| GMT Month 3 | 8 | 57,028 | 49,302 | 49,706 | 52,095 |
| 95% CI | n = 29 | n = 30 | n = 22 | n = 32 | n = 84 |
|  | — | 36,725; 88,554 | 32,141; 75,627 | 35,792; 69,029 | 41,773; 64,967 |
| GMT/CMV-seropositive baseline Month 3 | — | 15.7 | 13.4 | 12.7 | 13.3 |

CMV-seronegative
Neutralizing Antibodies Against Fibroblast Infection
(P202 seropositive cohort baseline GMT = 3,955)

|  | Placebo<br>N = 29 | 50 μg<br>N = 30 | 100 μg<br>N = 23 | 150 μg<br>N = 32 | Total mRNA<br>N = 85 |
|---|---|---|---|---|---|
| GMT baseline | 8 | 8 | 8 | 8 | 8 |
|  | n = 29 | n = 30 | n = 23 | n = 32 | n = 85 |
| GMT Month 1 | 8 | 73 | 175 | 136 | 116 |
| 95% CI | n = 28 | n = 30 | n = 23 | n = 30 | n = 83 |
|  | — | 35, 151 | 86, 356 | 68, 272 | 78; 174 |
| GMT Month 2 | 8 | 37 | 71 | 83 | 60 |
| 95% CI | n = 29 | n = 29 | n = 22 | n = 32 | n = 83 |
|  | — | 19; 71 | 31;166 | 50; 137 | 42; 86 |
| GMT Month 3 | 8 | 3,856 | 3,242 | 4,638 | 3953 |
| 95% CI | n = 29 | n = 30 | n = 22 | n = 32 | n = 84 |
|  | — | 2,726; 5,455 | 2,009; 5,233 | 3,417; 6,296 | 3223; 4849 |
| GMT/CMV-seropositive baseline Month 3 | — | 1.0 | 0.8 | 1.2 | 1.0 |

N = number of subjects in treatment group;
n = number of subjects with non-missing data at corresponding timepoint;
GMT = Geometric Mean Titer;
GMR = Geometric Mean Ration (post-baseline/baseline titers);
CI = Confidence intervals.

In CMV-seropositive participants, neutralizing antibodies against epithelial cell infection (FIG. 17) boosted in a dose-related manner after the 1 st vaccination to GMTs at Month 1 (1 month after the 1st vaccination) of 27,062 (95% CI 7,392, 99,073); 52,989 (95% CI 24,882,112,847); and 116,899 (95% CI 60,899, 224,392) with corresponding GMRs of 12.0, 8.9, and 15.6 in the 50 μg, 100 μg, and 150 μg treatment groups, respectively (Table 2). Within each mRNA treatment group, nAb against epithelial cell infection was boosted further after the 2nd vaccination to GMTs at Month 3 (1 month after the 2nd vaccination) of 102,850 (95% CI 64,178, 164,826); 81,111 (95% CI 40,570, 162, 167); and 126,075 (95% CI 73,077, 217,509) with corresponding GMRs of 51.4, 13.7, and 16.9 in the 50 μg, 100 μg, and 150 μg treatment groups, respectively (Table 2).

In CMV-seropositive participants, neutralizing antibodies against fibroblast infection (FIG. 18) boosted in a dose-related manner after the 1st vaccination to GMTs at Month 1 (1 month after the 1st vaccination) of 5,686 (95% CI 1,680, 19,252); 14,251 (95% CI 5,790, 35,077); and 21,341 (95% CI 13,468, 33,817 with corresponding GMRs of 2.3, 2.2, and 3.0 in the 50 μg, 100 μg, and 150 μg treatment groups, respectively (Table 2). Within each mRNA treatment group, nAb against fibroblast infection was boosted further after the 2nd vaccination to GMTs at Month 3 (1 month after the 2nd vaccination) of 9,970 (95% CI 6,487, 15,325); 11,652 (95% CI 6,323, 21,475); and 13,208 (95% CI 8,875, 19,657) with corresponding GMRs of 4.4, 1.8, and 1.9 in the 50 μg, 100 μg, and 150 μg treatment groups, respectively (Table 2).

TABLE 2

Neutralizing Antibody Responses in CMV-Seropositive Participants

CMV-seropositive
Neutralizing Antibodies Against Epithelial Cell Infection
(P202 seropositive cohort baseline GMT = 3,924)

|  | Placebo<br>N = 10 | 50 µg<br>N = 15 | 100 µg<br>N = 10 | 150 µg<br>N = 11 | Total mRNA<br>N = 36 |
|---|---|---|---|---|---|
| GMT Baseline | 2,938 | 2,250 | 5,935 | 7,480 | 4,252 |
| 95% CI | n = 10 | n = 15 | n = 10 | n = 11 | n = 36 |
|  | 589; 14,664 | 589; 8,591 | 3,159; 11,150 | 3,600; 15,542 | 2,325; 7,778 |
| GMT Month 1 | 9,157 | 27,062 | 52,989 | 116,889 | 51,002 |
| 95% CI | n = 9 | n = 15 | n = 10 | n = 11 | n = 36 |
|  | 3,157; 26,560 | 7,392; 99,073 | 24,882; 112,847 | 60,889; 224,392 | 27,998; 92,906 |
| GMT Month 2 | 27,677 | 30,228 | 51,008 | 88,939 | 48,545 |
| 95% CI | n = 10 | n = 15 | n = 9 | n = 11 | n = 35 |
|  | 4,204; 14,019 | 7,730;118,211 | 22,109;117,682 | 50,343; 157,126 | 26,247; 89,785 |
| GMT Month 3 | 7,245 | 102,850 | 81,111 | 126,075 | 102,455 |
| 95% CI | n = 10 | n = 14 | n = 10 | n = 11 | n = 35 |
|  | 4121; 12736 | 64,178; 164,826 | 40,570; 162,167 | 73,077; 177,509 | 76,439; 137,325 |
| GMR Month 1 | 3.3 | 12.0 | 8.9 | 15.6 | 12.0 |
| 95% CI | 0.7,16.4 | 7.3,19.8 | 4.8,16.7 | 6.0,41.1 | 8.3,17.3 |
| GMR Month 2 | 2.6 | 13.4 | 8.7 | 11.9 | 11.6 |
| 95% CI | 0.7, 10.3 | 7.6, 23.9 | 3.7, 20.2 | 6.1, 23.3 | 8.1, 16.5 |
| GMR Month 3 | 2.5 | 51.4 | 13.7 | 16.9 | 24.8 |
| 95% CI | 0.6; 10.2 | 13.3; 198.9 | 6.6; 28.3 | 9.2; 31.0 | 13.7; 44.9 |

CMV-seropositive
Neutralizing Antibodies Against Fibroblast Infection
(P202 seropositive cohort baseline GMT = 3,955)

|  | Placebo<br>N = 10 | 50 µg<br>N = 15 | 100 µg<br>N = 10 | 150 µg<br>N = 11 | Total mRNA<br>N = 36 |
|---|---|---|---|---|---|
| GMT Baseline | 2,545 | 2,507 | 6,377 | 7,117 | 4,470 |
| 95% CI | n = 10 | n = 15 | n = 10 | n = 11 | n = 36 |
|  | 440; 14,733 | 651; 9,655 | 2,484; 16,371 | 3,368; 15,039 | 2,391; 8,356 |
| GMT Month 1 | 6,452 | 5,686 | 14,251 | 21,341 | 10,994 |
| 95% CI | n = 9 | n = 15 | n = 10 | n = 11 | n = 36 |
|  | 3,276; 12,705 | 1,680; 19,252 | 5,790; 35,077 | 13,468; 33,817 | 6,225; 19,417 |
| GMT Month 2 | 5,710 | 5,449 | 14,735 | 11,983 | 9,015 |
| 95% CI | n = 10 | n = 15 | n = 9 | n = 11 | n = 35 |
|  | 3,301; 9,879 | 1,548; 19,182 | 5,913; 36.716 | 7,109; 20,199 | 5,054; 16,081 |
| GMT Month 3 | 8,138 | 9,970 | 11,652 | 13,208 | 11,388 |
| 95% CI | n = 10 | n = 14 | n = 9 | n = 11 | n = 35 |
|  | 5,610; 11,808 | 6,487; 15,325 | 6,323; 21,475 | 8,875; 19,657 | 3,223; 4,849 |
| GMR Month 1 | 3.1 | 2.3 | 2.2 | 3.0 | 2.5 |
| 95% CI | 0.6, 14.9 | 1.4, 3.7 | 1.3, 3.9 | 1.7, 5.4 | 1.9, 3.3 |
| GMR Month 2 | 2.2 | 2.2 | 2.1 | 1.7 | 2.0 |
| 95% CI | 0.6, 8.8 | 1.4, 3.3 | 1.3, 3.4 | 1.0, 2.7 | 1.6, 2.5 |
| GMR Month 3 | 3.2 | 4.4 | 1.8 | 1.9 | 2.6 |
| 95% CI | 0.7; 14.5 | 1.3; 14.9 | 1.1; 3.1 | 1.1; 3.1 | 1.6; 4.4 |

N = number of subjects in treatment group;
n = Number of subjects with non-missing data at corresponding timepoint GMT = Geometric Mean Titer;
GMR = Geometric Mean Ration (post-baseline/baseline titers);
CI = Confidence intervals Immunogenicity Conclusions
CMV-Seronegative Participants
(a) Neutralizing antibodies against epithelial cell infection (a measure of immune response to intact CMV pentamer antigen) increased in a generally dose-related manner after the $1^{st}$ vaccination (Month 1). After the $2^{nd}$ vaccination (Month 3), nAb GMTs against epithelial cell infection were boosted to at least 12-fold over the baseline GMT of CMV-seropositive participants (a measure of previous naturally-acquired CMV infection). The Month 3 nAb GMTs against epithelial cell infection in the 50 gg, 100 µg, and 150 µg treatment groups were generally numerically similar.
(b) Neutralizing antibodies against fibroblast infection (a measure of immune response to CMV gB antigen) did not show an appreciable increase after the $1^{st}$ vaccination (Month 1). After the $2^{nd}$ vaccination (Month 3), nAb against fibroblast infection were boosted to GMTs generally equivalent to the baseline GMT in CMV-seropositive participants (a measure of previous naturally-acquired CMV infection). The Month 3 GMTs in the 50 µg, 100 µg, and 150 µg treatment groups were generally numerically similar.

CMV-Seropositive Participants
(a) Baseline nAb GMTs against epithelial cell infection varied across treatment groups, and GMTs generally increased in the Placebo treatment group between baseline and Month 3. Within each hCMV mRNA vaccine treatment group, nAb GMTs against epithelial cell infection boosted to levels at least 8-fold over the respective baseline GMT after the $1^{st}$ vaccination (Month 1), and to GMTs at least 13-fold to greater than 51-fold over the respective baseline GMT after the $2^{nd}$ vaccination (Month 3). A dose-related GMR response after either the $1^{st}$ or $2^{nd}$ vaccinations was not apparent.

(b) Baseline nAb GMTs against fibroblast infection varied across treatment groups, and GMTs generally increased in the Placebo treatment group between baseline and Month 3. Within each hCMV mRNA vaccine treatment group, nAb GMTs against fibroblast infection boosted to levels at least 2-fold over the respective baseline GMT after the 1$^{st}$ and 2$^{nd}$ vaccinations (Month 1 and Month 3), but due to the increasing nAb GMTs in the Placebo treatment group, there was no notable increase in GMR compared to Placebo after either vaccination. A dose-related GMR response across the mRNA treatment groups compared to the Placebo treatment group was not apparent.

Solicited Safety

Solicited adverse reactions (AR) post 1$^{st}$ vaccination were recorded (Table 3). Injection site pain was the most commonly reported solicited local adverse reaction. The most common solicited systemic ARs were headache, fatigue, and myalgia in both CMV-seronegative and CMV-seropositive treatment groups. No serious adverse events (SAEs) were reported. No unsolicited events leading to study discontinuation occurred.

TABLE 3

Solicited adverse reactions (AR) post 1$^{st}$ vaccination

| | | CMV-seronegative | | | | CMV-seropositive | | | |
|---|---|---|---|---|---|---|---|---|---|
| | | Placebo N = 30 | 50 µg N = 31 | 100 µg N = 24 | 150 µg N = 32 | Placebo N = 12 | 50 µg N = 15 | 100 µg N = 10 | 150 µg N = 11 |
| Local ARs | Pain | 4/30 (13%) | 26/31 (84%) | 23/24 (96%) | 29/32 (91%) | 3/12 (25) | 12/15 (80%) | 8/10 (80%) | 7/11 (64%) |
| | | — | — | 2 (8) | 2 (6) | — | 2 (13) | — | — |
| | Redness | — | 1/31 (3) | — | 3/32 (9) | — | — | — | 1/11 (9) |
| | Swelling (injection site) | — | 1/31 (3) | — | 2/32 (6) | — | — | — | 1/11 (9) |
| | Swelling (Axillary) | — | 1/31 (3) | 8/24 (33) | 4/32 (13) | 2/12 (17) | 1/15 (7) | — | 3/11 (27) |
| Most common systemic ARs | Fever | — | — | — | 1/32 (3) | | | | 3/11 (27) |
| | | | | | | | | | 1 (9) |
| | Headache | 10/30 (33) | 7/31 (23) | 10/24 (42) | 10/32 (31) | 4/12 (33) | 7/15 (47) | 4/10 (4) | 6/11 (55) |
| | | 2 (7) | — | — | — | — | — | — | — |
| | Fatigue | 9/30 (30) | 9/31 (29) | 8/24 (33) | 14/32 (44) | 3/12 (25) | 11/15 (73) | 4/10 (40) | 4/11 (27) |
| | | 1 (3) | — | — | — | — | 2 (13) | — | — |
| | Myaigla | 4/30 (13) | 2/31 (7) | 6/24 (25) | 11/32 (34) | 1/12 (8) | 8/15 (53) | 5/10 (5) | 6/11 (55) |
| | | 2 (7) | — | — | — | — | 3 (20) | — | — |
| | Arthralgia | 2/30 (7) | — | 3/24 (13) | 5/32 (16) | 1/12 (8) | 7/15 (47) | 4/10 (40) | 2/11 (18) |
| | | 2 (7) | — | — | — | — | — | — | — |
| | Nausea | 3/30 (10) | 2/31 (7) | 1/24 (4) | 2/32 (6) | — | 4/15 (27) | 1/10 (10) | 1/11 (9) |
| | | 1 (3) | — | — | — | — | — | — | — |
| | Chills | 3/30 (10) | 3/31 (10) | 4/24 (7) | 5/32 (6) | — | 6/15 (40) | 2/10 (2) | 4/11 (26) |
| | | 1 (3) | — | — | — | — | — | — | — |
| | Rash | 2/30 (7) | 2/31 (7) | 3/24 (13) | 1/32 (3) | 3/12 (25) | 2/15 (13) | — | 1/11 (9) |

Values represent n (%) participants reporting each AR, bold text = grade 3 ARs

Solicited adverse reactions post $2^{st}$ vaccination were recorded (Table 4). After the $2^{nd}$ vaccination, the rate and severity distribution of solicited ARs in the CMV-seronegative and CMV-seropositive treatment groups were generally similar.

TABLE 4

Solicited adverse reactions (AR) post $2^{nd}$ vaccination

| | | CMV Serostatus at Baseline | | | | | | | |
|---|---|---|---|---|---|---|---|---|---|
| | | CMV-seronegative | | | | CMV-seropositive | | | |
| | | Placebo N = 30 | 50 µg N = 31 | 100 µg N = 24 | 150 µg N = 32 | Placebo N = 12 | 50 µg N = 15 | 100 µg N = 10 | 150 µg N = 11 |
| Local ARs | Pain | 5/30 (17%) | 28/31 (90%) 2 (7) | 23/24 (96%) | 30/32 (94%) | — | 13/15 (80%) 1 (7) | 7/10 (70%) | 8/11 (64%) 1 (9) |
| | Redness | — | — | 2/24 (8) | 5/32 (16) 1 (3) | — | — | — | 2/11 (18) 1 (9) |
| | Swelling (injection site) | — | — | 1/24 (4) | 5/32 (16) 1 (6) | — | 2/15 (13) | — | 1/11 (9) |
| | Swelling (Axillary) | 1 (3) | 4/31 (13) | 7/24 (29) | 6/32 (19) | — | 3/15 (20) | 2/10 (20) | 2/11 (18) |
| Most common systemic ARs | Fever | — | 1 (3) | — | 3/32 (9) | — | — | — | 2/11 (18) 1 (9) |
| | Headache | 11/30 (37) | 14/31 (45) 2 (7) | 13/24 (54) 3 (13) | 17/32 (53) | 6/12 (50) 2 (17) | 9/15 (60) | 5/10 (50) | 4/11 (36) 1 (9) |
| | Fatigue | 7/30 (23) | 14/31 (45) 1 (3) | 9/24 (38) 1 (4) | 17/32 (53) 2 (6) | 2/12 (17) | 11/15 (73) 1 (7) | 3/10 (30) | 7/11 (63) 1 (9) |
| | Myaigla | 1/30 (3) | 16/31 (52) 2 (7) | 12/24 (50) 2 (8) | 15/32 (47) 3 (9) | 1/12 (8) | 11/15 (73) 1 (7) | 6/10 (60) | 6/11 (55) 1 (9) |
| | Arthralgia | 2/30 (7) | 12/39 1 (3) | 10/24 (42) 1 (4) | 11/32 (34) | 1/12 (8) | 6/15 (40) 1 (7) | 5/10 (50) | 4/11 (36) |
| | Nausea | — | 6/31 (19) | 3/24 (13) | 7/32 (22) | 1/12 (8) | 4/15 (27) | 2/10 (20) | 2/11 (18) |
| | Chills | 1/30 (3) | 8/31 (26) 1 (3) | 9/24 (38) 1 (4) | 16/32 (50) | — | 6/15 (40) | 3/10 (30) | 6/11 (55) 1 (9) |
| | Rash | — | — | 2/24 (8) | 6/32 (19) | 1/12 (8) | 1/15 (7) | 1/10 (10) | — |

Values represent n (%) participants reporting each AR, bold text = grade 3 ARs

Safety Conclusions
  (a) The vaccine was generally well-tolerated across all doses regardless of serostatus.
  (b) No SAEs were reported.
  (c) There were no unsolicited events leading to study discontinuation.
  (d) Generally similar proportions of CMV-seronegative and CMV-seropositive participants in the treatment groups reported at least one solicited AR after the 1st vaccination and after the 2nd vaccination.
  (e) Overall, there did not appear to be a dose-related pattern in proportions of participants reporting solicited ARs after the 1st or 2nd vaccinations in either the CMV-seronegative or CMV-seropositive treatment groups.
  (f) Overall, the most common solicited local AR was injection site pain. The most common solicited systemic ARs were headache, fatigue, and myalgia in both CMV-seronegative and CMV-seropositive treatment groups.
  (g) After the 1st vaccination, rates of solicited systemic ARs were generally numerically lower in CMV-seronegative participants. Reports of Grade 3 solicited systemic ARs were low and limited to the CMV-seropositive treatment group. A dose-related pattern in rates of solicited ARs was not apparent in either the CMV-seronegative or CMV-seropositive treatment group.
  (h) After the 2nd vaccination, the rate and severity distribution of solicited ARs in the CMV-seronegative and CMV-seropositive treatment groups were generally similar.
  (i) The proportion of participants reporting unsolicited AEs overall and Grade 3 unsolicited AEs were generally numerically similar in CMV-seronegative and CMV-seropositive participants in the treatment groups. The proportion of CMV-seronegative participants reporting treatment-related unsolicited AEs was numerically higher in CMV-seropositive participants. There was no apparent dose-related or CMV serostatus-related pattern of reported unsolicited AEs.

Example 6: Evaluation of Immunogenicity 1 Month Post-$3^{rd}$ Vaccination in Phase II Study This Example describes results from the 7-month (1 month post-3rd vaccination) interim analysis of immunogenicity of the hCMV mRNA vaccine.

Immunogenicity in CMV-seronegative and CMV-seropositive participants was measured as neutralizing antibody (nAb) responses against epithelial cell infection (a measure of immune response to pentamer antigen); nAb responses against fibroblast infection (a measure of immune response to gB antigen); anti-pentamer binding antibody titers; and anti-gB binding antibody titers. Results were summarized by mean, median, min, max, geometric mean titer (GMT), geometric mean ratio (GMR) with respect to baseline, and corresponding 95% confidence intervals for GMT and GMR.

Figure 20:
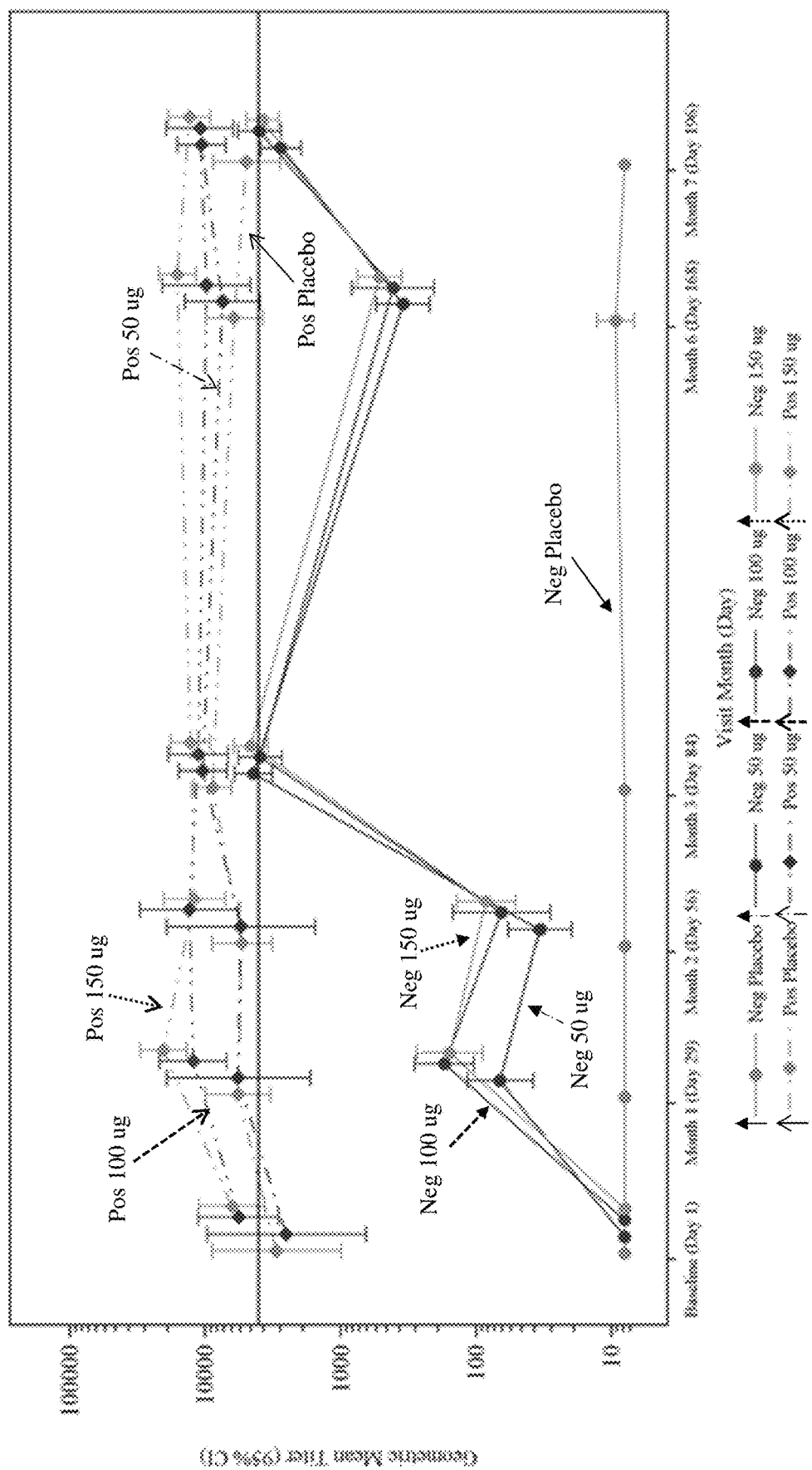
FIG. 20 shows neutralizing antibody titers against fibroblast infection through month 7 (1 month after the second vaccination) in a Phase II trial, by CMV serostatus and vaccination group, per-protocol set for antibody-mediated immunogenicity. Neg: CMV-seronegative, Pos: CMV-seropositive. 50 μg, 100 μg, and 150 μg refer to the dose of mRNA vaccine. Confidence intervals (CIs) were calculated using t-distribution of the log transformed values. The solid black reference line indicates the baseline GMT of all CMV seropositive subjects at baseline.

A microneutralization assay for measurement of nAb against epithelial cell infection utilized CMV isolate VR1814 and ARPE-19 cells. A microneutralization assay for measurement of nAb against fibroblast infection utilized CMV isolate AD169 and HEL299 cells. A binding ELISA assay for measurement of pentamer utilized recombinant human CMV pentamer protein complex consisting of full length UL75 (gH), UL115 (gL), UL128, UL130 and UL131A derived from VR1814 isolate. A binding ELISA assay for measurement of gB utilized recombinant human CMV gB encoding extracellular domain linked to the cytoplasmic domain.

again after the 3rd vaccination to GMTs exceeding the seropositive benchmark GMTs in all treatment groups by over 20-fold (FIG. 20).

Within each mRNA treatment group, nAb against fibroblast infection increased after the 2nd vaccination to GMTs approaching or exceeding the seropositive benchmark GMT in all treatment groups. After the 3rd vaccination, GMTs in the 100 μg and 150 μg treatment groups were comparable to GMTs after the 2nd vaccination (FIG. 20).

TABLE 5

Neutralizing Antibody Responses in CMV-Seropositive Participants

|  | Placebo<br>N = 43 | 50 μg<br>N = 44 | 100 μg<br>N = 39 | 150 μg<br>N = 44 | Total mRNA<br>N = 127 |
|---|---|---|---|---|---|
| | | CMV-Seronegative<br>Neutralizing Antibodies Against Epithelial Cell Infection | | | |
| GMT Baseline | 8 | 8 | 8 | 8 | 8 |
|  | n = 43 | n = 44 | n = 39 | n = 44 | n = 127 |
| Post $1^{st}$ Dose GMT Month 1 | 9.1 | 1,121 | 2,592 | 3,802 | 2,155 |
|  | n = 41 | n = 44 | n = 39 | n = 38 | n = 121 |
| 95% CI | 7; 12 | 684; 1,836 | 1,702; 3,948 | 2,713; 5,328 | 1,663; 2,793 |
| Post $2^{nd}$ Dose GMT Month 3 | 8 | 61,759 | 45,696 | 49,581 | 51,473 |
|  | n = 35 | n = 27 | n = 30 | n = 36 | n = 93 |
| 95% CI | — | 39,400; 96,807 | 32,940; 63,394 | 36,690; 67,001 | 42,231; 62,736 |
| Post $3^{rd}$ Dose GMT Month 7 | 8 | 117,022 | 112,325 | 101,114 | 109,654 |
|  | n = 29 | n = 27 | n = 18 | n = 27 | n = 72 |
| 95% CI | — | 71,909; 190,439 | 75,155; 167,878 | 75,957; 134,602 | 87,666; 137,1157 |
| | | CMV-Seronegative<br>Neutralizing Antibodies Against Fibroblast Infection | | | |
| GMT baseline | 8 | 8 | 8 | 8 | 8 |
|  | n = 43 | n = 44 | n = 39 | n = 44 | n = 127 |
| Post $1^{st}$ Dose GMT Month 1 | 8 | 66 | 171 | 156 | 118 |
|  | n = 41 | n = 44 | n = 39 | n = 38 | n = 121 |
| 95% CI | — | 38, 116 | 104, 282 | 89, 274 | 86; 161 |
| Post $2^{nd}$ Dose GMT Month 3 | 8 | 4,395 | 3,915 | 4,597 | 4,308 |
|  | n = 35 | n = 27 | n = 30 | n = 36 | n = 93 |
| 95% CI | — | 3,195; 6,047 | 2,703; 5,672 | 3,438; 6,146 | 3,592; 5,168 |
| Post $3^{rd}$ Dose GMT Month 7 | 8 | 2,758 | 3,965 | 3,761 | 3,393 |
|  | n = 29 | n = 27 | n = 18 | n = 27 | n = 72 |
| 95% CI | — | 1,958; 3,886 | 2,742; 5,735 | 2,849; 4,965 | 2,822; 4,079 |

CMV-seropositive group GMT of nAb against epithelial call infection at Baseline = 4,732 (95% CI: 3,059; 7,321)
CMV-seropositive group GMT of nAb against fibroblast infection at Baseline = 4,045 (95% CI: 2,566; 6.374)
CI = confidence intervals; CMV = cytomegalovirus; GMT = geometric mean titer; GMR = geometric mean ratio (post-baseline/baseline titers); N = number of participants in treatment group; n = number of participants with non-missing data at corresponding timepoint.

Baseline Neutralizing Antibody

In CMV-seronegative participants (n=127), nAb GMTs against epithelial cell infection and against fibroblast infection at Baseline (prior to the first vaccination) were below the LLOQ (reported as 8, representing 0.5×LLOQ) in all treatment groups. This is indicative of the absence of CMV infection prior to immunization.

In CMV-seropositive participants (n=62), the Baseline GMT of nAb against epithelial cell infection was 4,732 (95% CI: 3,059; 7,321) and the Baseline GMT of nAb against fibroblast infection was 4,045 (95% CI: 2,566; 6,374). These values represent the nAb GMTs of naturally acquired immunity for this PP immunogenicity set and a benchmark against which neutralizing antibody responses in the CMV-seronegative group could be compared.

Neutralizing Antibody (nAb) Responses

Figure 19:
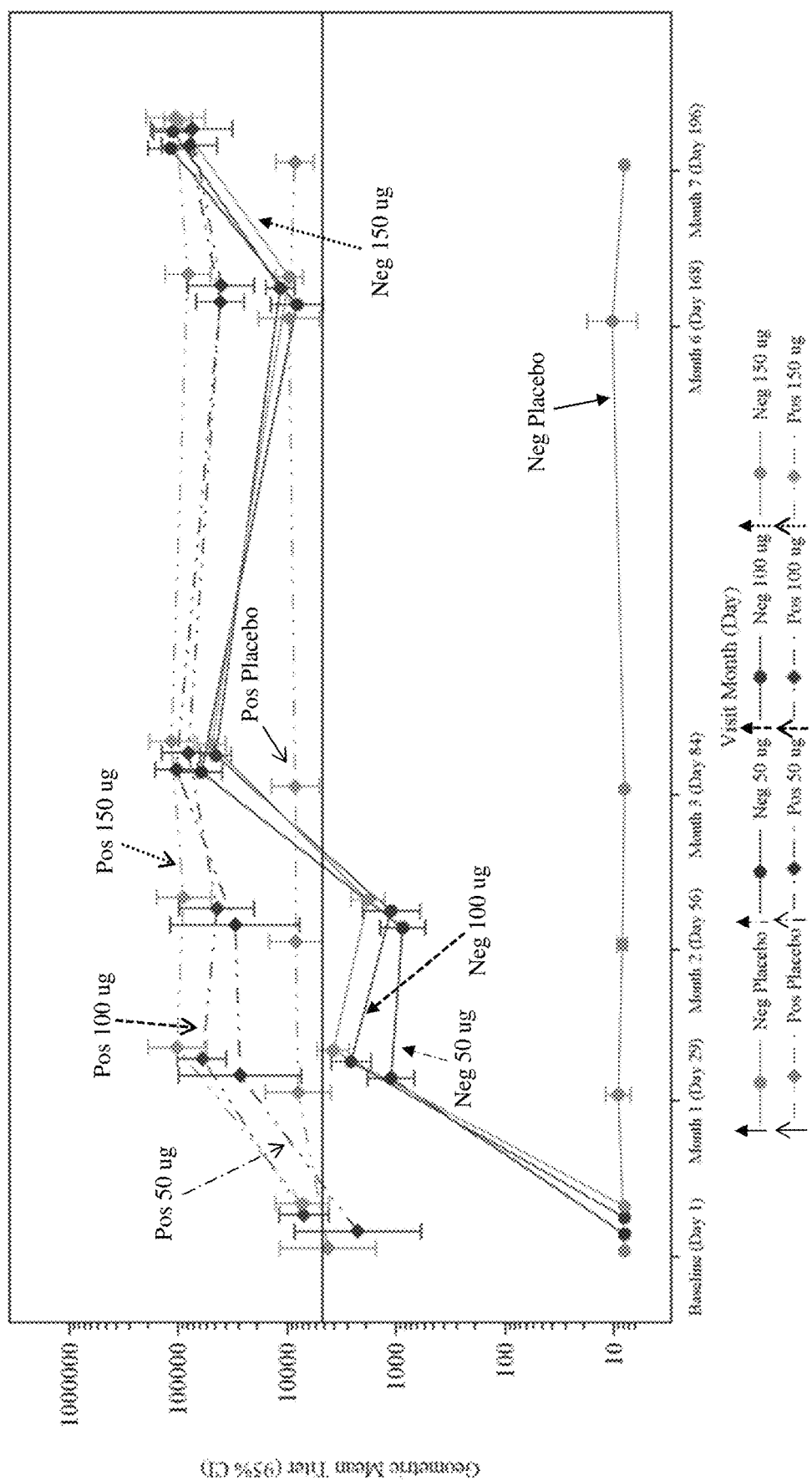
FIG. 19 shows neutralizing antibody titers against epithelial cell infection through month 7 (1 month after third vaccination) in a Phase II trial, by CMV serostatus and vaccination group, per-protocol set for antibody-mediated immunogenicity. Neg: CMV-seronegative, Pos: CMV-seropositive. 50 μg, 100 μg, and 150 μg refer to the dose of mRNA vaccine. Confidence intervals (CIs) were calculated using t-distribution of the log transformed values. The solid black reference line indicates the baseline GMT of all CMV seropositive subjects at baseline.

In CMV-seronegative participants, neutralizing antibodies against epithelial cell infection increased in a dose-related manner after the 1st vaccination (FIG. 19, Table 5). Within each mRNA treatment group, nAb against epithelial cell infection increased further after the 2nd vaccination and In CMV-seropositive participants, neutralizing antibodies against epithelial cell infection increased in a dose-related manner after the 1st vaccination (FIG. 19, Table 6). Within each mRNA treatment group, nAb against epithelial cell infection after the 3rd vaccination were comparable to GMTs after the 2nd vaccination in the 100 and 150 μg groups (FIG. 19).

Within each mRNA treatment group, nAb against fibroblast infection after the 3rd vaccination were comparable to GMTs after the 2nd vaccination (FIG. 20).

It is of note that baseline GMTs varied across treatment groups for both nAb against epithelial cell infection and nAb against fibroblast infection. In particular, the baseline GMTs in the 50 μg treatment group were numerically lower relative to the 100 μg and 150 μg treatment groups, which may have contributed to the relatively higher GMRs in the 50 μg treatment group. Additionally, the post-baseline GMTs in the Placebo treatment groups were higher compared to the respective baseline GMTs.

TABLE 6

Neutralizing Antibody Responses in CMV-Seropositive Participants

| | Placebo<br>N = 16 | 50 µg<br>N = 15 | 100 µg<br>N = 16 | 150 µg<br>N = 15 | Total mRNA<br>N = 46 |
|---|---|---|---|---|---|
| | | | CMV-Seropositive<br>Neutralizing Antibodies Against Epithelial Cell Infection | | |
| GMT Baseline | 4,244 | 2,250 | 7,059 | 7,296 | 4,915 |
| | n = 16 | n = 15 | n = 16 | n = 15 | n = 46 |
| 95% CI | 1,534; 11,747 | 589; 8,591 | 4,183; 11,914 | 4,109; 12,953 | 2,996; 8,063 |
| Post 1st Dose GMT Month 1 | 7,966 | 27,062 | 60,667 | 102,921 | 53,858 |
| | n = 14 | n = 15 | n = 16 | n = 13 | n = 44 |
| 95% CI | 3,967; 15,995 | 7,392; 99,073 | 36,408; 101,091 | 55,937; 189,371 | 32,712; 88,675 |
| Post 2nd Dose GMT Month 3 | 8,491 | 104,606 | 81,198 | 115,517 | 100,128 |
| | n = 13 | n = 15 | n = 12 | n = 13 | n = 40 |
| 95% CI | 5,117; 14,092 | 67,546; 161,999 | 46,508; 141,762 | 72,280; 184,620 | 77,414; 129,508 |
| Post 3rd Dose GMT Month 7 | 8,551 | 79,508 | 75,875 | 105,862 | 86,238 |
| | n = 12 | n = 12 | n = 10 | n = 11 | n = 33 |
| 95% CI | 5,745; 12,729 | 44,701; 141,419 | 32,204; 178,764 | 57,020; 196,541 | 60,784; 122,352 |
| GMR Month 1 | 2.1 | 12.0 | 8.6 | 12.8 | 10.9 |
| 95% CI | 0.8; 5.8 | 7.3; 19.8 | 4.8; 15.5 | 5.2; 31.4 | 7.6; 15.4 |
| GMR Month 3 | 2.2 | 46.5 | 14.0 | 17.1 | 23.4 |
| 95% CI | 0.8; 6.4 | 13.1; 165.5 | 7.8; 25.2 | 9.6; 30.4 | 13.8; 39.6 |
| GMR Month 7 | 2.1 | 23 | 12.4 | 12.9 | 15.7 |
| 95% CI | 0.6; 7.3 | 6.4; 82.6 | 4.6; 33.5 | 7.4; 22.5 | 9.3; 26.7 |
| | | | CMV-Seropositive<br>Neutralizing Antibodies Against Fibroblast Infection | | |
| GMT Baseline | 2,970 | 2,507 | 5,642 | 6,359 | 4,503 |
| | n = 16 | n = 15 | n = 16 | n = 15 | n = 46 |
| 95% CI | 993; 8,884 | 651; 9,655 | 2,832; 11,242 | 3,264; 11,158 | 2,717; 7,464 |
| Post 1st Dose GMT Month 1 | 5,698 | 5,686 | 12,294 | 20,365 | 10,972 |
| | n = 14 | n = 15 | n = 16 | n = 13 | n = 44 |
| 95% CI | 3,277; 9,908 | 1,680; 19,252 | 6,958; 21,722 | 13,679; 30,319 | 6,872; 17,520 |
| Post 2nd Dose GMT Month 3 | 8,804 | 10,410 | 11,282 | 12,868 | 11,425 |
| | n = 13 | n = 15 | n = 12 | n = 13 | n = 40 |
| 95% CI | 6,403; 12,107 | 6,923; 15,654 | 6,776; 18,786 | 9,234; 17,933 | 9,160; 14,250 |
| Post 3rd Dose GMT Month 7 | 4,936 | 10,604 | 10,972 | 13,123 | 11,503 |
| | n = 11 | n = 12 | n = 10 | n = 11 | n = 33 |
| 95% CI | 2,796; 8,714 | 6,997; 16,072 | 6,194; 19,435 | 9,168; 18,784 | 9,129; 14,495 |
| GMR Month 1 | 2.4 | 2.3 | 2.2 | 2.9 | 2.4 |
| 95% CI | 0.9; 6.5 | 1.4; 3.7 | 1.5; 3.3 | 1.8; 4.7 | 1.9; 3.1 |
| GMR Month 3 | 3.3 | 4.2 | 2.1 | 2.1 | 2.7 |
| 95% CI | 1.1; 10.3 | 1.3; 12.9 | 1.2; 3.5 | 1.3; 3.3 | 1.7; 4.2 |
| GMR Month 7 | 2.3 | 3.1 | 1.9 | 2.0 | 2.3 |
| 95% CI | 0.6; 8.9 | 0.8; 11.8 | 0.9; 4.1 | 1.1; 3.8 | 1.4; 3.9 |

CI = Confidence intervals; CMV = cytomegalovirus; GMR = Geometric Mean Ratio (post-baseline/baseline titers); GMT = Geometric Mean Titer; N = number of participants in treatment group; n = Number of participants with non-missing data at corresponding timepoint.

Binding Antibody (nAb) Responses

Figure 21:
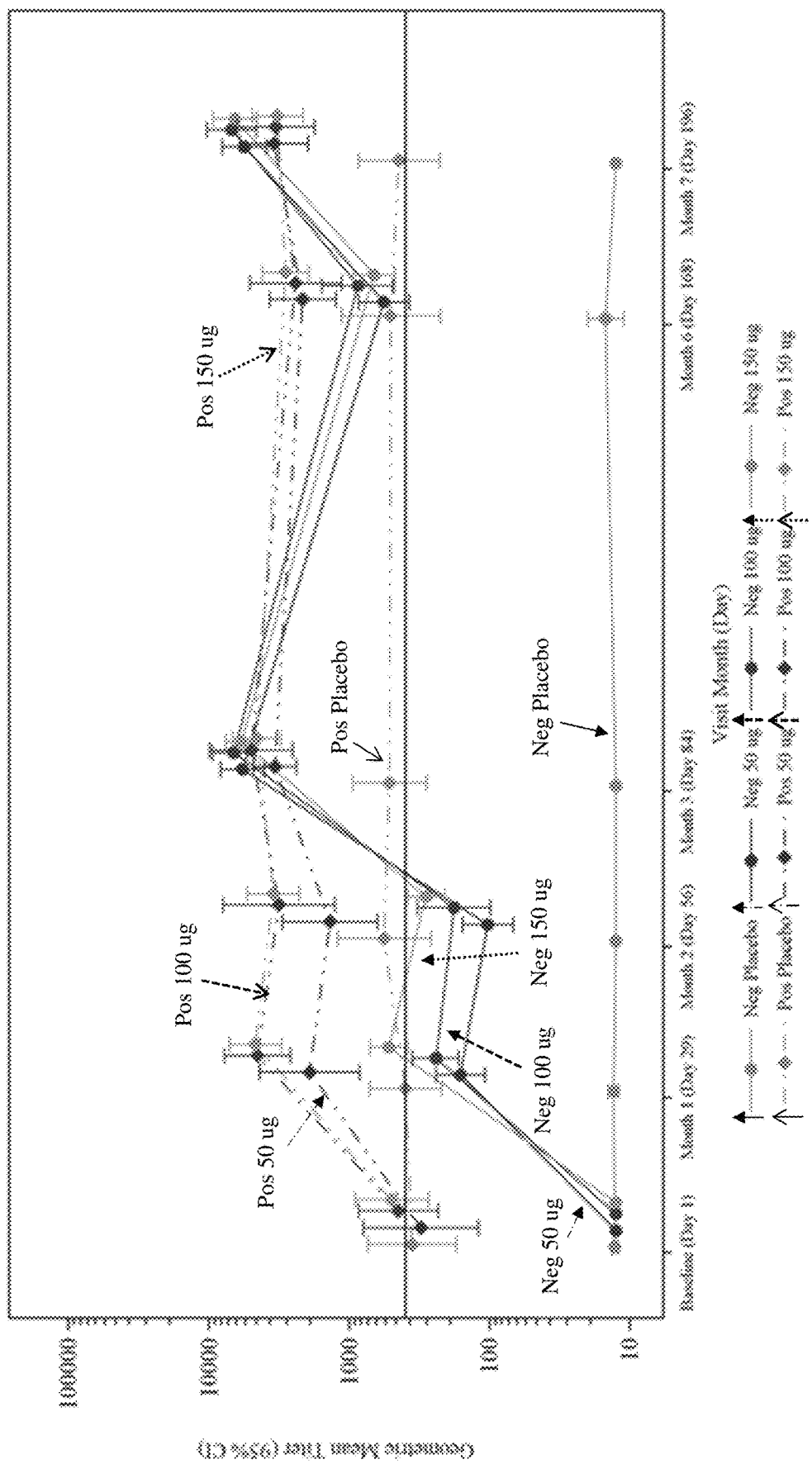
FIG. 21 shows anti-pentamer binding antibody titers through month 7 (1 month after the second vaccination) in a Phase II trial, by CMV serostatus and vaccination group, per-protocol set for antibody-mediated immunogenicity. Neg: CMV-seronegative, Pos: CMV-seropositive. 50 μg, 100 μg, and 150 μg refer to the dose of mRNA vaccine. Confidence intervals (CIs) were calculated using t-distribution of the log transformed values. The solid black reference line indicates the baseline GMT of all CMV seropositive subjects at baseline.

In CMV-seronegative participants, anti-pentamer bAb increased slightly after the 1st vaccination (FIG. 21, Table 7), then increased after the 2nd vaccination to GMTs over 10-fold that of the CMV-seropositive group at baseline with no apparent dose relationship. In all mRNA treatment groups, GMTs after the 3rd vaccination were comparable to the 2nd vaccination (FIG. 21).

Figure 22:
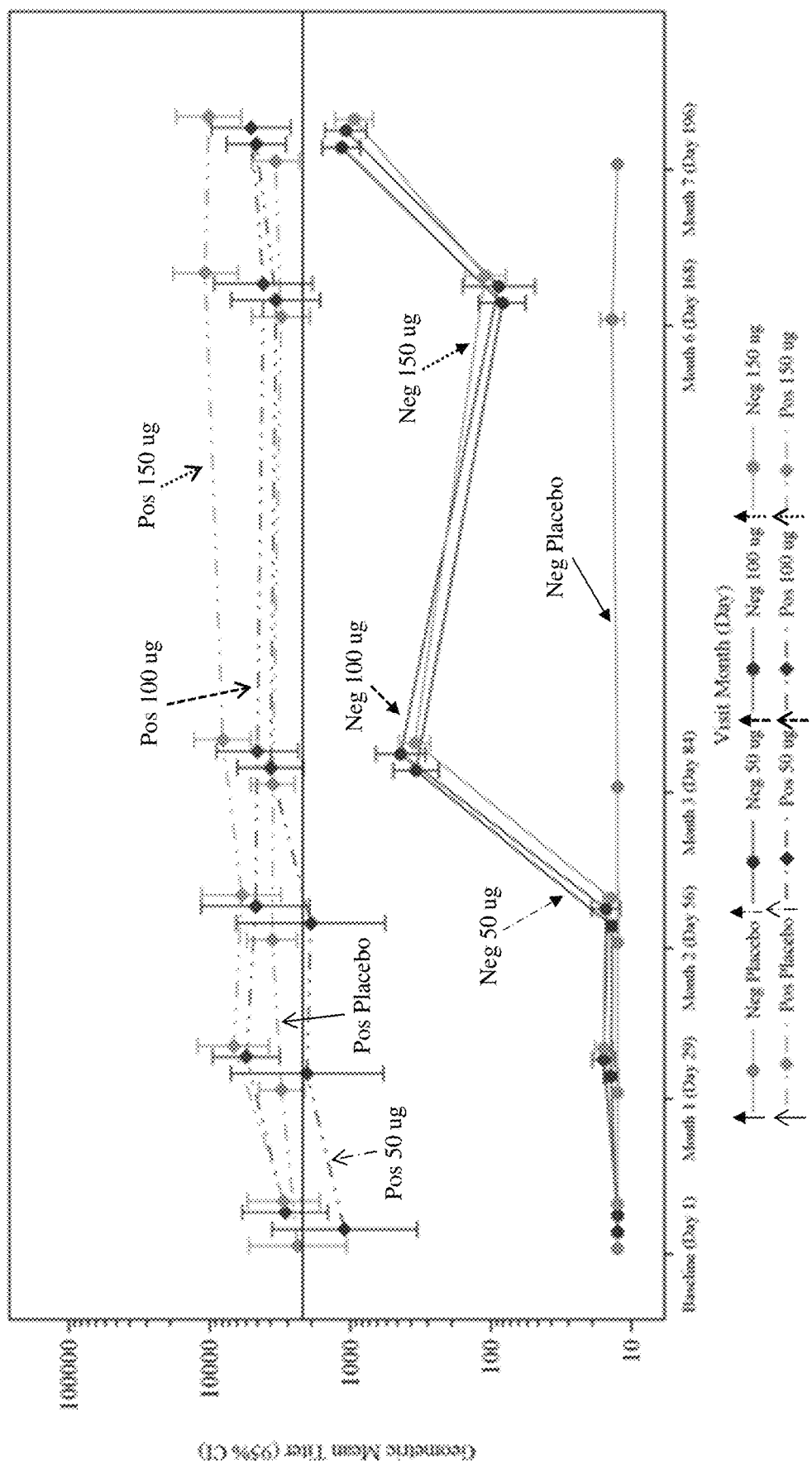
FIG. 22 shows anti-gB binding antibody titers through month 7 (1 month after the second vaccination) in a Phase II trial, by CMV serostatus and vaccination group, per-protocol set for antibody-mediated immunogenicity. Neg: CMV-seronegative, Pos: CMV-seropositive. 50 μg, 100 μg, and 150 μg refer to the dose of mRNA vaccine. Confidence intervals (CIs) were calculated using t-distribution of the log transformed values. The solid black reference line indicates the baseline GMT of all CMV seropositive subjects at baseline.
Figure 23:
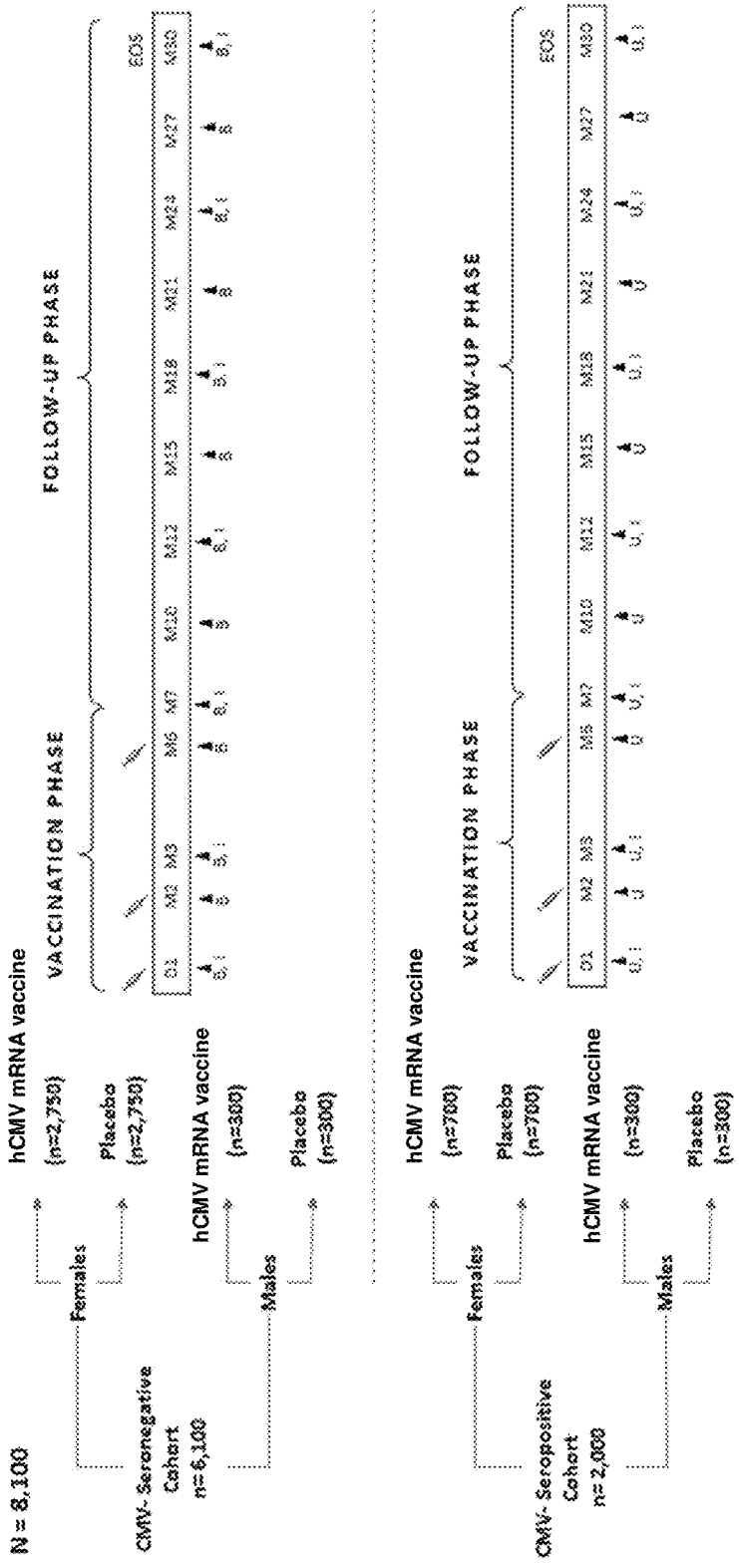
FIG. 23 is a schematic showing a study flow diagram for the Phase III study described in Example 7. Abbreviations: B=blood sampling for seroconversion due to primary CMV infection (CMV-seronegative cohort); CMV=cytomegalovirus; D=day; EOS=end of study; I=serum sampling for antibody mediated immunogenicity; M=month; n=total number of participants; U=urine sampling for CMV shedding in the CMV-seropositive cohort.

Within each mRNA treatment group, anti-gB did not appreciably increase after the 1st vaccination, then increased after the 2nd vaccination and further increased after the 3rd vaccination (FIG. 22, Table 7). GMTs after the 3rd vaccination were lower than the GMT of the CMV-seropositive group at baseline. There was no apparent dose relationship across the treatment groups.

TABLE 7

Binding Antibody Responses in CMV-Seronegative Participants

| | Placebo<br>N = 43 | 50 µg<br>N = 44 | 100 µg<br>N = 39 | 150 µg<br>N = 44 | Total mRNA<br>N = 127 |
|---|---|---|---|---|---|
| | | | CMV-Seronegative<br>Anti-Pentamer Binding Antibodies | | |
| GMT Baseline | 12.77 | 12.5 | 12.5 | 12.5 | 12.5 |
| | n = 43 | n = 44 | n = 39 | n = 44 | n = 127 |
| 95% CI | 12.23, 13.32 | — | — | — | — |
| GMT Month 1 | 13.04 | 161.60 | 242.00 | 518.75 | 265.49 |
| | n = 41 | n = 44 | n = 39 | n = 38 | n = 121 |
| 95% CI | 11.97, 14.21 | 108.21, 241.34 | 166.47, 351.81 | 381.33, 705.69 | 212.17, 332.20 |
| GMT Month 3 | 12.5 | 5749.97 | 6656.96 | 5841.76 | 6065.24 |
| | n = 35 | n = 27 | n = 30 | n = 36 | n = 93 |

TABLE 7-continued

Binding Antibody Responses in CMV-Seronegative Participants

|  | Placebo<br>N = 43 | 50 μg<br>N = 44 | 100 μg<br>N = 39 | 150 μg<br>N = 44 | Total mRNA<br>N = 127 |
|---|---|---|---|---|---|
| 95% CI | — | 4006.68, 8251.77 | 4704.85, 9419.05 | 4481.87, 7614.26 | 5077.14, 7245.63 |
| GMT Month 7 | 12.5 | 5572.61 | 6892.01 | 6512.61 | 6230.41 |
|  | n = 29 | n = 27 | n = 18 | n = 27 | n = 72 |
| 95% CI | — | 3871.16, 8021.88 | 4587.91, 10353.25 | 4542.74, 9336.67 | 5060.98, 7670.06 |

CMV-Seronegative
Anti-gB Binding Antibodies

| GMT Baseline | 12.5 | 12.5 | 12.5 | 12.5 | 12.5 |
|---|---|---|---|---|---|
| 95% CI | n = 43 | n = 44 | n = 39 | n = 44 | n = 127 |
| GMT Month 1 | 12.5 | 14.03 | 15.77 | 15.70 | 15.09 |
|  | n = 41 | n = 44 | n = 39 | n = 38 | n = 121 |
| 95% CI | — | 12.53, 15.70 | 13.09, 19.02 | 13.51, 18.25 | 13.87, 16.43 |
| GMT Month 3 | 12.5 | 339.83 | 436.76 | 347.45 | 371.66 |
|  | n = 35 | n = 27 | n = 30 | n = 36 | n = 93 |
| 95% CI | — | 234.71, 492.04 | 290.16, 657.43 | 268.76, 449.18 | 307.14, 449.74 |
| GMT Month 7 | 12.50 | 1154.82 | 1074.30 | 937.17 | 1048.71 |
|  | n = 29 | n = 27 | n = 18 | n = 27 | n = 72 |
| 95% CI | — | 848.30, 1572.11 | 763.56, 1511.51 | 686.85, 1278.70 | 878.23, 1252.29 |

CMV-seropositive group GMT of anti-pentamer binding Ab at Baseline = 395 (95% CI: 281; 554)
CMV-seropositive group GMT of anti-gB binding Ab at Baseline = 2,190 (95% CI: 1,469; 3,263)
CI = confidence intervals; CMV = cytomegalovirus; GMR = geometric mean ratio (post-baseline/baseline titers); GMT = geometric mean titer; N = number of participants in treatment group; n = number of participants with non-missing data at corresponding timepoint.

In seropositive participants, anti-pentamer bAb were boosted after the 1st vaccination in all mRNA treatment groups (FIG. 21, Table 8) and increased further after the 2nd vaccination with no apparent dose relationship. After the 3rd vaccination, anti-pentamer bAb was comparable to the 2nd vaccination for all mRNA treatment groups (FIG. 22). Across the mRNA treatment groups, GMRs were at least 6.2 after the 1st vaccination, at least 10.2 after the 2nd vaccination, and at least 6.8 after the 3rd vaccination.

Anti-gB bAb were boosted after the 1st vaccination in all mRNA treatment groups and increased after the 2nd and 3rd vaccinations. Across the mRNA treatment groups, GMRs were at least 1.8 after the each of the 3 vaccinations (FIG. 22, Table 8).

TABLE 8

Binding Antibody Responses in CMV-Seropositive Participants

|  | Placebo<br>N = 16 | 50 μg<br>N = 15 | 100 μg<br>N = 16 | 150 μg<br>N = 15 | Total mRNA<br>N = 46 |
|---|---|---|---|---|---|

CMV-Seropositive
Anti-Pentamer Binding Antibodies Against Epithelial Cell Infection

| GMT Baseline | 356.26 | 306.79 | 446.89 | 496.35 | 409.07 |
|---|---|---|---|---|---|
|  | n = 16 | n = 15 | n = 16 | n = 15 | n = 46 |
| 95% CI | 173.21, 732.76 | 119.73, 786.10 | 232.93, 857.42 | 273.08, 902.18 | 274.59, 609.41 |
| GMT Month 1 | 397.38 | 1905.20 | 4513.40 | 4655.22 | 3394.54 |
|  | n = 14 | n = 15 | n = 16 | n = 13 | n = 44 |
| 95% CI | 221.15, 714.03 | 836.52, 4339.16 | 2623.60, 7764.44 | 3036.52, 7136.80 | 2369.82, 4862.36 |
| GMT Month 3 | 513.54 | 3378.10 | 4994.21 | 4556.10 | 4186.35 |
|  | n = 13 | n = 15 | n = 12 | n = 13 | n = 40 |
| 95% CI | 280.84, 939.06 | 2377.28, 4800.27 | 2534.23, 9842.07 | 3063.50, 6775.93 | 3248.83, 5394.40 |
| GMT Month 7 | 439.53 | 3431.76 | 3333.40 | 3239.10 | 3336.77 |
|  | n = 12 | n = 12 | n = 10 | n = 11 | n = 33 |
| 95% CI | 226.15, 854.23 | 1964.00, 5996.43 | 1763.50, 6300.85 | 2121.37, 4945.75 | 2528.09, 4404.11 |
| GMR Month 1 (95% CI) | 1.25 (0.78, 2.01) | 6.21 (3.67, 10.50) | 10.09 (5.28, 19.29) | 8.01 (4.18, 15.34) | 7.99 (5.75, 11.10) |
| GMR Month 3 (95% CI) | 1.39 (0.81, 2.38) | 11.01 (4.11, 29.43) | 10.51 (6.01, 18.37) | 10.20 (5.09, 20.46) | 10.59 (6.93, 16.19) |
| GMR Month 7 (95% CI) | 1.07 (0.64, 1.77) | 7.57 (2.42, 23.65) | 7.29 (4.13, 12.86) | 6.84 (3.65, 12.79) | 7.23 (4.65, 11.26) |

CMV-Seropositive
Anti-gB Binding Antibodies Against Fibroblast Infection

| GMT Baseline | 2366.38 | 1096.31 | 2902.20 | 2981.12 | 2131.37 |
|---|---|---|---|---|---|
|  | n = 16 | n = 15 | n = 16 | n = 15 | n = 46 |
| 95% CI | 1062.33, 5271.21 | 333.05, 3608.80 | 1442.33, 5839.72 | 1649.35, 5388.25 | 1321.83, 3436.71 |
| GMT Month 1 | 3073.70 | 2028.11 | 5496.22 | 6754.86 | 4158.32 |
|  | n = 14 | n = 15 | n = 16 | n = 13 | n = 44 |
| 95% CI | 2110.13, 4477.28 | 581.02, 7079.33 | 3159.27, 9561.84 | 3799.57, 12008.74 | 2554.47, 6769.17 |
| GMT Month 3 | 3557.07 | 3699.02 | 4595.97 | 8112.05 | 5095.81 |
|  | n = 13 | n = 15 | n = 12 | n = 13 | n = 40 |
| 95% CI | 2480.93, 5099.99 | 2149.36, 6365.94 | 2349.99, 8988.51 | 5108.43, 12881.71 | 3728.42, 6964.67 |
| GMT Month 7 | 3404.68 | 4667.54 | 5054.78 | 10115.96 | 6188.00 |
|  | n = 12 | n = 12 | n = 10 | n = 11 | n = 33 |
| 95% CI | 2317.28, 5002.36 | 2859.43, 7618.98 | 2636.93, 9689.59 | 5983.30, 17103.06 | 4548.34, 8418.75 |

TABLE 8-continued

Binding Antibody Responses in CMV-Seropositive Participants

|  | Placebo<br>N = 16 | 50 μg<br>N = 15 | 100 μg<br>N = 16 | 150 μg<br>N = 15 | Total mRNA<br>N = 46 |
|---|---|---|---|---|---|
| GMR Month 1, 95% CI | 1.43 (0.69, 2.99) | 1.85 (1.28, 2.66) | 1.89 (1.46, 2.44) | 2.12 (1.52, 2.96) | 1.94 (1.64, 2.30) |
| GMR Month 3, 95% CI | 1.52 (0.68, 3.38) | 3.37 (1.53, 7.42) | 1.84 (1.27, 2.66) | 2.86 (1.87, 4.36) | 2.67 (1.92, 3.69) |
| GMR Month 7, 95% CI | 1.42 (0.55, 3.68) | 3.48 (1.19, 10.17) | 1.83 (1.15, 2.92) | 3.46 (1.74, 6.86) | 2.86 (1.85, 4.42) |

CI = Confidence intervals; GMR = Geometric Mean Ratio (post-baseline/baseline titers); GMT = Geometric Mean Titer; N = number of participants in treatment group; n = number of participants with non-missing data at corresponding timepoint.

Immunogenicity Conclusions
CMV-Seronegative Participants
  (a) Neutralizing antibody response. Neutralizing Ab GMTs against epithelial cell infection increased after the 3rd vaccination compared to the 2nd vaccination in all CMV seronegative mRNA treatment groups, with GMTs exceeding the baseline GMT of the CMV-seropositive group by over 20-fold. The nAb GMTs against fibroblast infection after the 2nd vaccination approached or exceeded the baseline GMT of the CMV seropositive group in all mRNA treatment groups. After the 3rd vaccination, nAb GMTs in the 100 μg and 150 μg treatment groups were comparable to GMTs after the 2nd vaccination.
  (b) Binding antibody response. Anti-pentamer binding Ab GMTs increased after the $2^{nd}$ vaccination to levels exceeding the baseline GMT of the CMV-seropositive group of over 10-fold, with comparable GMTs after the $3^{rd}$ vaccination compared to the $2^{nd}$ vaccination, and without an apparent dose relationship. Anti-gB binding Ab GMTs were numerically higher after the $3^{rd}$ vaccination compared to the $2^{nd}$ vaccination within mRNA treatment groups, without an apparent overall dose relationship, and were numerically lower than the baseline GMT of the CMV-seropositive group.
CMV-Seropositive Participants
  (a) Neutralizing antibody response. In the mRNA treatment groups, nAb GMRs against epithelial cell infection were boosted to at least 8.6 after the $1^{st}$ vaccination, at least 14.0 after the $2^{nd}$ vaccination, and at least 12.4 after the $3^{rd}$ vaccination, without an apparent overall dose relationship. Neutralizing Ab GMRs against fibroblast infection were boosted to GMRs of at least 2.2 after the $1^{st}$ vaccination, at least 2.1 after the $2^{nd}$ vaccination, and at least 1.9 after the $3^{rd}$ vaccination, without an apparent overall dose relationship.
  (b) Binding antibody response. In the mRNA treatment groups, anti-pentamer bAb GMTs were boosted to GMRs of at least 6.2 after the $1^{st}$ vaccination, at least 10.2 after the $2^{nd}$ vaccination, and at least 6.8 after the $3^{rd}$ vaccination, without an apparent overall dose relationship. Within each mRNA treatment group, anti-gB binding Ab GMTs were boosted after the $1^{st}$ vaccination to GMRs of at least 1.8 across the mRNA treatment groups, and GMRs were generally comparable after the $2^{nd}$ and $3^{rd}$ vaccinations without an apparent dose relationship.

Solicited Safety

The most common solicited systemic ARs were headache, fatigue, myalgia, arthralgia, and chills in both the CMV-seropositive and CMV-seronegative total mRNA groups. In the CMV seronegative total mRNA groups, rates of participants reporting headache, fatigue, myalgia, arthralgia, and chills after the 1st vaccination were 27%, 33%, 21%, 10%, and 13%, respectively, which numerically increased to 47%, 42%, 44%, 33%, and 35%, respectively, after the 2nd vaccination, and to 49%, 52%, 47%, 34%, and 31%, respectively, after the 3rd vaccination. In the CMV seropositive total mRNA groups, rates of participants reporting headache, fatigue, myalgia, arthralgia, and chills after the 1st vaccination (52%, 54%, 59%, 43%, and 37%, respectively) were generally numerically comparable compared to the 2nd vaccination (51%, 61%, 70%, 44%, and 47%, respectively) and the 3rd vaccination (56%, 62%, 46%, 41%, and 51%, respectively). In CMV-seronegative Placebo group, rates of headache, fatigue, myalgia, arthralgia, and chills were 37%, 33%, 16%, 7%, and 10%, respectively, after the 1st vaccination; 38%, 25%, 5%, 5%, and 2.5%, respectively, after the 2nd vaccination; and 22%, 8%, 0%, 0%, and 3%, respectively, after the 3rd vaccination. In the CMV-seropositive Placebo group, rates of headache, fatigue, myalgia, arthralgia, and chills were 35%, 25%, 10%, 5%, and 0%, respectively, after the 1st vaccination; in 43%, 14%, 7%, 7%, and 0%, respectively, after the 2nd vaccination; and in 20%, 7%, 0%, 0%, and 0%, respectively, after the 3rd vaccination (Table 9 and Table 10).

TABLE 9

Summary of Solicited Systemic Adverse Reactions in CMV-Seronegative Participants

|  | $1^{st}$ Vaccination | | $2^{nd}$ Vaccination | | $3^{rd}$ Vaccination | |
|---|---|---|---|---|---|---|
| Solicited Systemic<br>ARs | Placebo<br>(N = 43)<br>n (%) | Total mRNA<br>(N = 135)<br>n (%) | Placebo<br>(N = 40)<br>n (%) | Total mRNA<br>(N = 117)<br>n (%) | Placebo<br>(N = 36)<br>n (%) | Total mRNA<br>(N = 102)<br>n (%) |
| Fever | 0 | 1 (0.7) | 0 | 8 (6.8) | 0 | 14 (13.7) |
| Grade 3 | 0 | 0 | 0 | 2 (1.7) | 0 | 1 (1.0) |
| Headache | 16 (37.2) | 36 (26.7) | 15 (37.5) | 55 (47.0) | 8 (22.2) | 50 (49.0) |
| Grade 3 | 2 (4.7) | 0 | 0 | 8 (6.8) | 0 | 4 (3.9) |
| Fatigue | 14 (32.6) | 45 (33.3) | 10 (25.0) | 49 (41.9) | 3 (8.3) | 53 (52.0) |
| Grade 3 | 1 (2.3) | 0 | 0 | 4 (3.4) | 0 | 2 (2.0) |
| Myalgia | 7 (16.3) | 28 (20.7) | 2 (5.0) | 51 (43.6) | 0 | 48 (47.1) |
| Grade 3 | 2 (4.7) | 1 (0.7) | 0 | 7 (6.0) | 0 | 6 (5.9) |
| Arthralgia | 3 (7.0) | 14 (10.4) | 2 (5.0) | 38 (32.5) | 0 | 35 (34.3) |

TABLE 9-continued

Summary of Solicited Systemic Adverse Reactions in CMV-Seronegative Participants

| | 1st Vaccination | | 2nd Vaccination | | 3rd Vaccination | |
|---|---|---|---|---|---|---|
| Solicited Systemic ARs | Placebo (N = 43) n (%) | Total mRNA (N = 135) n (%) | Placebo (N = 40) n (%) | Total mRNA (N = 117) n (%) | Placebo (N = 36) n (%) | Total mRNA (N = 102) n (%) |
| Grade 3 | 2 (4.7) | 0 | 0 | 3 (2.6) | 0 | 4 (3.9) |
| Nausea/Vomiting | 3 (7.0) | 9 (6.7) | 0 | 22 (18.8) | 3 (8.3) | 18 (17.6) |
| Grade 3 | 2 (4.7) | 0 | 0 | 0 | 0 | 0 |
| Chills | 4 (9.3) | 18 (13.3) | 1 (2.5) | 41 (35.0) | 1 (2.8) | 32 (31.4) |
| Grade 3 | 1 (2.3) | 0 | 0 | 3 (2.6) | 0 | 0 |
| Rash | 3 (7.0) | 9 (6.7) | 0 | 9 (7.7) | 1 (2.8) | 5 (4.9) |

AR = adverse reaction; CMV = cytomegalovirus; n = number of participants in treatment group; Total mRNA = all mRNA treatment groups combined.

TABLE 10

Summary of Solicited Systemic Adverse Reactions in CMV-Seropositive Participants

| | 1st Vaccination | | 2nd Vaccination | | 3rd Vaccination | |
|---|---|---|---|---|---|---|
| Solicited Systemic ARs | Placebo (N = 20) n (%) | Total mRNA (N = 54) n (%) | Placebo (N = 14) n (%) | Total mRNA (N = 43) n (%) | Placebo (N = 15) n (%) | Total mRNA (N = 39) n (%) |
| Fever | 0 | 5 (9.3) | 0 | 5 (11.6) | 0 | 8 (20.5) |
| Grade 3 | 0 | 1 (1.9) | 0 | 2 (4.7) | 0 | 1 (2.6) |
| Headache | 7 (35.0) | 28 (51.9) | 6 (42.9) | 22 (51.2) | 3 (20.0) | 22 (56.4) |
| Grade 3 | 0 | 0 | 2 (14.3) | 1 (2.3) | 0 | 1 (2.6) |
| Fatigue | 5 (25.0) | 29 (53.7) | 2 (14.3) | 26 (60.5) | 1 (6.7) | 24 (61.5) |
| Grade 3 | 0 | 2 (3.7) | 0 | 4 (9.3) | 0 | 3 (7.7) |
| Myalgia | 2 (10.0) | 32 (59.3) | 1 (7.1) | 30 (69.8) | 0 | 18 (46.2) |
| Grade 3 | 0 | 4 (7.4) | 0 | 6 (14.0) | 0 | 6 (15.4) |
| Arthralgia | 1 (5.0) | 23 (42.6) | 1 (7.1) | 19 (44.2) | 0 | 16 (41.0) |
| Grade 3 | 0 | 1 (1.9) | 0 | 3 (7.0) | 0 | 2 (5.1) |
| Nausea/Vomiting | 2 (10.0) | 13 (24.1) | 1 (7.1) | 9 (20.9) | 1 (6.7) | 8 (20.5) |
| Grade 3 | 0 | 0 | 0 | 0 | 0 | 0 |
| Chills | 0 | 20 (37.0) | 0 | 20 (46.5) | 0 | 20 (51.3) |
| Grade 3 | 0 | 0 | 0 | 2 (4.7) | 0 | 1 (2.6) |
| Rash | 4 (20.0) | 5 (9.3) | 1 (7.1) | 3 (7.0) | 1 (6.7) | 2 (5.1) |

AR = adverse reaction; CMV = cytomegalovirus; n = number of participants in treatment group; Total mRNA = all mRNA treatment groups combined.

Safety Conclusions
(a) The vaccine was generally well tolerated across all doses regardless of serostatus. No protocol-defined pause rules have been met in the study to date.
(b) A single SAE was reported (follicular thyroid cancer) in a participant who received the vaccine that was not treatment-related.
(c) There were no unsolicited events leading to study discontinuation. TEAE leading to discontinuation of the study vaccine occurred infrequently.
(d) Generally comparable proportions of CMV-seronegative and CMV-seropositive participants in vaccine treatment groups reported at least one solicited AR after the $1^{st}$, $2^{nd}$, and $3^{rd}$ vaccinations.
(e) There did not appear to be a dose-related pattern in proportions of participants reporting solicited ARs after the $1^{st}$, $2^{nd}$, or $3^{rd}$ vaccinations in either the CMV-seronegative or CMV-seropositive vaccine treatment groups.
(f) In both CMV-seronegative and CMV-seropositive vaccine treatment groups, the most common solicited local AR was injection site pain. The overall frequency after the $3^{rd}$ vaccination was generally comparable to the frequency after the $2^{nd}$ vaccination in the vaccine treatment groups. The overall frequency of Grade 3 severity injection site pain was similar between the $2^{nd}$ and $3^{rd}$ vaccinations in the both CMV-seronegative mRNA treatment groups and numerically lower after the $3^{rd}$ vaccination compared to the $2^{nd}$ vaccination in the CMV-seropositive mRNA treatment groups.
(g) In both CMV-seronegative and CMV-seropositive vaccine treatment groups, the most common solicited systemic ARs were headache, fatigue, myalgia, arthralgia, and chills. Proportions of participants reporting solicited systemic ARs were generally numerically higher after the $2^{nd}$ vaccination compared to the 1st vaccination, and numerically comparable after the 3rd vaccination compared to the $2^{nd}$ vaccination. The frequency of fever after the $3^{rd}$ vaccination was numerically higher compared to the $2^{nd}$ vaccination but rates of Grade 3 fever were comparable (defined as oral temperature 39.0° C.-40.0° C./102.1-104.0° F.).
(h) There was no apparent overall pattern or difference in distribution of unsolicited AEs or MAAEs with generally comparable rates in the CMV-seronegative and CMV-seropositive groups.
(i) Analysis of laboratory results revealed no safety concerns.

Example 7: A Phase III, Randomized, Observer-Blind, Placebo-Controlled Study to Evaluate the Efficacy, Safety, and Immunogenicity of hCMV mRNA Cytomegalovirus (CMV) Vaccine in Healthy Subjects 16 to 40 Years of Age The purpose of this Phase III study is to evaluate the vaccine safety, efficacy, and immunogenicity to the hCMV mRNA vaccine against primary cytomegalovirus (CMV) infection in healthy women 16 to 40 years of age who were either CMV-seronegative or CMV-seropositive at enrolment.

Description of Study Vaccine

As described above, the hCMV mRNA vaccine consists of 6 distinct mRNA sequences encoding important targets of neutralizing antibody (nAb) response to human CMV infection (full length CMV glycoprotein B [gB] and pentameric gH/gL/UL128/UL130/UL131A glycoprotein complex [pentamer]) in a lipid nanoparticle (LNP) formulation.

The LNP formulation includes 4 lipid excipients: heptadecan-9-yl 8-((2-hydroxyethyl)(6-oxo-6(undecyloxy)hexyl) amino)octanoate, a proprietary ionizable amino lipid, and the commercially-available lipids cholesterol, 1,2-distearoyl-sn-glycero-3-phosphocholine (DSPC), and 1,2-dimyristoyl-rac-glycerol, methoxypolyethyleneglycol (PEG2000-DMG).

The hCMV mRNA vaccine injection is stored at 2° C. to 8° C. until use. Following appropriate dose preparation, the hCMV mRNA vaccine injection will be administered intramuscularly into the deltoid muscle, preferably in the non-dominant arm, in a volume of 0.5 mL.

The Phase III formulation of the hCMV mRNA vaccine will be filled and lyophilized in 2R Type I glass vials at a total mRNA content of 151 μg/vial. Prior to use, the lyophilized drug product is reconstituted with 0.7 mL of 0.9% sodium chloride injection, to form a uniform LNP dispersion with a concentration of 0.2 mg/mL for administration.

A 0.9% sodium chloride injection (normal saline) placebo will be administered intramuscularly into the deltoid muscle, preferably in the nondominant arm, in a volume of 0.5 mL.

Study Design

The primary efficacy objective is to demonstrate vaccine effect of the hCMV mRNA vaccine against primary cytomegalovirus (CMV) infection in female subjects who are CMV seronegative at enrollment. Primary CMV infection is defined as seroconversion from a negative result (baseline/Day 1) to a positive result for serum immunoglobin G (IgG) against CMV as measured by a platform-based automated immunoassay based on at least 1 of the 4 recombinant CMV antigens not encoded by the hCMV mRNA vaccine (pp150, pp28, pp52, pp38) assessed starting 28 days after the third injection. Female subjects who are CMV seropositive at baseline and male subjects will not be included for the primary efficacy analysis.

Approximately 8,100 total subjects will be enrolled in the study: a CMV-seronegative cohort: 5,500 female subjects and 600 male subjects and a CMV-seropositive cohort: 1,400 female subjects and 600 male subjects.

Subjects will be randomly assigned in a 1:1 ratio to receive either 100 μg of the hCMV mRNA vaccine or placebo. Randomization will be in a blinded manner using a centralized interactive response technology at the Day 1 visit, in accordance with pre-generated randomization schedules. For each serostatus cohort (CMV-seronegative, CMV-seropositive), randomization will be stratified by sex (female, male) and age (≥16 to <18 years, ≥18 to <20 years, and ≥20 to ≤40 years) to balance treatment assignments. At least 400 enrolled CMV seronegative female subjects will be in the ≥16 to <18 age group. Each participant will participate in 2 phases: Vaccination Phase (Day 1 to Month 7 [Day 197; 28 days following the third injection]) and a Follow-up Phase (post Month 7 [Day 198]) through Month 30 (Day 887; approximately 24 months after the third injection). Upon completing the Vaccination Phase, subjects will have scheduled study visits approximately every 3 months during the Follow up Phase for safety and study assessments.

All subjects will receive the first injection on Day 1 and will receive the same treatment for the second injection at Month 2 (Day 57) and the third injection at Month 6 (Day 169). Subjects will have approximately 14 study visits and approximately 18 safety telephone calls/electronic diary (eDiary) safety and surveillance prompts over the course of the study. During the Vaccination Phase, local and systemic solicited adverse reactions (ARs) will be collected through 7 days following each injection using an eDiary. Any solicited AR that is ongoing beyond Day 7 will be recorded until no longer reported, not exceeding 28 days. Unsolicited adverse events (AEs) will be collected starting the day of each injection and through 28 days following each injection. Medically-attended AEs (MAAEs) will be collected starting on Day 1 and through 6 months after the last injection. Serious adverse events (SAEs) will be collected from time of consent through end-of-study (EOS). Deaths, AESIs, and AEs leading to withdrawal from further injections or from study participation will be collected through EOS. Pregnancy safety and general outcome data will be collected in all subjects who become pregnant during the study from Day 1 to EOS, including spontaneous and voluntary terminations and congenital abnormalities. Pregnancy safety and general outcome data may be collected beyond EOS (ie, for pregnancies continuing beyond EOS visit).

Subjects will have scheduled blood samplings over the course of the study to assess eligibility, seroconversion due to primary CMV infection (CMV-seronegative cohort), vaccine induced antibody responses, and antibody persistence. A more detailed overview of procedures and visits can be found in the schedules of assessments (SOAs) (Table 11 and Table 12).

TABLE 11

Schedule of Assessment - Vaccination Phase (Screening - Day 197/Month 7)

| | Visit Number | | | | | | | | | |
|---|---|---|---|---|---|---|---|---|---|---|
| | 0 | 1 | | 2 | 3 | | 4 | 5, 6 | 7 | 8 |
| Timepoint (1 month = 28 days) | | D1 | | M 1 | M 2 | | M 3 | M 4, 5 | M 6 | M 7 |
| Type of Visit | S | S | N/A | SC | S | N/A | S | SC | S | N/A | S |
| Study Visit Day | Day 0 (Screening) | Day 1 (Baseline) | Day 8 | Day 29 | Day 57 | Day 64 | Day 85 | Day 113 Day 141 | Day 169 | Day 176 | Day 197 |

TABLE 11-continued

Schedule of Assessment - Vaccination Phase (Screening - Day 197/Month 7)

| | Visit Number | | | | | | | | | |
|---|---|---|---|---|---|---|---|---|---|---|
| | 0 | 1 | 2 | 3 | | 4 | 5, 6 | 7 | | 8 |
| Window Allowance (Days) | −28 | 0 | +3 | +/−7 | +/−7 | +3 | +/−7 | +/−7 | +/−7 | +3 | +/−7 |
| Days Since Most Recent Injection Visit (except M6/D169 which should be calculated from D1) | — | 0 | 7 | 28 | 56/0 | 7 | 28 | 56, 84 | 168/0 | 7 | 28 |
| ICF, demographics, concomitant medications, medical history, including pregnancy history | X | | | | | | | | | | |
| Serum for CMV IgG/IgM for eligibility | X | | | | | | | | | | |
| Confirmation of inclusion/exclusion criteria | X | X | | | | | | | | | |
| Physical examination and height and weight[a] | X | X | | | X | | X | | X | | X |
| Vital signs[b] | X | X | | | X | | X | | X | | X |
| Urine pregnancy testing[c] | X | X | | | X | | X | | X | | X |
| Randomization | | X | | | | | | | | | |
| Serum for antibody-mediated immunogenicity | | X | | | | | X | | | | X |
| CMV-Seronegative cohort only: Serum for CMV primary infection (IgG)[d] | | X | | | X | | X | | X | | X |
| CMV-Seropositive only: Urine for CMV shedding[e] | | X | | | X | | X | | X | | X |
| Study injection (vaccination) | | X | | | X | | | | X | | |
| eDiary activation for solicited AR (7 days) and 30-minute post-injection solicited AR assessments, vital signs, and eDiary entry review[f] | | X | | | X | | | | X | | |
| Review of solicited AR eDiary[g] | | | X | | | X | | | | X | |
| Follow-up safety telephone calls[h] | | | | X | | | | X | | | |
| Recording of Unsolicited AEs[i] | | X | X | X | X | X | X | | X | X | X |
| Recording of MAAEs | | X | X | X | X | X | X | X | X | X | X |
| Recording of SAEs | X | X | X | X | X | X | X | X | X | X | X |
| Recording of concomitant medications and nonstudy vaccinations[j] | | X | X | X | X | X | X | X | X | X | X |
| CMV-seronegative cohort only: CMV Illness Assessment if symptoms of possible primary CMV infection are reported[k] | | | | | | | X | ⟶ | | | |
| CMV-seronegative cohort only: Seroconversion Visit if seroconversion due to primary CMV infection is documented[l] | | | | | | | X | ⟶ | | | |

Abbreviations:
AE = adverse event;
AR = adverse reaction;
CMV = cytomegalovirus,
D = day;
eDiary = electronic diary.
ePRO = electronic patient-reported outcomes;
EQ-5D-5L = EuroQol-5 Dimension 5 Level;
ICF = informed consent form;
HRPQ = Health-Related Productivity Questionnaire;
IgG = Immunoglobulin G;
IgM = Immunoglobulin M;
M = month;
MAAE = medically-attended adverse event;
min = minute;
N/A = not applicable;
PCR = polymerase chain reaction;
SAE = serious adverse event;
S = study site visit;
SC = safety (telephone) call.

TABLE 12

Schedule of Assessment - Follow-up Phase (Post Month 7-Month 30)

| | Visit Number | | | | | | | | | |
|---|---|---|---|---|---|---|---|---|---|---|
| | 9, 10 | 11 | 12 | 13 | 14, 5 | 16 | 17, 18 | 19 | 20, 21 | 22 |
| Month Timepoint (1 Month = 30 days) | M8, 9 | M 10 | M 11 | M 12 | M 13, 14 | M 15 | M 16, 17 | M 18 | M 19, 20 | M 21 |
| Type of Visit | eD | S* | eD | S* | eD | S* | eD | S* | eD | S* |
| Study Visit Day | D 227 D 257 | D 287 | D 317 | D 347 | D 377 D 407 | D 437 | D 467 D 497 | D 527 | D 557 D 587 | D 617 |
| Window Allowance (Days) | +/-7 | +/-7 | +/-7 | +/-7 | +/-7 | +/-7 | +/-7 | +14 | +/-7 | +/-7 |
| Days since Study Day 1 | 226, 256 | 286 | 316 | 346 | 376, 406 | 436 | 466, 496 | 526 | 556, 586 | 616 |
| Physical examination and vital signs[a] | | X | | X | | X | | X | | X |
| Urine pregnancy[b] | | X | | X | | X | | X | | X |
| Serum for antibody-mediated immunogenicity | | | | X | | | | X | | |
| CMV-seronegative cohort only: Serum for primary CMV infection[c] | | X | | X | | X | | X | | X |
| CMV-seropositive only: Urine for CMV shedding[d] | | X | | X | | X | | X | | X |
| eDiary safety and surveillance/ Follow-up safety telephone calls[e] | X | | X | | X | | X | | X | |
| Recording of MAAEs and related concomitant medications relevant to or for the treatment of the MAAE | X | X | X | X | | | | | | |
| Recording of SAEs and related concomitant medications relevant to or for the treatment of the SAE | X | X | X | X | X | X | X | X | X | X |
| CMV-seronegative cohort only: Illness Assessment Visit if symptoms of possible primary CMV infection are reported[f] | ←—————————————————————————————————→ | | | | | | | | | |
| CMV-seronegative cohort only: Seroconversion Visit if seroconversion due to primary CMV infection is documented[g] | ←—————————————————————————————————→ | | | | | | | | | |

Study Completion

| | Visit Number | | | | | |
|---|---|---|---|---|---|---|
| | 23, 24 | 25 | 26, 27 | 28 | 29, 30 | 31 |
| Month Timepoint (1 Month = 30 days) | M 22, 23 | M 24 | M 25, 26 | M 27 | M 28, 29 | M 30 EOS |
| Type of Visit | eD | S* | eD | S* | eD | S* |
| Study Visit Day | D 647 D 677 | D 707 | D 737 D 767 | D 797 | D 827 D 857 | D 887 |
| Window Allowance (Days) | +/-7 | +/-7 | +/-7 | +/-7 | +/-7 | +14 |
| Days since Study | | | | | | |

TABLE 12-continued

| Schedule of Assessment - Follow-up Phase (Post Month 7-Month 30) | | | | | | |
|---|---|---|---|---|---|---|
| Day 1 | 646, 676 | 706 | 736, 766 | 796 | 826, 856 | 886 |
| Physical examination and vital signs[a] | | X | | X | | X |
| Urine pregnancy[b] | | X | | X | | X |
| Serum for antibody-mediated immunogenicity | | X | | | | X |
| CMV-seronegative cohort only: Serum for primary CMV infection[c] | | X | | X | | X |
| CMV-seropositive only: Urine for CMV shedding[d] | | X | | X | | X |
| eDiary safety and surveillance/ Follow-up safety telephone calls[e] | X | | X | | X | |
| Recording of MAAEs and related concomitant medications relevant to or for the treatment of the MAAE | | | | | | |
| Recording of SAEs and related concomitant medications relevant to or for the treatment of the SAE | X | X | X | X | X | X |
| CMV-seronegative cohort only: Illness Assessment Visit if symptoms of possible primary CMV infection are reported[f] | ←――――――――――――――――――――→ | | | | | |
| CMV-seronegative cohort only: Seroconversion Visit if seroconversion due to primary CMV infection is documented[g] | ←――――――――――――――――――――→ | | | | | |
| Study Completion | | | | | | X |

Abbreviations:
AE = adverse event;
CMV = cytomegalovirus;
D = day;
eD = electronic diary;
EOS = end of study;
ePRO = electronic patient-reported outcomes;
EQ-5D-5L = EuroQol-5 Dimension 5 Level;
HRPQ = Health-Related Productivity Questionnaire;
M = month;
MAAE = medically-attended adverse event;
SAE = serious adverse event;
S* = study site visit or home visit;
SC = safety (telephone) call.

The study is observer-blind where only delegated unblinded study personnel responsible for study vaccine preparation, administration and/or accountability will have access to study treatment assignments. Neither the participant nor participant's parent(s)/legally acceptable representative(s) (LAR[s]) nor the Investigator nor study site staff responsible for study assessments/safety will have access to the treatment assignment during the conduct of the study. The Investigator may unblind in the event of an emergency.

Subjects may experience AEs that necessitate an unscheduled visit; these AEs will be recorded as MAAEs. There may also be situations in which the Investigator asks a participant to return for an unscheduled visit following the report of an AE. Additional examinations may be conducted at these visits as necessary to ensure the safety and well-being of subjects during the study. Electronic case report forms should be completed for each unscheduled visit.

All subjects will be followed for safety for a minimum of 30 months (24 months after the third injection) for seroconversion due to primary CMV infection (CMV seronegative cohort), CMV shedding (CMV seropositive cohort), pregnancy outcomes, and for SAEs through to EOS and MAAEs for 6 months after the last injection (Table 12).

Subjects who discontinue from further vaccinations after either the first or second vaccination but do not withdraw consent will be followed for safety as noted above and will provide blood samples for immunogenicity and seroconversion due to primary CMV infection (CMV seronegative cohort) and CMV shedding (CMV seropositive cohort) (Table 12).

Cytomegalovirus-Seronegative Cohort:

Cytomegalovirus-seronegative cohort subjects will provide blood samples for assessment of seroconversion due to primary CMV infection and urine samples for pregnancy testing at the following study visits: Day 1, Month 2 (Day 57), Month 3 (Day 85), Month 6 (Day 169), Month 7 Day 197), Month 10 (Day 287), Month 12 (Day 347), Month 15 (Day 437), Month 18 (Day 527), Month 21 (Day 617), Month 24 (Day 707), Month 27 (Day 797), and Month 30 (Day 887, EOS). (Table 11 and Table 12.)

Subjects meeting the primary endpoint of seroconversion due to primary CMV infection from Month 3 through EOS will be contacted to be seen for an unscheduled study visit (Seroconversion Visit) for clinical assessment including blood, urine, and saliva sampling for CMV polymerase chain reaction (PCR), after which they will return to the planned visit schedule. After the Seroconversion Visit, urine will be collected for CMV PCR at all subsequent scheduled study visits through EOS. Once a participant meets the criteria of seroconversion due to primary CMV infection, serum collection to test for primary CMV infection will not be completed at subsequent visits.

In the CMV-seronegative cohort, it is anticipated that the majority of seroconversions due to primary CMV infection will be asymptomatic and will be detected by planned serological surveillance testing at scheduled study visits. Subjects will be assessed for symptoms meeting criteria for possible symptomatic primary CMV infection by protocol defined criteria at scheduled study visits starting at Month 3, safety telephone calls, and via eDiary safety surveillance prompts (beginning at Month 8). Subjects meeting protocol defined criteria for possible symptomatic primary CMV infection in between scheduled study visits, during safety telephone calls, or via eDiary during the Follow up Phase will be instructed to return to the study site for a CMV Illness Assessment Visit (unscheduled visit). The CMV Illness Assessment Visit will include physical examination; collection of blood samples for hematology, chemistry, seroconversion due to primary CMV infection, and Epstein-Barr virus (EBV) panel; and a urine sample for CMV PCR. At the discretion of the Investigator, testing for HIV antibodies, HIV viral load, and severe acute respiratory syndrome coronavirus 2 (SARS-CoV-2) may be performed. In addition, subjects reporting symptoms for possible symptomatic primary CMV infection by protocol-defined criteria may also receive electronic patient reported outcomes (ePRO) questionnaires to collect health status and health-related productivity information as reported by the participant. The questionnaires may include the EuroQol 5 Dimension 5 Level (EQ 5D 5L) and the Health-Related Productivity Questionnaire (HRPQ), which may be triggered based on the CMV Illness Assessment visit or on symptoms reported via the safety eDiary, and based on availability and implementation timelines for the ePRO questionnaires.

Cytomegalovirus-Seropositive Cohort:

Cytomegalovirus-seropositive cohort subjects will have urine sampling for CMV shedding and urine pregnancy testing at the following study visits: Day 1, Month 2 (Day 57), Month 3 (Day 85), Month 6 (Day 169), Month 7 (Day 197), Month 10 (Day 287), Month 12 (Day 347), Month 15 (Day 437), Month 18 (Day 527), Month 21 (Day 617), Month 24 (Day 707), Month 27 (Day 797), and Month 30 (Day 887, EOS). (Table 11 and Table 12).

Study Duration:

The study duration will be approximately 30 months for each participant.

Sample Size:

The sample size of CMV-seropositive subjects is driven by safety. Approximately 2,000 CMV seropositive female and male subjects will be randomly assigned in a 1:1 ratio to the hCMV vaccine and placebo. With 1,000 CMV-seropositive subjects exposed to the hCMV vaccine, the study has at least 90% probability to observe at least 1 CMV-seropositive participant with an AE at a true 0.25% AE rate.

The sample size of CMV seronegative male subjects is driven by safety. Approximately 600 CMV seronegative male subjects will be randomly assigned in a 1:1 ratio to the hCMV vaccine and placebo. With 300 CMV seronegative male subjects exposed to the hCMV vaccine, the study has at least 95% probability to observe at least 1 CMV seronegative male participant with an AE at a true 1% AE rate.

Objectives and Endpoints

Primary Objectives:

The primary objectives of this study are as follows:

1) To demonstrate the efficacy of the hCMV mRNA vaccine to prevent primary CMV infection in CMV seronegative female subjects 2) To evaluate the safety and reactogenicity of the hCMV mRNA vaccine when administered on a 3-dose injection schedule in all subjects.

Secondary Objectives:

The secondary objectives of this study are as follows:

1) To evaluate immunogenicity to the hCMV mRNA vaccine when administered on a 3-dose injection schedule in all subjects.

2) To evaluate persistence of immunogenicity to the hCMV mRNA vaccine through 24 months after the third injection in all subjects.

Exploratory Objectives:

The exploratory objectives of this study are as follows:

1) To evaluate the effect of the hCMV mRNA vaccine on CMV infection kinetics in CMV-seronegative subjects meeting the endpoint of seroconversion due to primary CMV infection as measured by CMV PCR in blood, urine, and saliva.

2) To evaluate the effect of the hCMV mRNA vaccine on the frequency and level of urinary CMV shedding in CMV seropositive subjects.

3) In CMV-seronegative female subjects receiving the hCMV mRNA vaccine, to assess levels of antigen specific nAb and binding antibodies in subjects meeting the endpoint of seroconversion due to primary CMV infection and subjects not meeting the endpoint of seroconversion due to primary CMV infection.

4) To evaluate the effect of the hCMV mRNA vaccine on incidence of symptomatic primary CMV infection in CMV seronegative subjects.

5) To evaluate immune markers after receipt of the hCMV mRNA vaccine as correlates of risk for primary CMV infection in CMV-seronegative subjects.

6) To describe the effect of the hCMV mRNA vaccine to prevent primary CMV infection in CMV seronegative subjects who received 2 doses of a 3-dose regimen.

7) To evaluate the impact of symptomatic primary CMV infection on participant reported health state and health related productivity in CMV seronegative subjects.

8) In CMV seronegative male subjects, to evaluate the effect of the hCMV mRNA vaccine on incidence of primary CMV infection.

Primary Endpoints:

The primary endpoints of this study are as follows:

1) Primary CMV infection, defined as seroconversion from a negative to a positive result for serum IgG as measured by a platform-based automated immunoassay based on at least 1 of the 4 recombinant CMV antigens not encoded by the hCMV mRNA vaccine (pp150, pp28, pp52, pp38) assessed starting 28 days after the third injection.

2) Solicited ARs through 7 days after each injection, unsolicited AEs through 28 days after each injection, MAAEs from Day 1 through 6 months after the last injection, AESIs from Day 1 through EOS, and SAEs from time of consent through EOS.

Secondary Endpoints:

The secondary endpoints of this study are as follows:

1) Antigen-specific nAb and binding antibody GMTs on Day 1, Month 3, Month 7, and Month 12.

2) Antigen-specific nAb and binding antibody GMTs on Month 18, Month 24, and Month 30.

Analyses

Immunogenicity Assessments

Immunogenicity for this study will be assessed as follows:

1) Serum functional antibody levels against vaccine antigens as measured by nAb titer against epithelial cell infection and nAb titer against fibroblast infection.

2) Serum binding antibody titers against vaccine antigens as measured by enzyme-linked immunosorbent assay specific to the gB and pentamer proteins.

Safety Assessments

Safety assessments will include monitoring and recording of the following for each subject:

1) Solicited local and systemic ARs that occur during the 7 days following each injection (ie, the day of injection and 6 subsequent days). Any solicited AR that is ongoing beyond Day 7 will be recorded until no longer reported, not exceeding 28 days. Solicited ARs will be recorded daily using eDiaries.

a) Solicited local ARs include injection site pain, injection site erythema [redness], injection site swelling/induration [hardness], and localized axillary swelling or tenderness ipsilateral to the vaccination arm.

b) Solicited systemic ARs include headache, fatigue, myalgia (muscle aches all over the body), arthralgia (aching in several joints), nausea, fever, and chills.

2) Beginning at Month 8, subjects will receive safety eDiary prompts at time points specified in the schedule of assessments. Safety eDiary will prompt the participant to report occurrence of relevant safety events. If eDiary prompt results in identification of a relevant safety event, trained study site personnel will call the participant within 1 business day, or within 2 business days after the window for eDiary completion has closed if the participant did not complete the eDiary, to collect information relating to MAAEs (up to 6 months after the last injection), AEs leading to withdrawal, SAEs, and information on concomitant medications associated with those events. For the CMV-seronegative cohort only, safety eDiary will also prompt the participant to report symptoms that may be consistent with symptomatic CMV. For CMV seronegative subjects who have not seroconverted due to primary CMV infection, site personnel will review symptoms reported in the safety eDiary and determine whether a CMV Illness Assessment Visit is required.

3) Unsolicited AEs observed or reported starting on Day 1 and during the 28 days following each injection (ie, the first day of each injection and 27 subsequent days).

4) AEs leading to discontinuation from dosing and/or study participation from Day 1 through Month 30 (Day 887) or withdrawal from the study.

5) MAAEs from Day 1 through 6 months after the last injection or withdrawal from the study.

6) AESIs from Day 1 through Month 30 (Day 887) or withdrawal from the study.

7) SAEs from time of consent through Month 30 (Day 887) or withdrawal from the study.

8) Vital sign measurements.

9) Physical examination findings.

10) Pregnancy testing at each study visit. For subjects who become pregnant during the study from Day 1 to EOS, pregnancy safety and outcome data will be collected; data may be collected beyond EOS for pregnancies continuing beyond the EOS visit.

Example 8: A Substudy of Infant Outcomes in Subjects Who Become Pregnant During Participation in Phase III The purpose of the substudy is to assess cytomegalovirus (CMV) related outcomes in live births of female subjects who become pregnant during the course of the hCMV mRNA vaccine main Phase III study described in Example 7. All objectives and endpoints in this substudy are exploratory.

The hCMV mRNA vaccine main study is enrolling a female population at risk for CMV infection and reinfection due to the enrollment requirement of close exposure to young children. Since an ultimate goal of developing the hCMV mRNA vaccine is to prevent congenital CMV infection by establishing or enhancing preconceptional immunity against CMV in prospective mothers, this substudy provides a unique opportunity to collect information on infant outcomes in a maternal population at increased risk for CMV infection or reinfection. The objectives of this hCMV mRNA vaccine substudy are to assess all enrolled newborns for CMV shedding, assess for diagnoses of congenital CMV (cCMV) based on clinical records, and assess placental transfer of vaccine induced antibodies in paired maternal/infant blood samples.

Figure 24:
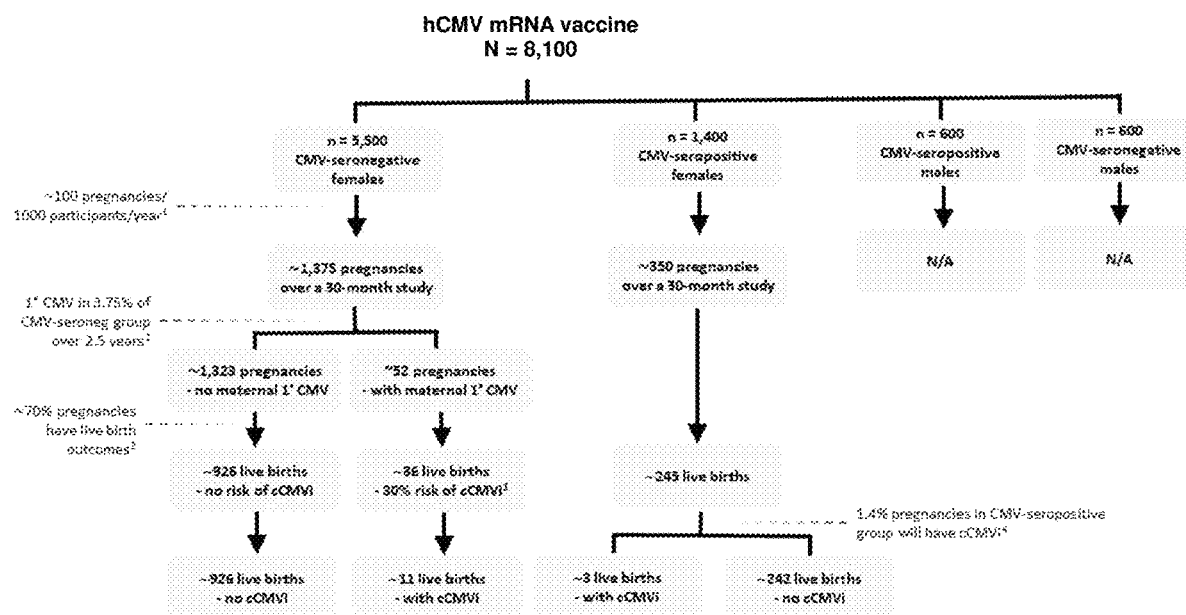
FIG. 24 is a schematic showing congenital CMV infection projections in the infant outcome substudy described in Example 8.
Figure 25:
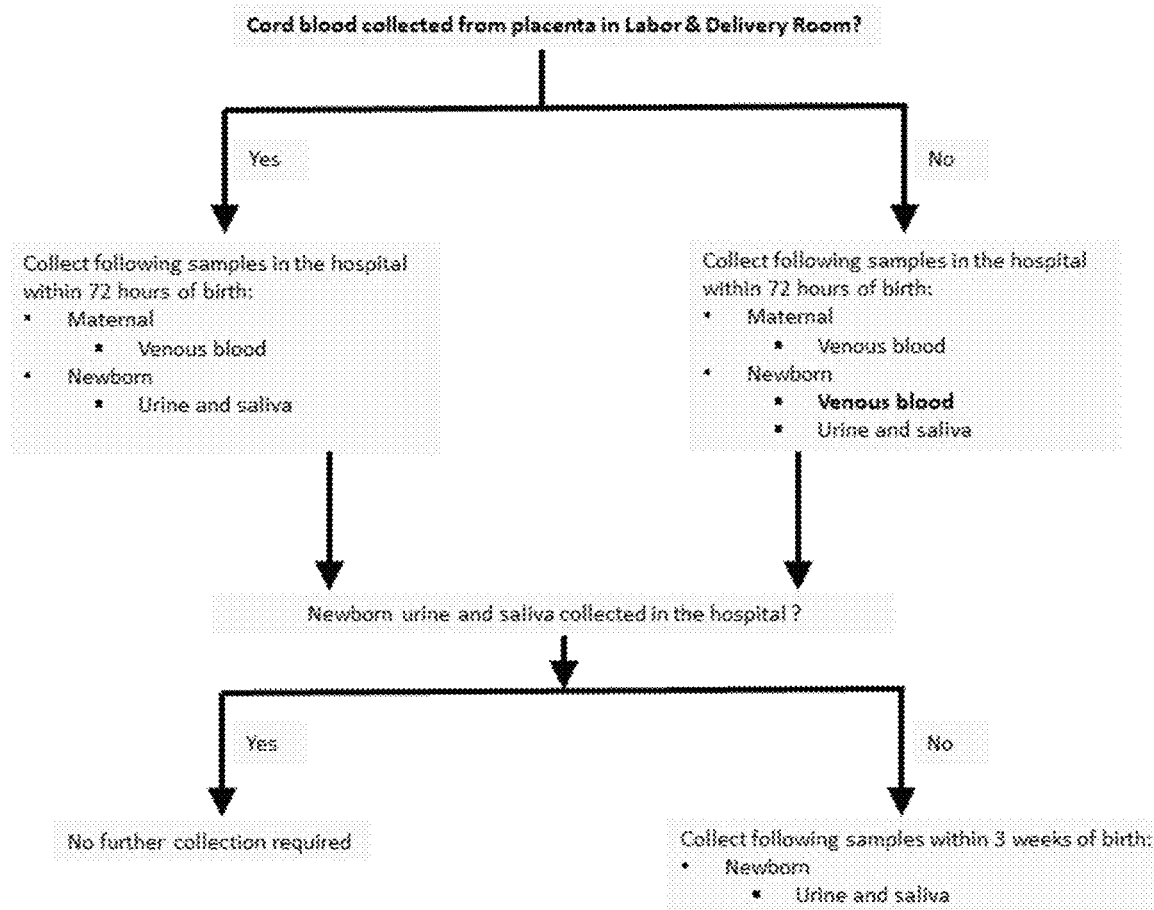
FIG. 25 is a schematic showing the sample collection schema in newborns in the infant outcome substudy described in Example 8.

Given an estimated enrollment of 6,900 (5,500 CMV seronegative and 1,400 CMV seropositive) females in the hCMV mRNA vaccine main Phase III study, and based on published estimates of annual pregnancy incidence, live births, primary CMV infection rates in CMV seronegative pregnant women, and cCMV infection rates in CMV seronegative and CMV seropositive pregnant women, it is estimated that a maximum of approximately 1,200 live births may occur during the course of participation in the hCMV mRNA vaccine main Phase III study and the number of newborns with cCMV infection is expected to be very low (FIG. 24).

Substudy Design

This substudy may enroll all subjects who have received at least 1 study vaccination in the hCMV mRNA vaccine main Phase III study and become pregnant at any point during study participation with plans to carry the pregnancy to term. Pregnancy is defined as a positive urine pregnancy test obtained during the course of participation in the hCMV mRNA vaccine main Phase III study. All subjects who become pregnant during participation in the hCMV mRNA vaccine main Phase III study will not receive any further study injections but will continue to be followed per the main protocol for safety, pregnancy outcome, immunogenicity, seroconversion due to primary CMV infection (CMV-seronegative subjects), CMV shedding (CMV-seropositive subjects), and will be offered in the hCMV mRNA vaccine substudy. In addition, as part of the hCMV mRNA vaccine main Phase III study, pregnant CMV-seronegative subjects will have the option of returning to the study site more frequently (on a monthly basis) to have blood testing for seroconversion due to primary CMV infection.

There are no randomization procedures in this substudy. All study site staff, the CRO blinded team, and the Sponsor will remain blinded to individual treatment assignments.

The duration of participation may begin from the time the hCMV mRNA vaccine subject meets the definition of pregnancy and provides consent and is determined to be eligible for participation in the hCMV mRNA vaccine substudy, through 6 weeks after delivery. Participation in this substudy may extend beyond the EOS visit on hCMV mRNA vaccine (parent study) if the delivery date is less than 6 weeks from the EOS visit or occurs after the EOS visit.

Up to approximately 1,200 subjects and their infants are anticipated to be eligible for participation in this substudy. Subjects will provide individual consent to each of the substudy procedures for themselves and their infant.

Substudy procedures may include the following:
1. Newborn sampling of urine and saliva on 1 occasion within 3 weeks after delivery.
2. Request for and review of subject and/or infant medical records.
3. If within the operational capacity of the subject's study site, collection of 1 set of paired samples* of maternal venous blood obtained ≤72 hours of delivery and newborn cord blood or newborn venous blood (if permissible) obtained ≤72 hours of delivery.

*Maternal sample and newborn sample do not need to be collected at the same time as long as both are taken ≤72 hours of delivery.

This substudy will be conducted in compliance with the protocol, GCP, and all applicable regulatory requirements.

Objectives and Endpoints

Exploratory Objectives
1. To assess the incidence of CMV shedding in newborns of all subjects who become pregnant during the hCMV mRNA vaccine Phase III main study, by treatment group.
2. To assess the a) presence of clinical diagnosis of cCMV infection and b) presence and severity of clinical diagnosis of cCMV disease in infants meeting any of the following criteria:
  i) have abnormalities reported on the hCMV mRNA vaccine main study Pregnancy Report Form;
  ii) meet the exploratory endpoint under Objective 1 for positive CMV PCR results;
  iii) are born to CMV seronegative subjects who meet the primary endpoint of seroconversion due to 1° CMV infection prior to or during the pregnancy.
3. To measure the efficiency of transplacental transfer of vaccine-induced pentamer specific and gB-specific IgG in live births of subjects who were CMV-seronegative at enrollment.

Exploratory Endpoints
1. Positive CMV PCR of newborn saliva and urine or positive CMV PCR of newborn urine sampled within 3 weeks of life.
2. Clinical diagnosis of cCMV infection based on review of infant and/or subject medical records documenting confirmed test results meeting published criteria for cCMV infection.

In infants meeting criteria for clinically diagnosed cCMV infection, assessment for clinical diagnosis of cCMV disease and cCMV disease severity based on review of infant medical records.

3. Newborn:maternal ratio of pentamer-specific and gB-specific binding antibody titers and nAb titers in paired samples of maternal blood obtained ≤72 hours of delivery and newborn cord blood or venous blood obtained ≤72 hours of delivery.

Analyses

Study Assessments and Procedures

The following study assessments and procedures may be completed for subjects in the substudy:

1. Urine pregnancy test (if a positive urine pregnancy test is not documented within the main hCMV mRNA vaccine main study or other medical records).

2. Newborn sampling of urine or saliva+/−urine for CMV PCR on 1 occasion within 3 weeks after delivery. These samples may be collected either at the birth facility or in the study clinic, as appropriate (FIG. 24). Saliva samples testing positive for CMV by PCR will have follow up urine sampling for CMV PCR testing. Newborn urine samples will be collected using a urine bag if performed at the study clinic. Saliva samples will be collected at least 90 minutes after the last breastfeeding using an oral swab. The Principal Investigator will immediately refer the subject and her infant to the subject's pediatrician and inform the subject's obstetrician of any infant urine or saliva sample returns a positive CMV PCR result.

A clinical diagnosis of cCMV infection and disease will be based on clinical assessment and diagnosis documented in infant ±subject medical records.

3. Request for and review of subject and/or infant medical records if any of the following occur or are reported:
a. infants with positive urine or saliva CMV PCR results from samples taken within 3 weeks after delivery (as above);
b. congenital anomaly or infant abnormalities reported on the Pregnancy Report Form completed as part of the hCMV mRNA vaccine main study;

c. infants born to CMV seronegative subjects who meet the primary endpoint of seroconversion due to primary CMV infection prior to or during pregnancy.

Medical records will be reviewed for criteria supporting the diagnosis of cCMV infection and disease.

4. If within the operational capability of the subject's study site, collection of 1 set of paired samples of maternal blood obtained ≤72 hours of delivery and newborn cord blood or newborn venous blood obtained ≤72 hours of delivery. Immunogenicity assessments of these samples may include:

a. Serum binding antibody levels to the pentamer and gB vaccine antigens as measured by enzyme-linked immunosorbent assay.

b. Serum functional antibody levels to the pentamer and gB vaccine antigens as measured by nAb titer against epithelial cell infection and nAb titer against fibroblast infection.

Immunogenicity Assessments

No assessment of clinical efficacy will be performed in this study. All objectives in this substudy are exploratory.

Safety Assessments

Safety will be assessed as described in the hCMV mRNA vaccine main Phase III study (Example 7).

Sequences

It should be understood that any of the mRNA sequences described herein may include a 5' UTR and/or a 3' UTR. The UTR sequences may be selected from the following sequences, or other known UTR sequences may be used. It should also be understood that any of the mRNA constructs described herein may further comprise a polyA tail and/or cap (e.g., 7mG(5')ppp(5')NlmpNp). Further, while many of the mRNAs and encoded antigen sequences described herein include a signal peptide and/or a peptide tag (e.g., C-terminal His tag), it should be understood that the indicated signal peptide and/or peptide tag may be substituted for a different signal peptide and/or peptide tag, or the signal peptide and/or peptide tag may be omitted.

5' UTR:

(SEQ ID NO: 13)
GGGAAAUAAGAGAGAAAAGAAGAGUAAGAAGAAAUAUAAGAGCCACC

3' UTR:

(SEQ ID NO: 14)
UGAUAAUAGGCUGGAGCCUCGGUGGCCAUGCUUCUUGCCCCUUGGGC

CUCCCCCCAGCCCCUCCUCCCCUUCCUGCACCCGUACCCCCGUGGUC

UUUGAAUAAAGUCUGAGUGGGCGGC

TABLE 13 hCMV mRNA and antigen sequences

| | | SEQ ID NO: |
|---|---|---|
| hCMV gB mRNA | | |
| SEQ ID NO: 1 consists of, from 5' end to 3' end, 5' UTR SEQ ID NO: 13, mRNA ORF SEQ ID NO: 7, and 3' UTR SEQ ID NO: 14. | | 1 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA AGAGCCACC | 13 |
| ORF of mRNA Construct (excluding the stop codon) | AUGGAAUCCAGGAUCUGGUGCCUGGUAGUCUGCGUUAAC UUGUGUAUCGUCUGUCUGGGUGCUGCGGUUUCCUCAUCU UCUACUCGUGGAACUUCUGCUACUCACAGUCACCAUUCC UCUCAUACGACGUCUGCUGCUCACUCUCGAUCCGGUUCA GUCUCUCAACGCGUAACUUCUUCCCAAACGGUCAGCCAU GGUGUUAACGAGACCAUCUACAACACUACCCUCAAGUAC GGAGAUGUGGUGGGGGUCAAUACCACCAAGUACCCCUAU CGCGUGUGUUCUAUGGCCCAGGGUACGGAUCUUAUUCGC UUUGAACGUAAUAUCGUCUGCACCUCGAUGAAGCCCAUC AAUGAAGACCUGGACGAGGGCAUCAUGGUGGUCUACAAA CGCAACAUCGUCGCGCACACCUUUAAGGUACGAGUCUAC CAGAAGGUUUUGACGUUUCGUCGUAGCUACGCUUACAUC CACACCACUUAUCUGCUGGGCAGCAACACGGAAUACGUG GCGCCUCCUAUGUGGGAGAUUCAUCAUAUCAACAGCCAC AGUCAGUGCUACAGUUCCUACAGCCGCGUUAUAGCAGGC ACGGUUUUCGUGGCUUAUCAUAGGGACAGCUAUGAAAAC AAAACCAUGCAAUUAAUGCCCGACGAUUAUUCCAACACC CACAGUACCCGUUACGUGACGGUCAAGGAUCAAUGGCAC AGCCGCGGCAGCACCUGGCUCUAUCGUGAGACCUGUAAU CUGAAUUGUAUGGUGACCAUCACUACUGCGCGCUCCAAA UAUCCUUAUCAUUUUUUCGCCACUUCCACGGGUGACGUG GUUGACAUUUCUCCUUUCUACAACGGAACCAAUCGCAAU GCCAGCUACUUUGGAGAAAACGCCGACAAGUUUUUCAUU UUUCCGAACUACACUAUCGUCUCCGACUUUGGAAGACCG AAUUCUGCGUUAGAGACCCACAGGUUGGUGGCUUUUCUU GAACGUGCGACUCGGUGAUCUCCUGGGAUAUACAGGAC GAAAAGAAUGUCACUUGUCAACUCACUUUCUGGGAAGCC UCGGAACGCACCAUUCGUUCCGAAGCCGAGGACUCGUAU CACUUUUCUUCUGCCAAAAUGACCGCCACUUUCUUAUCU | 7 |

TABLE 13-continued hCMV mRNA and antigen sequences

| | | SEQ ID NO: |
|---|---|---|
| | AAGAAGCAAGAGGUGAACAUGUCCGACUCUGCGCUGGAC UGCGUACGUGAUGAGGCUAUAAAUAAGUUACAGCAGAUU UUCAAUACUUCAUACAAUCAAACAUAUGAAAAAUAUGGA AACGUGUCCGUCUUUGAAACCACUGGUGGUUUGGUAGUG UUCUGGCAAGGUAUCAAGCAAAAAUCUCUGGUGGAACUC GAACGUUUGGCCAACCGCUCCAGUCUGAAUCUUACUCAU AAUAGAACCAAAAGAAGUACAGAUGGCAACAAUGCAACU CAUUUAUCCAACAUGGAAUCGGUGCACAAUCGGUCUAC GCCCAGCUGCAGUUCACCUAUGACACGUUGCGCGGUUAC AUCAACCGGGCGCUGGCGCAAAUCGCAGAAGCCUGGUGU GUGGAUCAACGGCGCACCCUAGAGGUCUUCAAGGAACUC AGCAAGAUCAACCCGUCAGCCAUUCUCUCGGCCAUUUAC AACAAACCGAUUGCCGCGCGUUUCAUGGGUGAUGUCUUG GGCCUGGCCAGCUGCGUGACCAUCAACCAAACCAGCGUCA AGGUGCUGCGUGAUAUGAACGUGAAGGAGUCGCCAGGAC GCUGCUACUCACGACCCGUGGUCAUCUUUAAUUUCGCCA ACAGCUCGUACGUGCAGUACGGUCAACUGGGCGAGGACA ACGAAAUCCUGUUGGGCAACCACCGCACUGAGGAAUGUC AGCUUCCCAGCCUCAAGAUCUUCAUCGCCGGGAACUCGGC CUACGAGUACGUGGACUACCUCUUCAAACGCAUGAUUGA CCUCAGCAGUAUCUCCACCGUCGACAGCAUGAUCGCCCUG GAUAUCGACCCGCUGGAAAAUACCGACUUCAGGGUACUG GAACUUUACUCGCAGAAAGAGCUGCGUUCCAGCAACGUU UUUGACCUCGAAGAGAUCAUGCGCGAAUUCAACUCGUAC AAGCAGCGGGUAAAGUACGUGGAGGACAAGGUAGUCGAC CCGCUACCGCCCUACCUCAAGGGUCUGGACGACCUCAUGA GCGGCCUGGGCGCCGCGGGAAAGGCCGUUGGCGUAGCCA UUGGGGCCGUGGGUGGCGCGGUGGCCUCCGUGGUCGAAG GCGUUGCCACCUUCCUCAAAAACCCCUUCGGAGCGUUCAC CAUCAUCCUCGUGGCCAUAGCUGUAGUCAUUAUCACUUA UUUGAUCUAUACUCGACAGCGGCGUUUGUGCACGCAGCC GCUGCAGAACCUCUUUCCCUAUCUGGUGUCCGCCGACGG GACCACCGUGACGUCGGGCAGCACCAAAGACACGUCGUU ACAGGCUCCGCCUUCCUACGAGGAAAGUGUUUAUAAUUC UGGUCGCAAAGGACCGGGACCACCGUCGUCUGAUGCAUC CACGGCGGCUCCGCCUUACACCAACGAGCAGGCUUACCAG AUGCUUCUGGCCCUGGCCCGUCUGGACGCAGAGCAGCGA GCGCAGCAGAACGGUACAGAUUCUUUGGACGGACGGACU GGCACGCAGGACAAGGGACAGAAGCCCAACCUACUAGAC CGACUGCGACAUCGCAAAAACGGCUACCGACACUUGAAA GACUCUGACGAAGAAGAGAACGUC | |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 14 |
| Corresponding amino acid sequence | MESRIWCLVVCVNLCIVCLGAAVSSSSTRGTSATHSHHSSHTT SAAHSRSGSVSQRVTSSQTVSHGVNETIYNTTLKYGDVVGVN TTKYPYRVCSMAQGTDLIRFERNIVCTSMKPINEDLDEGIMVV YKRNIVAHTFKVRVYQKVLTFRRSYAYIHTTYLLGSNTEYVA PPMWEIHHINSHSQCYSSYSRVIAGTVFVAYHRDSYENKTMQ LMPDDYSNTHSTRYVTVKDQWHSRGSTWLYRETCNLNCMV TITTARSKYPYHFFATSTGDVVDISPFYNGTNRNASYFGENAD KFFIFPNYTIVSDFGRPNSALETHRLVAFLERADSVISWDIQDE KNVTCQLTFWEASERTIRSEAEDSYHFSSAKMTATFLSKKQEV NMSDSALDCVRDEAINKLQQIFNTSYNQTYEKYGNVSVFETT GGLVVFWQGIKQKSLVELERLANRSSLNLTHNRTKRSTDGNN ATHLSNMESVHNLVYAQLQFTYDTLRGYINRALAQIAEAWC VDQRRTLEVFKELSKINPSAILSAIYNKPIAARFMGDVLGLASC VTINQTSVKVLRDMNVKESPGRCYSRPVVIFNFANSSYVQYG QLGEDNEILLGNHRTEECQLPSLKIFIAGNSAYEYVDYLFKRMI DLSSISTVDSMIALDIDPLENTDFRVLELYSQKELRSSNVFDLE EIMREFNSYKQRVKYVEDKVVDPLPPYLKGLDDLMSGLGAA GKAVGVAIGAVGGAVASVVEGVATFLKNPFGAFTIILVAIAV VIITYLIYTQRRLCTQPLQNLFPYLVSADGTTVTSGSTKDTSL QAPPSYEESVYNSGRKGPGPPSSDASTAAPPYTNEQAYQMLL ALARLDAEQRAQQNGTDSLDGRTGTQDKGQKPNLLDRLRHR KNGYRHLKDSDEEENV | 15 |
| PolyA tail | 100 nt | |

TABLE 13-continued hCMV mRNA and antigen sequences

| | | SEQ ID NO: |
|---|---|---|
| hCMV UL128 | | |
| SEQ ID NO: 2 consists of, from 5' end to 3' end, 5' UTR SEQ ID NO: 13, mRNA ORF SEQ ID NO: 8, and 3' UTR SEQ ID NO: 14. | | 2 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 13 |
| ORF of mRNA Construct (excluding the stop codon) | AUGAGUCCCAAAGAUCUGACGCCGUUCUUGACGGCGUUG UGGCUGCUAUUGGGUCACAGCCGCUGCCGCGGGUGCGC GCAGAAGAAUGUUGCGAAUUCAUAAACGUCAACCACCCG CCGGAACGCUGUUACGAUUUCAAAAUGUGCAAUCGCUUC ACCGUCGCGCUGCGGUGUCCGGACGGCGAAGUCUGCUAC AGUCCCGAGAAAACGGCUGAGAUUCGCGGGAUCGUCACC ACCAUGACCCAUUCAUUGACACGCCAGGUCGUACACAAC AAACUGACGAGCUGCAACUACAAUCCGUUAUACCUCGAA GCUGACGGGCGAAUACGCUGCGGCAAAGUAAACGACAAG GCGCAGUACCUGCUGGGCGCCGCUGGCAGCGUUCCCUAUC GAUGGAUCAAUCUGGAAUACGACAAGAUAACCCGGAUCG UGGGCCUGGAUCAGUACCUGGAGAGCGUUAAGAAACACA AACGGCUGGAUGUGUGCCGCGCUAAAAUGGGGCUAUAUGC UGCAG | 8 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 14 |
| Corresponding amino acid sequence | MSPKDLTPFLTALWLLLGHSRVPRVRAEECCEFINVNHPPERC YDFKMCNRFTVALRCPDGEVCYSPEKTAEIRGIVTTMTHSLTR QVVHNKLTSCNYNPLYLEADGRIRCGKVNDKAQYLLGAAGS VPYRWINLEYDKITRIVGLDQYLESVKKHKRLDVCRAKMGY MLQ | 16 |
| PolyA tail | 100 nt | |
| hCMV UL130 | | |
| SEQ ID NO: 3 consists of, from 5' end to 3' end, 5' UTR SEQ ID NO: 13, mRNA ORF SEQ ID NO: 9, and 3' UTR SEQ ID NO: 14. | | 3 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 13 |
| ORF of mRNA Construct (excluding the stop codon) | AUGCUGCGGCUUCUGCUUCGUCACCACUUUCACUGCCUGC UUCUGUGCGCGGUUUGGGCAACGCCCUGUCUGGCGUCUC CGUGGUCGACGCUAACAGCAAACCAGAAUCCGUCCCCGCC AUGGUCUAAACUGACGUAUUCCAAACCGCAUGACGCGGC GACGUUUUACUGUCCUUUUCUCUAUCCCUCGCCCCCACGA UCCCCCUUGCAAUUCUCGGGGUUCCAGCGGGUAUCAACG GGUCCCGAGUGUCGCAACGAGACCCUGUAUCUGCUGUAC AACCGGGAAGGCCAGACCUUGGUGGAGAGAAGCUCCACC UGGGUGAAAAAGGUGAUCUGGUACCUGAGCGGUCGGAAC CAAACCAUCCUCCAACGGAUGCCCCGAACGGCUUCGAAAC CGAGCGACGGAAACGUGCAGAUCAGCGUGGAAGACGCCA AGAUUUUUGGAGCGCACAUGGUGCCCAAGCAGACCAAGC UGCUACGCUUCGUCGUCAACGAUGGCACACGUUAUCAGA UGUGUGUGAUGAAGCUGGAGAGCUGGGCUCACGUCUCC GGGACUACAGCGUGUCUUUUCAGGUGCGAUUGACGUUCA CCGAGGCCAAUAACCAGACUUACACCUUCUGCACCCAUCC CAAUCUCAUCGUU | 9 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 14 |

TABLE 13-continued hCMV mRNA and antigen sequences

| | | SEQ ID NO: |
|---|---|---|
| Corresponding amino acid sequence | MLRLLLRHHFHCLLLCAVWATPCLASPWSTLTANQNPSPPWS KLTYSKPHDAATFYCPFLYPSPPRSPLQFSGFQRVSTGPECRNE TLYLLYNREGQTLVERSSTWVKKVIWYLSGRNQTILQRMPRT ASKPSDGNVQISVEDAKIFGAHMVPKQTKLLRFVVNDGTRYQ MCVMKLESWAHVFRDYSVSFQVRLTFTEANNQTYTFCTHPN LIV | 17 |
| PolyA tail | 100 nt | | hCMV UL131

| | | |
|---|---|---|
| SEQ ID NO: 4 consists of, from 5' end to 3' end, 5' UTR SEQ ID NO: 13, mRNA ORF SEQ ID NO: 10, and 3' UTR SEQ ID NO: 14. | | 4 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 13 |
| ORF of mRNA Construct (excluding the stop codon) | AUGCGGCUGUGUCGGGUGUGGCUGUCUGUUUGUCUGUGC GCCGUGGUGCUGGGUCAGUGCCAGCGGGAAACCGCGGAA AAGAACGAUUAUUACCGAGUACCGCAUUACUGGGACGCG UGCUCUCGCGCGCUGCCCGACCAAACCCGUUACAAGUAUG UGGAACAGCUCGUGGACCUCACGUUGAACUACCACUACG AUGCGAGCCACGGCUUGGACAACUUUGACGUGCUCAAGA GAAUCAACGUGACCGAGGUGUCGUUGCUCAUCAGCGACU UUAGACGUCAGAACCGUCGCGGCGGCACCAACAAAAGGA CCACGUUCAACGCCGCCGGUUCGCUGGCGCCACACGCCCG GAGCCUCGAGUUCAGCGUGCGGCUCUUUGCCAAC | 10 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 14 |
| Corresponding amino acid sequence | MRLCRVWLSVCLCAVVLGQCQRETAEKNDYYRVPHYWDAC SRALPDQTRYKYVEQLVDLTLNYHYDASHGLDNFDVLKRIN VTEVSLLISDFRRQNRRGGTNKRTTFNAAGSLAPHARSLEFSV RLFAN | 18 |
| PolyA tail | 100 nt | | hCMV gH

| | | |
|---|---|---|
| SEQ ID NO: 5 consists of, from 5' end to 3' end, 5' UTR SEQ ID NO: 13, mRNA ORF SEQ ID NO: 11, and 3' UTR SEQ ID NO: 14. | | 5 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 13 |
| ORF of mRNA Construct (excluding the stop codon) | AUGCGGCCAGGCCUCCCCUCCUACCUCAUCAUCCUCGCCG UCUGUCUCUUCAGCCACCUACUUUCGUCACGAUAUGGCG CAGAAGCCGUAUCCGAACCGCUGGACAAAGCGUUUCACC UACUGCUCAACACCUACGGGAGACCCAUCCGCUUCCUGCG UGAAAAUACCACCCAGUGUACCUACAACAGCAGCCUCCG UAACAGCACGGUCGUCAGGGAAAACGCCAUCAGUUUCAA CUUCUUCCAAAGCUAUAAUCAAUACUAUGUAUUCCAUAU GCCUCGAUGUCUCUUUGCGGGUCCUCUGGCGGAGCAGUU UCUGAACCAGGUAGAUCUGACCGAAACCCUGGAAAGAUA CCAACAGAGACUUAACACUUACGCGCUGGUAUCCAAGA CCUGGCCAGCUACCGAUCUUUCUCGCAGCAGCUAAAGGC ACAAGACAGCCUAGGUGAACAGCCCACCACUGUGCCACCG CCCAUUGACCUGUCAAUACCUCACGUUGGAUGCCACCGC AAACACUCCACACGGCUGGACAGAAUCACAUACCACCUC AGGACUACACCGACCACACUUUAACCAGACCUGUAUCCUC UUUGAUGGACACGAUCUACAUUCAGCACCGUCACACCU UGUUUGCACCAAGGCUUUUACCUCAUCGACGAACUACGU UACGUUAAAAUAACACUGACCGAGGACUUCUUCGUAGUU ACGGUGUCCAUAGACGACGACACACCCAUGCUGCUUAUC | 11 |

TABLE 13-continued hCMV mRNA and antigen sequences

| | | SEQ ID NO: |
|---|---|---|
| | UUCGGCCAUCUUCCACGCGUACUUUUCAAAGCGCCCUAUC<br>AACGCGACAACUUUAUACUACGACAAACUGAGAAACACG<br>AGCUCCUGGUGCUAGUUAAGAAAGAUCAACUGAACCGUC<br>ACUCUUAUCUCAAAGACCCGGACUUUCUUGACGCCGCAC<br>UUGACUUCAACUACCUAGACCUCAGCGCACUACUACGUA<br>ACAGCUUUCACCGUUACGCCGUGGAUGUACUCAAGAGCG<br>GUCGAUGUCAGAUGCUGGACCGCCGCACGGUAGAAAUGG<br>CCUUCGCCUACGCAUUAGCACUGUUCGCAGCAGCCCGACA<br>AGAAGAGGCCGGCGCCCAAGUCUCCGUCCCACGGGCCCUA<br>GACCGCCAGGCCGCACUCUUACAAAUACAAGAAUUUAUG<br>AUCACCUGCCUCUCACAAACACCACCACGCACCACGUUGC<br>UGCUGUAUCCCACGGCCGUGGACCUGGCCAAACGAGCCCU<br>UUGGACACCGAAUCAGAUCACCGACAUCACCAGCCUCGU<br>ACGCCUGGUCUACAUACUCUCUAAACAGAAUCAGCAACA<br>UCUCAUCCCCCAAUGGGCACUACGACAGAUCGCCGACUUU<br>GCCCUAAAACUACACAAAACGCACCUGGCCUCUUUUCUU<br>UCAGCCUUCGCACGCCAAGAACUCUACCUCAUGGGCAGCC<br>UCGUCCACUCCAUGCUGGUACAUACGACGGAGAGACGCG<br>AAAUCUUCAUCGUAGAAACGGGCCUCUGUUCAUUGGCCG<br>AGCUAUCACACUUUACGCAGUUGUUAGCUCAUCCACACC<br>ACGAAUACCUCAGCGACCUGUACACACCCUGUUCCAGUA<br>GCGGGCGACGCGAUCACUCGCUCGAACGCCUCACGCGUCU<br>CUUCCCCGAUGCCACCGUCCCCGCUACCGUUCCCGCCGCC<br>CUCUCCAUCCUAUCUACCAUGCAACCAAGCACGCUGGAAA<br>CCUUCCCCGACCUGUUUUGCUUGCCGCUCGGCGAAUCCUU<br>CUCCGCGCUGACCGUCUCCGAACACGUCAGUUAUAUCGU<br>AACAAACCAGUACCUGAUCAAAGGUAUCUCCUACCCUGU<br>CUCCACCACCGUCGUAGGCCAGAGCCUCAUCAUCACCCAG<br>ACGGACAGUCAAACUAAAUGCGAACUGACGCGCAACAUG<br>CAUACCACACAGCAUCACAGUGGCGCUCAACAUUUCGC<br>UAGAAAACUGCGCCUUUUGCCAAAGCGCCCUGCUAGAAU<br>ACGACGACACGCAAGGCGUCAUCAACAUCAUGUACAUGC<br>ACGACUCGGACGACGUCCUUUUCGCCCUGGAUCCCUACAA<br>CGAAGUGGUGGUCUCAUCUCCGCGAACUCACUACCUCAU<br>GCUUUUGAAGAACGGUACGGUACUAGAAGUAACUGACGU<br>CGUCGUGGACGCCACCGACAGUCGUCUCCUCAUGAUGUCC<br>GUCUACGCGCUAUCGGCCAUCAUCGGCAUCUAUCUGCUC<br>UACCGCAUGCUCAAGACAUGC | |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 14 |
| Corresponding amino acid sequence | MRPGLPSYLIILAVCLFSHLLSSRYGAEAVSEPLDKAFHLLLNT<br>YGRPIRFLRENTTQCTYNSSLRNSTVVRENAISFNFFQSYNQY<br>YVFHMPRCLFAGPLAEQFLNQVDLTETLERYQQRLNTYALVS<br>KDLASYRSFSQQLKAQDSLGEQPTTVPPPIDLSIPHVWMPPQT<br>TPHGWTESHTTSGLHRPHFNQTCILFDGHDLLFSTVTPCLHQG<br>FYLIDELRYVKITLTEDFFVVTVSIDDDTPMLLIFGHLPRVLFK<br>APYQRDNFILRQTEKHELLVLVKKDQLNRHSYLKDPDFLDAA<br>LDFNYLDLSALLRNSFHRYAVDVLKSGRCQMLDRRTVEMAF<br>AYALALFAAARQEEAGAQVSVPRALDRQAALLQIQEFMITCL<br>SQTPPRTTLLLYPTAVDLAKRALWTPNQITDITSLVRLVYILSK<br>QNQQHLIPQWALRQIADFALKLHKTHLASFLSAFARQELYLM<br>GSLVHSMLVHTTERREIFIVETGLCSLAELSHFTQLLAHPHHEY<br>LSDLYTPCSSSGRRDHSLERLTRLFPDATVPATVPAALSILSTM<br>QPSTLETFPDLFCLPLGESFSALTVSEHVSYIVTNQYLIKGISYP<br>VSTTVVGQSLIITQTDSQTKCELTRNMHTTHSITVALNISLENC<br>AFCQSALLEYDDTQGVINIMYMHDSDDVLFALDPYNEVVSS<br>PRTHYLMLLKNGTVLEVTDVVVDATDSRLLMMSVYALSAIIG<br>IYLLYRMLKTC | 19 |
| PolyA tail | 100 nt | | hCMV gL

| | | |
|---|---|---|
| SEQ ID NO: 6 consists of, from 5' end to 3' end, 5' UTR SEQ ID NO: 13, mRNA ORF SEQ ID NO: 12, and 3' UTR SEQ ID NO: 14. | | 6 |
| Chemistry | 1-methylpseudouridine | |
| Cap | 7mG(5')ppp(5')N1mpNp | |

TABLE 13-continued hCMV mRNA and antigen sequences

| | | SEQ ID NO: |
|---|---|---|
| 5' UTR | GGGAAAUAAGAGAGAAAAGAAGAGUAAGAAGAAAUAUA AGAGCCACC | 13 |
| ORF of mRNA Construct (excluding the stop codon) | AUGUGCCGCCGCCCGGAUUGCGGCUUCUCUUUCUCACCUG GACCGGUGAUACUGCUGUGGUGUUGCCUUCUGCUGCCCA UUGUUUCCUCAGCCGCCGUCAGCGUCGCUCCUACCGCCGC CGAGAAAGUCCCCGCGGAGUGCCCCGAACUAACGCGCCGA UGCUUGUUGGGUGAGGUGUUUGAGGGUGACAAGUAUGAA AGUUGGCUGCGCCCGUUGGUGAAUGUUACCGGGCGCGAU GGCCCGCUAUCGCAACUUAUCCGUUACCGUCCCGUUACGC CGGAGGCCGCCAACUCCGUGCUGUUGGACGAGGCUUUCC UGGACACUCUGGCCCUGCUGUACAACAAUCCGGAUCAAU UGCGGGCCCUGCUGACGCUGUUGAGCUCGGACACAGCGC CGCGCUGGAUGACGGUGAUGCGCGGCUACAGCGAGUGCG GCGAUGGCUCGCCGGCCGUGUACACGUGCGUGGACGACC UGUGCCGCGGCUACGACCUCACGCGACUGUCAUACGGGC GCAGCAUCUUCACGGAACACGUGUUAGGCUUCGAGCUGG UGCCACCGUCUCUCUUUAACGUGGUGGUGGCCAUACGCA ACGAAGCCACGCGUACCAACCGCGCCGUGCGUCUGCCCGU GAGCACCGCUGCCGCGCCCGAGGGCAUCACGCUCUUUUAC GGCCUGUACAACGCAGUGAAGGAAUUCUGCCUGCGUCAC CAGCUGGACCCGCCGCUGCUACGCCACCUAGAUAAAUACU ACGCCGGACUGCCGCCCGAGCUGAAGCAGACGCGCGUCAA CCUGCCGGCUCACUCGCGCUAUGGCCCUCAAGCAGUGGAU GCUCGC | 12 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 14 |
| Corresponding amino acid sequence | MCRRPDCGFSFSPGPVILLWCCLLLPIVSSAAVSVAPTAAEKV PAECPELTRRCLLGEVFEGDKYESWLRPLVNVTGRDGPLSQLI RYRPVTPEAANSVLLDEAFLDTLALLYNNPDQLRALLTLLSSD TAPRWMTVMRGYSECGDGSPAVYTCVDDLCRGYDLTRLSYG RSIFTEHVLGFELVPPSLFNVVVAIRNEATRTNRAVRLPVSTAA APEGITLFYGLYNAVKEFCLRHQLDPPLLRHLDKYYAGLPPEL KQTRVNLPAHSRYGPQAVDAR | 20 |
| PolyA tail | 100 nt | |

EQUIVALENTS

All references, patents and patent applications disclosed herein are incorporated by reference with respect to the subject matter for which each is cited, which in some cases may encompass the entirety of the document. This application incorporates by reference the entire contents, including all the drawings and all parts of the specification (including sequence listing or amino acid/polynucleotide sequences) of PCT Publication No. WO2017/070613, filed on Oct. 21, 2016, and entitled "HUMAN CYTOMEGALOVIRUS VACCINE," PCT Publication No. WO2018/075980, filed Oct. 20, 2017, and entitled "HUMAN CYTOMEGALOVIRUS VACCINE," PCT Publication No. WO2021/050864, filed on Sep. 11, 2020, and entitled "HUMAN CYTOMEGALOVIRUS VACCINE," U.S. Pat. No. 10,064,935, granted on Sep. 4, 2018, and entitled "HUMAN CYTOMEGALOVIRUS RNA VACCINES," U.S. Pat. No. 10,383,937, granted on Aug. 20, 2019, and entitled "HUMAN CYTOMEGALOVIRUS RNA VACCINES," U.S. Pat. No. 10,716,846, granted on Jul. 21, 2020, and entitled "HUMAN CYTOMEGALOVIRUS RNA VACCINES," and U.S. Pat. No. 10,695,419, granted on Jun. 30, 2020, and entitled "HUMAN CYTOMEGALOVIRUS VACCINE.

The indefinite articles "a" and "an," as used herein in the specification and in the claims, unless clearly indicated to the contrary, should be understood to mean "at least one." It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

Those skilled in the art will recognize, or be able to ascertain using no more than routine experimentation, many equivalents to the specific embodiments of the disclosure described herein. Such equivalents are intended to be encompassed by the following claims.

What is claimed is:

1. A human cytomegalovirus (hCMV) immunogenic composition comprising (a) a messenger ribonucleic acid (mRNA) polynucleotide comprising an open reading frame encoding a hCMV gH polypeptide; (b) a mRNA polynucleotide comprising an open reading frame encoding a hCMV gL polypeptide; (c) a mRNA polynucleotide comprising an open reading frame encoding a hCMV UL128 polypeptide; (d) a mRNA polynucleotide comprising an open reading frame encoding a hCMV UL130 polypeptide; (e) a mRNA polynucleotide comprising an open reading frame encoding a hCMV UL131A polypeptide; and (f) a mRNA polynucleotide comprising an open reading frame encoding a hCMV gB polypeptide, wherein:
   the molar ratio of (a):(f) within the immunogenic composition is about 1:1;
   the molar ratio of (b):(c):(d):(e) within the immunogenic composition is about 1:1:1:1; and
   the molar ratio of each of (a) and (f) to any one of (b), (c), (d) or (e) within the immunogenic composition is about 1.5:1 to 2:1.

2. The hCMV immunogenic composition of claim 1, wherein the molar ratio of (a):(b):(c):(d):(e):(f) is about 2:1:1:1:1:2.

3. The hCMV immunogenic composition of claim 1, wherein the hCMV immunogenic composition is maintained as a liquid formulation until use in administration to patients.

4. The hCMV immunogenic composition of claim 1, wherein the hCMV immunogenic composition is maintained as a lyophilized formulation until use in administration to patients.

5. The hCMV immunogenic composition of claim 1, wherein the hCMV immunogenic composition is stable for at least three months when stored at a temperature of greater than 0° C. and less than or equal to 10° C.

6. The hCMV immunogenic composition of claim 5, wherein the hCMV immunogenic composition is stable for at least twelve to eighteen months when stored at a temperature of greater than 0° C. and less than or equal to 10° C.

7. The hCMV immunogenic composition of claim 1, wherein the hCMV immunogenic composition is stable for at least three months when stored at a temperature of about 5° C.

8. The hCMV immunogenic composition of claim 1, wherein the hCMV immunogenic composition has increased stability relative to an hCMV immunogenic composition in which (a)-(f) are present in approximately equivalent masses.

9. The hCMV immunogenic composition of claim 8, wherein the hCMV immunogenic composition has increased stability when stored for at least three months, or at least twenty-four months, at a temperature of greater than 0° C.

and less than or equal to 10° C. relative to an hCMV immunogenic composition in which (a)-(f) are present in approximately equivalent masses.

10. The hCMV immunogenic composition of claim 1, wherein the hCMV immunogenic composition has:
   (i) increased pentamer expression relative to an hCMV immunogenic composition in which (a)-(f) are present in approximately equivalent masses;
   (ii) increased pentamer antibody levels relative to an hCMV immunogenic composition in which (a)-(f) are present in approximately equivalent masses;
   (iii) increased gB expression relative to an hCMV immunogenic composition in which (a)-(f) are present in approximately equivalent masses; and/or
   (iv) increased gB antibody levels relative to an hCMV immunogenic composition in which (a)-(f) are present in approximately equivalent masses.

11. The hCMV immunogenic composition of claim 1, wherein the mRNA polynucleotides of (a)-(f) are formulated in at least one lipid nanoparticle in an amount sufficient to induce an antigen-specific immune response to hCMV or a hCMV antigen in a subject.

12. The hCMV immunogenic composition of claim 1, wherein the mRNA polynucleotides of (a)-(f) are formulated in at least one lipid nanoparticle and lyophilized in an amount sufficient to induce an antigen-specific immune response to hCMV or a hCMV antigen in a subject.

13. The hCMV immunogenic composition of claim 1, wherein at least one of the mRNA polynucleotides of (a)-(f) comprises a chemical modification.

14. The hCMV immunogenic composition of claim 13, wherein at least 80% of the uracil in the open reading frame of mRNA polynucleotides (a)-(f) have a chemical modification selected from N1-methyl-pseudouridine or N1-ethyl-pseudouridine.

15. The hCMV immunogenic composition of claim 14, wherein the chemical modification is in the carbon-5 position of the uracil.

16. The hCMV immunogenic composition of claim 1, wherein at least one of the mRNA polynucleotides of (a)-(f) further comprises at least one 5' terminal cap, and wherein the 5' terminal cap is 7mG(5')ppp(5')N1mpNp.

17. The hCMV immunogenic composition of claim 11, wherein the lipid nanoparticle comprises a mixture of lipids comprising: an ionizable amino lipid; cholesterol; 1,2-distearoyl-sn-glycero-3-phosphocholine (DSPC); and 1,2 dimyristoyl-sn-glycerol, methoxypolyethyleneglycol (DMG-PEG).

18. The hCMV immunogenic composition of claim 17, wherein the ionizable amino lipid comprises Compound I:

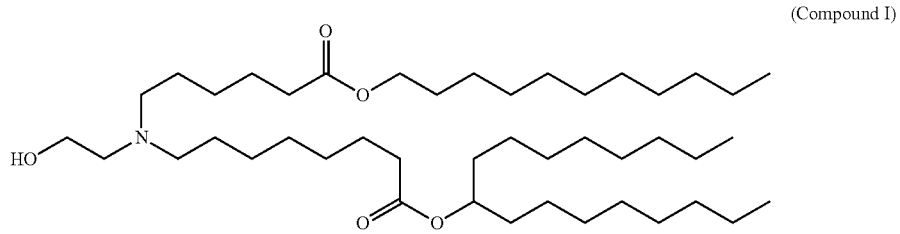 [SMILES: CCCCCCCCCCCOC(=O)CCCCCN(CCO)CCCCCCCC(=O)OC(CCCCCCCC)CCCCCCCC]

(Compound I)

19. The hCMV immunogenic composition of claim 17, wherein the lipid nanoparticle comprises a mixture of lipids comprising 20-60 mol % ionizable amino lipid, 25-55 mol % cholesterol, 5-25 mol % DSPC, and 0.5-15 mol % DMG-PEG.

20. The hCMV immunogenic composition of claim 19, wherein the lipid nanoparticle comprises a mixture of lipids comprising 45-55 mol % ionizable amino lipid, 35-40 mol % cholesterol, 5-15 mol % DSPC, and 1-2 mol % DMG-PEG.

21. The hCMV immunogenic composition of claim 1, wherein the molar ratio of mRNAs (a):(b):(c):(d):(e):(f) is about 2:1:1:1:1:2 and results in 10% less lipid administered to patients compared to when an equal mass of mRNAs (a):(b):(c):(d):(e):(f) is administered.

22. The hCMV immunogenic composition of claim 1, wherein the mRNA encoding hCMV gH protein comprises a nucleotide sequence having at least 90% identity to the nucleotide sequence of sequence of SEQ ID NO: 5, the mRNA encoding hCMV gL protein comprises a nucleotide sequence having at least 90% identity to the nucleotide sequence of sequence of SEQ ID NO: 6, the mRNA encoding hCMV UL128 protein comprises a nucleotide sequence having at least 90% identity to the nucleotide sequence of sequence of SEQ ID NO: 2, the mRNA encoding hCMV UL130 protein comprises a nucleotide sequence having at least 90% identity to the nucleotide sequence of sequence of SEQ ID NO: 3, the mRNA encoding hCMV UL131A protein comprises a nucleotide sequence having at least 90% identity to the nucleotide sequence of sequence of SEQ ID NO: 4, and/or the mRNA encoding hCMV gB protein comprises a nucleotide sequence having at least 90% identity to the nucleotide sequence of sequence of SEQ ID NO: 1.

23. The hCMV immunogenic composition of claim 22, wherein the mRNA encoding hCMV gH protein comprises the nucleotide sequence of sequence of SEQ ID NO: 5, the mRNA encoding hCMV gL protein comprises the nucleotide sequence of sequence of SEQ ID NO: 6, the mRNA encoding hCMV UL128 protein comprises the nucleotide sequence of sequence of SEQ ID NO: 2, the mRNA encoding hCMV UL130 protein comprises the nucleotide sequence of sequence of SEQ ID NO: 3, the mRNA encoding hCMV UL131A protein comprises the nucleotide sequence of sequence of SEQ ID NO: 4, and/or the mRNA encoding hCMV gB protein comprises the nucleotide sequence of sequence of SEQ ID NO: 1.

24. The hCMV immunogenic composition of claim 1, wherein the open reading frame encoding the hCMV gH polypeptide comprises a sequence having at least 90% identity to the sequence of SEQ ID NO: 11, the open reading frame encoding the hCMV gL polypeptide comprises a sequence having at least 90% identity to the sequence of SEQ ID NO: 12, the open reading frame encoding the hCMV UL128 polypeptide comprises a sequence having at least 90% identity to the sequence of SEQ ID NO: 8, the open reading frame encoding the hCMV UL130 polypeptide comprises a sequence having at least 90% identity to the sequence of SEQ ID NO: 9, the open reading frame encoding the hCMV UL131A polypeptide comprises a sequence having at least 90% identity to the of sequence of SEQ ID NO: 10, and/or the open reading frame encoding the hCMV gB polypeptide comprises a sequence having at least 90% identity to the sequence of SEQ ID NO: 7.

25. The hCMV immunogenic composition of claim 24, wherein the open reading frame encoding the hCMV gH polypeptide comprises SEQ ID NO: 11, the open reading frame encoding the hCMV gL polypeptide comprises SEQ ID NO: 12, the open reading frame encoding the hCMV UL128 polypeptide comprises SEQ ID NO: 8, the open reading frame encoding the hCMV UL130 polypeptide comprises SEQ ID NO: 9, the open reading frame encoding the hCMV UL131A polypeptide comprises SEQ ID NO: 10, and/or the open reading frame encoding the hCMV gB polypeptide comprises the sequence of SEQ ID NO: 7.

26. The hCMV immunogenic composition of claim 1, wherein each of the mRNA polynucleotides of (a)-(f) further comprises a polyA tail.

27. The hCMV immunogenic composition of claim 26, wherein the polyA tail is 100 nucleotides in length.

28. The hCMV immunogenic composition of claim 1, wherein the hCMV gH polypeptide comprises an amino acid sequence having at least 90% identity to the amino acid sequence of SEQ ID NO: 19, the hCMV gL polypeptide comprises an amino acid sequence having at least 90% identity to the amino acid sequence of SEQ ID NO: 20, the hCMV UL128 polypeptide comprises an amino acid sequence having at least 90% identity to the amino acid sequence of SEQ ID NO: 16, the hCMV UL130 polypeptide comprises an amino acid sequence having at least 90% identity to the amino acid sequence of SEQ ID NO: 17, the hCMV UL131A polypeptide comprises an amino acid sequence having at least 90% identity to the amino acid sequence of SEQ ID NO: 18, and/or the hCMV gB polypeptide comprises an amino acid sequence having at least 90% identity to the amino acid sequence of SEQ ID NO: 15.

29. A method for producing an antigen-specific immune response to human cytomegalovirus (hCMV) in a subject comprising administering to a human subject an effective amount of the hCMV immunogenic composition of claim 1 to thereby induce an antigen-specific immune response to hCMV or a hCMV antigen in the human subject.

30. The method of claim 29, wherein the hCMV immunogenic composition is administered at a total dose of 100 µg mRNA.

* * * * *